US010422005B2

(12) United States Patent
Nekarda et al.

(10) Patent No.: US 10,422,005 B2
(45) Date of Patent: Sep. 24, 2019

(54) METHODS FOR TREATING COLORECTAL CANCER USING PROGNOSTIC GENETIC MARKERS

(75) Inventors: Hjalmar Nekarda, Essen (DE); Jan Friederichs, München (DE); Bernhard Holzmann, München (DE); Robert Rosenberg, Munich (DE); Anthony Edmund Reeve, Dunedin (NZ); Michael Alan Black, Dunedin (NZ); John Lindsay McCall, Auckland (NZ); Yu-Hsin Lin, Dunedin (NZ); Robert Craig Pollock, Dunedin (NZ)

(73) Assignee: PACIFIC EDGE LIMITED, Dunedin (NZ)

( * ) Notice: Subject to any disclaimer, the term of this patent is extended or adjusted under 35 U.S.C. 154(b) by 363 days.

(21) Appl. No.: 12/214,782

(22) Filed: Jun. 20, 2008

(65) Prior Publication Data

US 2009/0181384 A1    Jul. 16, 2009

Related U.S. Application Data

(63) Continuation of application No. PCT/NZ2006/000343, filed on Dec. 22, 2006.

(30) Foreign Application Priority Data

Dec. 23, 2005 (NZ) ........................ 544432

(51) Int. Cl.
| C12Q 1/68 | (2018.01) |
| C12P 19/34 | (2006.01) |
| C12Q 1/6886 | (2018.01) |
| G01N 33/574 | (2006.01) |
| G16B 20/00 | (2019.01) |
| G16B 25/00 | (2019.01) |

(52) U.S. Cl.
CPC ..... *C12Q 1/6886* (2013.01); *G01N 33/57419* (2013.01); *G16B 20/00* (2019.02); *C12Q 2600/118* (2013.01); *C12Q 2600/158* (2013.01); *C12Q 2600/16* (2013.01); *G16B 25/00* (2019.02)

(58) Field of Classification Search
None
See application file for complete search history.

(56) References Cited

FOREIGN PATENT DOCUMENTS

| SG | 2008046195 | 8/2009 |
| WO | WO/2002/068677 | * 9/2002 |
| WO | WO2002/068677 | 9/2002 |
| WO | WO2004/090550 | 10/2004 |
| WO | WO2005/064009 | 7/2005 |

OTHER PUBLICATIONS

Wang et al. (J Clin Oncol., May 2004, 22:1564-1571).*
Butler et al. (Br J Cancer. Jan. 2000; 82(1): 131-135).*
Dieffenbach et al. (Genome Res.,1993, 3: S30-S37).*
"Affymatrix GeneChip Human Genome U133 Array Set HG-U133A" Geo Host, Mar. 11, 2002.
Eschrich, S et al., "Molecular staging for survival prediction of colorectal cancer patients"; Journal of Clinical Oncology (May 2005) vol. 23, No. 15, pp. 3526-3535.
Arango, D., et al.; "Gene expression profiling predicts recurrence in Dukes' C. colorectal cancer"; Gastroenterology (Sep. 2005) vol. 129, pp. 874-884.
Int'l Preliminary Exam Rp, Jul. 2, 2004, PCT/NZ2003/000045.
Database Medline Abstract, Database Accession No. PMID:16078572; Sichuan Da Xue Xue Bao Yi Xue Ban Jul. 2005; 36(4):503-5; Lin Man-Hua et al: "Expression and clinical significance of nm23-H1, Fas and FasL in colorectal carcinoma tissues".
Goo, Jian-Jun, "Evaluative significance of the expression of Fas antigen and P53 protein in colorectal cancer for the biological characters and prognosis," Basic Research, Reference Number XP008082293. (Best copy available.)
Eschrich, Steven; Molecular Staging or Survival Prediction of Colorectal Cancer Patients; Journal of Clinical Oncology; May 20, 2005; vol. 23, No. 15, pp. 3526-3535.
English Translation of Korean office action dated May 10, 2013; Korean Patent Appl. No. 7018020/2008.
Abstract with reference No. XP-002512619.
European Search Report dated Nov. 2, 2009; Application No. 06835771.4-1222/1977237; Pacific Edge Biotechnology Limited; reference FBP20410.

* cited by examiner

*Primary Examiner* — Young J Kim
(74) *Attorney, Agent, or Firm* — D. Benjamin Borson; Borson Law Group, PC

(57) ABSTRACT

This invention relates to prognostic signatures, and compositions and methods for determining the prognosis of cancer in a patient, particularly for colorectal cancer. Specifically, this invention relates to the use of genetic markers for the prediction of the prognosis of cancer, such as colorectal cancer, based on signatures of genetic markers. In various aspects, the invention relates to a method of predicting the likelihood of long-term survival of a cancer patient, a method of determining a treatment regime for a cancer patient, a method of preparing a treatment modality for a cancer patient, among other methods as well as kits and devices for carrying out these methods.

2 Claims, 9 Drawing Sheets

Number of Appearances in "Top 100" List

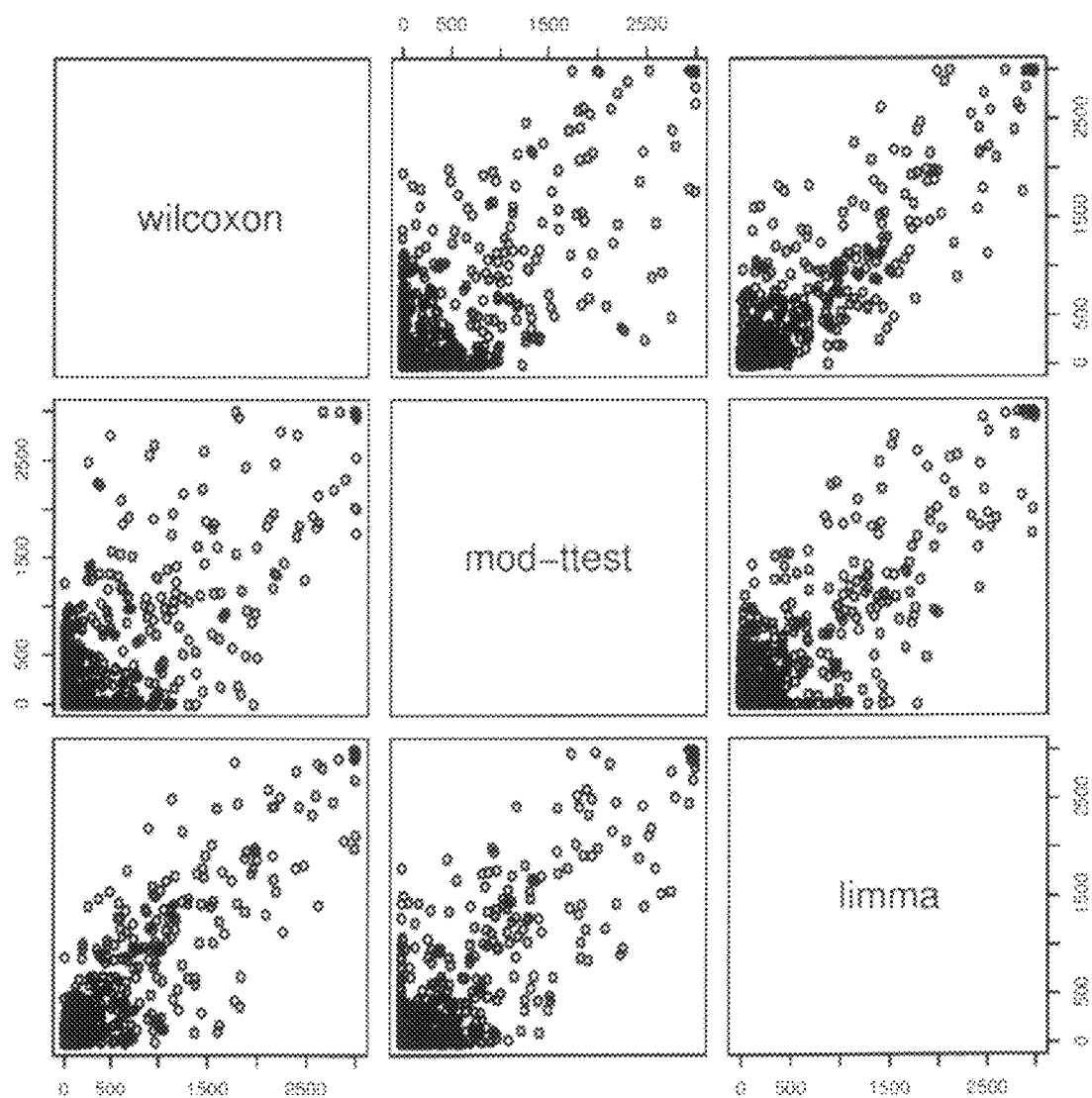

METHODS FOR TREATING COLORECTAL CANCER USING PROGNOSTIC GENETIC MARKERS

RELATED APPLICATIONS

This application is a Continuation under 35 U.S.C. § 1.111(a) of PCT/NZ2006/000343, International Filing Date 22 Dec. 2006, which claims the benefit of New Zealand Provisional Patent Application No. 544432 filed Dec. 23, 2005, both of which are incorporated by reference herein in their entirety.

FIELD OF THE INVENTION

This invention relates to methods and compositions for determining the prognosis of cancer, particularly colorectal cancer, in a patient. Specifically, this invention relates to the use of genetic markers for determining the prognosis of cancer, such as colorectal cancer, based on prognostic signatures.

BACKGROUND OF THE INVENTION

Colorectal cancer (CRC) is one of the most common cancers in the developed world, and its incidence is continuing to increase. Although the progression of colorectal cancer from benign polyp to adenoma to carcinoma is well studied (1), the molecular events influencing the transition and establishment of metastasis are less well understood. The prognosis and treatment of CRC currently depends on the clinico-pathological stage of disease at the time of diagnosis, and primary surgical treatment. Unfortunately disease stage alone does not allow accurate prediction of outcome for individual patients. If patient outcomes could be predicted more accurately treatments could be tailored to avoid under-treating patients destined to relapse, or over-treating patients who would be helped by surgery alone.

Many attempts have been made to identify markers that predict clinical outcome in CRC. Until recently most studies focused on single proteins or gene mutations with limited success in terms of prognostic information (2). Microarray technology enables the identification of sets of genes, called classifiers or signatures that correlate with cancer outcome. This approach has been applied to a variety of cancers, including CRC (3-5), but methodological problems and a lack of independent validation has cast doubt over the findings (6, 7). Furthermore, doubts about the ability of classifiers/signatures to predict outcome have arisen due to poor concordance of identified by different researchers using different array platforms and methodologies (8).

There is a need for further tools to predict the prognosis of colorectal cancer. This invention provides further methods, compositions, kits, and devices based on prognostic cancer markers, specifically colorectal cancer prognostic markers, to aid in the prognosis and treatment of cancer.

SUMMARY OF THE INVENTION

In certain embodiments there is provided a set of markers genes identified to be differentially expressed in recurrent and non-recurrent colorectal tumours. This set of genes can be used to generate prognostics signatures, comprising two or more markers, capable of predicting the progression of colorectal tumour in a patient.

The individual markers can differentially expressed depending on whether the tumour is recurrent or not. The accuracy of prediction can be enhanced by combining the markers together into a prognostic signature for, providing for much more effective individual tests than single-gene assays. Also provided for is the application of techniques, such as statistics, machine learning, artificial intelligence, and data mining to the prognostics signatures to generate prediction models. In another embodiment, expression levels of the markers of a particular prognostic signature in the tumour of a patient can then be applied to the prediction model to determine the prognosis.

In certain embodiments, the expression level of the markers can be established using microarray methods, quantitative polymerase chain reaction (qPCR), or immunoassays.

BRIEF DESCRIPTION OF THE FIGURES

This invention is described with reference to specific embodiments thereof and with reference to the figures, in which:

FIG. 2A depicts a graph of survival using the NZ 22-gene signature on 149 tumours from NZ patients. FIG. 2B depicts a graph of survival using the DE 19-gene signature on 55 tumours from DE patients. FIG. 2C depicts a graph of survival using the NZ prognostic signature validated on 55 tumours from DE patients. FIG. 2D depicts a graph of survival using the DE prognostic signature validated on 149 tumours from NZ patients. P-values were calculated using the log-rank test.

FIG. 3A depicts with Kaplan-Meier analysis using the 22-gene NZ signature on NZ patients with Stage II and Stage III disease. FIG. 3B depicts with Kaplan-Meier analysis using the 19-gene DE signature on NZ patients with Stage II and Stage III disease.

FIG. 4A depicts a graph of sensitivity (proportion of recurrent tumours correctly classified), with respect to number of genes/signature. FIG. 4B depicts a graph of specificity (proportion of non-recurrent tumours correctly classified), with respect to number of genes/signature. FIG. 4C depicts a graph of classification rate (proportion of tumours correctly classified), with respect to number of genes/signature. The nomenclature applied by the statistician is as follows: 1 refers to Stage I or Stage II colorectal cancer (with no progression), and IV refers to eventual progression to Stage IV metastases.

FIG. 5A depicts a graph of the sensitivity (proportion of recurrent tumours correctly classified), with respect to number of genes/signature. FIG. 5B depicts a graph of the specificity (proportion of non-recurrent tumours correctly classified), with respect to number of genes/signature. FIG. 5C depicts a graph of the classification rate (proportion of tumours correctly classified), with respect to number of genes/signature.

FIGS. 6A-6C depict graphs of top counts using the gema method. FIGS. 6D-6F depict graphs of top counts using the mas5 method. FIGS. 6G-6I depict graphs of top counts using the rma method. To compare methods, use row and column as defined on the diagonal to obtain the scatter plot between those two methods, analogous to reading distances off a distance chart on a map FIGS. 7A-7I show the pairs chart (39) of top counts (number of times each gene appeared in the "top-n" gene lists, i.e., top 10, top 20, top 100, and top 325 as described in Example 17) using three different filtering statistics. FIGS. 7A-7C depict two-sample Wilcoxon test (41). FIGS. 7D-7F depict t-test (modified using an ad-hoc correction factor in the denominator to abrogate the effect of low-variance genes falsely appearing as significant). FIGS. 7G-7I depict empirical Bayes as provided by the "limma" (10, 40, 42) package of Bioconductor (12, 40).

DETAILED DESCRIPTION

Definitions

Figure 1:
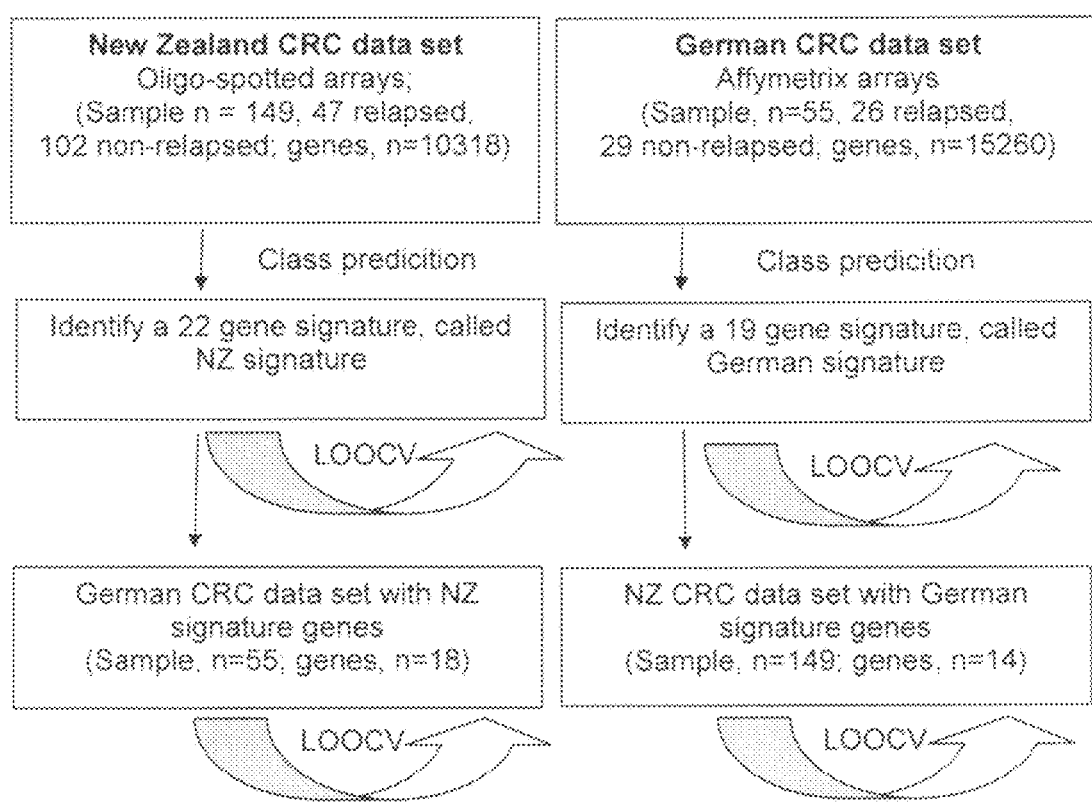
FIG. 1 depicts a flow chart showing the methodology for producing the prognostic signatures from 149 New Zealand (NZ) and 55 German (DE) colorectal cancer (CRC) samples. New Zealand RNA samples were hybridized to oligonucleotide spotted arrays, with a 22-gene signature produced via leave one out cross validation (LOOCV), and then independently validated by LOOCV using the 55 sample DE data set. German RNA samples were hybridized to Affymetrix arrays, with a 19-gene signature produced via LOOCV, and then independently validated by LOOCV using the NZ data set.

Before describing embodiments of the invention in detail, it will be useful to provide some definitions of terms used herein.

The term "marker" refers to a molecule that is associated quantitatively or qualitatively with the presence of a biological phenomenon. Examples of "markers" include a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments, whether related directly or indirectly to a mechanism underlying the phenomenon. The markers of the invention include the nucleotide sequences (e.g., GenBank sequences) as disclosed herein, in particular, the full-length sequences, any coding sequences, any fragments, or any complements thereof, and any measurable marker thereof as defined above.

The terms "CCPM" or "colorectal cancer prognostic marker" or "CCPM family member" refer to a marker with altered expression that is associated with a particular prognosis, e.g., a higher or lower likelihood of recurrence of cancer, as described herein, but can exclude molecules that are known in the prior art to be associated with prognosis of colorectal cancer. It is to be understood that the term CCPM does not require that the marker be specific only for colorectal tumours. Rather, expression of CCPM can be altered in other types of tumours, including malignant tumours.

The terms "prognostic signature," "signature," and the like refer to a set of two or more markers, for example CCPMs, that when analysed together as a set allow for the determination of or prediction of an event, for example the prognostic outcome of colorectal cancer. The use of a signature comprising two or more markers reduces the effect of individual variation and allows for a more robust prediction. Non-limiting examples of CCPMs are set forth in Tables 1, 2, 5, and 9, while non-limiting examples of prognostic signatures are set forth in Tables 3, 4, 8A, 8B, and 9, herein. In the context of the present invention, reference to "at least one," "at least two," "at least five," etc., of the markers listed in any particular set (e.g., any signature) means any one or any and all combinations of the markers listed.

The term "prediction method" is defined to cover the broader genus of methods from the fields of statistics, machine learning, artificial intelligence, and data mining, which can be used to specify a prediction model. These are discussed further in the Detailed Description section.

The term "prediction model" refers to the specific mathematical model obtained by applying a prediction method to a collection of data. In the examples detailed herein, such data sets consist of measurements of gene activity in tissue samples taken from recurrent and non-recurrent colorectal cancer patients, for which the class (recurrent or non-recurrent) of each sample is known. Such models can be used to (1) classify a sample of unknown recurrence status as being one of recurrent or non-recurrent, or (2) make a probabilistic prediction (i.e., produce either a proportion or percentage to be interpreted as a probability) which represents the likelihood that the unknown sample is recurrent, based on the measurement of mRNA expression levels or expression products, of a specified collection of genes, in the unknown sample. The exact details of how these gene-specific measurements are combined to produce classifications and probabilistic predictions are dependent on the specific mechanisms of the prediction method used to construct the model.

"Sensitivity", "specificity" (or "selectivity"), and "classification rate", when applied to the describing the effectiveness of prediction models mean the following:

"Sensitivity" means the proportion of truly positive samples that are also predicted (by the model) to be positive. In a test for CRC recurrence, that would be the proportion of recurrent tumours predicted by the model to be recurrent. "Specificity" or "selectivity" means the proportion of truly negative samples that are also predicted (by the model) to be negative. In a test for CRC recurrence, this equates to the proportion of non-recurrent samples that are predicted to by non-recurrent by the model. "Classification Rate" is the proportion of all samples that are correctly classified by the prediction model (be that as positive or negative).

As used herein "antibodies" and like terms refer to immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., a mouse or human sequence. Further included are camelid antibodies, shark antibodies or nanobodies.

The terms "cancer" and "cancerous" refer to or describe the physiological condition in mammals that is typically characterized by abnormal or unregulated cell growth. Cancer and cancer pathology can be associated, for example, with metastasis, interference with the normal functioning of neighbouring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. Specifically included are colorectal cancers, such as, bowel (e.g., large bowel), anal, and rectal cancers.

The term "colorectal cancer" includes cancer of the colon, rectum, and/or anus, and especially, adenocarcinomas, and may also include carcinomas (e.g., squamous cloacogenic carcinomas), melanomas, lymphomas, and sarcomas. Epidermoid (nonkeratinizing squamous cell or basaloid) carcinomas are also included. The cancer may be associated with particular types of polyps or other lesions, for example, tubular adenomas, tubulovillous adenomas (e.g., villoglandular polyps), villous (e.g., papillary) adenomas (with or without adenocarcinoma), hyperplastic polyps, hamartomas, juvenile polyps, polypoid carcinomas, pseudopolyps, lipomas, or leiomyomas. The cancer may be associated with familial polyposis and related conditions such as Gardner's syndrome or Peutz-Jeghers syndrome. The cancer may be associated, for example, with chronic fistulas, irradiated anal skin, leukoplakia, lymphogranuloma venereum, Bowen's disease (intraepithelial carcinoma), condyloma acuminatum, or human papillomavirus. In other aspects, the cancer may be associated with basal cell carcinoma, extramammary Paget's disease, cloacogenic carcinoma, or malignant melanoma.

The terms "differentially expressed," "differential expression," and like phrases, refer to a gene marker whose expression is activated to a higher or lower level in a subject (e.g., test sample) having a condition, specifically cancer, such as colorectal cancer, relative to its expression in a control subject (e.g., reference sample). The terms also include markers whose expression is activated to a higher or lower level at different stages of the same condition; in recurrent or non-recurrent disease; or in cells with higher or lower levels of proliferation. A differentially expressed marker may be either activated or inhibited at the polynucleotide level or polypeptide level, or may be subject to alternative splicing to result in a different polypeptide product. Such differences may be evidenced by a change in mRNA levels, surface expression, secretion or other partitioning of a polypeptide, for example.

Differential expression may include a comparison of expression between two or more markers (e.g., genes or their gene products); or a comparison of the ratios of the expression between two or more markers (e.g., genes or their gene products); or a comparison of two differently processed products (e.g., transcripts or polypeptides) of the same marker, which differ between normal subjects and diseased subjects; or between various stages of the same disease; or between recurring and non-recurring disease; or between cells with higher and lower levels of proliferation; or between normal tissue and diseased tissue, specifically cancer, or colorectal cancer. Differential expression includes both quantitative, as well as qualitative, differences in the temporal or cellular expression pattern in a gene or its expression products among, for example, normal and diseased cells, or among cells which have undergone different disease events or disease stages, or cells with different levels of proliferation.

The term "expression" includes production of polynucleotides and polypeptides, in particular, the production of RNA (e.g., mRNA) from a gene or portion of a gene, and includes the production of a polypeptide encoded by an RNA or gene or portion of a gene, and the appearance of a detectable material associated with expression. For example, the formation of a complex, for example, from a polypeptide-polypeptide interaction, polypeptide-nucleotide interaction, or the like, is included within the scope of the term "expression". Another example is the binding of a binding ligand, such as a hybridization probe or antibody, to a gene or other polynucleotide or oligonucleotide, a polypeptide or a protein fragment, and the visualization of the binding ligand. Thus, the intensity of a spot on a microarray, on a hybridization blot such as a Northern blot, or on an immunoblot such as a Western blot, or on a bead array, or by PCR analysis, is included within the term "expression" of the underlying biological molecule.

The terms "expression threshold," and "defined expression threshold" are used interchangeably and refer to the level of a marker in question outside which the polynucleotide or polypeptide serves as a predictive marker for patient survival without cancer recurrence. The threshold will be dependent on the predictive model established are derived experimentally from clinical studies such as those described in the Examples below. Depending on the prediction model used, the expression threshold may be set to achieve maximum sensitivity, or for maximum specificity, or for minimum error (maximum classification rate). For example a higher threshold may be set to achieve minimum errors, but this may result in a lower sensitivity. Therefore, for any given predictive model, clinical studies will be used to set an expression threshold that generally achieves the highest sensitivity while having a minimal error rate. The determination of the expression threshold for any situation is well within the knowledge of those skilled in the art.

The term "long-term survival" is used herein to refer to survival for at least 5 years, more preferably for at least 8 years, most preferably for at least 10 years following surgery or other treatment.

The term "microarray" refers to an ordered or unordered arrangement of capture agents, preferably polynucleotides (e.g., probes) or polypeptides on a substrate. See, e.g., Microarray Analysis, M. Schena, John Wiley & Sons, 2002; Microarray Biochip Technology, M. Schena, ed., Eaton Publishing, 2000; Guide to Analysis of DNA Microarray Data, S. Knudsen, John Wiley & Sons, 2004; and Protein Microarray Technology, D. Kambhampati, ed., John Wiley & Sons, 2004.

The term "oligonucleotide" refers to a polynucleotide, typically a probe or primer, including, without limitation, single-stranded deoxyribonucleotides, single- or double-stranded ribonucleotides, RNA: DNA hybrids, and double-stranded DNAs. Oligonucleotides, such as single-stranded DNA probe oligonucleotides, are often synthesized by chemical methods, for example using automated oligonucleotide synthesizers that are commercially available, or by a variety of other methods, including in vitro expression systems, recombinant techniques, and expression in cells and organisms.

The term "polynucleotide," when used in the singular or plural, generally refers to any polyribonucleotide or polydeoxribonucleotide, which may be unmodified RNA or DNA or modified RNA or DNA. This includes, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences. It will be understood that each reference to a "polynucleotide" or like term, herein, will include the full-length sequences as well as any fragments, derivatives, or variants thereof.

"Polypeptide," as used herein, refers to an oligopeptide, peptide, or protein sequence, or fragment thereof, and to naturally occurring, recombinant, synthetic, or semi-synthetic molecules. Where "polypeptide" is recited herein to refer to an amino acid sequence of a naturally occurring protein molecule, "polypeptide" and like terms, are not meant to limit the amino acid sequence to the complete, native amino acid sequence for the full-length molecule. It will be understood that each reference to a "polypeptide" or like term, herein, will include the full-length sequence, as well as any fragments, derivatives, or variants thereof.

The term "prognosis" refers to a prediction of medical outcome, for example, a poor or good outcome (e.g., likelihood of long-term survival); a negative prognosis, or poor outcome, includes a prediction of relapse, disease progression (e.g., tumour growth or metastasis, or drug resistance), or mortality; a positive prognosis, or good outcome, includes a prediction of disease remission, (e.g., disease-free status), amelioration (e.g., tumour regression), or stabilization.

The term "proliferation" refers to the processes leading to increased cell size or cell number, and can include one or more of: tumour or cell growth, angiogenesis, innervation, and metastasis.

The term "qPCR" or "QPCR" refers to quantative polymerase chain reaction as described, for example, in PCR Technique: Quantitative PCR, J. W. Larrick, ed., Eaton Publishing, 1997, and A-Z of Quantitative PCR, S. Bustin, ed., IUL Press, 2004.

The term "tumour" refers to all neoplastic cell growth and proliferation, whether malignant or benign, and all pre-cancerous and cancerous cells and tissues.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. Additional details and explanation of stringency of hybridization reactions, are found e.g., in Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×, Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash comprising 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, Molecular Cloning: A Laboratory Manual, 2nd edition, Sambrook et al., 1989; Oligonucleotide Synthesis, MJ Gait, ed., 1984; Animal Cell Culture, R. I. Freshney, ed., 1987; Methods in Enzymology, Academic Press, Inc.; Handbook of Experimental Immunology, 4th edition, D. M. Weir & C C. Blackwell, eds., Blackwell Science Inc., 1987; Gene Transfer Vectors for Mammalian Cells, J. M. Miller & M. P. Calos, eds., 1987; Current Protocols in Molecular Biology, F. M. Ausubel et al., eds., 1987; and PCR: The Polymerase Chain Reaction, Mullis et al., eds., 1994.

Description Of Embodiments Of The Invention

In colorectal cancer, discordant results have been reported for prognostic markers. The present invention discloses the use of microarrays to reach a firmer conclusion, and to determine the prognostic role of specific prognostic signatures in colorectal cancer. The microarray-based studies shown herein indicate that particular prognostic signatures in colorectal cancer are associated with a prognosis. The invention can therefore be used to identify patients at high risk of recurrence of cancer, or patients with a high likelihood of recovery.

The present invention provides for markers for the determination of disease prognosis, for example, the likelihood of recurrence of tumours, including colorectal tumours. Using the methods of the invention, it has been found that numerous markers are associated with the prognosis of colorectal cancer, and can be used to predict disease outcome. Microarray analysis of samples taken from patients with various stages of colorectal tumours has led to the surprising discovery that specific patterns of marker expression are associated with prognosis of the cancer. The present invention therefore provides for a set of genes, outlined in Table 1 and Table 2, that are differentially expressed in recurrent and non-recurrent colorectal cancers. The genes outlined in Table 1 and Table 2 provide for a set of colorectal cancer prognostic makers (CCPMs).

A decrease in certain colorectal cancer prognostic markers (CCPMs), for example, markers associated with immune responses, is indicative of a particular prognosis. This can include increased likelihood of cancer recurrence after standard treatment, especially for colorectal cancer. Conversely, an increase in other CCPMs is indicative of a particular prognosis. This can include disease progression or the increased likelihood of cancer recurrence, especially for colorectal cancer. A decrease or increase in expression can be determined, for example, by comparison of a test sample, e.g., patient's tumour sample, to a reference sample, e.g., a sample associated with a known prognosis. In particular, one or more samples from patient(s) with non-recurrent cancer could be used as a reference sample.

For example, to obtain a prognosis, expression levels in a patient's sample (e.g., tumour sample) can be compared to samples from patients with a known outcome. If the patient's sample shows increased or decreased expression of one or more CCPMs that compares to samples with good outcome (no recurrence), then a positive prognosis, or recurrence is unlikely, is implicated. If the patient's sample shows expression of one or more CCPMs that is comparable to samples with poor outcome (recurrence), then a positive prognosis, or recurrence of the tumour is likely, is implicated.

As further examples, the expression levels of a prognostic signature comprising two or more CCPMS from a patient's sample (e.g., tumour sample) can be compared to samples of recurrent/non-recurrent cancer. If the patient's sample shows increased or decreased expression of CCPMs by comparison to samples of non-recurrent cancer, and/or comparable expression to samples of recurrent cancer, then a negative prognosis is implicated. If the patient's sample shows expression of CCPMs that is comparable to samples of non-recurrent cancer, and/or lower or higher expression than samples of recurrent cancer, then a positive prognosis is implicated.

As one approach, a prediction method can be applied to a panel of markers, for example the panel of CCPMs outlined in Table 1 and Table 2, in order to generate a predictive model. This involves the generation of a prognostic signature, comprising two or more CCPMs.

The disclosed CCPMs in Table 1 and Table 2 therefore provide a useful set of markers to generate prediction signatures for determining the prognosis of cancer, and establishing a treatment regime, or treatment modality, specific for that tumour. In particular, a positive prognosis can be used by a patient to decide to pursue standard or less invasive treatment options. A negative prognosis can be used by a patient to decide to terminate treatment or to pursue highly aggressive or experimental treatments. In addition, a patient can chose treatments based on their impact on the expression of prognostic markers (e.g., CCPMs).

Levels of CCPMs can be detected in tumour tissue, tissue proximal to the tumour, lymph node samples, blood samples, serum samples, urine samples, or faecal samples, using any suitable technique, and can include, but is not limited to, oligonucleotide probes, quantitative PCR, or antibodies raised against the markers. It will be appreciated that by analyzing the presence and amounts of expression of a plurality of CCPMs in the form of prediction signatures, and constructing a prognostic signature (e.g., as set forth in Tables 3, 4, 8A, 8B, and 9), the sensitivity and accuracy of prognosis will be increased. Therefore, multiple markers according to the present invention can be used to determine the prognosis of a cancer.

The invention includes the use of archived paraffin-embedded biopsy material for assay of the markers in the set, and therefore is compatible with the most widely available type of biopsy material. It is also compatible with several different methods of tumour tissue harvest, for example, via core biopsy or fine needle aspiration. In certain aspects, RNA is isolated from a fixed, wax-embedded cancer tissue specimen of the patient. Isolation may be performed by any technique known in the art, for example from core biopsy tissue or fine needle aspirate cells.

In one aspect, the invention relates to a method of predicting a prognosis, e.g., the likelihood of long-term survival of a cancer patient without the recurrence of cancer, comprising determining the expression level of one or more prognostic markers or their expression products in a sample obtained from the patient, normalized against the expression level of other RNA transcripts or their products in the sample, or of a reference set of RNA transcripts or their expression products. In specific aspects, the prognostic marker is one or more markers listed in Tables 1, 2, or 5, or is included as one or more of the prognostic signatures derived from the markers listed in Tables 1, 2, and 5, or the prognostic signatures listed in Tables 3, 4, 8A, 8B, or 9.

In further aspects, the expression levels of the prognostic markers or their expression products are determined, e.g., for the markers listed in Tables 1, 2, or 5, a prognostic signature derived from the markers listed in Tables 1, 2, and 5, e.g., for the prognostic signatures listed in Tables 3, 4, 8A, 8B, or 9. In another aspect, the method comprises the determination of the expression levels of a full set of prognosis markers or their expression products, e.g., for the markers listed in Tables 1, 2, or 5, or, a prognostic signature derived from the markers listed in Tables 1, 2, and 5, e.g., for the prognostic signatures listed in Tables 3, 4, 8A, 8B, or 9.

In an additional aspect, the invention relates to an array (e.g., microarray) comprising polynucleotides hybridizing to two or more markers, e.g., for the markers listed in Tables 1, 2, and 5, or a prognostic signature derived from the markers listed in Tables 1, 2, and 5, e.g., the prognostic signatures listed in Tables 3, 4, 8A, 8B, and 9. In particular aspects, the array comprises polynucleotides hybridizing to prognostic signature derived from the markers listed in Tables 1, 2, and 5, or e.g., for the prognostic signatures listed in Tables 3, 4, 8A, 8B, or 9. In another specific aspect, the array comprises polynucleotides hybridizing to the full set of markers, e.g., for the markers listed in Tables 1, 2, or 5, or, e.g., for the prognostic signatures listed in Tables 3, 4, 8A, 8B, or 9.

For these arrays, the polynucleotides can be cDNAs, or oligonucleotides, and the solid surface on which they are displayed can be glass, for example. The polynucleotides can hybridize to one or more of the markers as disclosed herein, for example, to the full-length sequences, any coding sequences, any fragments, or any complements thereof. In particular aspects, an increase or decrease in expression levels of one or more CCPM indicates a decreased likelihood of long-term survival, e.g., due to cancer recurrence, while a lack of an increase or decrease in expression levels of one or more CCPM indicates an increased likelihood of long-term survival without cancer recurrence.

TABLE 1

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| ME2 | 210154_at, 210153_s_at, 209397_at | NM_002396 | malic enzyme 2, NAD(+)-dependent, mitochondrial | Hs.233119 | M55905, BC000147 | 0.74 |
| STAT1 | AFFX-HUMISGF3A/M97935_MA_at, AFFX-HUMISGF3A/M97935_MB_at, AFFX-HUMISGF3A/M97935_3_at, 200887_s_at, AFFX-HUMISGF3A/M97935_5_at, 209969_s_at | NM_007315, NM_139266 | signal transducer and activator of transcription 1, 91 kDa | Hs.470943 | NM_007315, BC002704 | 0.58 |
| CXCL10 | 204533_at | NM_001565 | chemokine (C—X—C motif) ligand 10 | Hs.413924 | NM_001565 | 0.29 |
| FAS | 215719_x_at, 216252_x_at, 204780_s_at, 204781_s_at | NM_000043, NM_152871, NM_152872, NM_152873, NM_152874, NM_152875, NM_152876, NM_152877 | Fas (TNF receptor superfamily, member 6) | Hs.244139 | X83493, Z70519, AA164751, NM_000043 | 0.68 |
| SFRS2 | 200753_x_at, 214882_s_at, 200754_x_at | NM_003016 | splicing factor, arginine/serine-rich 2 | Hs.73965 | BE866585, BG254869, NM_003016 | 0.82 |
| GUF1 | 218884_s_at | NM_021927 | GUF1 GTPase homolog (S. cerevisiae) | Hs.546419 | NM_021927 | 0.71 |
| CXCL9 | 203915_at | NM_002416 | chemokine (C—X—C motif) ligand 9 | Hs.77367 | NM_002416 | 0.33 |
| TYMS | 202589_at | NM_001071 | thymidylate synthetase | Hs.369762 | NM_001071 | 0.53 |
| SEC10L1 | 218748_s_at | NM_006544 | SEC10-like 1 (S. cerevisiae) | Hs.365863 | NM_006544 | 0.76 |
| PLK4 | 204887_s_at | NM_014264 | polo-like kinase 4 (Drosophila) | Hs.172052 | NM_014264 | 0.64 |
| MAP2K4 | 203265_s_at | NM_003010 | mitogen-activated protein kinase kinase 4 | Hs.514681 | AA810268 | 0.76 |
| EIF4E | 201435_s_at, 201436_at | NM_001968 | eukaryotic translation initiation factor 4E | Hs.249718 | AW268640, AI742789 | 0.69 |
| TLK1 | 210379_s_at | NM_012290 | tousled-like kinase 1 | Hs.470586 | AF162666 | 0.59 |
| CXCL11 | 210163_at, 211122_s_at | NM_005409 | chemokine (C—X—C motif) ligand 11 | Hs.518814 | AF030514, AF002985 | 0.15 |
| PSME2 | 201762_s_at | NM_002818 | proteasome (prosome, macropain) activator subunit 2 (PA28 beta) | Hs.434081, Hs.512410 | NM_002818 | 0.68 |
| hCAP-D3 | 212789_at | NM_015261 | non-SMC condensin II complex, subunit D3 | Hs.438550 | AI796581 | 0.83 |
| MPP5 | 219321_at | NM_022474 | membrane protein, palmitoylated 5 (MAGUK p55 subfamily member 5) | Hs.509699 | NM_022474 | 0.74 |
| DLGAP4 | 202570_s_at | NM_014902, NM_183006 | discs, large (Drosophila) homolog-associated protein 4 | Hs.249600 | BF346592 | 1.3 |
| WARS | 200628_s_at, 200629_at | NM_004184, NM_173701, NM_213645, NM_213646 | tryptophanyl-tRNA synthetase | Hs.497599 | M61715, NM_004184 | 0.66 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/ non-relapse) |
|---|---|---|---|---|---|---|
| ARF6 | 203312_x_at | NM_001663 | ADP-ribosylation factor 6 | Hs.525330 | NM_001663 | 0.77 |
| PBK | 219148_at | NM_018492 | PDZ binding kinase | Hs.104741 | NM_018492 | 0.41 |
| GMFB | 202543_s_at | NM_004124 | glia maturation factor, beta | Hs.151413 | BC005359 | 0.66 |
| NDUFA9 | 208969_at | NM_005002 | NADH dehydrogenase (ubiquinone) 1 alpha subcomplex, 9, 39 kDa | Hs.75227 | AF050641 | 0.77 |
| CDC40 | 203377_s_at | NM_015891 | cell division cycle 40 homolog (yeast) | Hs.428147 | NM_015891 | 0.8 |
| WHSC1 | 209053_s_at, 209054_s_at, 209052_s_at | NM_007331, NM_014919, NM_133330, NM_133331, NM_133332, NM_133333, NM_133334, NM_133335, NM_133336 | Wolf-Hirschhorn syndrome candidate 1 | Hs.113876 | BE793789, AF083389, BF111870 | 0.75 |
| C1QBP | 208910_s_at, 214214_s_at | NM_001212 | complement component 1, q subcomponent binding protein | Hs.555866 | L04636, AU151801 | 0.71 |
| RBM25 | 212031_at | NM_021239 | RNA binding motif protein 25 | Hs.531106 | AV757384 | 0.83 |
| SLC25A11 | 209003_at, 207088_s_at | NM_003562 | solute carrier family 25 (mitochondrial carrier, oxoglutarate carrier), member 11 | Hs.184877 | AF070548, NM_003562 | 0.83 |
| TK1 | 202338_at | NM_003258 | thymidine kinase 1, soluble | Hs.515122 | NM_003258 | 0.73 |
| ETNK1 | 222262_s_at, 219017_at | NM_018638 | ethanolamine kinase 1 | Hs.240056 | AL137750, NM_018638 | 0.66 |
| KLHL24 | 221985_at | NM_017644 | kelch-like 24 (Drosophila) | Hs.407709 | AW006750 | 1.4 |
| AK2 | 212175_s_at, 205996_s_at, 212174_at | NM_001625, NM_013411, | adenylate kinase 2 | Hs.470907 | AL513611, NM_013411, W02312 | 0.8 |
| HNRPD | 221481_x_at, 209330_s_at, 200073_s_at | NM_001003810, NM_002138, NM_031369, NM_031370 | heterogeneous nuclear ribonucleoprotein D (AU-rich element RNA binding protein 1, 37 kDa) | Hs.480073 | D55672, D55674, M94630 | 0.8 |
| GTPBP3 | 213835_x_at | NM_032620, NM_133644 | GTP binding protein 3 (mitochondrial) | Hs.334885 | AL524262 | 0.87 |
| PSAT1 | 220892_s_at | NM_021154, NM_058179 | phosphoserine aminotransferase 1 | Hs.494261 | NM_021154 | 0.54 |
| AP1G1 | 203350_at | NM_001030007, NM_001128 | adaptor-related protein complex 1, gamma 1 subunit | Hs.461253 | NM_001128 | 0.89 |
| SMCHD1 | 212577_at | | structural maintenance of chromosomes flexible hinge domain containing 1 | Hs.8118 | AA868754 | 0.74 |
| SLC4A4 | 210738_s_at, 203908_at, 211494_s_at, 210739_x_at | NM_003759 | solute carrier family 4, sodium bicarbonate cotransporter, member 4 | Hs.5462 | AF011390, NM_003759, AF157492, AF069510 | 0.7 |
| RBMS3 | 206767_at | NM_001003792, NM_001003793, NM_014483 | RNA binding motif, single stranded interacting protein | Hs.221436 | NM_014483 | 1.2 |
| LARP4 | 214155_s_at | NM_052879, NM_199188, NM_199190 | La ribonucleoprotein domain family, member 4 | Hs.26613 | AI743740 | 0.66 |

TABLE 1-continued

Colorectal Cancer Predictive Markers (corresponding to Affymetrix
GeneChip probes that show statistically significant differential expression,
$P < 0.05$, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| FANCA | 203805_s_at | NM_000135, NM_001018112 | Fanconi anemia, complementation group A | Hs.284153 | AW083279 | 0.78 |
| SOS1 | 212780_at | NM_005633 | son of sevenless homolog 1 (*Drosophila*) | Hs.278733 | AA700167 | 0.84 |
| IFT20 | 210312_s_at | NM_174887 | intraflagellar transport 20 homolog (*Chlamydomonas*) | Hs.4187 | BC002640 | 1.2 |
| NUP210 | 212316_at, 220035_at, 213947_s_at | NM_024923 | nucleoporin 210 kDa | Hs.475525 | AA502912, NM_024923, AI867102 | 0.78 |
| IRF8 | 204057_at | NM_002163 | interferon regulatory factor 8 | Hs.137427 | AI073984 | 0.75 |
| SGPP1 | 221268_s_at | NM_030791 | sphingosine-1-phosphate phosphatase 1 | Hs.24678 | NM_030791 | 0.76 |
| MAD2L1 | 203362_s_at | NM_002358 | MAD2 mitotic arrest deficient-like 1 (yeast) | Hs.509523, Hs.533185 | NM_002358 | 0.7 |
| PAICS | 201013_s_at, 201014_s_at | NM_006452 | phosphoribosylaminoimidazole carboxylase, phosphoribosylaminoimidazole succinocarboxamide synthetase | Hs.518774 | AA902652, NM_006452 | 0.71 |
| RPS2 | 217466_x_at | NM_002952 | ribosomal protein S2 | Hs.356366, Hs.381079, Hs.498569, Hs.506997, Hs.556270 | L48784 | 0.83 |
| TMED5 | 202195_s_at | NM_016040 | transmembrane emp24 protein transport domain containing 5 | Hs.482873 | NM_016040 | 0.86 |
| GTSE1 | 204317_at, 204318_s_at | NM_016426 | G-2 and S-phase expressed 1 | Hs.386189, Hs.475140 | BF305380, NM_016426 | 0.8 |
| DCK | 203302_at | NM_000788 | deoxycytidine kinase | Hs.709 | NM_000788 | 0.77 |
| DKFZp762E1312 | 218726_at | NM_018410 | hypothetical protein DKFZp762E1312 | Hs.532968 | NM_018410 | 0.81 |
| BAZ1A | 217986_s_at | NM_013448, NM_182648 | bromodomain adjacent to zinc finger domain, 1A | Hs.509140 | NM_013448 | 0.8 |
| HIP2 | 202346_at | NM_005339 | huntingtin interacting protein 2 | Hs.50308 | NM_005339 | 0.78 |
| HNRPA3P1 | 206809_s_at | | heterogeneous nuclear ribonucleoprotein A3 pseudogene 1 | Hs.524276 | NM_005758 | 0.83 |
| CDC42BPA | 214464_at | NM_003607, NM_014826 | CDC42 binding protein kinase alpha (DMPK-like) | Hs.35433 | NM_003607 | 1.4 |
| P15RS | 218209_s_at | NM_018170 | hypothetical protein FLJ10656 | Hs.464912 | NM_018170 | 0.79 |
| FLJ10534TSR1 | 218156_s_at | NM_018128 | TSR1, 20S rRNA accumulation, homolog (*S. cerevisiae*) | Hs.388170 | NM_018128 | 0.75 |
| RRM1 | 201476_s_at | NM_001033 | ribonucleotide reductase M1 polypeptide | Hs.383396 | AI692974 | 0.76 |
| USP4 | 202682_s_at | NM_003363, NM_199443 | ubiquitin specific peptidase 4 (proto-oncogene) | Hs.77500 | NM_003363 | 1.2 |
| ZNF304 | 207753_at | NM_020657 | zinc finger protein 304 | Hs.287374 | NM_020657 | 1.3 |
| CA2 | 209301_at | NM_000067 | carbonic anhydrase II | Hs.155097 | M36532 | 0.25 |
| LOC92249 | 212957_s_at | | hypothetical protein LOC92249 | Hs.31532 | AU154785 | 1.1 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| MARCH5 | 218582_at | NM_017824 | membrane-associated ring finger (C3HC4) 5 | Hs.549165 | NM_017824 | 0.81 |
| TRMT5 | 221952_x_at | NM_020810 | TRM5 tRNA methyltransferase 5 homolog (*S. cerevisiae*) | Hs.380159 | AB037814 | 0.81 |
| PRDX3 | 201619_at | NM_006793, NM_014098 | peroxiredoxin 3 | Hs.523302 | NM_006793 | 0.73 |
| RAP1GDS1 | 217457_s_at | NM_021159 | RAP1, GTP-GDP dissociation stimulator 1 | Hs.132858 | X63465 | 0.82 |
| NUMB | 209073_s_at | NM_001005743, NM_001005744, NM_001005745, NM_003744 | numb homolog (*Drosophila*) | Hs.509909 | AF015040 | 0.82 |
| KIF2 | 203087_s_at | NM_004520 | kinesin heavy chain member 2 | Hs.533222 | NM_004520 | 0.72 |
| ACADSB | 205355_at | NM_001609 | acyl-Coenzyme A dehydrogenase, short/branched chain | Hs.81934 | NM_001609 | 0.87 |
| IBRDC3 | 213038_at | NM_153341 | IBR domain containing 3 | Hs.546478 | AL031602 | 0.88 |
| TES | 202719_s_at | NM_015641, NM_152829 | testis derived transcript (3 LIM domains) | Hs.533391 | BC001451 | 1.3 |
| YDD19 | 37079_at | | YDD19 protein | Hs.525826 | U82319 | 0.92 |
| GZMB | 210164_at | NM_004131 | granzyme B (granzyme 2, cytotoxic T-lymphocyte-associated serine esterase 1) | Hs.1051 | J03189 | 0.66 |
| LAP3 | 217933_s_at | NM_015907 | leucine aminopeptidase 3 | Hs.479264 | NM_015907 | 0.67 |
| C17orf25 | 209092_s_at | NM_016080 | chromosome 17 open reading frame 25 | Hs.279061 | AF061730 | 0.72 |
| ZNF345 | 207236_at | NM_003419 | zinc finger protein 345 | Hs.362324 | NM_003419 | 1.1 |
| KITLG | 207029_at, 211124_s_at | NM_000899, NM_003994 | KIT ligand | Hs.1048 | NM_000899, AF119835 | 0.75 |
| CAMSAP1L1 | 212765_at | NM_203459 | calmodulin regulated spectrin-associated protein 1-like 1 | Hs.23585 | AB029001 | 1.3 |
| YTHDC2 | 205835_s_at, 205836_s_at | NM_022828 | YTH domain containing 2 | Hs.231942 | AW975818, NM_022828 | 0.84 |
| RABIF | 204477_at | NM_002871 | RAB interacting factor | Hs.90875 | U74324 | 1.2 |
| SERBP1 | 217725_x_at | NM_001018067, NM_001018068, NM_001018069, NM_015640 | SERPINE1 mRNA binding protein 1 | Hs.369448, Hs.519284, Hs.530412 | NM_015640 | 0.81 |
| KPNB1 | 208975_s_at | NM_002265 | karyopherin (importin) beta 1 | Hs.532793 | L38951 | 0.74 |
| BRIP1 | 221703_at | NM_032043 | BRCA1 interacting protein C-terminal helicase 1 | Hs.532799 | AF360549 | 0.86 |
| IRF1 | 202531_at | NM_002198 | interferon regulatory factor 1 | Hs.436061 | NM_002198 | 0.62 |
| TIPIN | 219258_at | NM_017858 | TIMELESS interacting protein | Hs.426696 | NM_017858 | 0.73 |
| SPFH1 | 202444_s_at | NM_006459 | SPFH domain family, member 1 | Hs.150087 | NM_006459 | 0.76 |
| SFPQ | 201586_s_at | NM_005066 | splicing factor proline/glutamine-rich (polypyrimidine tract binding protein associated) | Hs.355934 | NM_005066 | 0.83 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| MGAT2 | 211061_s_at | NM_001015883, NM_002408 | mannosyl (alpha-1,6-)-glycoprotein beta-1,2-N-acetylglucosaminyltransferase | Hs.93338 | BC006390 | 0.79 |
| MCCC2 | 209624_s_at | NM_022132 | methylcrotonoyl-Coenzyme A carboxylase 2 (beta) | Hs.167531 | AB050049 | 0.6 |
| DDAH2 | 215537_x_at, 214909_s_at | NM_013974 | dimethylarginine dimethylaminohydrolase 2 | Hs.247362 | AJ012008, AK026191 | 1.2 |
| NP | 201695_s_at | NM_000270 | nucleoside phosphorylase | Hs.75514 | NM_000270 | 0.79 |
| CHEK1 | 205393_s_at, 205394_at | NM_001274 | CHK1 checkpoint homolog (S. pombe) | Hs.24529 | NM_001274 | 0.7 |
| MYO1B | 212365_at | NM_012223 | myosin IB | Hs.439620 | BF215996 | 0.85 |
| ATP5A1 | 213738_s_at | NM_001001935, NM_001001937, NM_004046 | ATP synthase, H+ transporting, mitochondrial F1 complex, alpha subunit, isoform 1, cardiac muscle | Hs.298280, Hs.551998 | AI587323 | 0.82 |
| IL2RB | 205291_at | NM_000878 | interleukin 2 receptor, beta | Hs.474787 | NM_000878 | 0.73 |
| RPL39 | 217665_at | NM_001000 | ribosomal protein L39 (RPL39) | Hs.558387 | AA420614 | 1.3 |
| CD59 | 212463_at | NM_000611, NM_203329, NM_203330, NM_203331 | CD59 antigen p18-20 (antigen identified by monoclonal antibodies 16.3A5, EJ16, EJ30, EL32 and G344) | Hs.278573 | BE379006 | 1.5 |
| AMD1 | 201196_s_at | NM_001033059, NM_001634 | adenosylmethionine decarboxylase 1 | Hs.159118 | M21154 | 0.74 |
| GGA2 | 210658_s_at | NM_015044, NM_138640 | golgi associated, gamma adaptin ear containing, ARF binding protein 2 | Hs.460336 | BC000284 | 0.82 |
| MCM6 | 201930_at | NM_005915 | MCM6 minichromosome maintenance deficient 6 (MIS5 homolog, S. pombe) (S. cerevisiae) | Hs.444118 | NM_005915 | 0.75 |
| SCC-112 | 213983_s_at, 212138_at | NM_015200 | SCC-112 protein | Hs.331431 | AW991219, AK021757 | 0.8 |
| BCL7C | 219072_at | NM_004765 | B-cell CLL/lymphoma 7C | Hs.303197 | NM_004765 | 1.2 |
| HMGN2 | 208668_x_at | NM_005517 | high-mobility group nucleosomal binding domain 2 | Hs.181163 | BC003689 | 0.9 |
| RBBP4 | 210371_s_at, 217301_x_at | NM_005610 | retinoblastoma binding protein 4 | Hs.555890 | BC003092, X71810 | 0.8 |
| KIAA0090 | 212396_s_at | NM_015047 | KIAA0090 | Hs.439200 | AI143233 | 0.81 |
| SYNPO | 202796_at | NM_007286 | synaptopodin | Hs.435228 | NM_007286 | 1.2 |
| GPR161 | 214104_at | NM_007369, NM_153832 | G protein-coupled receptor 161 | Hs.271809 | AI703188 | 1.5 |
| TMEM113 | 215509_s_at | NM_025222 | transmembrane protein 113 | Hs.194110 | AL137654 | 0.72 |
| SMC2L1 | 204240_s_at | NM_006444 | SMC2 structural maintenance of chromosomes 2-like 1 (yeast) | Hs.119023 | NM_006444 | 0.65 |
| CCNA2 | 203418_at | NM_001237 | cyclin A2 | Hs.85137 | NM_001237 | 0.6 |
| VAPB | 202549_at | NM_004738 | VAMP (vesicle-associated membrane protein)-associated protein B and C | Hs.182625 | AK025720 | 1.2 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| EXOSC9 | 213226_at | NM_005033 | exosome component 9 | Hs.91728 | AI346350 | 0.73 |
| TRIM25 | 206911_at | NM_005082 | tripartite motif-containing 25 | Hs.528952, Hs.551516 | NM_005082 | 0.88 |
| SCYL2 | 221220_s_at | NM_017988 | SCY1-like 2 (*S. cerevisiae*) | Hs.506481 | NM_017988 | 0.85 |
| RYK | 214172_x_at | NM_001005861, NM_002958 | RYK receptor-like tyrosine kinase | Hs.245869 | BG032035 | 1.2 |
| MTHFD1 | 202309_at | NM_005956 | methylenetetrahydrofolate dehydrogenase (NADP+ dependent) 1, methenyltetrahydrofolate cyclohydrolase, formyltetrahydrofolate synthetase | Hs.435974 | NM_005956 | 0.74 |
| RUNX1 | 211180_x_at | NM_001001890, NM_001754 | runt-related transcription factor 1 (acute myeloid leukemia 1, aml1 oncogene) | Hs.149261, Hs.278446 | D89788 | 1.1 |
| KPNA2 | 201088_at, 211762_s_at | NM_002266 | karyopherin alpha 2 (RAG cohort 1, importin alpha 1) | Hs.159557, Hs.252712 | NM_002266, BC005978 | 0.77 |
| PSME1 | 200814_at | NM_006263, NM_176783 | proteasome (prosome, macropain) activator subunit 1 (PA28 alpha) | Hs.75348 | NM_006263 | 0.76 |
| TACC3 | 218308_at | NM_006342 | transforming, acidic coiled-coil containing protein 3 | Hs.104019 | NM_006342 | 0.78 |
| FEN1 | 204768_s_at | NM_004111 | flap structure-specific endonuclease 1 | Hs.409065 | NM_004111 | 0.73 |
| GTF3C4 | 219198_at | NM_012204 | general transcription factor IIIC, polypeptide 4, 90 kDa | Hs.549088 | NM_012204 | 0.87 |
| GEMIN4 | 217099_s_at | NM_015721 | gem (nuclear organelle) associated protein 4 | Hs.499620 | AF258545 | 0.76 |
| CTSS | 202902_s_at | NM_004079 | cathepsin S | Hs.181301 | NM_004079 | 0.74 |
| MCM2 | 202107_s_at | NM_004526 | MCM2 minichromosome maintenance deficient 2, mitotin (*S. cerevisiae*) | Hs.477481 | NM_004526 | 0.71 |
| GPHN | 220773_s_at | NM_001024218, NM_020806 | gephyrin | Hs.208765 | NM_020806 | 0.67 |
| NUP50 | 218295_s_at | NM_007172, NM_153645, NM_153684 | nucleoporin 50 kDa | Hs.475103 | NM_007172 | 0.78 |
| RANBP2L1 | 210676_x_at | NM_005054, NM_032260 | RAN binding protein 2-like 1 | Hs.469630 | U64675 | 0.83 |
| NR5A2 | 208337_s_at | NM_003822, NM_205860 | nuclear receptor subfamily 5, group A, member 2 | Hs.33446 | NM_003822 | 0.77 |
| PGD | 201118_at | NM_002631 | phosphogluconate dehydrogenase | Hs.464071 | NM_002631 | 0.75 |
| FUT4 | 209892_at, 209893_s_at | NM_002033 | fucosyltransferase 4 (alpha (1,3) fucosyltransferase, myeloid-specific) | Hs.390420 | AF305083, M58596 | 0.78 |
| RAB6A | 201048_x_at | NM_002869, NM_198896 | RAB6A, member RAS oncogene family | Hs.503222, Hs.535586 | NM_002869 | 0.81 |
| CCNT2 | 204645_at | NM_001241, NM_058241 | cyclin T2 | Hs.292754 | NM_001241 | 0.87 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| TFRC | 207332_s_at | NM_003234 | transferrin receptor (p90, CD71) | Hs.529618 | NM_003234 | 0.63 |
| BIRC5 | 202095_s_at | NM_001012270, NM_001012271, NM_001168 | baculoviral IAP repeat-containing 5 (survivin) | Hs.514527 | NM_001168 | 0.7 |
| PGGT1B | 206288_at | NM_005023 | protein geranylgeranyltransferase type I, beta subunit | Hs.254006 | NM_005023 | 0.8 |
| USP14 | 201672_s_at | NM_005151 | ubiquitin specific peptidase 14 (tRNA-guanine transglycosylase) | Hs.464416 | NM_005151 | 0.81 |
| PURA | 204020_at | NM_005859 | purine-rich element binding protein A | Hs.443121 | BF739943 | 1.2 |
| LMAN1 | 203293_s_at, 203294_s_at | NM_005570 | lectin, mannose-binding, 1 | Hs.465295 | NM_005570, U09716 | 0.82 |
| WDR45L | 209076_s_at | NM_019613 | WDR45-like | Hs.201390 | BC000974 | 0.82 |
| SGCD | 213543_at | NM_000337, NM_172244 | sarcoglycan, delta (35 kDa dystrophin-associated glycoprotein) | Hs.387207 | AA570453 | 1.2 |
| LRP8 | 205282_at | NM_001018054, NM_004631, NM_017522, NM_033300 | low density lipoprotein receptor-related protein 8, apolipoprotein e receptor | Hs.444637 | NM_004631 | 0.78 |
| ITGA4 | 205885_s_at | NM_000885 | integrin, alpha 4 (antigen CD49D, alpha 4 subunit of VLA-4 receptor) | Hs.555880 | L12002 | 0.74 |
| BUB3 | 201458_s_at | NM_001007793, NM_004725 | BUB3 budding uninhibited by benzimidazoles 3 homolog (yeast) | Hs.418533 | NM_004725 | 0.79 |
| KIF18A | 221258_s_at | NM_031217 | kinesin family member 18A | Hs.301052 | NM_031217 | 0.83 |
| FKBP9 | 212169_at | NM_007270 | FK506 binding protein 9, 63 kDa | Hs.103934 | AL050187 | 1.2 |
| ATF6 | 217550_at | NM_007348 | activating transcription factor 6 | Hs.492740 | AA576497 | 1.4 |
| TNFRSF11A | 207037_at | NM_003839 | tumor necrosis factor receptor superfamily, member 11a, NFKB activator | Hs.204044 | NM_003839 | 0.68 |
| KIAA0841 | 213054_at | | KIAA0841 | Hs.7426 | AA845355 | 0.9 |
| TGFB2 | 209909_s_at | NM_003238 | transforming growth factor, beta 2 | Hs.133379 | M19154 | 1.1 |
| ITGB5 | 201125_s_at, 201124_at, 214021_x_at | NM_002213 | integrin, beta 5 | Hs.13155 | NM_002213, AL048423, AI335208 | 1.2 |
| RABGEF1 | 218310_at | NM_014504 | RAB guanine nucleotide exchange factor (GEF) 1 | Hs.530053 | NM_014504 | 1.2 |
| PBX1 | 205253_at, 212148_at | NM_002585 | pre-B-cell leukemia transcription factor 1 | Hs.493096 | NM_002585, AL049381 | 1.2 |
| ZNF148 | 203318_s_at | NM_021964 | zinc finger protein 148 (pHZ-52) | Hs.380334 | NM_021964 | 1.2 |
| ZWINT | 204026_s_at | NM_001005413, NM_001005414, NM_007057, NM_032997 | ZW10 interactor | Hs.42650 | NM_007057 | 0.66 |
| ZDHHC3 | 213675_at | NM_016598 | zinc finger, DHHC-type containing 3 | Hs.61430 | W61005 | 1.3 |
| CDCA8 | 221520_s_at | NM_018101 | cell division cycle associated 8 | Hs.524571 | BC001651 | 0.76 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| CUTL1 | 214743_at | NM_001913, NM_181500, NM_181552 | cut-like 1, CCAAT displacement protein (*Drosophila*) | Hs.438974 | BE046521 | 1.3 |
| C18orf9 | 219311_at | NM_024899 | chromosome 18 open reading frame 9 | Hs.236940 | NM_024899 | 0.73 |
| TXNDC | 209476_at | NM_030755 | thioredoxin domain containing | Hs.125221 | AL080080 | 0.75 |
| POLE2 | 205909_at | NM_002692 | polymerase (DNA directed), epsilon 2 (p59 subunit) | Hs.162777 | NM_002692 | 0.73 |
| SPCS3 | 218817_at | NM_021928 | signal peptidase complex subunit 3 homolog (*S. cerevisiae*) | Hs.42194 | NM_021928 | 0.7 |
| CAND1 | 208839_s_at | NM_018448 | cullin-associated and neddylation-dissociated 1 | Hs.546407 | AL136810 | 0.84 |
| U2AF2 | 218381_s_at | NM_001012478, NM_007279 | U2 (RNU2) small nuclear RNA auxiliary factor 2 | Hs.528007 | NM_007279 | 0.83 |
| WDHD1 | 204728_s_at | NM_001008396, NM_007086 | WD repeat and HMG-box DNA binding protein 1 | Hs.385998 | NM_007086 | 0.73 |
| HEM1 | 209734_at | NM_005337 | hematopoietic protein 1 | Hs.182014 | BC001604 | 0.9 |
| RABEP1 | 214552_s_at | NM_004703 | rabaptin, RAB GTPase binding effector protein 1 | Hs.551518 | AF098638 | 0.84 |
| SYDE1 | 44702_at | NM_033025 | synapse defective 1, Rho GTPase, homolog 1 (*C. elegans*) | Hs.528701 | R77097 | 1.1 |
| WFDC1 | 219478_at | NM_021197 | WAP four-disulfide core domain 1 | Hs.36688 | NM_021197 | 1.2 |
| TBX2 | 40560_at | NM_005994 | T-box 2 | Hs.531085 | U28049 | 1.1 |
| GART | 210005_at | NM_000819, NM_175085 | phosphoribosylglycinamide formyltransferase, phosphoribosylglycinamide synthetase, phosphoribosylaminoimidazole synthetase | Hs.473648 | D32051 | 0.84 |
| H2AFZ | 213911_s_at, 200853_at | NM_002106 | H2A histone family, member Z | Hs.119192 | BF718636, NM_002106 | 0.8 |
| CD7 | 214551_s_at | NM_006137 | CD7 antigen (p41) | Hs.36972 | NM_006137 | 0.8 |
| ELOVL6 | 210868_s_at | NM_024090 | ELOVL family member 6, elongation of long chain fatty acids (FEN1/Elo2, SUR4/Elo3-like, yeast) | Hs.412939 | BC001305 | 0.81 |
| CACNB3 | 34726_at | NM_000725 | calcium channel, voltage-dependent, beta 3 subunit | Hs.250712 | U07139 | 1.2 |
| TAP1 | 202307_s_at | NM_000593 | transporter 1, ATP-binding cassette, sub-family B (MDR/TAP) | Hs.352018 | NM_000593 | 0.68 |
| NUP98 | 210793_s_at | NM_005387, NM_016320, NM_139131, NM_139132 | nucleoporin 98 kDa | Hs.524750 | U41815 | 0.75 |
| CHAF1A | 214426_x_at, 203976_s_at | NM_005483 | chromatin assembly factor 1, subunit A (p150) | Hs.79018 | BF062223, NM_005483 | 0.83 |
| EPAS1 | 200878_at | NM_001430 | endothelial PAS domain protein 1 | Hs.468410 | AF052094 | 1.3 |
| RNGTT | 204207_s_at | NM_003800 | RNA guanylyltransferase and 5'-phosphatase | Hs.127219 | AB012142 | 0.8 |

TABLE 1-continued

Colorectal Cancer Predictive Markers (corresponding to Affymetrix
GeneChip probes that show statistically significant differential expression,
$P < 0.05$, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| KLF7 | 204334_at | NM_003709 | Kruppel-like factor 7 (ubiquitous) | Hs.471221 | AA488672 | 1.1 |
| C4orf16 | 219023_at | NM_018569 | chromosome 4 open reading frame 16 | Hs.435991 | NM_018569 | 0.77 |
| YBX2 | 219704_at | NM_015982 | Y box binding protein 2 | Hs.380691 | NM_015982 | 0.75 |
| IVD | 216958_s_at | NM_002225 | isovaleryl Coenzyme A dehydrogenase | Hs.513646 | AK022777 | 0.81 |
| PEG3 | 209242_at | NM_006210 | paternally expressed 3 | Hs.201776 | AL042588 | 1.2 |
| FBXL14 | 213145_at | NM_152441 | F-box and leucine-rich repeat protein 14 | Hs.367956 | BF001666 | 0.83 |
| TMEPAI | 217875_s_at | NM_020182, NM_199169, NM_199170, NM_199171 | transmembrane, prostate androgen induced RNA | Hs.517155 | NM_020182 | 1.4 |
| RNF138 | 218738_s_at | NM_016271, NM_198128 | ring finger protein 138 | Hs.302408, Hs.501040 | NM_016271 | 0.82 |
| DNM1L | 203105_s_at | NM_005690, NM_012062, NM_012063 | dynamin 1-like | Hs.550499 | NM_012062 | 0.87 |
| LHCGR | 215306_at | NM_000233 | luteinizing hormone/choriogonadotropin receptor | Hs.468490 | AL049443 | 1.3 |
| SOCS6 | 214462_at, 206020_at | NM_004232 | suppressor of cytokine signaling 6 (SOCS6) | Hs.591068 | NM_004232, NM_016387 | 0.85 |
| CEP350 | 213956_at | NM_014810 | centrosomal protein 350 kDa | Hs.413045 | AW299294 | 1.3 |
| PTGER3 | 210374_x_at, 210831_s_at | NM_000957, NM_198712, NM_198713, NM_198714, NM_198715, NM_198716, NM_198717, NM_198718, NM_198719, NM_198720 | prostaglandin E receptor 3 (subtype EP3) | Hs.445000 | D38300, L27489 | 1.1 |
| M11S1 | 200723_s_at | NM_005898, NM_203364 | membrane component, chromosome 11, surface marker 1 | Hs.471818 | NM_005898 | 0.9 |
| RFC5 | 203210_s_at | NM_007370, NM_181578 | replication factor C (activator 1) 5, 36.5 kDa | Hs.506989 | NM_007370 | 0.79 |
| INDO | 210029_at | NM_002164 | indoleamine-pyrrole 2,3 dioxygenase | Hs.840 | M34455 | 0.74 |
| KIAA0286 | 212619_at | NM_015257 | NA | Hs.533787 | AW205215 | 0.77 |
| MOBK1B | 201298_s_at | NM_018221 | MOB1, Mps One Binder kinase activator-like 1B (yeast) | Hs.196437 | BC003398 | 0.84 |
| FLJ20273 | 218035_s_at | NM_019027 | RNA-binding protein | Hs.518727 | NM_019027 | 0.73 |
| HADHSC | 211569_s_at | NM_005327 | L-3-hydroxyacyl-Coenzyme A dehydrogenase, short chain | Hs.438289 | AF001903 | 0.62 |
| SSPN | 204964_s_at | NM_005086 | sarcospan (Kras oncogene-associated gene) | Hs.183428 | NM_005086 | 1.6 |
| AP2B1 | 200615_s_at | NM_001030006, NM_001282 | adaptor-related protein complex 2, beta 1 subunit | Hs.514819 | AL567295 | 0.77 |
| EIF4A1 | 201530_x_at, 214805_at | NM_001416 | eukaryotic translation initiation factor 4A, isoform 1 | Hs.129673 | NM_001416, U79273 | 0.79 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| DEPDC1 | 220295_x_at | NM_017779 | DEP domain containing 1 | Hs.445098 | NM_017779 | 0.66 |
| AGPAT5 | 218096_at | NM_018361 | 1-acylglycerol-3-phosphate O-acyltransferase 5 (lysophosphatidic acid acyltransferase, epsilon) | Hs.490899 | NM_018361 | 0.68 |
| HNRPDL | 201993_x_at | NM_005463, NM_031372 | heterogeneous nuclear ribonucleoprotein D-like | Hs.527105 | NM_005463 | 0.86 |
| GBP1 | 202270_at | NM_002053 | guanylate binding protein 1, interferon-inducible, 67 kDa | Hs.62661, Hs.443527 | NM_002053 | 0.61 |
| AMIGO2 | 222108_at | NM_181847 | adhesion molecule with Ig-like domain 2 | Hs.121520 | AC004010 | 1.6 |
| XPO7 | 208459_s_at | NM_015024 | exportin 7 | Hs.172685 | NM_015024 | 0.78 |
| PAWR | 204005_s_at | NM_002583 | PRKC, apoptosis, WT1, regulator | Hs.406074 | NM_002583 | 0.71 |
| NARS | 200027_at | NM_004539 | asparaginyl-tRNA synthetase | Hs.465224 | NM_004539 | 0.84 |
| CENPA | 204962_s_at | NM_001809 | centromere protein A, 17 kDa | Hs.1594 | NM_001809 | 0.69 |
| KIF15 | 219306_at | NM_020242 | kinesin family member 15 | Hs.307529 | NM_020242 | 0.78 |
| ZNF518 | 204291_at | NM_014803 | zinc finger protein 518 | Hs.147895 | NM_014803 | 0.88 |
| LPP | 202821_s_at | NM_005578 | LIM domain containing preferred translocation partner in lipoma | Hs.444362 | AL044018 | 1.3 |
| BRRN1 | 212949_at | NM_015341 | barren homolog (*Drosophila*) | Hs.308045 | D38553 | 0.76 |
| C5orf4 | 48031_r_at | NM_016348, NM_032385 | chromosome 5 open reading frame 4 | Hs.519694 | H93077 | 1.2 |
| UBAP1 | 46270_at | NM_016525 | ubiquitin associated protein 1 | Hs.268963 | AL039447 | 1.1 |
| SH3GLB1 | 209090_s_at | NM_016009 | SH3-domain GRB2-like endophilin B1 | Hs.136309 | AL049597 | 1.2 |
| CDKN1C | 213182_x_at | NM_000076 | cyclin-dependent kinase inhibitor 1C (p57, Kip2) | Hs.106070 | R78668 | 1.4 |
| MCM10 | 220651_s_at | NM_018518, NM_182751 | MCM10 minichromosome maintenance deficient 10 (*S. cerevisiae*) | Hs.198363 | NM_018518 | 0.74 |
| KIAA0265 | 209254_at | NM_014997 | KIAA0265 protein | Hs.520710 | AI808625 | 1.2 |
| BUB1 | 209642_at | NM_004336 | BUB1 budding uninhibited by benzimidazoles 1 homolog (yeast) | Hs.469649 | AF043294 | 0.68 |
| LGALS3BP | 200923_at | NM_005567 | lectin, galactoside-binding, soluble, 3 binding protein | Hs.514535 | NM_005567 | 0.8 |
| NCAPD2 | 201774_s_at | NM_014865 | non-SMC condensin I complex, subunit D2 | Hs.5719 | AK022511 | 0.73 |
| CD86 | 205686_s_at | NM_006889, NM_175862 | CD86 antigen (CD28 antigen ligand 2, B7-2 antigen) | Hs.171182 | NM_006889 | 0.88 |
| C16orf30 | 219315_s_at | NM_024600 | chromosome 16 open reading frame 30 | Hs.459652 | NM_024600 | 1.2 |
| RBBP8 | 203344_s_at | NM_002894, NM_203291, NM_203292 | retinoblastoma binding protein 8 | Hs.546282 | NM_002894 | 0.79 |

TABLE 1-continued

Colorectal Cancer Predictive Markers (corresponding to Affymetrix
GeneChip probes that show statistically significant differential expression,
P < 0.05, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| FEM1C | 213341_at | NM_020177 | fem-1 homolog c (C. elegans) | Hs.47367 | AI862658 | 0.82 |
| NUP160 | 214962_s_at | NM_015231 | nucleoporin 160 kDa | Hs.372099 | AK026236 | 0.84 |
| VAMP4 | 213480_at | NM_003762, NM_201994 | vesicle-associated membrane protein 4 | Hs.6651 | AF052100 | 1.1 |
| C9orf76 | 218979_at | NM_024945 | chromosome 9 open reading frame 76 | Hs.284137 | NM_024945 | 0.8 |
| DHX15 | 201386_s_at | NM_001358 | DEAH (Asp-Glu-Ala-His) box polypeptide 15 | Hs.5683 | AF279891 | 0.83 |
| RIG | 221127_s_at | | regulated in glioma | Hs.292156 | NM_006394 | 1.2 |
| HBP1 | 209102_s_at | NM_012257 | HMG-box transcription factor 1 | Hs.162032 | AF019214 | 1.2 |
| ABCE1 | 201873_s_at, 201872_s_at | NM_002940 | ATP-binding cassette, sub-family, E (OABP), member 1 | Hs.12013 | NM_002940, AI002002 | 0.79 |
| PPA2 | 220741_s_at | NM_006903, NM_176866, NM_176867, NM_176869 | pyrophosphatase (inorganic) 2 | Hs.480452 | NM_006903 | 0.81 |
| CPD | 201942_s_at | NM_001304 | carboxypeptidase D | Hs.446079 | D85390 | 0.68 |
| KIAA0828 | 215672_s_at | NM_015328 | adenosylhomocysteinase 3 | Hs.195058 | AK025372 | 0.73 |
| K-ALPHA-1 | 211058_x_at | NM_006082 | alpha tubulin | Hs.524390 | BC006379 | 0.85 |
| RNMT | 202684_s_at | NM_003799 | RNA (guanine-7-) methyltransferase | Hs.8086 | AB020966 | 0.9 |
| MIS12 | 221559_s_at | NM_024039 | MIS12 homolog (yeast) | Hs.267194 | BC000229 | 0.8 |
| AURKB | 209464_at | NM_004217 | aurora kinase B | Hs.442658 | AB011446 | 0.71 |
| FAM64A | 221591_s_at | NM_019013 | family with sequence similarity 64, member A | Hs.404323 | BC005004 | 0.8 |
| TAP2 | 204770_at | NM_000544, NM_018833 | transporter 2, ATP-binding cassette, sub-family B (MDR/TAP) | Hs.502 | NM_000544 | 0.82 |
| PCDHGC3 | 205717_x_at | NM_002588, NM_032402, NM_032403 | protocadherin gamma subfamily C, 3 | Hs.368160 | NM_002588 | 1.2 |
| AVEN | 219366_at | NM_020371 | apoptosis, caspase activation inhibitor | Hs.555966 | NM_020371 | 1.1 |
| HMGB2 | 208808_s_at | NM_002129 | high-mobility group box 2 | Hs.434953 | BC000903 | 0.76 |
| CDC2 | 203214_x_at | NM_001786, NM_033379 | cell division cycle 2, G1 to S and G2 to M | Hs.334562 | NM_001786 | 0.72 |
| RIF1 | 214700_x_at | NM_018151 | RAP1 interacting factor homolog (yeast) | Hs.536537 | AK000323 | 0.84 |
| TCF7L2 | 216511_s_at | NM_030756 | transcription factor 7-like 2 (T-cell specific, HMG-box) | Hs.501080 | AJ270770 | 0.8 |
| KIF11 | 204444_at | NM_004523 | kinesin family member 11 | Hs.8878 | NM_004523 | 0.68 |
| TTC19 | 217964_at | NM_017775 | tetratricopeptide repeat domain 19 | Hs.462316 | NM_017775 | 0.67 |
| MDS032 | 221706_s_at | NM_018467 | uncharacterized hematopoietic stem/progenitor cells protein MDS032 | Hs.16187 | BC006005 | 1.2 |
| PSMA3 | 201532_at | NM_002788, NM_152132 | proteasome (prosome, macropain) subunit, alpha type, 3 | Hs.531089 | NM_002788 | 0.76 |
| PDGFA | 205463_s_at | | platelet-derived growth factor alpha polypeptide | Hs.376032, Hs.521331 | NM_002607 | 1.3 |

TABLE 1-continued

Colorectal Cancer Predictive Markers (corresponding to Affymetrix
GeneChip probes that show statistically significant differential expression,
$P < 0.05$, as ascertained by BRB Array Tools)

| Gene Symbol | Affymetrix Probe IDs | Refseq Access. | Gene Description | Unigene Access. | Other Genbank Access. | Expression Fold Difference (relapse/non-relapse) |
|---|---|---|---|---|---|---|
| GTF2H2 | 221540_x_at | NM_001515 | general transcription factor IIH, polypeptide 2, 44 kDa | Hs.191356, Hs.398348 | AF078847 | 0.86 |
| CXCL13 | 205242_at | NM_006419 | chemokine (C—X—C motif) ligand 13 (B-cell chemoattractant) | Hs.100431 | NM_006419 | 0.36 |
| FOXM1 | 202580_x_at | NM_021953, NM_202002, NM_202003 | forkhead box M1 | Hs.239 | NM_021953 | 0.7 |
| YARS | 212048_s_at | NM_003680 | tyrosyl-tRNA synthetase | Hs.213264 | AW245400 | 0.87 |
| SE57-1 | 220180_at | NM_025214 | coiled-coil domain containing 68 | Hs.120790 | NM_025214 | 0.77 |
| CLCA4 | 220026_at | NM_012128 | chloride channel, calcium activated, family member 4 | Hs.546343 | NM_012128 | 0.64 |
| MCAM | 211340_s_at | NM_006500 | melanoma cell adhesion molecule | Hs.511397 | M28882 | 1.2 |
| PBXIP1 | 214177_s_at | NM_020524 | pre-B-cell leukemia transcription factor interacting protein 1 | Hs.505806 | AI935162 | 1.2 |
| PPM1D | 204566_at | NM_003620 | protein phosphatase 1D magnesium-dependent, delta isoform | Hs.286073 | NM_003620 | 0.88 |
| FLJ22471 | 218175_at | NM_025140 | NA | Hs.114111 | NM_025140 | 1.2 |
| ZBTB20 | 205383_s_at | NM_015642 | zinc finger and BTB domain containing 20 | Hs.122417 | NM_015642 | 1.4 |
| RRM2 | 209773_s_at | NM_001034 | ribonucleotide reductase M2 polypeptide | Hs.226390 | BC001886 | 0.69 |

TABLE 2

Markers with expression correlating to that of the 22 genes from NZ signature.

| Gene Symbol | Affymetrix Probe IDs | Refseq Access | Gene Description | Unigene Access | Genbank Access | Expression Fold Difference (relapse/non-relapse) |
|---|---|---|---|---|---|---|
| CCL5 | 1405_i_at, 204655_at | NM_002985 | chemokine (C-C motif) ligand 5 | Hs.514821 | M21121, NM_002985 | 0.69 |
| SFRS10 | 200893_at | NM_004593 | splicing factor, arginine/serine-rich 10 (transformer 2 homolog, *Drosophila*) | Hs.533122 | NM_004593 | 0.96 |
| HLA-E | 200904_at | NM_005516 | major histocompatibility complex, class I, E | Hs.381008 | X56841 | 1 |
| K-ALPHA-1 | 201090_x_at | NM_006082 | alpha tubulin | Hs.524390 | NM_006082 | 0.87 |
| PSMA5 | 201274_at | NM_002790 | proteasome (prosome, macropain) subunit, alpha type, 5 | Hs.485246 | NM_002790 | 0.95 |
| TOP2A | 201292_at | NM_001067 | topoisomerase (DNA) II alpha 170 kDa | Hs.156346 | AL561834 | 0.77 |
| EBNA1BP2 | 201323_at | NM_006824 | EBNA1 binding protein 2 | Hs.346868 | NM_006824 | 0.98 |
| SNRPC | 201342_at | NM_003093 | small nuclear ribonucleoprotein polypeptide C | Hs.1063 | NM_003093 | 1 |
| UBE2L6 | 201649_at | NM_004223, NM_198183 | ubiquitin-conjugating enzyme E2L 6 | Hs.425777 | NM_004223 | 0.75 |

TABLE 2-continued

Markers with expression correlating to that of the 22 genes from NZ signature.

| Gene Symbol | Affymetrix Probe IDs | Refseq Access | Gene Description | Unigene Access | Genbank Access | Expression Fold Difference (relapse/non-relapse) |
|---|---|---|---|---|---|---|
| LAPTM5 | 201720_s_at | NM_006762 | lysosomal associated multispanning membrane protein 5 | Hs.371021 | AI589086 | 0.89 |
| CTSL | 202087_s_at | NM_001912, NM_145918 | cathepsin L | Hs.418123 | NM_001912 | 0.97 |
| GBP1 | 202269_x_at | NM_002053 | guanylate binding protein 1, interferon-inducible, 67 kDa | Hs.62661, Hs.443527 | BC002666 | 0.69 |
| TNFAIP2 | 202510_s_at | NM_006291 | tumor necrosis factor, alpha-induced protein 2 | Hs.525607 | NM_006291 | 0.91 |
| CCNB2 | 202705_at | NM_004701 | cyclin B2 | Hs.194698 | NM_004701 | 0.83 |
| GBP2 | 202748_at | NM_004120 | guanylate binding protein 2, interferon-inducible | Hs.386567 | NM_004120 | 0.87 |
| CDC20 | 202870_s_at | NM_001255 | CDC20 cell division cycle 20 homolog (*S. cerevisiae*) | Hs.524947 | NM_001255 | 0.78 |
| HAT1 | 203138_at | NM_001033085, NM_003642 | histone acetyltransferase | Hs.470611 | NM_003642 | 0.95 |
| SPAG5 | 203145_at | NM_006461 | sperm associated antigen 5 | Hs.514033 | NM_006461 | 0.87 |
| RFC5 | 203209_at | NM_007370, NM_181578 | replication factor C (activator 1) 5, 36.5 kDa | Hs.506989 | BC001866 | 0.79 |
| MYCBP | 203360_s_at | NM_012333 | c-myc binding protein | Hs.370040 | D50692 | 1 |
| BUB1B | 203755_at | NM_001211 | BUB1 budding uninhibited by benzimidazoles 1 homolog beta (yeast) | Hs.36708 | NM_001211 | 0.85 |
| SLA | 203761_at | NM_006748 | Src-like-adaptor | Hs.75367 | NM_006748 | 0.97 |
| VRK1 | 203856_at | NM_003384 | vaccinia related kinase 1 | Hs.422662 | NM_003384 | 0.72 |
| PIK3CD | 203879_at | NM_005026 | phosphoinositide-3-kinase, catalytic, delta polypeptide | Hs.518451 | U86453 | 0.99 |
| HLA-DMB | 203932_at | NM_002118 | major histocompatibility complex, class II, DM beta | Hs.1162 | NM_002118 | 0.82 |
| TRIP13 | 204033_at | NM_004237 | thyroid hormone receptor interactor 13 | Hs.436187 | NM_004237 | 0.78 |
| RARRES3 | 204070_at | NM_004585 | retinoic acid receptor responder (tazarotene induced) 3 | Hs.17466 | NM_004585 | 0.96 |
| CKS2 | 204170_s_at | NM_001827 | CDC28 protein kinase regulatory subunit 2 | Hs.83758 | NM_001827 | 0.8 |
| APOBEC3G | 204205_at | NM_021822 | apolipoprotein B mRNA editing enzyme, catalytic polypeptide-like 3G | Hs.474853 | NM_021822 | 0.74 |
| PSMB9 | 204279_at | NM_002800, NM_148954 | proteasome (prosome, macropain) subunit, beta type, 9 (large multifunctional peptidase 2) | Hs.381081 | NM_002800 | 0.63 |
| FUSIP1 | 204299_at | NM_054016 | FUS interacting protein (serine/arginine-rich) 1 | Hs.3530 | NM_021993 | 0.9 |
| SELL | 204563_at | NM_000655 | selectin L (lymphocyte adhesion molecule 1) | Hs.82848 | NM_000655 | 0.88 |
| DKK1 | 204602_at | NM_012242 | dickkopf homolog 1 (*Xenopus laevis*) | Hs.40499 | NM_012242 | 0.95 |
| KIF23 | 204709_s_at | NM_004856, NM_138555 | kinesin family member 23 | Hs.270845 | NM_004856 | 0.9 |
| TTK | 204822_at | NM_003318 | TTK protein kinase | Hs.169840 | NM_003318 | 0.8 |
| ECGF1 | 204858_s_at | NM_001953 | endothelial cell growth factor 1 (platelet-derived) | Hs.546251 | NM_001953 | 0.85 |
| LCP2 | 205269_at, 205270_s_at | NM_005565 | lymphocyte cytosolic protein 2 (SH2 domain containing leukocyte protein of 76 kDa) | Hs.304475 | AI123251, NM_005565 | 0.91 |
| BTN2A2 | 205298_s_at | NM_006995, NM_181531 | butyrophilin, subfamily 2, member A2 | Hs.373938 | W58757 | 0.94 |
| BMP5 | 205431_s_at | NM_021073 | bone morphogenetic protein 5 | Hs.296648 | NM_021073 | 0.9 |

TABLE 2-continued

Markers with expression correlating to that of the 22 genes from NZ signature.

| Gene Symbol | Affymetrix Probe IDs | Refseq Access | Gene Description | Unigene Access | Genbank Access | Expression Fold Difference (relapse/non-relapse) |
|---|---|---|---|---|---|---|
| GZMA | 205488_at | NM_006144 | granzyme A (granzyme 1, cytotoxic T-lymphocyte-associated serine esterase 3) | Hs.90708 | NM_006144 | 0.68 |
| SMURF2 | 205596_s_at | NM_022739 | SMAD specific E3 ubiquitin protein ligase 2 | Hs.515011 | AY014180 | 1 |
| CD8A | 205758_at | NM_001768, NM_171827 | CD8 antigen, alpha polypeptide (p32) | Hs.85258 | AW006735 | 0.78 |
| CD2 | 205831_at | NM_001767 | CD2 antigen (p50), sheep red blood cell receptor | Hs.523500 | NM_001767 | 0.87 |
| JAK2 | 205842_s_at | NM_004972 | Janus kinase 2 (a protein tyrosine kinase) | Hs.434374 | AF001362 | 0.86 |
| UBD | 205890_s_at | NM_006398 | ubiquitin D | Hs.44532 | NM_006398 | 0.41 |
| ADH1C | 206262_at | NM_000669 | alcohol dehydrogenase 1C (class I), gamma polypeptide | Hs.2523 | NM_000669 | 0.33 |
| AIM2 | 206513_at | NM_004833 | absent in melanoma 2 | Hs.281898 | NM_004833 | 0.91 |
| SI | 206664_at | NM_001041 | sucrase-isomaltase (alpha-glucosidase) | Hs.429596 | NM_001041 | 0.39 |
| NAT2 | 206797_at | NM_000015 | N-acetyltransferase 2 (arylamine N-acetyltransferase) | Hs.2 | NM_000015 | 0.82 |
| SP110 | 208012_x_at | NM_004509, NM_004510, NM_080424 | SP110 nuclear body protein | Hs.145150 | NM_004509 | 0.95 |
| PRDX1 | 208680_at | NM_002574, NM_181696, NM_181697 | peroxiredoxin 1 | Hs.180909 | L19184 | 1 |
| PSMA6 | 208805_at | NM_002791 | proteasome (prosome, macropain) subunit, alpha type, 6 | Hs.446260 | BC002979 | 0.87 |
| IFI16 | 208966_x_at | NM_005531 | interferon, gamma-inducible protein 16 | Hs.380250 | AF208043 | 1.2 |
| PPIG | 208995_s_at | NM_004792 | peptidyl-prolyl isomerase G (cyclophilin G) | Hs.470544 | U40763 | 0.98 |
| KIF2C | 209408_at, 211519_s_at | NM_006845 | kinesin family member 2C | Hs.69360 | U63743, AY026505 | 0.75 |
| APOL1 | 209546_s_at | NM_003661, NM_145343, NM_145344 | apolipoprotein L, 1 | Hs.114309 | AF323540 | 0.98 |
| CD74 | 209619_at | NM_001025158, NM_001025159, NM_004355 | CD74 antigen (invariant polypeptide of major histocompatibility complex, class II antigen-associated) | Hs.436568 | K01144 | 0.76 |
| HMMR | 209709_s_at | NM_012484, NM_012485 | hyaluronan-mediated motility receptor (RHAMM) | Hs.72550 | U29343 | 0.84 |
| CDKN3 | 209714_s_at | NM_005192 | cyclin-dependent kinase inhibitor 3 (CDK2-associated dual specificity phosphatase) | Hs.84113 | AF213033 | 0.71 |
| BUB3 | 209974_s_at | NM_001007793, NM_004725 | BUB3 budding uninhibited by benzimidazoles 3 homolog (yeast) | Hs.418533 | AF047473 | 0.84 |
| SOCS1 | 210001_s_at | NM_003745 | suppressor of cytokine signaling 1 | Hs.50640 | AB005043 | 0.93 |
| CD3Z | 210031_at | NM_000734, NM_198053 | CD3Z antigen, zeta polypeptide (TiT3 complex) | Hs.156445 | J04132 | 0.87 |
| CACYBP | 210691_s_at | NM_001007214, NM_014412 | calcyclin binding protein | Hs.508524 | AF275803 | 0.97 |
| HLA-DRA | 210982_s_at | NM_019111 | major histocompatibility complex, class II, DR alpha | Hs.520048 | M60333 | 0.74 |
| NEK2 | 211080_s_at | NM_002497 | NIMA (never in mitosis gene a)-related kinase 2 | Hs.153704 | Z25425 | 0.77 |

TABLE 2-continued

Markers with expression correlating to that of the 22 genes from NZ signature.

| Gene Symbol | Affymetrix Probe IDs | Refseq Access | Gene Description | Unigene Access | Genbank Access | Expression Fold Difference (relapse/non-relapse) |
|---|---|---|---|---|---|---|
| NF2 | 211091_s_at | NM_000268, NM_016418, NM_181825, NM_181826, NM_181827, NM_181828, NM_181829, NM_181830, NM_181831, NM_181832, NM_181833, NM_181834, NM_181835 | neurofibromin 2 (bilateral acoustic neuroma) | Hs.187898 | AF122828 | 0.96 |
| FYB | 211795_s_at | NM_001465, NM_199335 | FYN binding protein (FYB-120/130) | Hs.370503 | AF198052 | 0.83 |
| HLA-DPA1 | 211991_s_at | NM_033554 | major histocompatibility complex, class II, DP alpha 1 | Hs.347270 | M27487 | 0.75 |
| PTPRC | 212587_s_at, 212588_at | NM_002838, NM_080921, NM_080922, NM_080923 | protein tyrosine phosphatase, receptor type, C | Hs.192039 | AI809341, Y00062 | 0.77 |
| SP3 | 213168_at | NM_001017371, NM_003111 | Sp3 transcription factor | Hs.531587 | AU145005 | 0.98 |
| ITGAL | 213475_s_at | NM_002209 | integrin, alpha L (antigen CD11A (p180), lymphocyte function-associated antigen 1, alpha polypeptide) | Hs.174103 | AC002310 | 0.85 |
| RAC2 | 213603_s_at | NM_002872 | ras-related C3 botulinum toxin substrate 2 (rho family, small GTP binding protein Rac2) | Hs.517601 | BE138888 | 0.92 |
| DNA2L | 213647_at | | DNA2 DNA replication helicase 2-like (yeast) | Hs.532446 | D42046 | 0.87 |
| TRAF3IP3 | 213888_s_at | NM_025228 | TRAF3 interacting protein 3 | Hs.147434 | AL022398 | 0.86 |
| NKG7 | 213915_at | NM_005601 | natural killer cell group 7 sequence | Hs.10306 | NM_005601 | 0.72 |
| SFRS7 | 214141_x_at | NM_001031684, NM_006276 | splicing factor, arginine/serine-rich 7, 35 kDa | Hs.309090 | BF033354 | 0.88 |
| ZG16 | 214142_at | NM_152338 | zymogen granule protein 16 | Hs.184507 | AI732905 | 0.18 |
| PRF1 | 214617_at | NM_005041 | perforin 1 (pore forming protein) | Hs.2200 | AI445650 | 0.81 |
| CCNB1 | 214710_s_at | NM_031966 | cyclin B1 | Hs.23960 | BE407516 | 0.63 |
| KIAA0907 | 214995_s_at | NM_014949 | KIAA0907 | Hs.24656 | BF508948 | 0.82 |
| GTSE1 | 215942_s_at | NM_016426 | G-2 and S-phase expressed 1 | Hs.386189, Hs.475140 | BF973178 | 0.86 |
| HMGB3 | 216548_x_at | NM_005342 | high-mobility group box 3 | Hs.19114 | AL049709 | 0.97 |
| HLA-DMA | 217478_s_at | NM_006120 | major histocompatibility complex, class II, DM alpha | Hs.351279 | X76775 | 0.8 |
| C20orf45 | 217851_s_at | NM_016045 | chromosome 20 open reading frame 45 | Hs.3945 | NM_016045 | 1.1 |
| MRPL42 | 217919_s_at | NM_014050, NM_172177, NM_172178 | mitochondrial ribosomal protein L42 | Hs.199579 | BE782148 | 0.79 |
| NUSAP1 | 218039_at, 219978_s_at | NM_016359, NM_018454 | nucleolar and spindle associated protein 1 | Hs.511093 | NM_016359, NM_018454 | 0.92 |
| TMEM48 | 218073_s_at | NM_018087 | transmembrane protein 48 | Hs.476525 | NM_018087 | 0.71 |
| DHX40 | 218277_s_at | NM_024612 | DEAH (Asp-Glu-Ala-His) box polypeptide 40 | Hs.29403 | NM_024612 | 1.1 |
| NFS1 | 218455_at | NM_021100, NM_181679 | NFS1 nitrogen fixation 1 (S. cerevisiae) | Hs.194692 | NM_021100 | 1 |
| C10orf3 | 218542_at | NM_018131 | chromosome 10 open reading frame 3 | Hs.14559 | NM_018131 | 0.77 |
| NCAPG | 218663_at | NM_022346 | non-SMC condensin I complex, subunit G | Hs.446201, Hs.479270 | NM_022346 | 0.73 |

TABLE 2-continued

Markers with expression correlating to that of the 22 genes from NZ signature.

| Gene Symbol | Affymetrix Probe IDs | Refseq Access | Gene Description | Unigene Access | Genbank Access | Expression Fold Difference (relapse/non-relapse) |
|---|---|---|---|---|---|---|
| FBXO5 | 218875_s_at | NM_012177 | F-box protein 5 | Hs.520506 | NM_012177 | 0.89 |
| SLAMF8 | 219385_at | NM_020125 | SLAM family member 8 | Hs.438683 | NM_020125 | 0.94 |
| CENPN | 219555_s_at | NM_018455 | centromere protein N | Hs.283532 | NM_018455 | 0.81 |
| ATP13A3 | 219558_at | | ATPase type 13A3 | Hs.529609 | NM_024524 | 0.75 |
| ECT2 | 219787_s_at | NM_018098 | epithelial cell transforming sequence 2 oncogene | Hs.518299 | NM_018098 | 0.75 |
| ASPM | 219918_s_at | NM_018136 | asp (abnormal spindle)-like, microcephaly associated (*Drosophila*) | Hs.121028 | NM_018123 | 0.89 |
| ZC3HAV1 | 220104_at | NM_020119, NM_024625 | zinc finger CCCH-type, antiviral 1 | Hs.133512 | NM_020119 | 0.93 |
| CLEC2D | 220132_s_at | NM_001004419, NM_001004420, NM_013269 | C-type lectin superfamily 2, member D | Hs.268326 | NM_013269 | 0.91 |
| MS4A12 | 220834_at | NM_017716 | membrane-spanning 4-domains, subfamily A, member 12 | Hs.272789 | NM_017716 | 0.5 |
| C1orf112 | 220840_s_at | NM_018186 | chromosome 1 open reading frame 112 | Hs.443551 | NM_018186 | 0.96 |
| TPRT | 220865_s_at | NM_014317 | trans-prenyltransferase | Hs.555924 | NM_014317 | 0.92 |
| APOL3 | 221087_s_at | NM_014349, NM_030644, NM_145639, NM_145640, NM_145641, NM_145642 | apolipoprotein L, 3 | Hs.474737 | NM_014349 | 0.84 |
| C14orf156 | 221434_s_at | NM_031210 | chromosome 14 open reading frame 156 | Hs.324521 | NM_031210 | 0.9 |
| YTHDF3 | 221749_at | NM_152758 | YTH domain family, member 3 | Hs.491861 | AU157915 | 0.95 |
| LOC146909 | 222039_at | | hypothetical protein LOC146909 | Hs.135094 | AA292789 | 0.83 |
| TRAFD1 | 35254_at | NM_006700 | TRAF-type zinc finger domain containing 1 | Hs.5148 | AB007447 | 0.98 |
| ESPL1 | 38158_at | NM_012291 | extra spindle poles like 1 (*S. cerevisiae*) | Hs.153479 | D79987 | 0.87 |
| BTN3A3 | 38241_at | NM_006994, NM_197974 | butyrophilin, subfamily 3, member A3 | Hs.167741 | U90548 | 0.9 |

General Approaches to Prognostic Marker Detection

The following approaches are non-limiting methods that can be used to detect the proliferation markers, including CCPM family members: microarray approaches using oligonucleotide probes selective for a CCPM; real-time qPCR on tumour samples using CCPM specific primers and probes; real-time qPCR on lymph node, blood, serum, faecal, or urine samples using CCPM specific primers and probes; enzyme-linked immunological assays (ELISA); immunohistochemistry using anti-marker antibodies; and analysis of array or qPCR data using computers.

Other useful methods include northern blotting and in situ hybridization (Parker and Barnes, Methods in Molecular Biology 106: 247-283 (1999)); RNase protection assays (Hod, BioTechniques 13: 852-854 (1992)); reverse transcription polymerase chain reaction (RT-PCR; Weis et al., Trends in Genetics 8: 263-264 (1992)); serial analysis of gene expression (SAGE; Velculescu et al., Science 270: 484-487 (1995); and Velculescu et al., Cell 88: 243-51 (1997)), MassARRAY technology (Sequenom, San Diego, Calif.), and gene expression analysis by massively parallel signature sequencing (MPSS; Brenner et al., Nature Biotechnology 18: 630-634 (2000)). Alternatively, antibodies may be employed that can recognize specific complexes, including DNA duplexes, RNA duplexes, and DNA-RNA hybrid duplexes or DNA-polypeptide duplexes.

Primary data can be collected and fold change analysis can be performed, for example, by comparison of marker expression levels in tumour tissue and non-tumour tissue; by comparison of marker expression levels to levels determined in recurring tumours and non-recurring tumours; by comparison of marker expression levels to levels determined in tumours with or without metastasis; by comparison of marker expression levels to levels determined in differently staged tumours; or by comparison of marker expression levels to levels determined in cells with different levels of proliferation. A negative or positive prognosis is determined based on this analysis. Further analysis of tumour marker expression includes matching those markers exhibiting increased or decreased expression with expression profiles of known colorectal tumours to provide a prognosis.

A threshold for concluding that expression is increased will be dependent on the particular marker and also the particular predictive model that is to be applied. The threshold is generally set to achieve the highest sensitivity and selectivity with the lowest error rate, although variations may be desirable for a particular clinical situation. The desired threshold is determined by analysing a population of sufficient size taking into account the statistical variability of any predictive model and is calculated from the size of the sample used to produce the predictive model. The same applies for the determination of a threshold for concluding that expression is decreased. It can be appreciated that other thresholds, or methods for establishing a threshold, for concluding that increased or decreased expression has occurred can be selected without departing from the scope of this invention.

It is also possible that a prediction model may produce as it's output a numerical value, for example a score, likelihood value or probability. In these instances, it is possible to apply thresholds to the results produced by prediction models, and in these cases similar principles apply as those used to set thresholds for expression values.

Once the expression level, or output of a prediction model, of a predictive signature in a tumour sample has been obtained, the likelihood of the cancer recurring can then be determined.

From the markers identified, prognostic signatures comprising one or more CCPMs can be used to determine the prognosis of a cancer, by comparing the expression level of the one or more markers to the disclosed prognostic signature. By comparing the expression of one or more of the CCPMs in a tumour sample with the disclosed prognostic signature, the likelihood of the cancer recurring can be determined. The comparison of expression levels of the prognostic signature to establish a prognosis can be done by applying a predictive model as described previously.

Determining the likelihood of the cancer recurring is of great value to the medical practitioner. A high likelihood of re-occurrence means that a longer or higher dose treatment should be given, and the patient should be more closely monitored for signs of recurrence of the cancer. An accurate prognosis is also of benefit to the patient. It allows the patient, along with their partners, family, and friends to also make decisions about treatment, as well as decisions about their future and lifestyle changes. Therefore, the invention also provides for a method establishing a treatment regime for a particular cancer based on the prognosis established by matching the expression of the markers in a tumour sample with the differential expression signature.

It will be appreciated that the marker selection, or construction of a prognostic signature, does not have to be restricted to the CCPMs disclosed in Tables 1, 2, or 5, herein, or the prognostic signatures disclosed in Tables 3, 4, 8A, 8B, and 9, but could involve the use of one or more CCPMs from the disclosed signatures, or a new signature may be established using CCPMs selected from the disclosed marker lists. The requirement of any signature is that it predicts the likelihood of recurrence with enough accuracy to assist a medical practitioner to establish a treatment regime.

Reverse Transcription PCR (RT-PCR)

Of the techniques listed above, the most sensitive and most flexible quantitative method is RT-PCR, which can be used to compare RNA levels in different sample populations, in normal and tumour tissues, with or without drug treatment, to characterize patterns of expression, to discriminate between closely related RNAs, and to analyze RNA structure.

For RT-PCR, the first step is the isolation of RNA from a target sample. The starting material is typically total RNA isolated from human tumours or tumour cell lines, and corresponding normal tissues or cell lines, respectively. RNA can be isolated from a variety of samples, such as tumour samples from breast, lung, colon (e.g., large bowel or small bowel), colorectal, gastric, esophageal, anal, rectal, prostate, brain, liver, kidney, pancreas, spleen, thymus, testis, ovary, uterus, etc., tissues, from primary tumours, or tumour cell lines, and from pooled samples from healthy donors. If the source of RNA is a tumour, RNA can be extracted, for example, from frozen or archived paraffin-embedded and fixed (e.g., formalin-fixed) tissue samples.

The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukaemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man (q) PCR typically utilizes the 5' nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan RT-PCR can be performed using commercially available equipment, such as, for example, ABI PRISM 7700 Sequence Detection System (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700tam Sequence Detection System. The system consists of a thermocycler, laser, charge-coupled device (CCD), camera, and computer. The system amplifies samples in a 96-well format on a thermocycler. During amplification, laser-induced fluorescent signal is collected in real-time through fibre optics cables for all 96 wells, and detected at the CCD. The system includes software for running the instrument and for analyzing the data.

5' nuclease assay data are initially expressed as Ct, or the threshold cycle. As discussed above, fluorescence values are recorded during every cycle and represent the amount of product amplified to that point in the amplification reaction.

The point when the fluorescent signal is first recorded as statistically significant is the threshold cycle.

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and-actin.

Real-time Quantitative PCR (qPCR)

A more recent variation of the RT-PCR technique is the real time quantitative PCR, which measures PCR product accumulation through a dual-labeled fluorigenic probe (i.e., TaqMan probe). Real time PCR is compatible both with quantitative competitive PCR and with quantitative comparative PCR. The former uses an internal competitor for each target sequence for normalization, while the latter uses a normalization gene contained within the sample, or a housekeeping gene for RT-PCR. Further details are provided, e.g., by Held et al., Genome Research 6: 986-994 (1996).

Expression levels can be determined using fixed, paraffin-embedded tissues as the RNA source. According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W. J., Genome Res. 12 (4): 656-64 (2002), or by the BLAST software including its variations. Subsequent steps follow well established methods of PCR primer and probe design.

In order to avoid non-specific signals, it is useful to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers in: Krawetz S, Misener S (eds) Bioinformatics Methods and Protocols: Methods in Molecular Biology. Humana Press, Totowa, N.J., pp 365-386).

The most important factors considered in PCR primer design include primer length, melting temperature ($T_m$), and G/C content, specificity, complementary primer sequences, and 3' end sequence. In general, optimal PCR primers are generally 17-30 bases in length, and contain about 20-80%, such as, for example, about 50-60% G+C bases. Melting temperatures between 50 and 80° C., e.g., about 50 to 70° C., are typically preferred. For further guidelines for PCR primer and probe design see, e.g., Dieffenbach, C. W. et al., General Concepts for PCR Primer Design in: PCR Primer, A Laboratory Manual, Cold Spring Harbor Laboratory Press, New York, 1995, pp. 133-155; Innis and Gelfand, Optimization of PCRs in: PCR Protocols, A Guide to Methods and Applications, CRC Press, London, 1994, pp. 5-11; and Plasterer, T. N. Primerselect: Primer and probe design. Methods Mol. Biol. 70: 520-527 (1997), the entire disclosures of which are hereby expressly incorporated by reference.

Microarray Analysis

Differential expression can also be identified, or confirmed using the microarray technique. Thus, the expression profile of CCPMs can be measured in either fresh or paraffin-embedded tumour tissue, using microarray technology. In this method, polynucleotide sequences of interest (including cDNAs and oligonucleotides) are plated, or arrayed, on a microchip substrate. The arrayed sequences (i.e., capture probes) are then hybridized with specific polynucleotides from cells or tissues of interest (i.e., targets). Just as in the RT-PCR method, the source of RNA typically is total RNA isolated from human tumours or tumour cell lines, and corresponding normal tissues or cell lines. Thus RNA can be isolated from a variety of primary tumours or tumour cell lines. If the source of RNA is a primary tumour, RNA can be extracted, for example, from frozen or archived formalin fixed paraffin-embedded (FFPE) tissue samples and fixed (e.g., formalin-fixed) tissue samples, which are routinely prepared and preserved in everyday clinical practice.

In a specific embodiment of the microarray technique, PCR amplified inserts of cDNA clones are applied to a substrate. The substrate can include up to 1, 2, 5, 10, 15, 20, 25, 30, 35, 40, 45, 50, or 75 nucleotide sequences. In other aspects, the substrate can include at least 10,000 nucleotide sequences. The microarrayed sequences, immobilized on the microchip, are suitable for hybridization under stringent conditions. As other embodiments, the targets for the microarrays can be at least 50, 100, 200, 400, 500, 1000, or 2000 bases in length; or 50-100, 100-200, 100-500, 100-1000, 100-2000, or 500-5000 bases in length. As further embodiments, the capture probes for the microarrays can be at least 10, 15, 20, 25, 50, 75, 80, or 100 bases in length; or 10-15, 10-20, 10-25, 10-50, 10-75, 10-80, or 20-80 bases in length.

Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual colour fluorescence, separately labeled cDNA probes generated from two sources of RNA are hybridized pairwise to the array. The relative abundance of the transcripts from the two sources corresponding to each specified gene is thus determined simultaneously. An exemplary protocol for this is described in detail in Example 4.

The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93 (2): 106-149 (1996)). Microarray analysis can be performed by commercially available equipment, following manufacturer's protocols, such as by using the Affymetrix GenChip technology, Illumina microarray technology or Incyte's microarray technology. The development of microarray methods for large-scale analysis of gene expression makes it possible to search systematically for molecular markers of cancer classification and outcome prediction in a variety of tumour types.

RNA Isolation, Purification, and Amplification

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56: A67 (1987), and De Sandres et al., BioTechniques 18: 42044 (1995). In particular, RNA isolation can be performed using purification kit, buffer set, and protease from commercial manufacturers, such as Qiagen, according to the manufacturer's instructions. For example, total RNA from cells in culture can be isolated using Qiagen RNeasy mini-columns. Other commercially available RNA isolation kits include MasterPure Complete DNA and RNA Purification Kit (EPICENTRE (D, Madison, Wis.), and Paraffin Block RNA Isolation Kit (Ambion, Inc.). Total RNA from tissue samples can be isolated using RNA Stat-60 (Tel-Test). RNA prepared from tumour can be isolated, for example, by cesium chloride density gradient centrifugation.

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 µm thick sections of paraffin-embedded tumour tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumour sample examined.

Immunohistochemistry and Proteomics

Immunohistochemistry methods are also suitable for detecting the expression levels of the proliferation markers of the present invention. Thus, antibodies or antisera, preferably polyclonal antisera, and most preferably monoclonal antibodies specific for each marker, are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomics can be used to analyze the polypeptides present in a sample (e.g., tissue, organism, or cell culture) at a certain point of time. In particular, proteomic techniques can be used to assess the global changes of polypeptide expression in a sample (also referred to as expression proteomics). Proteomic analysis typically includes: (1) separation of individual polypeptides in a sample by 2-D gel electrophoresis (2-D PAGE); (2) identification of the individual polypeptides recovered from the gel, e.g., by mass spectrometry or N-terminal sequencing, and (3) analysis of the data using bioinformatics. Proteomics methods are valuable supplements to other methods of gene expression profiling, and can be used, alone or in combination with other methods, to detect the products of the proliferation markers of the present invention.

Once the expression level of one or more prognostic markers in a tumour sample has been assessed the likelihood of the cancer recurring can then be determined. The inventors have identified a number of markers that are differentially expressed in non-recurring colorectal cancers compared to recurring colorectal cancers in patient data sets. The markers are set out in Tables 1, 2, and 9, in the examples below.

Selection of Differentially Expressed Genes.

An early approach to the selection of genes deemed significant involved simply looking at the "fold change" of a given gene between the two groups of interest. While this approach hones in on genes that seem to change the most spectacularly, consideration of basic statistics leads one to realize that if the variance (or noise level) is quite high (as is often seen in microarray experiments), then seemingly large fold-change can happen frequently by chance alone.

Microarray experiments, such as those described here, typically involve the simultaneous measurement of thousands of genes. If one is comparing the expression levels for a particular gene between two groups (for example recurrent and non-recurrent tumours), the typical tests for significance (such as the t-test) are not adequate. This is because, in an ensemble of thousands of experiments (in this context each gene constitutes an "experiment"), the probability of at least one experiment passing the usual criteria for significance by chance alone is essentially unity. In a test for significance, one typically calculates the probability that the "null hypothesis" is correct. In the case of comparing two groups, the null hypothesis is that there is no difference between the two groups. If a statistical test produces a probability for the null hypothesis below some threshold (usually 0.05 or 0.01), it is stated that we can reject the null hypothesis, and accept the hypothesis that the two groups are significantly different. Clearly, in such a test, a rejection of the null hypothesis by chance alone could be expected 1 in 20 times (or 1 in 100). The use of t-tests, or other similar statistical tests for significance, fail in the context of microarrays, producing far too many false positives (or type 1 errors)

In this type of situation, where one is testing multiple hypotheses at the same time, one applies typical multiple comparison procedures, such as the Bonferroni Method (43). However such tests are too conservative for most microarray experiments, resulting in too many false negative (type II) errors.

A more recent approach is to do away with attempting to apply a probability for a given test being significant, and establish a means for selecting a subset of experiments, such that the expected proportion of Type I errors (or false discovery rate; 47) is controlled for. It is this approach that has been used in this investigation, through various implementations, namely the methods provided with BRB Array Tools (48), and the limma (11, 42) package of Bioconductor (that uses the R statistical environment; 10, 39).

General Methodology for Data Mining: Generation of Prognostic Signatures

Data Mining is the term used to describe the extraction of "knowledge", in other words the "know-how", or predictive ability from (usually) large volumes of data (the dataset). This is the approach used in this study to generate prognostic signatures. In the case of this study the "know-how" is the ability to accurately predict prognosis from a given set of gene expression measurements, or "signature" (as described generally in this section and in more detail in the examples section).

The specific details used for the methods used in this study are described in Examples 17-20. However, application of any of the data mining methods (both those described in the Examples, and those described here) can follow this general protocol.

Data mining (49), and the related topic machine learning (40) is a complex, repetitive mathematical task that involves the use of one or more appropriate computer software packages (see below). The use of software is advantageous on the one hand, in that one does not need to be completely familiar with the intricacies of the theory behind each technique in order to successfully use data mining techniques, provided that one adheres to the correct methodology. The disadvantage is that the application of data mining can often be viewed as a "black box": one inserts the data and receives the answer. How this is achieved is often masked from the end-user (this is the case for many of the techniques described, and can often influence the statistical method chosen for data mining. For example, neural networks and support vector machines have a particularly complex implementation that makes it very difficult for the end user to extract out the "rules" used to produce the decision. On the other hand, k-nearest neighbours and linear discriminant analysis have a very transparent process for decision making that is not hidden from the user.

There are two types of approach used in data mining: supervised and unsupervised approaches. In the supervised approach, the information that is being linked to the data is known, such as categorical data (e.g. recurrent vs. non recurrent tumours). What is required is the ability to link the observed response (e.g. recurrence vs. non-recurrence) to the input variables. In the unsupervised approach, the classes within the dataset are not known in advance, and data mining methodology is employed to attempt to find the classes or structure within the dataset.

In the present example the supervised approach was used and is discussed in detail here, although it will be appreciated that any of the other techniques could be used.

The overall protocol involves the following steps:

Data representation. This involves transformation of the data into a form that is most likely to work successfully with the chosen data mining technique. In where the data is numerical, such as in this study where the data being investigated represents relative levels of gene expression, this is fairly simple. If the data covers a large dynamic range (i.e. many orders of magnitude) often the log of the data is taken. If the data covers many measurements of separate samples on separate days by separate investigators, particular care has to be taken to ensure systematic error is minimised. The minimisation of systematic error (i.e. errors resulting from protocol differences, machine differences, operator differences and other quantifiable factors) is the process referred to here as "normalisation".

Feature Selection. Typically the dataset contains many more data elements than would be practical to measure on a day-to-day basis, and additionally many elements that do not provide the information needed to produce a prediction model. The actual ability of a prediction model to describe a dataset is derived from some subset of the full dimensionality of the dataset. These dimensions the most important components (or features) of the dataset. Note in the context of microarray data, the dimensions of the dataset are the individual genes.

Feature selection, in the context described here, involves finding those genes which are most "differentially expressed". In a more general sense, it involves those groups which pass some statistical test for significance, i.e. is the level of a particular variable consistently higher or lower in one or other of the groups being investigated. Sometimes the features are those variables (or dimensions) which exhibit the greatest variance. The application of feature selection is completely independent of the method used to create a prediction model, and involves a great deal of experimentation to achieve the desired results. Within this invention, the selection of significant genes, and those which correlated with the earlier successful model (the NZ classifier), entailed feature selection. In addition, methods of data reduction (such as principal component analysis) can be applied to the dataset.

Training. Once the classes (e.g. recurrence/non-recurrence) and the features of the dataset have been established, and the data is represented in a form that is acceptable as input for data mining, the reduced dataset (as described by the features) is applied to the prediction model of choice. The input for this model is usually in the form a multi-dimensional numerical input, (known as a vector), with associated output information (a class label or a response). In the training process, selected data is input into the prediction model, either sequentially (in techniques such as neural networks) or as a whole (in techniques that apply some form of regression, such as linear models, linear discriminant analysis, support vector machines). In some instances (e.g. k-nearest neighbours) the dataset (or subset of the dataset obtained after feature selection) is itself the model. As discussed, effective models can be established with minimal understanding of the detailed mathematics, through the use of various software packages where the parameters of the model have been pre-determined by expert analysts as most likely to lead to successful results.

Validation. This is a key component of the data-mining protocol, and the incorrect application of this frequently leads to errors. Portions of the dataset are to be set aside, apart from feature selection and training, to test the success of the prediction model. Furthermore, if the results of validation are used to effect feature selection and training of the model, then one obtains a further validation set to test the model before it is applied to real-life situations. If this process is not strictly adhered to the model is likely to fail in real-world situations. The methods of validation are described in more detail below.

Application. Once the model has been constructed, and validated, it must be packaged in some way as it is accessible to end users. This often involves implementation of some form a spreadsheet application, into which the model has been imbedded, scripting of a statistical software package, or refactoring of the model into a hard-coded application by information technology staff.

Examples of software packages that are frequently used are:
Spreadsheet plugins, obtained from multiple vendors.
The R statistical environment.
The commercial packages MatLab, S-plus, SAS, SPSS, STATA.
Free open-source software such as Octave (a MatLab clone) many and varied C++ libraries, which can be used to implement prediction models in a commercial, closed-source setting.

Examples of Data Mining Methods.

The methods can be by first performing the step of data mining process (above), and then applying the appropriate known software packages. Further description of the process of data mining is described in detail in many extremely well-written texts. (49)

- Linear models (49, 50): The data is treated as the input of a linear regression model, of which the class labels or responses variables are the output. Class labels, or other categorical data, must be transformed into numerical values (usually integer). In generalised linear models, the class labels or response variables are not themselves linearly related to the input data, but are transformed through the use of a "link function". Logistic regression is the most common form of generalized linear model.
- Linear Discriminant analysis (49, 51, 52). Provided the data is linearly separable (i.e. the groups or classes of data can be separated by a hyperplane, which is an n-dimensional extension of a threshold), this technique can be applied. A combination of variables is used to separate the classes, such that the between group variance is maximised, and the within-group variance is minimised. The byproduct of this is the formation of a classification rule. Application of this rule to samples of unknown class allows predictions or classification of class membership to be made for that sample. There are variations of linear discriminant analysis such as nearest shrunken centroids which are commonly used for microarray analysis.
- Support vector machines (53): A collection of variables is used in conjunction with a collection of weights to determine a model that maximizes the separation between classes in terms of those weighted variables. Application of this model to a sample then produces a classification or prediction of class membership for that sample.
- Neural networks (52): The data is treated as input into a network of nodes, which superficially resemble biological neurons, which apply the input from all the nodes to which they are connected, and transform the input into an output. Commonly, neural networks use the "multiply and sum" algorithm, to transform the inputs from multiple connected input nodes into a single output. A node may not necessarily produce an output unless the inputs to that node exceed a certain threshold. Each node has as its input the output from several other nodes, with the final output node usually being linked to a categorical variable. The number of nodes, and the topology of the nodes can be varied in almost infinite ways, providing for the ability to classify extremely noisy data that may not be possible to categorize in other ways. The most common implementation of neural networks is the multi-layer perceptron.
- Classification and regression trees (54): In these. variables are used to define a hierarchy of rules that can be followed in a stepwise manner to determine the class of a sample. The typical process creates a set of rules which lead to a specific class output, or a specific statement of the inability to discriminate. A example classification tree is an implementation of an algorithm such as:

```
if gene A> x and gene Y > x and gene Z = z
then
    class A
else if geneA = q
    then
class B
```

- Nearest neighbour methods (51, 52). Predictions or classifications are made by comparing a sample (of unknown class) to those around it (or known class), with closeness defined by a distance function. It is possible to define many different distance functions. Commonly used distance functions are the Euclidean distance (an extension of the Pythagorean distance, as in triangulation, to n-dimensions), various forms of correlation (including Pearson Correlation co-efficient). There are also transformation functions that convert data points that would not normally be interconnected by a meaningful distance metric into euclidean space, so that Euclidean distance can then be applied (e.g. Mahalanobis distance). Although the distance metric can be quite complex, the basic premise of k-nearest neighbours is quite simple, essentially being a restatement of "find the k-data vectors that are most similar to the unknown input, find out which class they correspond to, and vote as to which class the unknown input is".
- Other methods:
    - Bayesian networks. A directed acyclic graph is used to represent a collection of variables in conjunction with their joint probability distribution, which is then used to determine the probability of class membership for a sample.
    - Independent components analysis, in which independent signals (e.g., class membership) re isolated (into components) from a collection of variables. These components can then be used to produce a classification or prediction of class membership for a sample.
    - Ensemble learning methods in which a collection of prediction methods are combined to produce a joint classification or prediction of class membership for a sample There are many variations of these methodologies that can be explored (49), and many new methodologies are constantly being defined and developed. It will be appreciated that any one of these methodologies can be applied in order to obtain an acceptable result. Particular care must be taken to avoid overfitting, by ensuring that all results are tested via a comprehensive validation scheme.

Validation

Application of any of the prediction methods described involves both training and cross-validation (43, 55) before the method can be applied to new datasets (such as data from a clinical trial). Training involves taking a subset of the dataset of interest (in this case gene expression measurements from colorectal tumours), such that it is stratified across the classes that are being tested for (in this case recurrent and non-recurrent tumours). This training set is used to generate a prediction model (defined above), which is tested on the remainder of the data (the testing set).

It is possible to alter the parameters of the prediction model so as to obtain better performance in the testing set, however, this can lead to the situation known as overfitting, where the prediction model works on the training dataset but not on any external dataset. In order to circumvent this, the process of validation is followed. There are two major types of validation typically applied, the first (hold-out validation) involves partitioning the dataset into three groups: testing, training, and validation. The validation set has no input into the training process whatsoever, so that any adjustment of parameters or other refinements must take place during application to the testing set (but not the validation set). The second major type is cross-validation, which can be applied in several different ways, described below.

There are two main sub-types of cross-validation: K-fold cross-validation, and leave-one-out cross-validation K-fold cross-validation: The dataset is divided into K subsamples, each subsample containing approximately the same proportions of the class groups as the original. In each round of validation, one of the K subsamples is set aside, and training is accomplished using the remainder of the dataset. The effectiveness of the training for that round is gauged by how correctly the classification of the left-out group is. This procedure is repeated K-times, and the overall effectiveness ascertained by comparison of the predicted class with the known class.

Leave-one-out cross-validation: A commonly used variation of K-fold cross validation, in which K=n, where n is the number of samples.

Combinations of CCPMS, such as those described above in Tables 1 and 2, can be used to construct predictive models for prognosis.

Prognostic Signatures

Prognostic signatures, comprising one or more of these markers, can be used to determine the outcome of a patient, through application of one or more predictive models derived from the signature. In particular, a clinician or researcher can determine the differential expression (e.g., increased or decreased expression) of the one or more markers in the signature, apply a predictive model, and thereby predict the negative prognosis, e.g., likelihood of disease relapse, of a patient, or alternatively the likelihood of a positive prognosis (continued remission).

A set of prognostic signatures have been developed. In the first instance, there are two signatures developed by cross-comparison of predictive ability between two datasets: the set of microarray experiments encompassing the German colorectal cancer samples, and the set of microarray experiments encompassing the New Zealand samples (discussed in example 6). In the second instance there has been an exhaustive statistical search for effective signatures based solely on the German dataset (discussed in example 17).

As described in Example 6 below, a prognostic signature comprising 19 genes has been established from a set of colorectal samples from Germany (Table 4). Another prognostic signature, of 22 genes, has also been established from samples of colorectal tumours from patients in New Zealand (Table 3). By obtaining a patient sample (e.g., tumour sample), and matching the expression levels of one or more markers in the sample to the differential expression profile, the likelihood of the cancer recurring can be determined.

TABLE 3

New Zealand prognostic signature

| | | | | |
|---|---|---|---|---|
| WDR44 | WD repeat domain 44 | 0.81 | Hs.98510 | NM_019045 |
| RBMS1 | rna binding motif, single stranded interacting protein 1, isoform d | 1.27 | Hs.470412 | NM_016836 |
| SACM1L | Ras-GTPase activating protein SH3 domain-binding protein 2 | 0.84 | Hs.156509 | NM_014016 |
| SOAT1 | sterol o-acyltransferase acyl-coenzyme a: cholesterol acyltransferase 1 | 1.21 | Hs.496383 | NM_003101 |
| PBK | pdz-binding kinase | 0.76 | Hs.104741 | NM_018492 |
| G3BP2 | ras-gtpase activating protein sh3 domain-binding protein 2 | 0.86 | Hs.303676 | NM_012297 |
| ZBTB20 | zinc finger and BTB domain containing 20 | 1.2 | Hs.477166 | NM_015642 |
| ZNF410 | zinc finger protein 410 | 0.84 | Hs.270869 | NM_021188 |
| COMMD2 | COMM domain containing 2 | 1.09 | Hs.591315 | NM_016094 |
| PSMC1 | proteasome (prosome, macropain) 26s subunit, atpase, 1 | 0.79 | Hs.356654 | NM_002802 |
| COX10 | COX10 homolog, cytochrome c oxidase assembly protein, heme A: farnesyltransferase (yeast) | 0.9 | Hs.462278 | NM_001303 |
| GTF3C5 | general transcription factor iiic, polypeptide 5 (63 kd) | 0.84 | Hs.495417 | NM_012087 |
| HMMR | hyaluronan-mediated motility receptor (rhamm) | 0.78 | Hs.72550 | NM_012485 |
| UBE2L3 | ubiquitin-conjugating enzyme e2l 3 | 0.83 | Hs.108104 | NM_003347 |
| GNAS | gnas complex locus | 1.26 | Hs.125898 | NM_000516 |
| PPP2R2A | protein phosphatase 2 (formerly 2a), regulatory subunit b (pr 52), alpha isoform | 0.91 | Hs.146339 | NM_002717 |
| RNASE2 | ribonuclease, rnase a family, 2 (liver, eosinophil-derived neurotoxin) | 0.83 | Hs.728 | NM_002934 |
| SCOC | short coiled-coil protein | 0.78 | Hs.480815 | NM_032547 |
| PSMD9 | proteasome (prosome, macropain) 26s subunit, non-atpase, 9 | 0.89 | Hs.131151 | NM_002813 |

TABLE 3-continued

New Zealand prognostic signature

| | | | | |
|---|---|---|---|---|
| EIF3S7 | eukaryotic translation initiation factor 3, subunit 7 (zeta, 66/67 kd) | 0.85 | Hs.55682 | NM_003753 |
| ATP2B4 | ATPase, Ca++ transporting, plasma membrane 4 | 1.11 | Hs.343522 | NM_001001396 NM_001684 |
| ABCC9 | atp-binding cassette, sub-family c, member 9, isoform sur2a-delta-14 | 0.9 | Hs.446050 | NM_020298 |

TABLE 4

German prognostic signature

| Gene Symbol | Gene Description | Expression fold difference (relapse/non-relapse) | UniGene Cluster | GenBank Acc. No. |
|---|---|---|---|---|
| CXCL10 | Chemokine (C—X—C motif) ligand 10 | 0.87 | Hs.413924 | NM_001565 |
| FAS | FAS (TNF receptor superfamily, member 6) | 0.9 | Hs.244139 | NM_000043 NM_152871 NM_152872 NM_152873 NM_152874 NM_152875 NM_152876 NM_152877 |
| CXCL9 | chemokine (C—X—C motif) ligand 9 | 0.87 | Hs.77367 | NM_002416 |
| TLK1 | tousled-like kinase 1 | 0.91 | Hs.470586 | NM_012290 |
| CXCL11 | chemokine (C—X—C motif) ligand 11 | 0.75 | Hs.518814 | NM_005409 |
| PBK | T-LAK cell-originated protein kinase | 0.86 | Hs.104741 | NM_018492 |
| PSAT1 | phosphoserine aminotransferase 1 | 0.91 | Hs.494261 | NM_021154 |
| MAD2L1 | MAD2 mitotic arrest deficient-like 1 (yeast) | 0.89 | Hs.533185 | NM_002358 |
| CA2 | carbonic anhydrase II | 0.84 | Hs.155097 | NM_000067 |
| GZMB | granzyme B (granzyme 2, cytotoxic T-lymphocyte-associated serine esterase 1) | 0.9 | Hs.1051 | NM_004131 |
| SLC4A4 | solute carrier family 4, sodium bicarbonate cotransporter, member 4 | 0.86 | Hs.5462 | NM_003759 |
| DLG7 | discs, large homolog 7 (*Drosophila*) | 0.89 | Hs.77695 | NM_014750 |
| TNFRSF11A | tumor necrosis factor receptor superfamily, member 11a, activator of NFKB | 0.9 | Hs.204044 | NM_003839 |
| KITLG | KIT ligand | 0.91 | Hs.1048 | NM_000899 |
| INDO | indoleamine-pyrrole 2,3 dioxygenase | 0.91 | Hs.840 | NM_002164 |
| GBP1 | guanylate binding protein 1, interferon-inducible, 67 kDa | 0.9 | Hs.62661 | NM_002053 |
| CXCL13 | chemokine (C—X—C motif) ligand 13 (B-cell chemoattractant) | 0.86 | Hs.100431 | NM_006419 |
| CLCA4 | chloride channel, calcium activated, family member 4 | 0.84 | Hs.546343 | NM_012128 |
| PCP4 | Purkinje cell protein 4 | 1.14 | Hs.80296 | NM_006198 |

TABLE 5

Immune response genes

| Gene Symbol | Gene Description | Expression fold difference (relapse/non-relapse) | UniGene Cluster | GenBank Acc. No. |
|---|---|---|---|---|
| CXCL9 | chemokine (C—X—C motif) ligand 9 | 0.87 | Hs.77367 | NM_002416 |
| CXCL10 | Chemokine (C—X—C motif) ligand 10 | 0.87 | Hs.413924 | NM_001565 |
| CXCL11 | chemokine (C—X—C motif) ligand 11 | 0.75 | Hs.518814 | AF030514 |
| CXCL13 | chemokine (C—X—C motif) ligand 13 (B-cell chemoattractant) | 0.86 | Hs.100431 | NM_006419 |
| PBK | T-LAK cell-originated protein kinase | 0.86 | Hs.104741 | NM_018492 |
| INDO | indoleamine-pyrrole 2,3 dioxygenase | 0.91 | Hs.840 | M34455 |
| GBP1 | guanylate binding protein 1, interferon-inducible, 67 kDa | 0.9 | Hs.62661 | NM_002053 |
| GZMB | granzyme B (granzyme 2, cytotoxic T-lymphocyte-associated serine esterase 1) | 0.9 | Hs.1051 | J03189 |
| KITLG | KIT ligand | 0.91 | Hs.1048 | NM_000899 |
| TNFRSF11A | tumor necrosis factor receptor superfamily, member 11a, activator of NFKB | 0.9 | Hs.204044 | NM_003839 |
| FAS | FAS (TNF receptor superfamily, member 6) | 0.9 | Hs.244139 | Z70519 |

In certain aspects, this invention provides methods for determining the prognosis of a cancer, comprising: (a) providing a sample of the cancer; (b) detecting the expression level of a CCPM family member in said sample; and (c) determining the prognosis of the cancer. In one aspect, the cancer is colorectal cancer.

In other aspects, the invention includes a step of detecting the expression level of a CCPM mRNA. In other aspects, the invention includes a step of detecting the expression level of a CCPM polypeptide. In yet a further aspect, the invention includes a step of detecting the level of a CCPM peptide. In yet another aspect, the invention includes detecting the expression level of more than one CCPM family member in said sample. In a further aspect the CCPM is a gene associated with an immune response. In a further aspect the CCPM is selected from the markers set forth in Tables 3, 4, 8A, 8B, or 9. In a still further aspect, the CCPM is included in a signature selected from the signatures set forth in Tables 3, 4, 8A, 8B, or 9.

In a further aspect the invention comprises detecting the expression level of; WDR44, RBMS1, SACM1L, SOAT1, PBK, G3BP2, ZBTB20, ZNF410, COMMD2, PSMC1, COX10, GTF3C5, HMMR, UBE2L3, GNAS, PPP2R2A, RNASE2, SCOC PSMD9, EIF3S7, ATP2B4, and ABCC9. In a further aspect the invention comprises detecting the expression level of; CXCL10, FAS, CXCL0, TLK1, CXCL11, PBK, PSAT1, MAD2L1, CA2, GZMB, SLC4A4, DLG7, TNFRSF11A, KITLG, INDO, GBP1, CXCL13, CLCA4, and PCP4.

In still further aspects, the invention includes a method of determining a treatment regime for a cancer comprising: (a) providing a sample of the cancer; (b) detecting the expression level of a CCPM family member in said sample; (c) determining the prognosis of the cancer based on the expression level of a CCPM family member; and (d) determining the treatment regime according to the prognosis.

In still further aspects, the invention includes a device for detecting a CCPM, comprising: a substrate having a CCPM capture reagent thereon; and a detector associated with said substrate, said detector capable of detecting a CCPM associated with said capture reagent. Additional aspects include kits for detecting cancer, comprising: a substrate; a CCPM capture reagent; and instructions for use. Yet further aspects of the invention include method for detecting a CCPM using qPCR, comprising: a forward primer specific for said CCPM; a reverse primer specific for said CCPM; PCR reagents; a reaction vial; and instructions for use.

Additional aspects of this invention comprise a kit for detecting the presence of a CCPM polypeptide or peptide, comprising: a substrate having a capture agent for said CCPM polypeptide or peptide; an antibody specific for said CCPM polypeptide or peptide; a reagent capable of labeling bound antibody for said CCPM polypeptide or peptide; and instructions for use.

In yet further aspects, this invention includes a method for determining the prognosis of colorectal cancer, comprising the steps of: providing a tumour sample from a patient suspected of having colorectal cancer; measuring the presence of a CCPM polypeptide using an ELISA method. In specific aspects of this invention the CCPM of the invention is selected from the markers set forth in Tables 1, 2, 5, or 9. In still further aspects, the CCPM is included in a prognostic signature selected from the signatures set forth in Tables 3, 4, 8A, 8B, or 10.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

Example 1

Patients and Methods

Two cohorts of patients were included in this study, one set from New Zealand (NZ) and the second from Germany (DE). The NZ patients were part of a prospective cohort study that included all disease stages, whereas the DE samples were selected from a tumour bank. Clinical information is shown in Table 6, while FIG. 1 summarises the experimental design.

Example 2

Tumour Samples

Primary colorectal tumor samples from 149 NZ patients were obtained from patients undergoing surgery at Dunedin Hospital and Auckland Hospital between 1995-2000. Tumor samples were snap frozen in liquid nitrogen. All surgical specimens were reviewed by a single pathologist (H-S Y) and were estimated to contain an average of 85% tumor cells. Among the 149 CRC patients, 12 had metastatic disease at presentation, 35 developed recurrent disease, and 102 were disease-free after a minimum of 5-year follow up.

Primary colorectal tumor samples from DE patients were obtained from patients undergoing surgery at the Surgical Department of the Technical University of Munich between 1995-2001. A group of 55 colorectal carcinoma samples was selected from banked tumours which had been obtained fresh from surgery, snap frozen in liquid nitrogen. The samples were obtained from 11 patients with stage I cancer and 44 patients with stage II cancer. Twenty nine patients were recurrence-free and 26 patients had experienced disease recurrence after a minimum of 5-year follow up.

Tumor content ranged between 70 and 100% with an average of 87%.

TABLE 6

Clinical characteristics of New Zealand and German colorectal tumours
1. Persisting disease

|  | Relapse free | Relapse |
|---|---|---|
| New Zealand data | | |
| Number of patients | 102 | 47 |
| Age | 68.5 (SD: 15.1) | 69.8 (SD: 8.7) |
| Gender | | |
| male | 48 (47%) | 22 (47%) |
| female | 54 (53%) | 25 (53%) |
| Tumor localization | | |
| right colon | 41 (40%) | 18 (38%) |
| left colon | 12 (12%) | 4 (9%) |
| sigmoid | 31 (30%) | 17 (36%) |
| rectum | 18 (18%) | 8 (17%) |
| Tumor stage | | |
| Stage I | 16 | 0 |
| Stage II | 61 | 13 |
| Stage III | 25 | 22 |
| Stage IV | 0 | 12[1] |
| Median follow up period/median recurrence free period (months) | 72 (range: 60-80) | 15 (range: 0-59) |

TABLE 6-continued

Clinical characteristics of New Zealand and German colorectal tumours
1. Persisting disease

|  | Relapse free | Relapse |
|---|---|---|
| German data | | |
| Number of patients | 29 | 26 |
| Age | 64.3 (SD: 12.8) | 61.8 (SD: 10.7) |
| Gender | | |
| male | 17 (59%) | 16 (62%) |
| female | 12 (41%) | 10 (38%) |
| Tumor localization | | |
| right colon | 8 (28%) | 4 (15%) |
| left colon | 7 (24%) | 5 (19%) |
| sigmoid | 6 (21%) | 7 (27%) |
| rectum | 8 (28%) | 10 (38%) |
| Tumor stage | | |
| Stage I | 5 | 6 |
| Stage II | 24 | 20 |
| Median follow up period/median recurrence free period (months) | 83.1 (range: 64-99) | 27.4 (range: 3-60) |

Example 3

RNA Extraction and Target Labeling

NZ tumours: Tumours were homogenized and RNA was extracted using Tri-Reagent (Progenz, Auckland, New Zealand). The RNA was then further purified using RNeasy mini column (Qiagen, Victoria, Australia). Ten micrograms of RNA was labelled with Cy5 dUTP using the indirect aminoallyl cDNA labelling protocol.

A reference RNA from 12 different cell lines was labelled with Cy3 dUTP. The fluorescently labelled cDNA were purified using a QiaQuick PCR purification kit (Qiagen, Victoria, Australia) according to the manufacturer's protocol.

DE tumours: Tumours were homogenized and RNA was isolated using RNeasy Mini Kit (Qiagen, Hilden, Germany). cRNA preparation was performed as described previously (9), purified on RNeasy Columns (Qiagen, Hilden, Germany), and eluted in 55 µl of water. Fifteen micrograms of cRNA was fragmented for 35 minutes at 95° C. and double stranded cDNA was synthesized with a oligo-dT-T7 primer (Eurogentec, Koln, Germany) and transcribed using the Promega RiboMax T7-kit (Promega, Madison, Wis.) and Biotin-NTP labelling mix (Loxo, Dossenheim, Germany).

Example 4

Microarray Experiments

NZ tumours: Hybridisation of the labelled target cDNA was performed using MWG Human 30K Array oligonucleotides printed on epoxy coated slides. Slides were blocked with 1% BSA and the hybridisation was done in prehybridisation buffer at 42° C. for at least 12 hours followed by a high stringency wash. Slides were scanned with a GenePix Microarray Scanner and data was analyzed using GenePix Pro 4.1 Microarray Acquisition and Analysis Software (Axon, Calif.).

DE tumours: cRNA was mixed with B2-control oligonucleotide (Affymetrix, Santa Clara, Calif.), eukaryotic hybridization controls (Affymetrix, Santa Clara, Calif.), herring sperm (Promega, Madison, Wis.), buffer and BSA to a final volume of 300 μl and hybridized to one microarray chip (Affymetrix, Santa Clara, Calif.) for 16 hours at 45° C. Washing steps and incubation with streptavidin (Roche, Mannheim, Germany), biotinylated goat-anti streptavidin antibody (Serva, Heidelberg, Germany), goat-IgG (Sigma, Taufkirchen, Germany), and streptavidin-phycoerythrin (Molecular Probes, Leiden, Netherlands) was performed in an Affymetrix Fluidics Station according to the manufacturer's protocol. The arrays were then scanned with a HP-argon-ion laser confocal microscope and the digitized image data were processed using the Affymetrix® Microarray Suite 5.0 Software.

Example 5

Data Pre-Processing

NZ data: Data pre-processing and normalization was performed in the R computing environment (10). A $\log_2$ transformation was applied to the foreground intensities from each channel of each array. Data from each spot was used on a per array basis to perform print-tip loss normalization via the limma package (11) from the Bioconductor suite of analysis tools (12). Scale normalization (13) was then used to standardize the distribution of log intensity ratios across arrays. Post-normalization cluster analysis revealed the presence of a gene-specific print-run effect present in the data. Analysis of variance (ANOVA) normalization was used to estimate and remove print run effects from the data for each gene. Replicate array data was available for 46 of the 149 samples. Cluster analysis of the entire data set indicated that the duplicate arrays clustered well with each other suggesting internal consistency of the array platform. Genes with low intensity, large differences between replicates (mean $\log_2$ difference between duplicates higher than 0.5), and unknown proteins were removed from the data set. After the initial normalization procedure, a subset of 10,318 genes was chosen for further analysis.

DE data: All Affymetrix U133A GeneChips passed quality control to eliminate scans with abnormal characteristics, that is, abnormal low or high dynamic range, high perfect match saturation, high pixel noise, grid misalignment problems, and low mean signal to noise ratio. Background correction and normalization were performed in the R computing environment (10, 40). Background corrected and normalized expression measures from probe level data (cel-files) were obtained using the robust multi-array average function (14) implemented in the Bioconductor package affy.

Example 6

Prognostic Signatures and Cross Validation

Data analysis was performed using the BRB Array-Tools package. Gene selection was performed using a random variance model t-test. In the DE data, 318 genes were found to be differentially expressed when using a significance threshold of 0.001. As most of the differentially expressed genes exhibited relatively small changes in expression, a condition requiring the mean $\log_2$ fold change between the two classes to be higher than 1.1 was added to the gene selection process for the DE data. Gene-based prognostic signatures were produced using leave one out cross validation (LOOCV) in each of the NZ and DE data sets. To avoid the problem of over-fitting, both the gene selection and signature construction were performed during each LOOCV iteration. After LOOCV, the prediction rate was estimated by the fraction of samples correctly predicted. In order to find a gene set that could make the best prediction for unknown samples, different t-test thresholds using a random variance model were investigated in conjunction with six classification methods: compound covariate classifier (CCP), diagonal linear discriminant analysis (DLD), 3-nearest neighbours (3-NN), 1-nearest neighbours (1-NN), nearest centroid (NC), and support vector machines (SVM).

To establish the validity of the NZ and DE prognosis signatures, reciprocal validation was performed, with the NZ signature validated using the DE data set, and vice versa. To test the NZ genes, probes relating to the 22 genes from the NZ signature were identified in the DE data, and LOOCV was used to assess the performance of a signature for the DE samples, based only on these probes. Similarly, probes relating to the 19 genes in the DE signature were identified in the NZ data and LOOCV was used to assess the performance of a signature for the NZ samples. In both cases a significance threshold of 0.999 was used to ensure that all genes were used in each LOOCV iteration. Differences between the platforms (in particular, log-ratio data versus log-intensity data) meant that direct application of a prediction rule across data sets was not feasible. The consequence of this is that only the gene sets, and not the prediction rules used, can be generalized to new samples. The significance of the LOOCV prediction results was calculated by permuting the class labels of the samples and finding the proportion of times that the permuted data resulted in a higher LOOCV prediction rate than that obtained for the unpermuted data. All permutation analysis involved 2000 permutations, with small P-values indicating that prediction results were unlikely to be due to chance.

Example 7

Survival Analysis

Kaplan-Meier survival analysis for censored data was performed using the survival package within the R computing environment. Survival was defined to be "disease free survival" post surgery. For each analysis, survival curves were constructed, and the log-rank test (15) was used to assess the presence of significant differences between the curves for the two groups in question. Censoring was taken into account for both the NZ and DE data sets. For the disease-free survival data, right censoring prior to five years could only occur for non-recurrent patients as a result of either death, or the last clinical follow-up occurring at less than five years. Odds ratios and confidence intervals were produced using the epitools package for R.

Example 8

Identification of Markers Co-Expressed with Chemokine Ligands

Genes in the DE data which had a Pearson correlation coefficient greater than 0.75 with at least one of the four chemokines appearing in the predictor in the non-relapse group were selected for ontology analysis. Ontology was performed using DAVID (hypertext transfer protocol:// apps1.niaid.nih.gov/david/).

Example 9

Results and Analysis

To identify robust prognostic signatures to predict disease relapse for CRC, two independent sets of samples from NZ and DE were used to generate array expression data sets from separate series of primary tumours with clinical follow-up of five or more years. After normalization, each data set was analyzed using the same statistical methods to generate a prognostic signature, which was then validated on the alternate series of patients. As such, the DE prognostic signature was validated on the NZ data set and the NZ prognostic signature was validated on the DE data set.

Example 10

Exhaustive Identification of Differentially Expressed Markers

DE Data Set: The BRB Array Tools class comparison procedure was used to detect probes exhibiting statistically significant differences in average intensity between relapse and non-relapse samples. The RVM (random variance model) was again used to produce p-values for each probe in the data set. In this second round, a total of 325 probes were found to be significantly differentially expressed between the two sample classes using an arbitrary significance threshold of 0.05. Note this selection of genes did not apply any fold-change threshold, and used a significance cut off of 0.05, rather than the threshold of 0.001 that was used in Example 6. The purpose of this less stringent threshold (p=0.05 instead of p=0.001) was to put forward a larger number of genes for construction of the second round of signatures (see example 17) These probes represent 270 unique genes (Table 1 and Table 2).

Explicitly, the test for significance (random variance model) comprises the following: generating a test statistic for each gene which was identical to that of a standard two sample t-test (45) except that the estimate of the pooled variance was obtained by representing the variance structure across all genes as an F-distribution, and then using the parameters, a and b, of this distribution (obtained via maximization of the empirical likelihood function) to form the following estimate of the pooled variance (see next page), $$s^2 = \frac{(n-2)s^2_{pooled} + 2b^{-1}}{(n-2) + 2a}$$

where $S^2$ is the new estimate of the pooled variance, $S^2_{pooled}$ is the standard estimate of pooled variance (45), n is the number of samples, and a and b are the parameters of the F-distribution (46). Based on the t-statistic formed, a t-distribution with n−2+2a degrees of freedom was used to obtain a p-value for each gene. To adjust for multiple hypothesis testing, the False Discovery Rate controlling procedure of Benjamini and Hochberg (7) was used to produce adjusted p-values for each gene. A gene was considered to have undergone significant differential expression if its adjusted p-value was less than 0.05.

Example 11

Identification of Correlated Markers

In order to identify additional genes that can be used as prognostic predictors, correlation analysis was carried out using the R statistical computing software package. This analysis revealed 167 probes that had a Pearson correlation coefficient (40, 44, 45) of at least 0.8. Of these probes, 51 were already present in the set of 325 significantly differentially expressed probes, while the remaining 116 were reported as non-significant (using a 0.05 threshold for the FDR, or "false-discovery rate" (47) controlling procedure, the RVM, or rando variance model). These 116 probes represent 111 distinct genes (Table 2).

Example 12

Construction of Prognostic Signatures

The NZ data set was generated using oligonucleotide printed microarrays. Six different signatures were constructed, with a support vector machine (SVM) using a gene selection threshold of 0.0008 yielding the highest LOOCV prediction rate, and producing a 22-gene signature (77% prediction rate, 53% sensitivity, 88% specificity; p=0.002, Tables 7, 8A, and 8B). For Tables 8A and 8B, the gene descriptions are shown in Tables 3 and 4, respectively.

TABLE 7

Construction of prognostic signatures

| Data set | Prediction rate | Sensitivity | Specificity | P value* | Odd ratio |
|---|---|---|---|---|---|
| 22 gene NZ signature tested on German data | | | | | |
| NZ data (training; SVM) | 0.77 (0.66, 0.86)§ | 0.53 (0.33, 0.73) | 0.88 (0.77, 0.95) | 0.002 | 8.4 (3.5, 21.4) |
| NZ data minus 4 genes not found in German data were removed from NZ data set (training; SVM) | 0.72 | 0.38 | 0.87 | 0.011 | |
| German data (test; SVM) | 0.71 (0.51, 0.86) | 0.62 (0.32, 0.86) | 0.79 (0.52, 0.95) | 0.002 | 5.9 (1.6, 24.5) |
| 19 gene German signature tested on NZ data | | | | | |
| German data (training; 3-NN) | 0.84 (0.65, 0.95) | 0.85 | 0.83 | <0.0001 | 24.1 (5.3, 144.7) |

TABLE 7-continued

Construction of prognostic signatures

| Data set | Prediction rate | Sensitivity | Specificity | P value* | Odd ratio |
|---|---|---|---|---|---|
| German data minus 5 genes not found in NZ data were removed from German data set (training; 3-NN) | 0.67 | 0.65 | 0.66 | 0.046 | |
| NZ data (test; 3-NN) | 0.67 (0.55, 0.78) | 0.42 (0.22, 0.64) | 0.78 (0.65, 0.89) | 0.045 | 2.6 (1.2, 6.0) |

SVM: support vector machine signature;
3-NN: 3 nearest neighbour signature.
§95% confidence interval
*P values were calculated from 2,000 permutation of class labels

TABLE 8A

NZ prognostic signature
New Zealand 22-gene prognostic signature

| p-value | Gene Symbol | GenBank Acc. No. | Genes not found in German data at time of analysis |
|---|---|---|---|
| 2.30E-05 | WDR44 | NM_019045 | * |
| 3.30E-05 | RBMS1 | NM_016836 | |
| 4.60E-05 | SACM1L | NM_014016 | |
| 6.80E-05 | SOAT1 | NM_003101 | |
| 7.90E-05 | PBK | NM_018492 | |
| 0.00014 | G3BP2 | NM_012297 | |
| 0.000163 | ZBTB20 | NM_015642 | |
| 0.000214 | ZNF410 | NM_021188 | * |
| 0.00022 | COMMD2 | NM_016094 | * |
| 0.000293 | PSMC1 | NM_002802 | |
| 0.000321 | COX10 | NM_001303 | |
| 0.000334 | GTF3C5 | NM_012087 | |
| 0.000367 | HMMR | NM_012485 | |
| 0.000405 | UBE2L3 | NM_003347 | |
| 0.000417 | GNAS | NM_000516 | |
| 0.000467 | PPP2R2A | NM_002717 | |
| 0.000493 | RNASE2 | NM_002934 | |
| 0.000532 | SCOC | NM_032547 | * |
| 0.000578 | PSMD9 | NM_002813 | |
| 0.000593 | EIF3S7 | NM_003753 | |
| 0.000649 | ATP2B4 | NM_001001396 NM_001684 | |
| 0.000737 | ABCC9 | NM_020298 | |

TABLE 8B

DE prognostic signature
German 19-gene prognostic signature

| p-value | Gene Symbol | GenBank Acc. No. | Genes not found in NZ data at time of analysis |
|---|---|---|---|
| 3.00E-06 | CXCL10 | NM_001565 | |
| 4.00E-06 | FAS | NM_000043 NM_152871 NM_152872 NM_152873 NM_152874 NM_152875 NM_152876 NM_152877 | |
| 8.00E-06 | CXCL9 | NM_002416 | * |
| 1.20E-05 | TLK1 | NM_012290 | |
| 1.30E-05 | CXCL11 | NM_005409 | |
| 2.10E-05 | PBK | NM_018492 | |
| 4.20E-05 | PSAT1 | NM_021154 | |
| 7.60E-05 | MAD2L1 | NM_002358 | |
| 9.80E-05 | CA2 | NM_000067 | |
| 0.000128 | GZMB | NM_004131 | * |
| 0.000177 | SLC4A4 | NM_003759 | |
| 0.000215 | DLG7 | NM_014750 | * |
| 0.000376 | TNFRSF11A | NM_003839 | |
| 0.00038 | KITLG | NM_000899 | |
| 0.000579 | INDO | NM_002164 | |
| 0.000634 | GBP1 | NM_002053 | |
| 0.000919 | CXCL13 | NM_006419 | * |
| 0.000942 | CLCA4 | NM_012128 | * |
| 0.001636 | PCP4 | NM_006198 | |

The NZ signature had an odds ratio for disease recurrence in the NZ patients of 8.4 (95% CI 3.5-21.4).

The DE data set was generated using Affymetrix arrays resulting in a 19-gene (22-probe) and 3-nearest neighbour (3-NN) signature (selection threshold 0.002, $\log_2$ fold change>1.1, 84% classification rate, 85% sensitivity, 83% specificity, p<0.0001, Tables 3, 4, 7). The DE signature had an odds ratio for recurrence in the DE patients of 24.1 (95% CI 5.3-144.7). Using Kaplan-Meier analysis, disease-free survival in NZ and DE patients was significantly different for those predicted to recur or not recur (NZ signature, p<0.0001, FIG. 2A; DE signature, p<0.0001, FIG. 2B).

Example 13

External Validation of the NZ and DE Prognostic Signatures

To validate the NZ signature, the 22 genes were used to construct a SVM signature in the DE data set by LOOCV. A prediction rate of 71% was achieved, which was highly significant (p=0.002; Table 7). The odds ratio for recurrence in DE patients, using the NZ signature, was 5.9 (95% CI 1.6-24.5). We surmise that the reduction in prediction rate, from 77% in NZ patients to 71% in DE patients (Table 7), was due to four genes from the NZ signature not being present in the DE data. Disease-free survival for DE patients predicted to relapse, according to the NZ signature, was significantly lower than disease-free survival for patients predicted not to relapse (p=0.0049, FIG. 2C).

Figure 2:
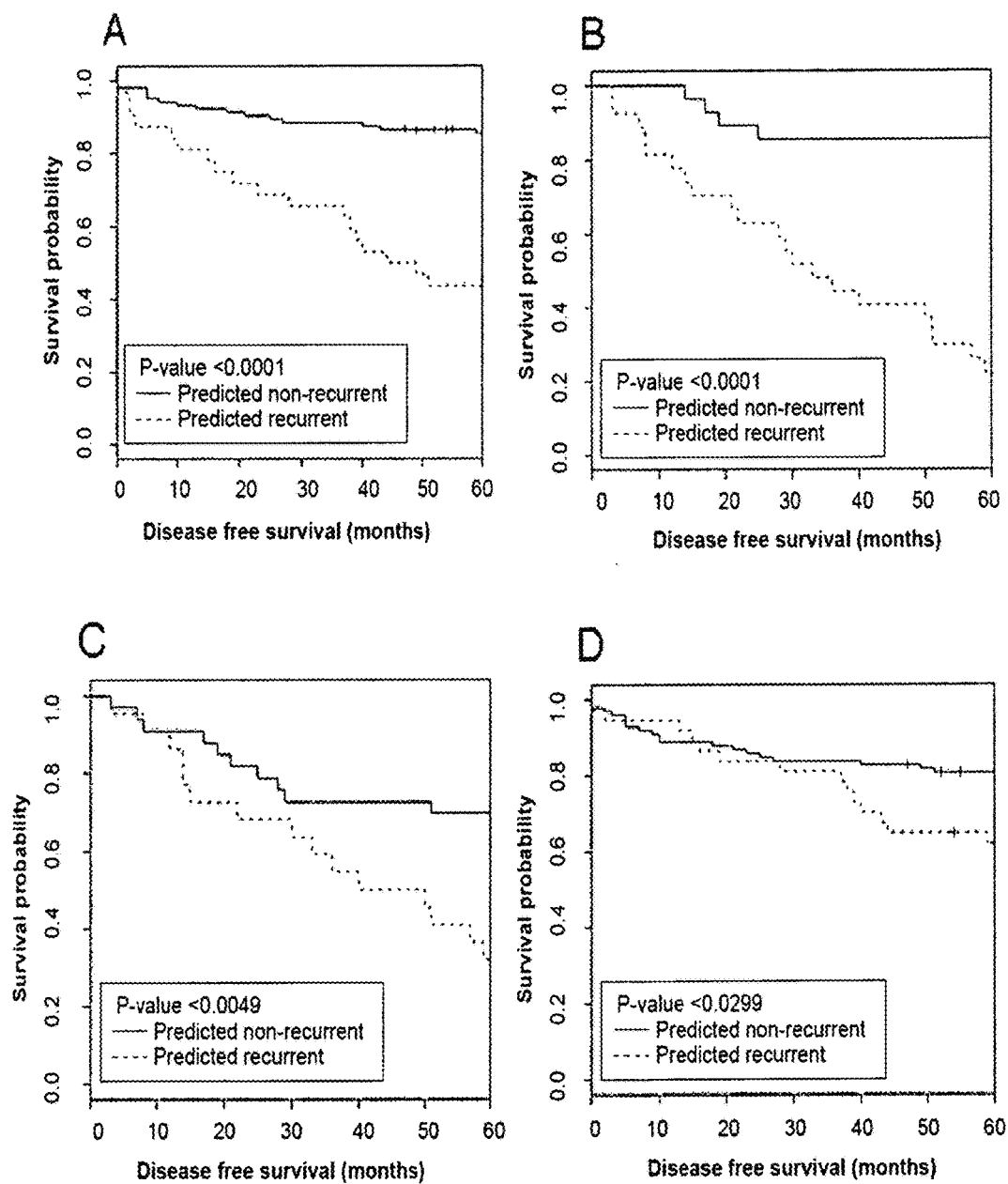
FIGS. 2A-2D depict Kaplan-Meier analyses of disease-free survival time with patients predicted as high versus low risk of tumour recurrence.

The DE signature was next validated by using the 19 genes to construct a 3-NN signature in the NZ data set by LOOCV. The prediction rate of 67% was again significant (p=0.046; Table 7), confirming the validity of the DE signature. The odds ratio for recurrence in NZ patients, using the DE signature, was 2.6 (95% CI 1.2-6.0). We consider that the reduction of the prediction rate was due to five genes from DE signature not being present in the NZ data set. This was confirmed when removal of these five genes from the DE data set resulted in a reduction of the LOOCV prediction rate from 84% to 67% (Table 7). Disease-free survival for NZ patients predicted to relapse, according to the DE signature, was significantly lower than disease-free survival for patients predicted not to relapse (p=0.029; FIG. 2D).

Example 14

Comparison of NZ and DE Prognostic Signatures with Current Staging System

Figure 3:
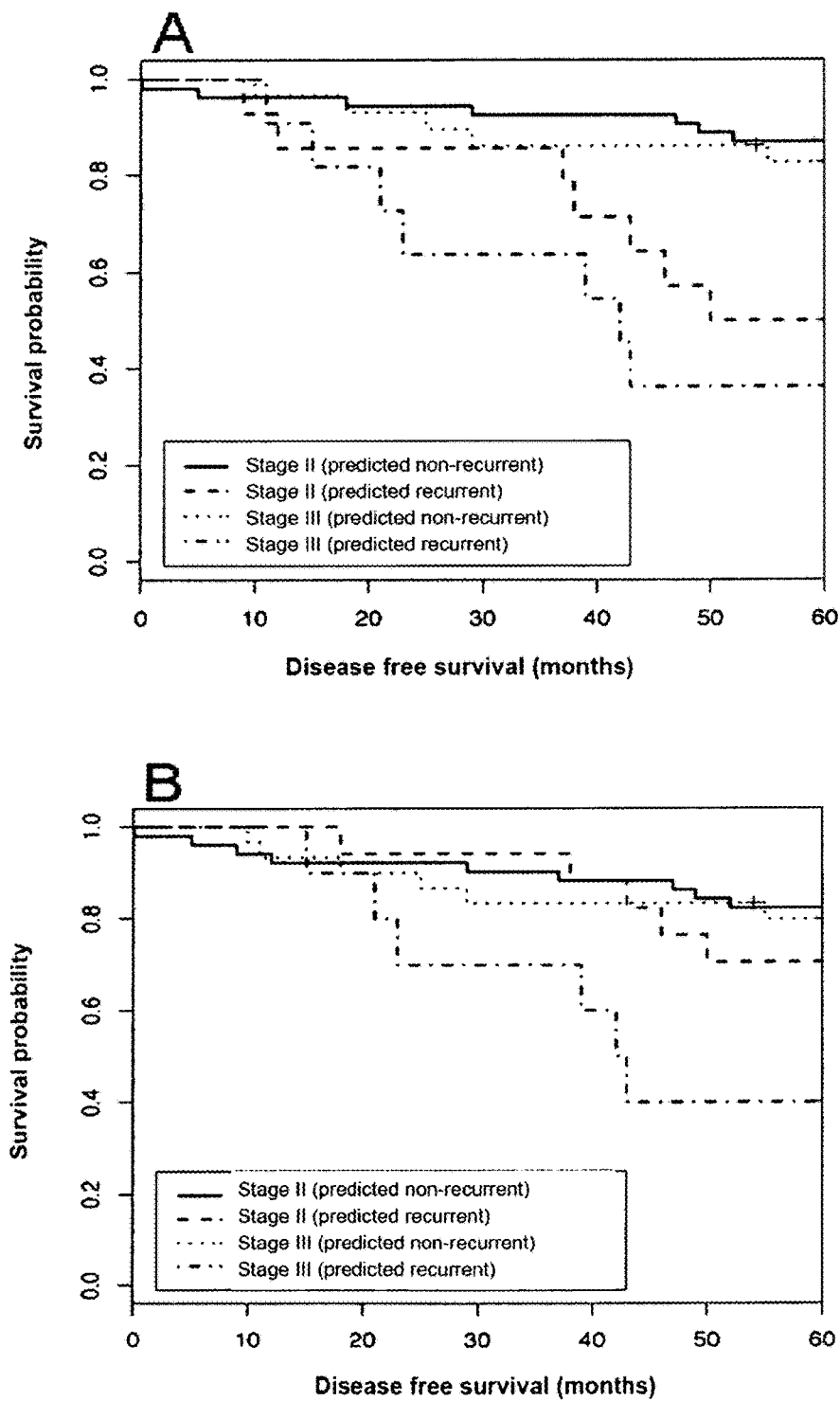
FIGS. 3A-3B depict Kaplan-Meier analyses of disease free survival time with patients predicted as high versus low risk of tumour recurrence.

Significant differences in disease-free survival between patients predicted to relapse or not relapse were also observed within the same clinico-pathological stage (FIG. 3). When patient predictions were stratified according to disease stage, the NZ signature was able to identify patients who were more likely to recur in both Stage II (p=0.0013, FIG. 3A), and Stage III subgroups (p=0.0295, FIG. 3A). This was mirrored to a lesser extent when the DE signature was applied to the NZ data set, where the difference was only observed for Stage III patients (p=0.0491, FIG. 3B). Again, the decreased predictive accuracy of the DE signature was likely due to the absence of five genes from the NZ data that decreased the LOOCV prediction rate.

Example 15

Genes in Signatures are Related to CRC Disease Progression

A number of genes in the NZ signature (Table 3) including G3BP2 (16), RBMS1 (17), HMMR (18), UBE2L3 (19), GNAS (20), RNASE2 (21) and ABCC9 (22) have all been reported to be involved in cancer progression, while RBMS1 (23), EIF3S7 (24) and GTF3C5 (25) are involved in transcription or translation. PBK is a protein kinase, which is involved in the process of mitosis (26), and the only gene common to the NZ and DE signatures. Eleven of 19 genes in the DE signature (Table 4) are involved in the immune response including 4 chemokine ligands (CXCL9, CXCL10, CXCL11, CXCL13; (27)), PBK (28), INDO (29), GBP1 (30), GZMB (31), KITLG (32), and two receptors of the tumor necrosis factor family (TNFRSF11A, FAS; 33)).

Eighty six genes were found to be moderately correlated (Pearson correlation coefficient >0.75) with at least one of the four chemokine ligands in the DE data. Ontology analysis found that 39 of these 65 genes were in the category of immune response (p<10-26). This result suggests a key role for the host immune response in determining CRC recurrence.

Example 16

Discussion of NZ and DE Prognostic Signatures

It has been shown that the two different prognostic signatures can be used to improve the current prognosis of colorectal cancer.

For the DE signature, it was surprising and unexpected that the stage I/II samples could be used to predict stage III outcome. It was also surprising that many genes associated with recurrent disease are related to the immune response. The immune response has an important role in the progression of different cancers and T-lymphocyte infiltration in CRC patients is an indicator of good prognosis (36-38). All of the eleven immune response (Table 5) genes were down-regulated in recurrent patients which would be unexpected based on known biological mechanisms.

To further confirm these results, 4 chemokine genes were chosen for further analysis. Chemokine ligands not only reflect the activity of the immune system and mediate leukocyte recruitment but also are involved in chemotaxis, cell adhesion and motility, and angiogenesis (36). To investigate the role of the immune response genes, 86 genes co-expressed with the chemokine ligands were identified. Almost half of these genes had a Gene Ontology classification within the "immune response" category suggesting that the primary function of these genes in the recurrence process is the modulation of the immune response. Furthermore, CD4+ and CD8+ T cell antigens (CD8A, CD3, PRF1, TRA@, TRB@) or functionally related antigens, for example, major histocompatibility molecules, interferon gamma induced proteins, and IL2RB, were found in the co-expressed gene list. The activation of tumor specific CD4+ T cells and CD8+ T cells has been shown to result in tumour rejection in a mouse colorectal cancer model (37). Collectively, these findings suggest that the lymphocytes form part of a tumor-specific host response involved in minimising the spread of cells from the primary tumour.

Example 17

Selection of Additional Prognostic Signatures

The performance of the two prognostic signatures described above was excellent in terms of cross-validation between the two data sets. Further studies were carried out, using a purely statistical approach, to develop a range of signatures, in addition to the aforementioned, that would also predict prognosis for other data sets. One of the additional goals of these studies was to ensure that the method used to normalize the microarray data (robust multi-array average) was not exerting undue influence on the choice of genes.

Figure 4:
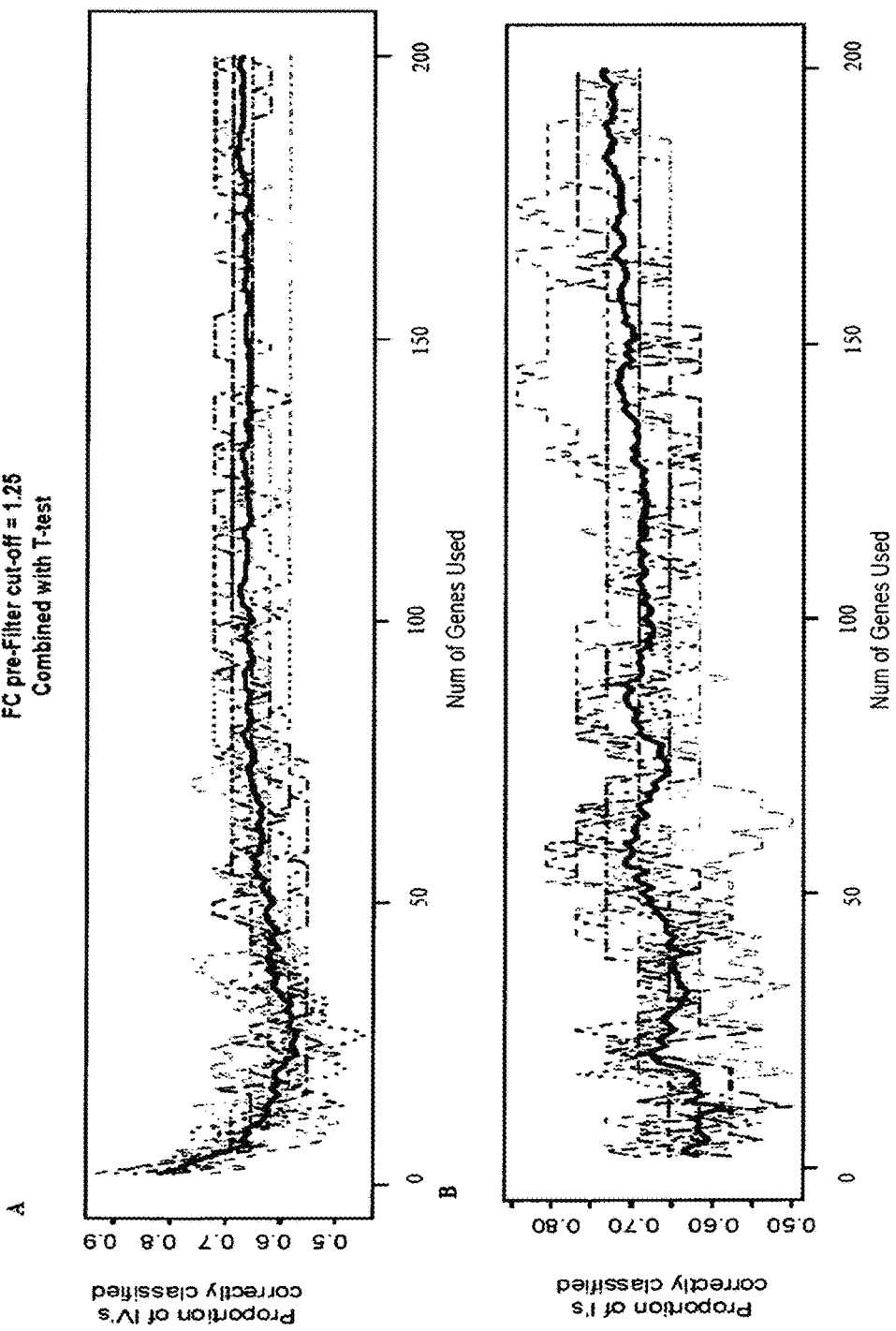
FIGS. 4A-4C show the predictive value of signatures of varying lengths for prognosis of colorectal cancer. These signatures were derived from 10 replicate runs of 11-fold cross validation. Each replicate 11-fold validation run is indicated by the various dashed lines; the mean across replicates by the bold line. In each fold of the cross-validation, genes were removed if the fold-change across classes was <1.1 (for the remaining samples not removed in that particular fold). The genes were then ranked using a modified t-statistic, obtaining a different set of genes for each fold, and classifiers using the top n-genes (where n=2 to 200) were constructed for each fold. The genes therefore may differ for each fold of each replicate 11-fold cross validation.
Figure 4:
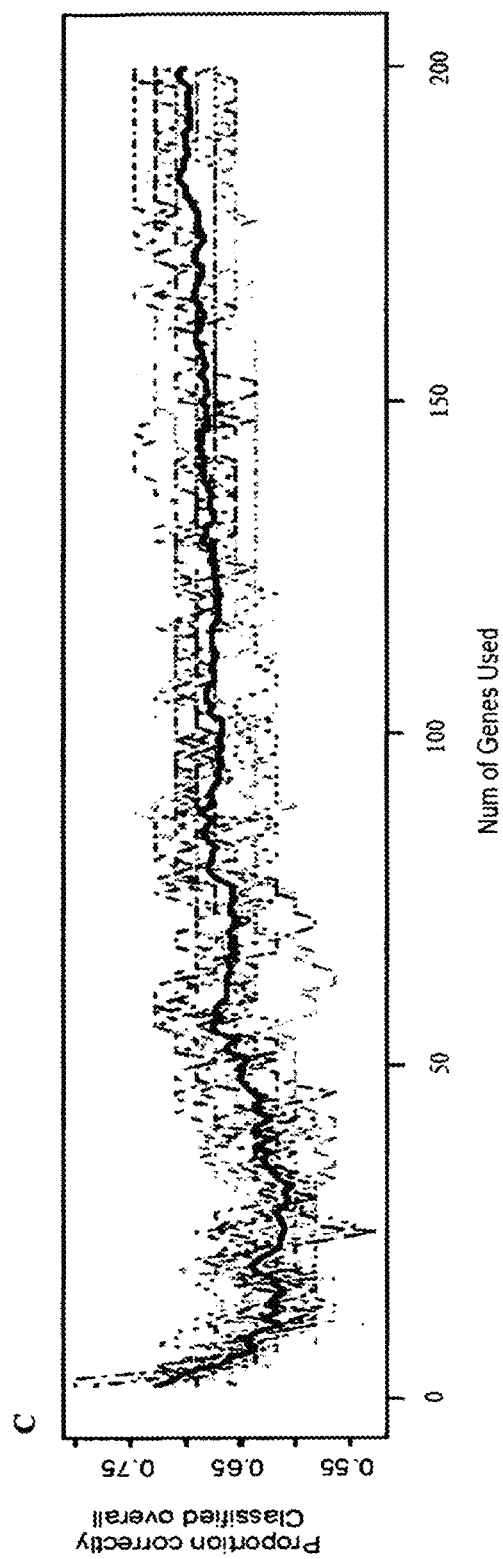
Figure 5:
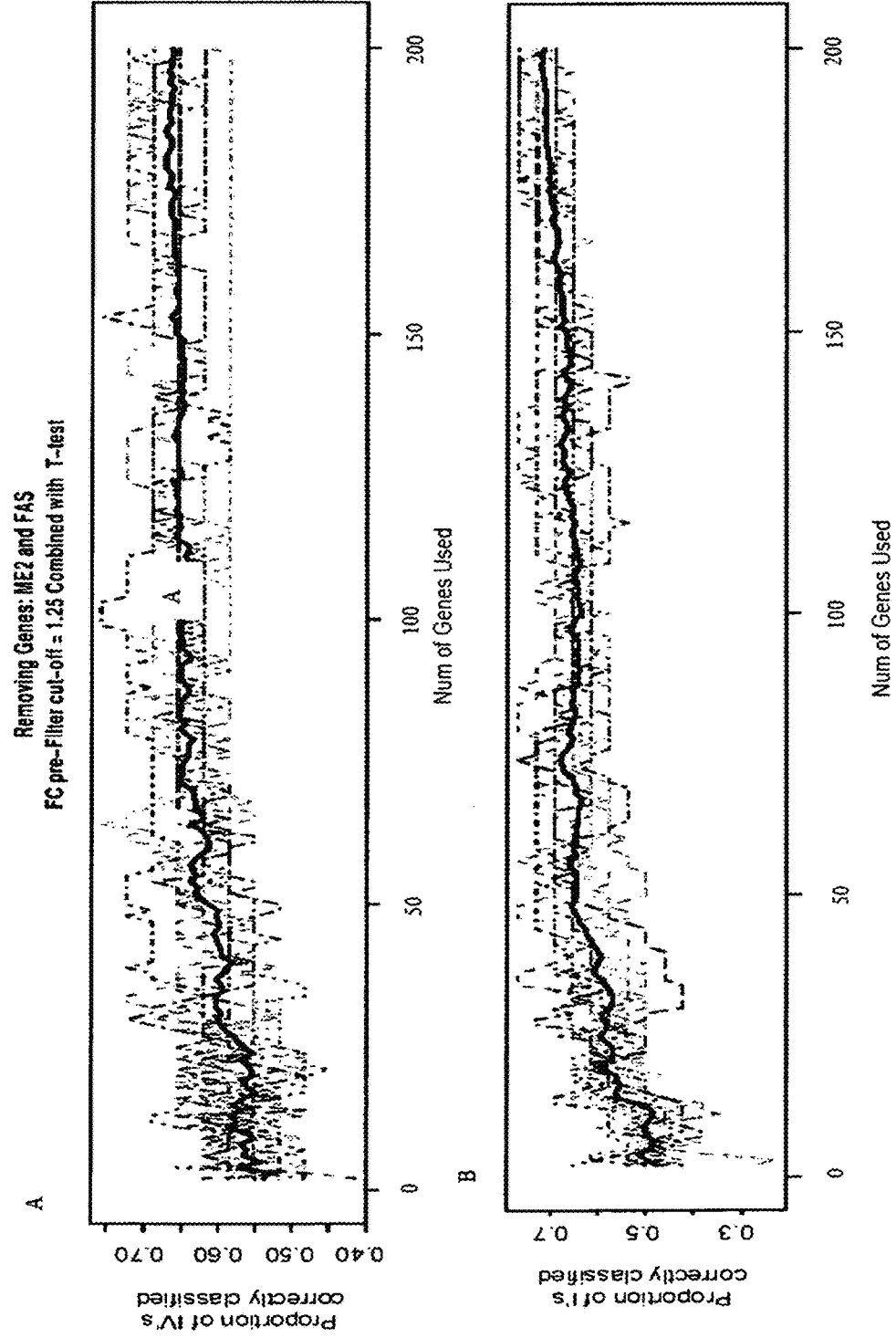
FIGS. 5A-5C depict graphs showing the decreased predictive value of signatures for the prognosis of colorectal cancer, in a repeat of the experiment of FIG. 4, except with the two genes, FAS and ME2 removed from the data set.
Figure 5:
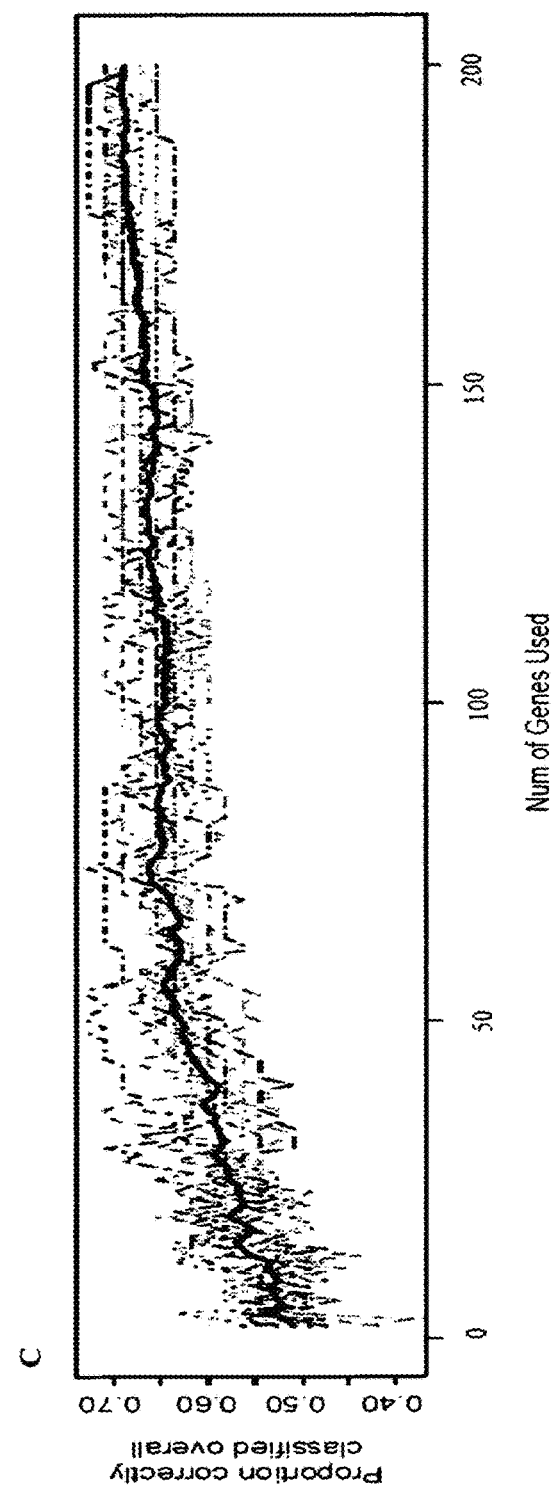

FIG. 4 shows the classification rates obtained from signatures of varying lengths. The classification rate is the proportion of correct relapse predictions (expressed as a percentage of total predictions), i.e., the proportion of samples correctly classified. The classification rates were determined using 11-fold cross validation. For this cross validation, a randomly selected stratified sample (i.e. same ratio of recurrent to non-recurrent tumours as the full data set) was removed as a validation set prior to gene selection of the genes, and model construction (using the training set of the remaining 50 samples). Cross-validation was then repeated a further ten times so that all 55 samples appeared in one validation set each. This 11-fold cross-validation process was repeated as 10 replicates, and the results plotted in FIG. 4 and FIG. 5. The classification rates shown were corrected using bootstrap bias correction (43), to give the expected classification rates for the signatures to be applied to another data set. From this analysis, it was ascertained that shorter signatures produced the best classification rate. In addition, analysis of the genes that most frequently appeared in classifiers show that the discriminatory power was mostly due to the effectiveness of two genes: FAS and ME2. This is illustrated most clearly by FIG. 5 shows the effectiveness of the signatures, once the two genes FAS and ME2 were removed from the data set. For more detail see the legend to FIG. 5.

Figure 6:
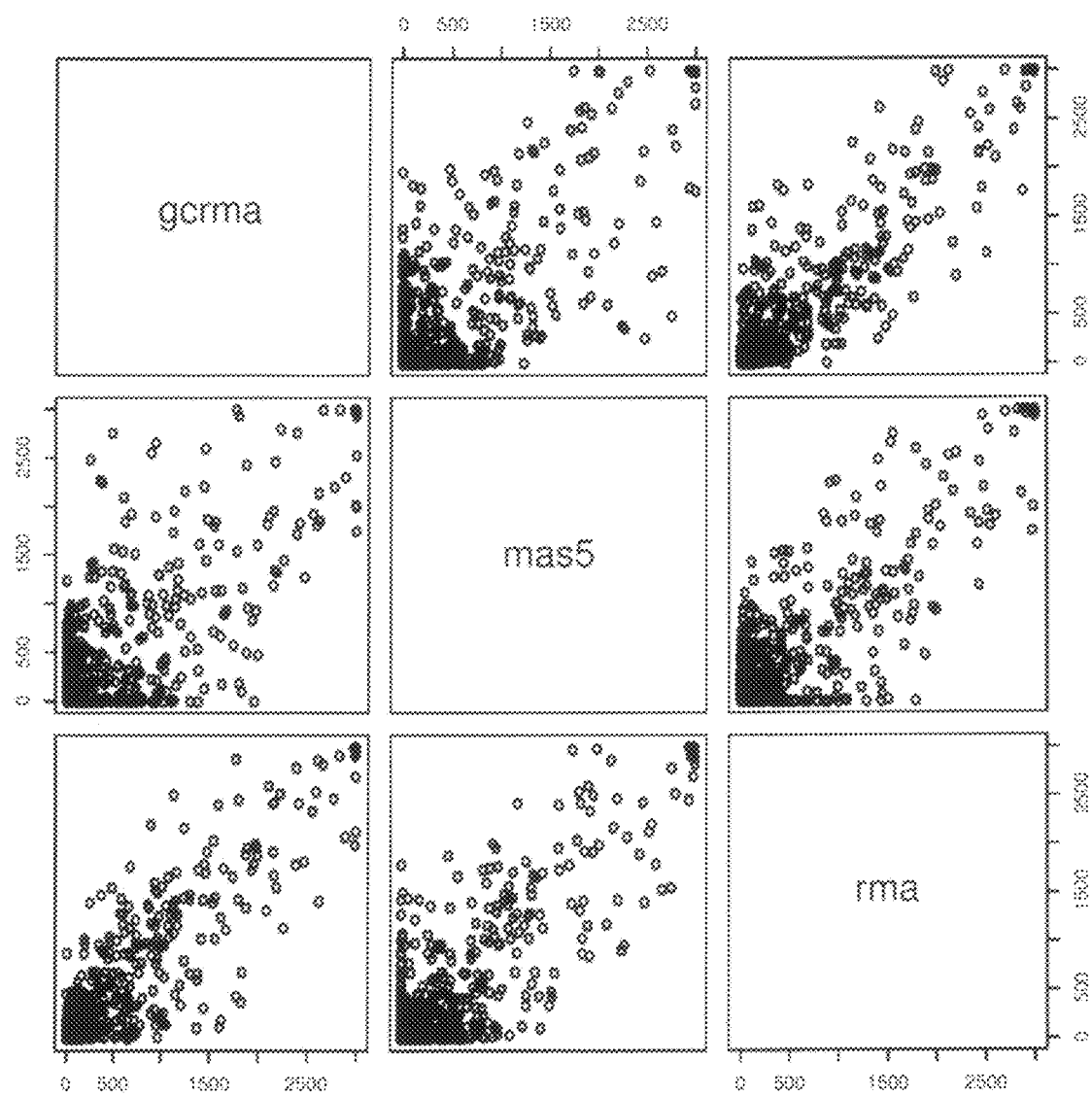
FIGS. 6A-6I shows a pairs chart of "top counts" (number of times each gene appeared in the "top-n" gene lists, i.e., top 10, top 20, top 100, and top 325 as described in Example 17) using three different normalization methods produced using the R statistical computing package (10, 39), in accordance with Example 17, below. The "pairs" chart is described in by Becker et al, in their treatise on the S Language (upon which R is based; see reference 39).

The effect of normalization on feature selection was thoroughly investigated by generating gene lists from 1000 stratified sub-samples of the original set of tumours, each time removing 5 samples (i.e. 1/11 of the total number of samples) from the data set. (This is effectively the same as performing 11-fold cross-validation). A tally was made of the number of times each gene appeared in the "top-n" gene lists (i.e., top 10, top 20, top 100, and top 325). This value was termed the "top count". Top counts were generated using three different normalization methods (40) (FIGS. 6A-6C (gcma), 6D-6F (mas5), and 6G-6I (rma), and three different filtering statistics (FIGS. 7A-7C (Wilcoxon), 7D-7F (modified ttest), and 7G-7I (limma). There was substantial correlation in the top count between normalization schemes and filtering statistics (41, 42) used. Thus, while normalization and feature selection methods were important, many genes appeared in the gene lists independently of the method used to pre-process the data. This indicates that the choice of normalization method had only a minimal effect on which genes were selected for use in signature construction. The top count, summed across all normalization methods and statistics, was found to be a robust measure of a gene's differential expression between recurrent and non-recurrent tumours.

Genes from the gene lists (see Table 1 and Table 2), were used to generate signatures by random sampling. The generation of samples was weighted, such that genes with higher "top count" were more likely to be selected. A range of signatures was generated, using between 2 and 55 Affymetrix probes. Signatures were selected if they exhibited >80% median classification rate, using three methods of classifiers: k-nearest neighbours, with k=1; k-nearest neighbours, with k=3; and support vector machines, with a linear kernel function, and using leave-one-out cross-validation.

On average, longer prognostic signatures were preferred over shorter signatures in terms of ability to predict prognosis for new data sets (FIG. 4 and FIG. 5). The genes FAS and ME2 were also important (discussed, above). These two facts were used, along with the fact that short signatures that do not contain either FAS or ME2 perform less effectively, to select candidate signatures as shown in Table 9, below. Signatures were selected (from the pool of randomly generated signatures) if they exhibited >80% median classification rate (using three methods of classifiers: k-nearest neighbours, with k=1; k-nearest neighbours, with k=3; and support vector machines, with a linear kernel function), using leave-one-out cross-validation.

In addition, because, on average, longer signatures (>10 genes/signature) tended to perform better, we selected signatures with 20 or more genes/signatures from a pool of signatures with 30 or more probes/signature. It is expected that these signatures (Table 10) will perform with a classification rate of around 70% when applied to other data sets, on the basis of the results shown in FIGS. 4 and 5. It was found that all of the signatures generated in this way contained both ME2, and all but one contained FAS, which may be due to the importance of these genes in providing prediction of prognosis. It was noted that the high classification rate obtained using this approach on the in-house data set did not necessarily mean that these signatures that would be expected to perform better than those set forth in Example 12, on other data sets. Rather, the purpose was to produce a range of signatures expected to apply to other data sets as least as well as the previous signatures. The markers comprising the prognostic signatures are set forth in Table 9.

TABLE 9

Additional Prognostic signatures (note SVM = support vector machine, 3NN = 3 nearest neighbours, 1NN = 1 nearest neighbour, Sens = sensitivity, Spec = specificity, for prediction of recurrence)

| Signature Number | Signature Genes (as gene symbols) | SVM | | 3NN | | 1NN | |
|---|---|---|---|---|---|---|---|
| | | Sens | Spec | Sens | Spec | Sens | Spec |
| 1 | WARS, STAT1, EIF4E, PRDX3, PSME2, GMFB, DLGAP4, TYMS, CTSS, MAD2L1, CXCL10, C1QBP, NDUFA9, SLC25A11, HNRPD, ME2, CXCL11, RBM25, CAMSAP1L1, hCAP-D3, BRRN1, ATP5A1, FAS, FLJ13220, PBK, BRIP1 | 81% | 86% | 73% | 90% | 77% | 83% |
| 2 | WARS, SFRS2, EIF4E, MTHFD2, PSME2, GMFB, DLGAP4, TYMS, LMAN1, CDC40, CXCL10, NDUFA9, SLC25A11, CA2, ME2, IFT20, TLK1, CXCL11, RBM25, AK2, FAS, FLJ13220, PBK, PSAT1, STAT1 | 77% | 86% | 85% | 79% | 81% | 86% |
| 3 | WARS, SFRS2, PRDX3, GMFB, DLGAP4, TYMS, LMAN1, CDC40, CXCL10, NDUFA9, KPNB1, SLC25A11, CA2, ME2, FUT4, CXCL11, GZMB, RBM25, ATP5A1, CDC42BPA, FAS, RBBP4, HNRPD, BRIP1, STAT1 | 85% | 86% | 92% | 76% | 85% | 79% |
| 4 | WARS, PRDX3, MTHFD2, PSME2, TES, DCK, CDC40, CXCL10, PLK4, NDUFA9, SLC25A11, WHSC1, ME2, CXCL11, SLC4A4, RBM25, ATP5A1, CDC42BPA, FAS, BAZ1A, AGPAT5, FLJ13220, HNRPD, KLHL24, STAT1 | 81% | 79% | 77% | 69% | 77% | 79% |
| 5 | HNRPD, WARS, MTHFD2, GMFB, DLGAP4, TYMS, CXCL9, IRF8, GTSE1, RABIF, CXCL10, FAS, TRIM25, KITLG, C1QBP, SLC25A11, C17orf25, CA2, ME2, SLC4A4, CXCL11, RBM25, KLHL24, STAT1 | 88% | 83% | 88% | 83% | 88% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 6 | HNRPD, WARS, STAT1, PRDX3, MTHFD2, PSME2, TK1, GMFB, DLGAP4, TYMS, CXCL9, PLK4, KITLG, NDUFA9, ME2, CXCL11, SLC4A4, AK2, FAS, AGPAT5, FLJ13220, PBK, ETNK1 | 73% | 83% | 81% | 79% | 65% | 66% |
| 7 | WARS, EIF4E, PRDX3, TK1, GMFB, DLGAP4, TYMS, LMAN1, ARF6, FAS, CHEK1, NDUFA9, SLC25A11, WHSC1, CA2, ME2, CXCL11, IFT20, SLC4A4, RBM25, hCAP-D3, CDC42BPA, FLJ13220, HNRPD, STAT1 | 88% | 90% | 88% | 90% | 85% | 86% |
| 8 | WARS, EPAS1, EIF4E, PRDX3, PSME2, TK1, GMFB, DLGAP4, TYMS, DCK, CDC40, CXCL9, CXCL10, C1QBP, NDUFA9, SLC25A11, WHSC1, ME2, TLK1, RBM25, BRRN1, FAS, BRIP1, TRMT5, KLHL24, STAT1 | 77% | 86% | 85% | 79% | 77% | 79% |
| 9 | HNRPD, WARS, PRDX3, MTHFD2, PSME2, GMFB, DLGAP4, TYMS, TES, CDC40, IRF8, CXCL10, FAS, CHEK1, KITLG, WHSC1, CA2, ME2, TLK1, RBM25, AK2, NUP210, ATP5A1, BRIP1 STAT1 | 69% | 79% | 85% | 83% | 77% | 79% |
| 10 | HNRPD, EPAS1, EIF4E, PRDX3, DLGAP4, TES, CTSS, DCK, CXCL9, CXCL10, FAS, PLK4, HNRPA3P1, SLC25A11, C1QBP, C17orf25, CA2, ME2, RBM25, AK2, SEC10L1, FLJ13220, TRMT5, STAT1 | 85% | 79% | 85% | 79% | 77% | 72% |
| 11 | HNRPD, WARS, EIF4E, PRDX3, PSME2, GBP1, GMFB, DLGAP4, TYMS, TES, RABIF, CXCL10, C1QBP, NDUFA9, SLC25A11, C17orf25, ME2, FUT4, CXCL11, RBM25, AK2, hCAP-D3, FAS, AGPAT5, SEC10L1, PBK, STAT1 | 85% | 83% | 92% | 76% | 85% | 76% |
| 12 | HNRPD, MTHFD2, PSME2, GMFB, DLGAP4, TYMS, DCK, IRF8, NDUFA9, SLC25A11, C17orf25, CA2, ME2, CXCL11, GZMB, RBM25, NUP210, SOCS6, DDAH2, FAS, RBBP4, MARCH5, SEC10L1, KLHL24, STAT1 | 88% | 79% | 92% | 69% | 92% | 83% |
| 13 | WARS, EPAS1, STAT1, MTHFD2, MCM6, GBP1, GMFB, DLGAP4, TYMS, ARF6, CXCL10, FAS, KITLG, NDUFA9, CA2, ME2, GZMB, CXCL11, RBM25, RBBP4, PBK, PSAT1, HNRPD | 88% | 90% | 88% | 76% | 77% | 69% |
| 14 | WARS, EPAS1, EIF4E, PRDX3, PSME2, GBP1, TK1, GMFB, TYMS, CXCL9, FAS, CHEK1, SLC25A11, NDUFA9, WHSC1, CA2, ME2, FUT4, CXCL11, RBM25, CAMSAP1L1, SFRS2, DDAH2, AGPAT5, HNRPD, BRIP1, ETNK1 | 85% | 83% | 92% | 76% | 92% | 79% |
| 15 | SFRS2, EIF4E, PRDX3, MTHFD2, MCM6, TK1, GMFB, TYMS, TES, CTSS, ARF6, CXCL9, RABIF, CXCL10, FAS, KITLG, SLC25A11, ME2, IFT20, SLC4A4, CXCL11, RBM25, PSAT1, HNRPD, TRMT5, STAT1 | 81% | 83% | 81% | 83% | 77% | 79% |
| 16 | WARS, SFRS2, EPAS1, EIF4E, PRDX3, TYMS, LMAN1, CDC40, CXCL9, CXCL10, PLK4, CHEK1, SLC25A11, C1QBP, NDUFA9, ME2, IFT20, SLC4A4, CXCL11, RBM25, DDAH2, FAS, HNRPD, BRIP1, STAT1 | 92% | 93% | 81% | 83% | 81% | 83% |
| 17 | WARS, EIF4E, GMFB, DLGAP4, TYMS, CTSS, MAD2L1, SLC4A4, CXCL9, IRF8, CXCL10, FAS, TRIM25, KPNB1, SLC25A11, HNRPD, ME2, CXCL11, RBM25, AK2, hCAP-D3, DDAH2, SEC10L1, ETNK1, STAT1 | 92% | 90% | 85% | 79% | 81% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 18 | HNRPD, WARS, SFRS2, MTHFD2, PSME2, TK1, GMFB, DLGAP4, ARF6, CXCL10, TRIM25, NDUFA9, SLC25A11, WHSC1, ME2, CXCL11, TLK1, RBM25, CAMSAP1L1, hCAP-D3, CDC42BPA, FAS, AGPAT5, STAT1 | 81% | 79% | 85% | 90% | 81% | 93% |
| 19 | HNRPD, WARS, SFRS2, STAT1, EIF4E, PSME2, TYMS, USP4, DCK, ARF6, CXCL9, RABIF, CXCL10, C1QBP, SLC25A11, ME2, IFT20, SLC4A4, CXCL11, RBM25, AK2, SOCS6, FAS, ETNK1 | 96% | 86% | 73% | 76% | 73% | 66% |
| 20 | WARS, EPAS1, EIF4E, PRDX3, MTHFD2, PSME2, GMFB, TES, ARF6, CXCL10, FAS, KITLG, C1QBP, SLC25A11, C17orf25, ME2, FUT4, CXCL11, RBM25, ATP5A1, FLJ13220, PSAT1, HNRPD, STAT1 | 77% | 79% | 73% | 83% | 81% | 86% |
| 21 | WARS, PSME2, GMFB, DLGAP4, USP4, ARF6, CDC40, CXCL9, IRF8, RABIF, CXCL10, PLK4, KITLG, C1QBP, NDUFA9, SLC25A11, WHSC1, C17orf25, ME2, TLK1, SLC4A4, RBM25, hCAP-D3, SOCS6, FAS, AGPAT5, SEC10L1, KLHL24, STAT1 | 77% | 72% | 85% | 83% | 85% | 79% |
| 22 | WARS, MTHFD2, PSME2, GBP1, TK1, GMFB, DLGAP4, CXCL9, CXCL10, CHEK1, TRIM25, SLC25A11, C17orf25, HNRPD, ME2, SLC4A4, RBM25, AK2, BRRN1, FAS, DKFZp762E1312, SEC10L1, PBK, TRMT5, STAT1 | 77% | 79% | 77% | 76% | 81% | 72% |
| 23 | HNRPD, WARS, STAT1, EIF4E, PRDX3, DLGAP4, TYMS, ARF6, CXCL9, CXCL10, FAS, HNRPA3P1, C1QBP, NDUFA9, SLC25A11, WHSC1, ME2, CXCL11, RBM25, MARCH5, SEC10L1, BRIP1 | 85% | 83% | 92% | 90% | 85% | 76% |
| 24 | WARS, PRDX3, PSME2, GMFB, DLGAP4, CTSS, LMAN1, CXCL9, CXCL10, HNRPA3P1, SLC25A11, NDUFA9, C17orf25, ME2, FUT4, SLC4A4, RBM25, AK2, FAS, MARCH5, PBK, HNRPD, KLHL24, ETNK1, STAT1 | 85% | 83% | 77% | 69% | 81% | 69% |
| 25 | WARS, PRDX3, MTHFD2, PSME2, GMFB, DLGAP4, TYMS, USP4, CDC40, CXCL9, CXCL10, TRIM25, NDUFA9, CA2, ME2, TLK1, CXCL11, SLC4A4, RBM25, AK2, ATP5A1, SOCS6, DDAH2, FAS, MARCH5, PBK, STAT1 | 81% | 83% | 77% | 83% | 81% | 72% |
| 26 | WARS, EIF4E, MTHFD2, PSME2, GMFB, DLGAP4, TYMS, ARF6, CXCL10, PLK4, CHEK1, HNRPA3P1, C1QBP, NDUFA9, SLC25A11, WHSC1, CA2, ME2, CXCL11, RBM25, CAMSAP1L1, FAS, SEC10L1, FLJ13220, STAT1 | 81% | 83% | 92% | 86% | 81% | 79% |
| 27 | WARS, SFRS2, EIF4E, MTHFD2, PSME2, TK1, TYMS, LMAN1, CDC40, CXCL10, C1QBP, NDUFA9, KPNB1, CA2, ME2, GZMB, TLK1, SLC4A4, RBM25, ATP5A1, FAS, AGPAT5, SEC10L1, FLJ13220, HNRPD, STAT1 | 85% | 90% | 85% | 86% | 81% | 79% |
| 28 | HNRPD, WARS, EPAS1, MTHFD2, PSME2, TK1, TYMS, CXCL9, CXCL10, FAS, TRIM25, KITLG, C1QBP, NDUFA9, CA2, ME2, CXCL11, RBM25, AK2, BRRN1, FLJ10534, SEC10L1, PBK, ETNK1, STAT1 | 88% | 86% | 81% | 86% | 81% | 76% |
| 29 | EIF4E, PRDX3, PSME2, DLGAP4, CTSS, CXCL9, GTSE1, CXCL10, FAS, PLK4, KITLG, SLC25A11, CA2, ME2, GZMB, CXCL11, RBM25, AK2, AGPAT5, MARCH5, FLJ13220, PBK, HNRPD, STAT1 | 88% | 86% | 88% | 76% | 77% | 69% |
| 30 | WARS, SFRS2, EIF4E, PRDX3, MTHFD2, PSME2, DLGAP4, TYMS, CTSS, CDC40, CXCL9, CXCL10, FAS, PLK4, NDUFA9, ME2, CXCL11, RBM25, AK2, BRRN1, RBBP4, HNRPD, KLHL24, ETNK1, STAT1 | 77% | 79% | 81% | 79% | 65% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM | | 3NN | | 1NN | |
|---|---|---|---|---|---|---|---|
| | | Sens | Spec | Sens | Spec | Sens | Spec |
| 31 | WARS, SFRS2, EIF4E, MTHFD2, PSME2, GMFB, DLGAP4, TYMS, ARF6, CDC40, CXCL9, TRIM25, SLC25A11, CA2, ME2, IFT20, CXCL11, RBM25, BRRN1, CDC42BPA, FAS, AGPAT5, FLJ10534, HNRPD, TRMT5, STAT1 | 85% | 83% | 92% | 76% | 92% | 72% |
| 32 | HNRPD, WARS, SFRS2, EPAS1, EIF4E, MTHFD2, PSME2, GMFB, DLGAP4, TYMS, CTSS, DCK, CXCL9, CXCL10, FAS, KITLG, NDUFA9, ME2, CXCL11, RBM25, ATP5A1, PBK, ETNK1, STAT1 | 85% | 79% | 77% | 83% | 77% | 72% |
| 33 | WARS, SFRS2, MTHFD2, PSME2, MCM6, GMFB, DLGAP4, TYMS, LMAN1, CDC40, SLC4A4, CXCL10, FAS, CHEK1, SLC25A11, C1QBP, WHSC1, C17orf25, CA2, ME2, RBM25, SOCS6, AGPAT5, HNRPD, STAT1 | 73% | 79% | 92% | 90% | 88% | 79% |
| 34 | HNRPD, WARS, MTHFD2, PSME2, GMFB, DLGAP4, RABIF, CXCL10, TRIM25, KITLG, C1QBP, KPNB1, SLC25A11, WHSC1, ME2, RBM25, CAMSAP1L1, BRRN1, CDC42BPA, FAS, AGPAT5, SEC10L1, ETNK1, STAT1 | 85% | 86% | 92% | 90% | 81% | 86% |
| 35 | HNRPD, WARS, SFRS2, SFPQ, MTHFD2, DLGAP4, TYMS, USP4, LMAN1, ARF6, CDC40, C1QBP, C17orf25, CA2, ME2, CXCL11, SLC4A4, RBM25, AK2, ATP5A1, FAS, SEC10L1, FLJ13220, ETNK1, STAT1 | 81% | 83% | 85% | 79% | 73% | 79% |
| 36 | WARS, SFRS2, EIF4E, PRDX3, MTHFD2, PSME2, GMFB, DLGAP4, LMAN1, ARF6, MAD2L1, GTSE1, CXCL10, FAS, KITLG, SLC25A11, WHSC1, ME2, FUT4, IFT20, RBM25, AGPAT5, HNRPD, STAT1 | 85% | 83% | 85% | 90% | 88% | 90% |
| 37 | WARS, SFRS2, EIF4E, MTHFD2, TK1, GMFB, DLGAP4, TYMS, LMAN1, CXCL10, CHEK1, HNRPA3P1, C1QBP, NDUFA9, SLC25A11, ME2, CXCL11, RBM25, BRRN1, CDC42BPA, FAS, SEC10L1, PSAT1, HNRPD, KLHL24, STAT1 | 73% | 79% | 92% | 83% | 85% | 86% |
| 38 | WARS, EPAS1, EIF4E, PRDX3, MTHFD2, GMFB, DLGAP4, TYMS, CTSS, LMAN1, DCK, CDC40, RABIF, CXCL10, HNRPA3P1, C1QBP, C17orf25, ME2, CXCL11, TLK1, RBM25, FAS, FLJ13220, HNRPD, KLHL24, STAT1 | 85% | 86% | 77% | 90% | 85% | 90% |
| 39 | WARS, SFRS2, EIF4E, PRDX3, MTHFD2, GMFB, DLGAP4, TYMS, CTSS, SLC4A4, CXCL10, SLC25A11, C17orf25, HNRPD, ME2, CXCL11, RBM25, AK2, CDC42BPA, FAS, AGPAT5, SEC10L1, TRMT5, STAT1 | 88% | 83% | 88% | 79% | 85% | 72% |
| 40 | SFRS2, EIF4E, PRDX3, PSME2, GMFB, DLGAP4, TYMS, CXCL9, IRF8, RABIF, CXCL10, FAS, TRIM25, SLC25A11, NDUFA9, ME2, CXCL11, RBM25, AGPAT5, FLJ13220, HNRPD, BRIP1, ETNK1, STAT1 | 85% | 93% | 88% | 83% | 81% | 69% |
| 41 | HNRPD, WARS, EIF4E, PRDX3, TK1, DLGAP4, TYMS, CDC40, CXCL9, GTSE1, CXCL10, FAS, KITLG, SLC25A11, NDUFA9, ME2, IFT20, SLC4A4, RBM25, NUP210, BAZ1A, SEC10L1, TRMT5, KLHL24, STAT1 | 85% | 83% | 96% | 79% | 92% | 72% |
| 42 | WARS, SFRS2, EIF4E, PRDX3, PSME2, DLGAP4, TYMS, CTSS, CXCL9, IRF8, CXCL10, FAS, C1QBP, NDUFA9, KPNB1, SLC25A11, ME2, SLC4A4, RBM25, SOCS6, MARCH5, SEC10L1, HNRPD, BRIP1, STAT1 | 81% | 79% | 85% | 83% | 92% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 43 | WARS, EPAS1, PRDX3, PSME2, TK1, GMFB, DLGAP4, TYMS, CTSS, CDC40, CXCL9, CXCL10, SLC25A11, C1QBP, WHSC1, ME2, GZMB, RBM25, SFRS2, FAS, AGPAT5, SEC10L1, PSAT1, KLHL24, ETNK1, STAT1 | 77% | 83% | 88% | 62% | 92% | 72% |
| 44 | WARS, PSME2, GMFB, DLGAP4, TYMS, CDC40, CXCL10, FAS, PLK4, C1QBP, NDUFA9, SLC25A11, CA2, ME2, CXCL11, IFT20, TLK1, RBM25, NUP210, BAZ1A, MARCH5, PSAT1, TRMT5, STAT1 | 85% | 86% | 96% | 79% | 81% | 83% |
| 45 | WARS, PRDX3, MTHFD2, PSME2, TYMS, CXCL10, FAS, CHEK1, TRIM25, C1QBP, NDUFA9, C17orf25, CA2, ME2, CXCL11, IFT20, RBBP4, RBM25, AK2, CDC42BPA, AGPAT5, DKFZp762E1312, HNRPD, STAT1 | 88% | 90% | 85% | 79% | 88% | 66% |
| 46 | WARS, SFRS2, EIF4E, SFPQ, PRDX3, MTHFD2, PSME2, DLGAP4, TYMS, USP4, CDC40, CXCL10, FAS, HNRPA3P1, KITLG, NDUFA9, KPNB1, SLC25A11, WHSC1, CA2, ME2, CXCL11, SLC4A4, RBM25, hCAP-D3, BRRN1, CDC42BPA, AGPAT5, MARCH5, SEC10L1, FLJ13220, BRIP1, ETNK1, STAT1 | 81% | 79% | 81% | 79% | 77% | 72% |
| 47 | HNRPD, WARS, EIF4E, PRDX3, MTHFD2, PSME2, GMFB, DLGAP4, TYMS, CTSS, MAD2L1, CDC40, CXCL9, CXCL10, KITLG, NDUFA9, SLC25A11, WHSC1, C17orf25, CA2, ME2, SLC4A4, CXCL11, RBM25, AK2, ATP5A1, CDC42BPA, FAS, BAZ1A, AGPAT5, SEC10L1, BRIP1, TRMT5, STAT1 | 81% | 83% | 88% | 86% | 88% | 69% |
| 48 | WARS, EIF4E, SFPQ, PRDX3, MTHFD2, PSME2, GMFB, DLGAP4, TYMS, USP4, ARF6, CXCL9, CXCL10, FAS, HNRPA3P1, C1QBP, NDUFA9, KPNB1, SLC25A11, ME2, CXCL11, IFT20, TLK1, RBM25, RBBP4, AGPAT5, MARCH5, SEC10L1, PBK, PSAT1, HNRPD, BRIP1, STAT1 | 77% | 83% | 81% | 79% | 73% | 69% |
| 49 | HNRPD, WARS, SFRS2, EIF4E, SFPQ, PRDX3, MTHFD2, PSME2, TK1, GMFB, DLGAP4, TYMS, TES, DCK, ARF6, CXCL9, CXCL10, HNRPA3P1, C1QBP, NDUFA9, SLC25A11, ME2, CXCL11, IFT20, TLK1, RBM25, AK2, hCAP-D3, ATP5A1, FAS, MARCH5, KLHL24, STAT1 | 77% | 83% | 77% | 79% | 81% | 83% |
| 50 | WARS, STAT1, EIF4E, SFPQ, PRDX3, MTHFD2, TK1, GMFB, DLGAP4, TYMS, CTSS, CXCL9, IRF8, CXCL10, PLK4, TRIM25, C1QBP, NDUFA9, SLC25A11, C17orf25, ME2, SLC4A4, AK2, CAMSAP1L1, FAS, BAZ1A, MARCH5, FLJ13220, PBK, BRIP1, KLHL24, ETNK1 | 81% | 79% | 85% | 83% | 77% | 66% |
| 51 | HNRPD, WARS, EIF4E, PRDX3, MTHFD2, GMFB, DLGAP4, TYMS, TES, ARF6, CXCL9, CXCL10, TRIM25, SLC25A11, NDUFA9, WHSC1, CA2, ME2, SLC4A4, CXCL11, RBM25, hCAP-D3, ATP5A1, FAS, RBBP4, SEC10L1, FLJ13220, PBK, BRIP1, KLHL24, ETNK1, STAT1 | 77% | 79% | 85% | 79% | 85% | 72% |
| 52 | WARS, EPAS1, STAT1, EIF4E, MTHFD2, PSME2, GBP1, GMFB, DLGAP4, TYMS, DCK, CDC40, CXCL9, CXCL10, FAS, HNRPA3P1, SLC25A11, C1QBP, ME2, FUT4, CXCL11, SLC4A4, RBM25, AK2, CAMSAP1L1, SFRS2, DDAH2, RBBP4, AGPAT5, FLJ10534, DKFZp762E1312, PSAT1, HNRPD | 77% | 83% | 81% | 86% | 69% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature | | SVM | | 3NN | | 1NN | |
|---|---|---|---|---|---|---|---|
| Number | Signature Genes (as gene symbols) | Sens | Spec | Sens | Spec | Sens | Spec |
| 53 | HNRPD, WARS, SFRS2, SFPQ, PRDX3, MTHFD2, PSME2, GMFB, DLGAP4, TYMS, LMAN1, CDC40, CXCL9, GTSE1, FAS, HNRPA3P1, SLC25A11, NDUFA9, KPNB1, CA2, ME2, CXCL11, SLC4A4, RBM25, BRRN1, CDC42BPA, RBBP4, BAZ1A, SEC10L1, BRIP1, KLHL24, STAT1 | 88% | 83% | 92% | 79% | 92% | 72% |
| 54 | HNRPD, WARS, EPAS1, PAICS, EIF4E, PRDX3, MTHFD2, PSME2, MCM6, GMFB, DLGAP4, TYMS, USP4, LMAN1, MAD2L1, CDC40, SLC4A4, CXCL9, CXCL10, FAS, KITLG, C1QBP, SLC25A11, ME2, CXCL11, RBM25, AK2, CDC42BPA, SFRS2, SEC10L1, STAT1 | 77% | 79% | 85% | 83% | 85% | 79% |
| 55 | WARS, EPAS1, STAT1, EIF4E, SFPQ, MTHFD2, PSME2, TK1, GMFB, DLGAP4, TYMS, TES, CXCL9, IRF8, CXCL10, FAS, NDUFA9, C17orf25, CA2, HNRPD, ME2, CXCL11, IFT20, RBM25, CDC42BPA, FLJ10534, SEC10L1, PBK, BRIP1, TRMT5 | 88% | 90% | 88% | 76% | 88% | 79% |
| 56 | SFRS2, PAICS, EIF4E, PRDX3, MTHFD2, PSME2, GMFB, DLGAP4, TYMS, TES, LMAN1, SLC4A4, CXCL9, CXCL10, FAS, PLK4, TRIM25, SLC25A11, NDUFA9, WHSC1, C17orf25, ME2, FUT4, CXCL11, IFT20, RBM25, ATP5A1, CDC42BPA, FLJ10534, SEC10L1, HNRPD, KLHL24, STAT1 | 85% | 79% | 85% | 79% | 81% | 86% |
| 57 | SFRS2, PAICS, EIF4E, SFPQ, PRDX3, MTHFD2, PSME2, MCM6, GMFB, DLGAP4, TYMS, CTSS, LMAN1, SLC4A4, CXCL9, IRF8, CXCL10, TRIM25, NDUFA9, C17orf25, CA2, HNRPD, ME2, CXCL11, IFT20, RBM25, AK2, ATP5A1, FAS, PBK, BRIP1, TRMT5, ETNK1, STAT1 | 81% | 86% | 85% | 79% | 85% | 83% |
| 58 | HNRPD, WARS, SFRS2, STAT1, EIF4E, MTHFD2, PSME2, DLGAP4, TYMS, DCK, CDC40, CXCL9, IRF8, CXCL10, PLK4, SLC25A11, NDUFA9, KPNB1, WHSC1, C17orf25, CA2, ME2, NUP210, SOCS6, CDC42BPA, FAS, AGPAT5, SEC10L1, FLJ13220, BRIP1, KLHL24, ETNK1 | 81% | 76% | 92% | 79% | 88% | 72% |
| 59 | WARS, SFRS2, MTHFD2, PSME2, GMFB, DLGAP4, TYMS, CDC40, CXCL9, GTSE1, CXCL10, FAS, PLK4, TRIM25, SLC25A11, C1QBP, NDUFA9, KPNB1, WHSC1, C17orf25, CA2, ME2, CXCL11, TLK1, RBM25, BRRN1, AGPAT5, MARCH5, HNRPD, BRIP1, TRMT5, KLHL24, STAT1 | 81% | 79% | 88% | 86% | 85% | 83% |
| 60 | HNRPD, WARS, SFRS2, EIF4E, SFPQ, MTHFD2, PSME2, MCM6, TK1, GMFB, DLGAP4, TYMS, LMAN1, CDC40, CXCL9, CXCL10, FAS, CHEK1, C1QBP, NDUFA9, SLC25A11, WHSC1, ME2, TLK1, CXCL11, RBM25, CDC42BPA, AGPAT5, FLJ10534, FLJ13220, PSAT1, STAT1 | 92% | 79% | 77% | 86% | 69% | 76% |
| 61 | WARS, EPAS1, EIF4E, MTHFD2, PSME2, GMFB, DLGAP4, TYMS, TES, LMAN1, ARF6, CDC40, CXCL9, CXCL10, FAS, PLK4, TRIM25, C1QBP, C17orf25, CA2, ME2, CXCL11, SLC4A4, RBM25, AK2, ATP5A1, CDC42BPA, AGPAT5, FLJ10534, DKFZp762E1312, SEC10L1, PBK, PSAT1, STAT1 | 77% | 83% | 85% | 72% | 85% | 69% |
| 62 | HNRPD, WARS, STAT1, EIF4E, SFPQ, PSME2, TK1, GMFB, DLGAP4, TYMS, TES, CXCL9, GTSE1, CXCL10, FAS, CHEK1, C1QBP, NDUFA9, SLC25A11, WHSC1, C17orf25, CA2, ME2, CXCL11, SLC4A4, RBM25, CDC42BPA, DDAH2, AGPAT5, FLJ13220, PBK, TRMT5, KLHL24, ETNK1 | 85% | 76% | 88% | 83% | 77% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature | | SVM | | 3NN | | 1NN | |
|---|---|---|---|---|---|---|---|
| Number | Signature Genes (as gene symbols) | Sens | Spec | Sens | Spec | Sens | Spec |
| 63 | WARS, EIF4E, PRDX3, PSME2, TK1, GMFB, DLGAP4, TYMS, USP4, DCK, MAD2L1, CXCL10, TRIM25, C1QBP, NDUFA9, SLC25A11, C17orf25, HNRPD, ME2, CXCL11, IFT20, RBBP4, TLK1, SLC4A4, RBM25, AK2, CAMSAP1L1, SOCS6, FAS, FLJ10534, FLJ13220, PBK, BRIP1, ETNK1, STAT1 | 81% | 83% | 65% | 83% | 73% | 72% |
| 64 | WARS, SFRS2, EIF4E, SFPQ, PRDX3, MTHFD2, PSME2, TK1, GMFB, DLGAP4, TYMS, LMAN1, CXCL9, IRF8, RABIF, CXCL10, CHEK1, NDUFA9, ME2, FUT4, CXCL11, SLC4A4, RBM25, AK2, CAMSAP1L1, FAS, RBBP4, MARCH5, SEC10L1, PBK, PSAT1, HNRPD, TRMT5, KLHL24, STAT1 | 69% | 79% | 73% | 83% | 85% | 83% |
| 65 | HNRPD, WARS, SFPQ, MTHFD2, PSME2, GMFB, DLGAP4, CTSS, LMAN1, ARF6, CDC40, SLC4A4, CXCL9, CXCL10, FAS, CHEK1, KITLG, C1QBP, NDUFA9, SLC25A11, WHSC1, ME2, FUT4, GZMB, IFT20, RBM25, CAMSAP1L1, BAZ1A, AGPAT5, SEC10L1, PBK, KLHL24, ETNK1, STAT1 | 85% | 72% | 88% | 79% | 77% | 72% |
| 66 | HNRPD, WARS, SFRS2, STAT1, PRDX3, MTHFD2, PSME2, GMFB, DLGAP4, TYMS, LMAN1, ARF6, IRF8, RABIF, CXCL10, PLK4, HNRPA3P1, SLC25A11, C1QBP, CA2, ME2, GZMB, CXCL11, RBM25, NUP210, ATP5A1, DDAH2, FAS, PSAT1, BRIP1, TRMT5, KLHL24, ETNK1 | 81% | 76% | 96% | 69% | 81% | 66% |
| 67 | WARS, EPAS1, STAT1, EIF4E, SFPQ, PSME2, GMFB, DLGAP4, TYMS, CTSS, DCK, SLC4A4, CXCL9, CXCL10, C1QBP, NDUFA9, SLC25A11, C17orf25, CA2, ME2, FUT4, CXCL11, RBM25, AK2, NUP210, CAMSAP1L1, FAS, AGPAT5, FLJ13220, PBK, HNRPD, ETNK1 | 77% | 83% | 92% | 79% | 77% | 69% |
| 68 | HNRPD, WARS, SFRS2, EIF4E, PRDX3, MTHFD2, GMFB, TYMS, TES, CDC40, SLC4A4, CXCL9, CXCL10, PLK4, HNRPA3P1, SLC25A11, C1QBP, NDUFA9, C17orf25, CA2, ME2, CXCL11, RBM25, NUP210, hCAP-D3, SOCS6, FAS, SEC10L1, PBK, TRMT5, KLHL24, STAT1 | 77% | 76% | 88% | 79% | 92% | 79% |
| 69 | HNRPD, WARS, EIF4E, PRDX3, MTHFD2, PSME2, GBP1, GMFB, DLGAP4, TYMS, TES, CTSS, CXCL9, CXCL10, FAS, CHEK1, C1QBP, NDUFA9, SLC25A11, CA2, ME2, GZMB, TLK1, CXCL11, RBM25, BRRN1, MARCH5, FLJ13220, PBK, TRMT5, KLHL24, ETNK1, STAT1 | 81% | 83% | 92% | 72% | 77% | 79% |
| 70 | HNRPD, WARS, SFRS2, EPAS1, EIF4E, MTHFD2, PSME2, TK1, GMFB, DLGAP4, USP4, TES, LMAN1, CDC40, CXCL9, IRF8, CXCL10, KITLG, NDUFA9, SLC25A11, WHSC1, CA2, ME2, CXCL11, RBM25, AK2, CAMSAP1L1, FAS, SEC10L1, PBK, BRIP1, TRMT5, STAT1 | 81% | 79% | 85% | 83% | 85% | 79% |
| 71 | HNRPD, WARS, PAICS, EIF4E, MTHFD2, PSME2, GMFB, DLGAP4, TYMS, USP4, TES, CXCL9, CXCL10, FAS, TRIM25, C1QBP, SLC25A11, C17orf25, CA2, ME2, CXCL11, IFT20, RBBP4, RBM25, AK2, hCAP-D3, ATP5A1, BAZ1A, PBK, BRIP1, KLHL24, ETNK1, STAT1 | 85% | 86% | 88% | 76% | 81% | 72% |

TABLE 9-continued

Additional Prognostic signatures (note SVM = support vector machine, 3NN = 3 nearest neighbours, 1NN = 1 nearest neighbour, Sens = sensitivity, Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 72 | WARS, SFRS2, EIF4E, PRDX3, MTHFD2, PSME2, MCM6, GMFB, TYMS, USP4, CXCL9, GTSE1, RABIF, CXCL10, FAS, PLK4, CHEK1, SLC25A11, C1QBP, NDUFA9, C17orf25, CA2, ME2, FUT4, IFT20, RBBP4, SLC4A4, CXCL11, RBM25, hCAP-D3, FLJ10534, MARCH5, HNRPD, TRMT5, STAT1 | 81% | 83% | 85% | 86% | 88% | 83% |
| 73 | HNRPD WARS, EIF4E, PRDX3, PSME2, TK1, DLGAP4, TYMS, CTSS, LMAN1, ARF6, CXCL9, CXCL10, CHEK1, TRIM25, NDUFA9, KPNB1, SLC25A11, WHSC1, ME2, SLC4A4, RBM25, AK2, SFRS2, DDAH2, FAS, FLJ10534, MARCH5, FLJ13220, BRIP1, TRMT5, KLHL24, ETNK1, STAT1 | 73% | 79% | 81% | 79% | 77% | 76% |
| 74 | WARS, SFRS2, EIF4E, MTHFD2, PSME2, DLGAP4, TYMS, USP4, TES, MAD2L1, SLC4A4, CXCL9, CXCL10, CHEK1, HNRPA3P1, TRIM25, NDUFA9, SLC25A11, WHSC1, C17orf25, CA2, ME2, IFT20, TLK1, CXCL11, RBM25, BRRN1, ATP5A1, FAS, AGPAT5, PBK, HNRPD, ETNK1, STAT1 | 92% | 86% | 81% | 83% | 88% | 76% |
| 75 | HNRPD, WARS, MTHFD2, PSME2, GMFB, DLGAP4, TYMS, TES, LMAN1, CDC40, GTSE1, CXCL10, FAS, KITLG, C1QBP, NDUFA9, SLC25A11, CA2, ME2, CXCL11, GZMB, IFT20, TLK1, SLC4A4, RBM25, hCAP-D3, BRRN1, DDAH2, MARCH5, FLJ13220, PBK, BRIP1, KLHL24, STAT1 | 85% | 86% | 88% | 79% | 85% | 76% |
| 76 | HNRPD, WARS, EIF4E, MTHFD2, PSME2, MCM6, GMFB, DLGAP4, TYMS, TES, CTSS, LMAN1, CDC40, SLC4A4, IRF8, GTSE1, CXCL10, CHEK1, HNRPA3P1, TRIM25, NDUFA9, WHSC1, CA2, ME2, CXCL11, RBM25, NUP210, ATP5A1, CDC42BPA, SFRS2, FAS, MARCH5, SEC10L1, BRIP1, STAT1 | 85% | 83% | 88% | 86% | 85% | 83% |
| 77 | HNRPD, WARS, EPAS1, EIF4E, PRDX3, MTHFD2, PSME2, GMFB, DLGAP4, TYMS, ARF6, SLC4A4, CXCL10, PLK4, CHEK1, HNRPA3P1, KPNB1, SLC25A11, WHSC1, C17orf25, CA2, ME2, CXCL11, IFT20, RBBP4, TLK1, RBM25, CDC42BPA, SFRS2, FAS, AGPAT5, FLJ10534, SEC10L1, TRMT5, STAT1 | 96% | 83% | 92% | 83% | 88% | 79% |
| 78 | WARS, SFRS2, STAT1, PAICS, EIF4E, PRDX3, MTHFD2, PSME2, GMFB, DLGAP4, TYMS, LMAN1, MAD2L1, SLC4A4, CXCL9, CXCL10, SLC25A11, C17orf25, CA2, ME2, FUT4, GZMB, CXCL11, RBM25, CAMSAP1L1, BRRN1, CDC42BPA, FAS, FLJ10534, SEC10L1, PBK, TRMT5, KLHL24 | 81% | 83% | 92% | 76% | 85% | 76% |
| 79 | HNRPD, WARS, SFRS2, PRDX3, MTHFD2, PSME2, GMFB, DLGAP4, TYMS, USP4, TES, CXCL9, CXCL10, FAS, KITLG, C1QBP, NDUFA9, C17orf25, CA2, ME2, RBM25, SOCS6, CDC42BPA, BAZ1A, AGPAT5, DKFZp762E1312, SEC10L1, FLJ13220, PSAT1, BRIP1, TRMT5, KLHL24, STAT1 | 81% | 72% | 88% | 79% | 88% | 69% |
| 80 | WARS, SFRS2, EPAS1, EIF4E, MTHFD2, PSME2, TK1, DLGAP4, TYMS, TES, CTSS, ARF6, CXCL9, CXCL10, FAS, HNRPA3P1, TRIM25, SLC25A11, C1QBP, NDUFA9, HNRPD, ME2, CXCL11, RBBP4, RBM25, AK2, AGPAT5, FLJ10534, DKFZp762E1312, SEC10L1, PBK, KLHL24, STAT1 | 85% | 86% | 81% | 69% | 69% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 81 | EIF4E, SFPQ, MTHFD2, PSME2, GMFB, DLGAP4, TYMS, TES, CTSS, CXCL9, CXCL10, FAS, PLK4, NDUFA9, WHSC1, C17orf25, CA2, HNRPD, ME2, IFT20, RBM25, NUP210, CDC42BPA, DDAH2, BAZ1A, AGPAT5, FLJ10534, DKFZp762E1312, SEC10L1, FLJ13220, PBK, BRIP1, TRMT5, STAT1 | 81% | 79% | 85% | 76% | 81% | 66% |
| 82 | WARS, SFRS2, STAT1, EIF4E, PRDX3, MTHFD2, PSME2, GMFB, DLGAP4, TYMS, TES, LMAN1, DCK, CDC40, CXCL9, CXCL10, FAS, TRIM25, C1QBP, NDUFA9, SLC25A11, CA2, ME2, CXCL11, SLC4A4, RBM25, AK2, BRRN1, AGPAT5, DKFZp762E1312, FLJ13220, PBK | 81% | 90% | 85% | 76% | 85% | 72% |
| 83 | SFRS2, STAT1, EIF4E, PRDX3, MTHFD2, PSME2, GMFB, DLGAP4, TYMS, USP4, TES, CTSS, LMAN1, ARF6, CDC40, IRF8, CXCL10, CHEK1, C1QBP, SLC25A11, WHSC1, ME2, SLC4A4, CXCL11, RBM25, NUP210, FAS, FLJ10534, MARCH5, FLJ13220, PSAT1, HNRPD, BRIP1, TRMT5, KLHL24 | 65% | 79% | 77% | 83% | 77% | 79% |
| 84 | HNRPD, WARS, SFRS2, EIF4E, PRDX3, MTHFD2, PSME2, TK1, GMFB, DLGAP4, TYMS, CTSS, ARF6, MAD2L1, CXCL10, TRIM25, KITLG, NDUFA9, WHSC1, CA2, ME2, GZMB, IFT20, CXCL11, RBM25, FAS, AGPAT5, MARCH5, PSAT1, BRIP1, TRMT5, STAT1 | 85% | 83% | 88% | 76% | 73% | 72% |
| 85 | HNRPD, SFRS2, STAT1, PRDX3, MTHFD2, PSME2, GMFB, DLGAP4, USP4, CTSS, ARF6, SLC4A4, CXCL9, RABIF, CXCL10, FAS, TRIM25, KITLG, C1QBP, SLC25A11, WHSC1, CA2, ME2, GZMB, RBBP4, CXCL11, RBM25, AGPAT5, MARCH5, SEC10L1, PBK, BRIP1, TRMT5 | 88% | 76% | 92% | 76% | 81% | 69% |
| 86 | WARS, STAT1, EIF4E, MTHFD2, PSME2, DLGAP4, TYMS, USP4, LMAN1, CDC40, CXCL9, IRF8, CXCL10, PLK4, TRIM25, C1QBP, NDUFA9, SLC25A11, CA2, ME2, CXCL11, RBM25, ATP5A1, SFRS2, FAS, AGPAT5, MARCH5, FLJ13220, PBK, HNRPD, BRIP1, TRMT5, KLHL24, ETNK1 | 85% | 76% | 81% | 83% | 81% | 76% |
| 87 | HNRPD, WARS, EPAS1, STAT1, EIF4E, MTHFD2, PSME2, TK1, GMFB, DLGAP4, TYMS, USP4, SLC4A4, CXCL9, IRF8, GTSE1, RABIF, CXCL10, FAS, PLK4, HNRPA3P1, TRIM25, SLC25A11, C1QBP, NDUFA9, WHSC1, ME2, CXCL11, TLK1, RBM25, AK2, NUP210, BRRN1, ATP5A1, SFRS2, AGPAT5, FLJ10534, MARCH5, PSAT1, BRIP1, KLHL24 | 73% | 79% | 88% | 83% | 69% | 72% |
| 88 | WARS, SFRS2, EPAS1, STAT1, EIF4E, PRDX3, MTHFD2, PSME2, TK1, GMFB, DLGAP4, TYMS, LMAN1, MAD2L1, CDC40, CXCL9, IRF8, CXCL10, FAS, CHEK1, NDUFA9, KPNB1, SLC25A11, WHSC1, C17orf25, CA2, ME2, CXCL11, IFT20, SLC4A4, RBM25, CDC42BPA, BAZ1A, AGPAT5, MARCH5, PBK, PSAT1, HNRPD, BRIP1, TRMT5, ETNK1 | 73% | 83% | 85% | 79% | 81% | 72% |
| 89 | HNRPD, WARS, SFRS2, STAT1, EIF4E, PRDX3, MTHFD2, PSME2, GMFB, TYMS, USP4, CTSS, DCK, CDC40, SLC4A4, CXCL9, CXCL10, FAS, CHEK1, SLC25A11, C1QBP, NDUFA9, WHSC1, CA2, ME2, GZMB, RBBP4, RBM25, ATP5A1, SOCS6, AGPAT5, MARCH5, DKFZp762E1312, SEC10L1, PBK, BRIP1, TRMT5, KLHL24 | 77% | 76% | 88% | 79% | 85% | 66% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 90 | WARS, SFRS2, EIF4E, PRDX3, MTHFD2, PSME2, TK1, GMFB, DLGAP4, TYMS, USP4, CTSS, SLC4A4, CXCL9, IRF8, GTSE1, CXCL10, PLK4, CHEK1, HNRPA3P1, KITLG, SLC25A11, C1QBP, NDUFA9, C17orf25, CA2, ME2, GZMB, CXCL11, RBM25, AK2, SOCS6, DDAH2, FAS, RBBP4, FLJ10534, MARCH5, DKFZp762E1312, PBK, HNRPD, BRIP1, KLHL24, STAT1 | 77% | 79% | 88% | 76% | 88% | 76% |
| 91 | HNRPD, WARS, SFRS2, EPAS1, STAT1, EIF4E, SFPQ, PRDX3, MTHFD2, PSME2, GMFB, DLGAP4, TYMS, USP4, TES, DCK, ARF6, MAD2L1, CDC40, SLC4A4, CXCL9, RABIF, CXCL10, FAS, SLC25A11, C1QBP, NDUFA9, WHSC1, C17orf25, ME2, FUT4, CXCL11, IFT20, RBBP4, RBM25, CAMSAP1L1, SEC10L1, PBK, PSAT1, KLHL24 | 69% | 83% | 81% | 79% | 77% | 76% |
| 92 | HNRPD, WARS, STAT1, EIF4E, MTHFD2, PSME2, TK1, GMFB, DLGAP4, TYMS, TES, CTSS, MAD2L1, SLC4A4, CXCL9, CXCL10, FAS, CHEK1, HNRPA3P1, SLC25A11, C1QBP, NDUFA9, WHSC1, CA2, ME2, GZMB, CXCL11, RBM25, AK2, CAMSAP1L1, DDAH2, BAZ1A, AGPAT5, SEC10L1, FLJ13220, PBK, BRIP1, TRMT5 | 77% | 83% | 92% | 83% | 77% | 66% |
| 93 | HNRPD, WARS, SFRS2, EPAS1, STAT1, EIF4E, MTHFD2, PSME2, GMFB, DLGAP4, TYMS, TES, CTSS, DCK, MAD2L1, CDC40, RABIF, CXCL10, FAS, PLK4, KITLG, SLC25A11, NDUFA9, WHSC1, CA2, ME2, CXCL11, IFT20, TLK1, RBM25, CDC42BPA, DDAH2, RBBP4, MARCH5, DKFZp762E1312, PBK, PSAT1, BRIP1, KLHL24, ETNK1 | 73% | 83% | 77% | 79% | 77% | 76% |
| 94 | HNRPD, WARS, STAT1, PAICS, EIF4E, PRDX3, MTHFD2, PSME2, TK1, GMFB, DLGAP4, TYMS, USP4, TES, CTSS, DCK, ARF6, CDC40, CXCL9, IRF8, RABIF, CXCL10, FAS, HNRPA3P1, TRIM25, SLC25A11, NDUFA9, WHSC1, CA2, ME2, CXCL11, GZMB, IFT20, SLC4A4, SFRS2, AGPAT5, FLJ10534, MARCH5, PBK, BRIP1 | 88% | 83% | 85% | 76% | 85% | 69% |
| 95 | WARS, SFRS2, STAT1, EIF4E, MTHFD2, PSME2, GMFB, DLGAP4, TYMS, TES, CTSS, LMAN1, DCK, MAD2L1, CDC40, SLC4A4, CXCL9, IRF8, CXCL10, FAS, C1QBP, NDUFA9, WHSC1, CA2, ME2, CXCL11, IFT20, RBM25, hCAP-D3, ATP5A1, DDAH2, FLJ10534, MARCH5, DKFZp762E1312, SEC10L1, PBK, HNRPD, BRIP1, TRMT5, KLHL24 | 73% | 79% | 85% | 83% | 85% | 79% |
| 96 | HNRPD, WARS, SFRS2, EPAS1, STAT1, EIF4E, PRDX3, MTHFD2, PSME2, GBP1, TK1, GMFB, DLGAP4, TYMS, USP4, ARF6, CXCL9, CXCL10, FAS, PLK4, CHEK1, HNRPA3P1, SLC25A11, C1QBP, WHSC1, CA2, ME2, CXCL11, GZMB, IFT20, RBM25, NUP210, SOCS6, AGPAT5, MARCH5, SEC10L1, PBK, BRIP1, ETNK1 | 85% | 86% | 92% | 76% | 77% | 69% |
| 97 | HNRPD, WARS, SFRS2, EPAS1, STAT1, EIF4E, MTHFD2, PSME2, MCM6, GMFB, DLGAP4, TYMS, TES, DCK, CDC40, SLC4A4, CXCL9, CXCL10, FAS, TRIM25, NDUFA9, SLC25A11, WHSC1, CA2, ME2, GZMB, IFT20, TLK1, CXCL11, RBM25, AK2, hCAP-D3, BRRN1, AGPAT5, MARCH5, FLJ13220, TRMT5, KLHL24 | 92% | 90% | 88% | 76% | 77% | 66% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature | | SVM | | 3NN | | 1NN | |
|---|---|---|---|---|---|---|---|
| Number | Signature Genes (as gene symbols) | Sens | Spec | Sens | Spec | Sens | Spec |
| 98 | HNRPD, WARS, EIF4E, SFPQ, MTHFD2, PSME2, TK1, GMFB, DLGAP4, TYMS, DCK, CDC40, SLC4A4, CXCL9, GTSE1, CXCL10, FAS, PLK4, CHEK1, KITLG, SLC25A11, C1QBP, NDUFA9, KPNB1, WHSC1, C17orf25, CA2, ME2, CXCL11, TLK1, RBM25, NUP210, RBBP4, AGPAT5, MARCH5, SEC10L1, FLJ13220, PBK, TRMT5, KLHL24, ETNK1, STAT1 | 73% | 76% | 92% | 83% | 81% | 83% |
| 99 | WARS, EPAS1, PRDX3, MTHFD2, GMFB, DLGAP4, TYMS, USP4, CTSS, CDC40, SLC4A4, CXCL9, IRF8, RABIF, CXCL10, FAS, HNRPA3P1, TRIM25, SLC25A11, NDUFA9, WHSC1, C17orf25, HNRPD, ME2, FUT4, CXCL11, GZMB, RBM25, AK2, ATP5A1, CDC42BPA, SFRS2, BAZ1A, AGPAT5, MARCH5, FLJ13220, BRIP1, KLHL24, ETNK1, STAT1 | 85% | 86% | 92% | 72% | 77% | 69% |
| 100 | HNRPD, WARS, SFRS2, PAICS, PRDX3, MTHFD2, PSME2, TK1, GMFB, DLGAP4, TYMS, LMAN1, ARF6, MAD2L1, CDC40, SLC4A4, CXCL9, IRF8, GTSE1, CXCL10, HNRPA3P1, SLC25A11, C1QBP, NDUFA9, WHSC1, C17orf25, CA2, ME2, CXCL11, RBM25, hCAP-D3, CDC42BPA, FAS, AGPAT5, FLJ10534, MARCH5, DKFZp762E1312, SEC10L1, PBK, BRIP1, TRMT5, ETNK1, STAT1 | 77% | 79% | 88% | 83% | 88% | 76% |
| 101 | HNRPD, WARS, STAT1, PAICS, EIF4E, PRDX3, MTHFD2, PSME2, TK1, GMFB, DLGAP4, TYMS, TES, ARF6, CXCL9, IRF8, CXCL10, FAS, PLK4, HNRPA3P1, TRIM25, C1QBP, NDUFA9, SLC25A11, WHSC1, C17orf25, ME2, CXCL11, IFT20, RBBP4, TLK1, SLC4A4, RBM25, AK2, NUP210, CAMSAP1L1, DDAH2, AGPAT5, MARCH5, SEC10L1, KLHL24, ETNK1 | 73% | 83% | 88% | 86% | 85% | 76% |
| 102 | HNRPD, WARS, SFRS2, EPAS1, EIF4E, PRDX3, MTHFD2, PSME2, DLGAP4, TYMS, USP4, CTSS, ARF6, CDC40, CXCL10, FAS, PLK4, TRIM25, KITLG, SLC25A11, C1QBP, NDUFA9, WHSC1, C17orf25, CA2, ME2, IFT20, RBBP4, TLK1, SLC4A4, CXCL11, RBM25, AK2, BAZ1A, MARCH5, SEC10L1, FLJ13220, PBK, BRIP1, KLHL24, STAT1 | 85% | 86% | 81% | 83% | 85% | 79% |
| 103 | WARS, SFRS2, EIF4E, SFPQ, PRDX3, MTHFD2, PSME2, MCM6, TK1, GMFB, DLGAP4, TYMS, USP4, LMAN1, DCK, SLC4A4, CXCL9, CXCL10, FAS, PLK4, TRIM25, C1QBP, NDUFA9, SLC25A11, WHSC1, CA2, HNRPD, ME2, GZMB, IFT20, TLK1, CXCL11, RBM25, RBBP4, MARCH5, PBK, PSAT1, BRIP1, TRMT5, KLHL24, ETNK1, STAT1 | 81% | 86% | 85% | 76% | 77% | 76% |
| 104 | HNRPD, WARS, SFRS2, EIF4E, MTHFD2, PSME2, MCM6, GMFB, DLGAP4, TYMS, USP4, LMAN1, ARF6, CDC40, CXCL9, GTSE1, CXCL10, FAS, CHEK1, HNRPA3P1, SLC25A11, C1QBP, WHSC1, CA2, ME2, GZMB, IFT20, SLC4A4, CXCL11, RBM25, BAZ1A, AUPAT5, SEC10L1, FLJ13220, PBK, PSAT1, BRIP1, TRMT5, ETNK1, STAT1 | 85% | 86% | 88% | 72% | 77% | 72% |

TABLE 9-continued

Additional Prognostic signatures (note SVM = support vector machine, 3NN = 3 nearest neighbours, 1NN = 1 nearest neighbour, Sens = sensitivity, Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 105 | WARS, PAICS, EIF4E, MTHFD2, PSME2, MCM6, GMFB, DLGAP4, TYMS, CTSS, MAD2L1, CDC40, SLC4A4, CXCL9, IRF8, RABIF, CXCL10, FAS, CHEK1, HNRPA3P1, TRIM25, NDUFA9, SLC25A11, CA2, HNRPD, ME2, CXCL11, IFT20, RBM25, AK2, CAMSAP1L1, BRRN1, SFRS2, DDAH2, RBBP4, SEC10L1, PBK, PSAT1, BRIP1, TRMT5, KLHL24, STAT1 | 88% | 86% | 81% | 83% | 81% | 83% |
| 106 | HNRPD, WARS, SFRS2, EPAS1, EIF4E, PRDX3, MTHFD2, PSME2, TK1, GMFB, DLGAP4, TYMS, TES, LMAN1, DCK, SLC4A4, CXCL9, CXCL10, PLK4, HNRPA3P1, C1QBP, NDUFA9, SLC25A11, WHSC1, C17orf25, CA2, ME2, CXCL11, GZMB, 1FT20, RBBP4, TLK1, RBM25, CAMSAP1L1, FAS, MARCH5, DKFZp762E1312, SEC10L1, PBK, STAT1 | 81% | 90% | 85% | 83% | 81% | 76% |
| 107 | WARS, SFRS2, EPAS1, EIF4E, PRDX3, MTHFD2, PSME2, TK1, GMFB, DLGAP4, TYMS, MAD2L1, CDC40, SLC4A4, CXCL9, CXCL10, FAS, KITLG, C1QBP, NDUFA9, SLC25A11, ME2, CXCL11, IFT20, TLK1, RBM25, AK2, BRRN1, ATP5A1, CDC42BPA, RBBP4, AGPAT5, MARCH5, SEC10L1, PBK, HNRPD, BRIP1, TRMT5, ETNK1, STAT1 | 85% | 83% | 81% | 86% | 81% | 72% |
| 108 | WARS, EPAS1, EIF4E, PRDX3, MTHFD2, PSME2, TK1, GMFB, DLGAP4, TYMS, TES, CTSS, LMAN1, CXCL9, GTSE1, RABIF, CXCL10, FAS, PLK4, SLC25A11, NDUFA9, KPNB1, HNRPD, ME2, FUT4, CXCL11, GZMB, IFT20, RBBP4, RBM25, CAMSAP1L1, hCAP-D3, SFRS2, DDAH2, AGPAT5, MARCH5, PBK, BRIP1, TRMT5, ETNK1, STAT1 | 81% | 83% | 85% | 69% | 73% | 79% |
| 109 | HNRPD, WARS, SFRS2, EPAS1, EIF4E, PRDX3, MTHFD2, PSME2, GMFB, DLGAP4, TYMS, TES, CTSS, DCK, CDC40, RABIF, CXCL10, FAS, CHEK1, HNRPA3P1, TRIM25, KPNB1, SLC25A11, WHSC1, C17orf25, CA2, ME2, CXCL11, TLK1, RBM25, ATP5A1, CDC42BPA, FLJ10534, MARCH5, DKFZp762E1312, SEC10L1, PBK, PSAT1, KLHL24, STAT1 | 77% | 79% | 88% | 79% | 77% | 72% |
| 110 | HNRPD, WARS, SFRS2, STAT1, EIF4E, PRDX3, MTHFD2, PSME2, TK1, GMFB, DLGAP4, TYMS, TES, ARF6, MAD2L1, CDC40, CXCL9, GTSE1, CXCL10, FAS, PLK4, CHEK1, HNRPA3P1, C1QBP, NDUFA9, SLC25A11, WHSC1, CA2, ME2, CXCL11, IFT20, TLK1, RBM25, ATP5A1, SOCS6, AGPAT5, SEC10L1, PBK, TRMT5, KLHL24 | 73% | 79% | 85% | 83% | 88% | 83% |
| 111 | HNRPD, WARS, SFRS2, EPAS1, EIF4E, PRDX3, MTHFD2, PSME2, GBP1, TK1, GMFB, DLGAP4, TYMS, TES, CTSS, MAD2L1, CXCL9, CXCL10, FAS, PLK4, CHEK1, SLC25A11, C1QBP, WHSC1, C17orf25, CA2, ME2, CXCL11, GZMB, TLK1, SLC4A4, RBM25, AK2, hCAP-D3, FLJ10534, SEC10L1, FLJ13220, PBK, BRIP1, KLHL24, STAT1 | 81% | 90% | 88% | 83% | 77% | 76% |
| 112 | WARS, SFRS2, EPAS1, EIF4E, MTHFD2, PSME2, GMFB, DLGAP4, TYMS, USP4, TES, CTSS, MAD2L1, CXCL9, CXCL10, TRIM25, NDUFA9, KPNB1, SLC25A11, WHSC1, C17orf25, CA2, HNRPD, ME2, CXCL11, GZMB, TLK1, RBM25, AK2, CAMSAP1L1, BRRN1, CDC42BPA, DDAH2, FAS, MARCH5, SEC10L1, PBK, PSAT1, BRIP1, KLHL24, ETNK1, STAT1 | 96% | 90% | 81% | 76% | 77% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 113 | HNRPD, WARS, SFRS2, STAT1, EIF4E, PRDX3, MTHFD2, PSME2, MCM6, GBP1, GMFB, DLGAP4, TYMS, USP4, LMAN1, DCK, ARF6, CDC40, CXCL9, CXCL10, FAS, PLK4, KITLG, C1QBP, NDUFA9, SLC25A11, WHSC1, C17orf25, CA2, ME2, FUT4, TLK1, CXCL11, SLC4A4, RBM25, AK2, ATP5A1, AGPAT5, FLJ10534, MARCH5, SEC10L1, PBK, PSAT1 | 65% | 76% | 88% | 76% | 85% | 83% |
| 114 | HNRPD, WARS, SFRS2, STAT1, MTHFD2, PSME2, MCM6, TK1, GMFB, TYMS, USP4, LMAN1, ARF6, CXCL10, FAS, PLK4, SLC25A11, C1QBP, NDUFA9, WHSC1, C17orf25, CA2, ME2, GZMB, RBBP4, CXCL11, RBM25, AK2, BRRN1, ATP5A1, CDC42BPA, DDAH2, BAZ1A, AGPAT5, MARCH5, SEC10L1, PBK, BRIP1 | 81% | 76% | 81% | 79% | 85% | 62% |
| 115 | HNRPD, WARS, EPAS1, STAT1, EIF4E, SFPQ, PRDX3, MTHFD2, PSME2, TK1, GMFB, DLGAP4, TYMS, TES, LMAN1, DCK, ARF6, CXCL9, IRF8, GTSE1, CXCL10, KITLG, NDUFA9, KPNB1, C17orf25, CA2, ME2, FUT4, CXCL11, GZMB, IFT20, TLK1, SLC4A4, RBM25, AK2, BRRN1, DDAH2, FAS, FLJ13220, PBK, PSAT1, BRIP1 | 81% | 86% | 81% | 76% | 81% | 79% |
| 116 | WARS, SFRS2, EPAS1, PAICS, EIF4E, PRDX3, MTHFD2, PSME2, GBP1, TK1, GMFB, DLGAP4, TYMS, CTSS, ARF6, CDC40, CXCL9, CXCL10, FAS, HNRPA3P1, TRIM25, SLC25A11, NDUFA9, WHSC1, HNRPD, ME2, FUT4, CXCL11, SLC4A4, RBM25, CAMSAP1L1, hCAP-D3, DDAH2, MARCH5, FLJ13220, PBK, PSAT1, TRMT5, ETNK1, STAT1 | 81% | 79% | 73% | 90% | 73% | 69% |
| 117 | WARS, SFRS2, EPAS1, EIF4E, SFPQ, PRDX3, MTHFD2, PSME2, GMFB, DLGAP4, TYMS, USP4, CTSS, LMAN1, ARF6, MAD2L1, CDC40, SLC4A4, CXCL9, CXCL10, FAS, PLK4, HNRPA3P1, TRIM25, NDUFA9, SLC25A11, WHSC1, C17orf25, CA2, ME2, CXCL11, GZMB, IFT20, TLK1, RBM25, ATP5A1, RBBP4, AGPAT5, PSAT1, HNRPD, KLHL24, STAT1 | 92% | 90% | 88% | 79% | 81% | 72% |
| 118 | WARS, EPAS1, EIF4E, PRDX3, MTHFD2, PSME2, GBP1, DLGAP4, TYMS, DCK, ARF6, MAD2L1, CDC40, CXCL9, IRF8, GTSE1, RABIF, CXCL10, FAS, CHEK1, TRIM25, C1QBP, NDUFA9, KPNB1, SLC25A11, WHSC1, C17orf25, CA2, ME2, GZMB, IFT20, TLK1, CXCL11, RBM25, AK2, SFRS2, BAZ1A, SEC10L1, FLJ13220, PBK, PSAT1, HNRPD, BRIP1, KLHL24, STAT1 | 77% | 90% | 88% | 76% | 73% | 79% |
| 119 | HNRPD, WARS, SFRS2, EPAS1, EIF4E, SFPQ, PRDX3, MTHFD2, PSME2, GBP1, GMFB, DLGAP4, TYMS, DCK, CDC40, CXCL9, CXCL10, PLK4, CHEK1, KITLG, C1QBP, NDUFA9, KPNB1, SLC25A11, WHSC1, CA2, ME2, FUT4, CXCL11, RBM25, AK2, hCAP-D3, BRRN1, FAS, AGPAT5, FLJ10534, MARCH5, SEC10L1, PBK, TRMT5, KLHL24, STAT1 | 77% | 76% | 92% | 83% | 92% | 76% |
| 120 | WARS, SFRS2, EPAS1, EIF4E, SFPQ, MTHFD2, PSME2, GMFB, TYMS, USP4, CTSS, LMAN1, DCK, MAD2L1, CDC40, SLC4A4, CXCL9, CXCL10, FAS, KITLG, SLC25A11, C1QBP, NDUFA9, CA2, ME2, IFT20, CXCL11, RBM25, AK2, CAMSAP1L1, hCAP-D3, ATP5A1, CDC42BPA, BAZ1A, AGPAT5, SEC10L1, PBK, HNRPD, BRIP1, KLHL24, STAT1 | 81% | 86% | 88% | 83% | 85% | 72% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM | | 3NN | | 1NN | |
|---|---|---|---|---|---|---|---|
| | | Sens | Spec | Sens | Spec | Sens | Spec |
| 121 | HNRPD, WARS, SFRS2, EPAS1, EIF4E, MTHFD2, PSME2, GMFB, DLGAP4, TYMS, LMAN1, MAD2L1, CDC40, CXCL9, CXCL10, CHEK1, TRIM25, SLC25A11, WHSC1, CA2, ME2, CXCL11, IFT20, RBBP4, SLC4A4, RBM25, AK2, NUP210, hCAP-D3, DDAH2, FAS, BAZ1A, FLJ10534, FLJ13220, PBK, BRIP1, TRMT5, ETNK1, STAT1 | 85% | 90% | 88% | 90% | 85% | 76% |
| 122 | HNRPD, WARS, EPAS1, STAT1, EIF4E, PRDX3, MTHFD2, PSME2, GMFB, DLGAP4, TYMS, TES, CTSS, LMAN1, CDC40, CXCL9, CXCL10, FAS, PLK4, KITLG, C1QBP, NDUFA9, SLC25A11, WHSC1, C17orf25, ME2, CXCL11, RBM25, hCAP-D3, BRRN1, ATP5A1, CDC42BPA, FLJ10534, MARCH5, SEC10L1, FLJ13220, PBK, BRIP1, TRMT5, KLHL24, ETNK1 | 69% | 76% | 77% | 86% | 69% | 69% |
| 123 | WARS, SFRS2, EPAS1, EIF4E, PRDX3, MTHFD2, PSME2, TK1, GMFB, DLGAP4, TYMS, USP4, LMAN1, ARF6, CDC40, CXCL9, IRF8, CXCL10, FAS, PLK4, CHEK1, HNRPA3P1, C1QBP, NDUFA9, SLC25A11, WHSC1, C17orf25, CA2, HNRPD, ME2, SLC4A4, CXCL11, RBM25, AK2, NUP210, AGPAT5, FLJ10534, MARCH5, DKFZp762E1312, PSAT1, BRIP1, TRMT5, STAT1 | 73% | 83% | 85% | 76% | 81% | 79% |
| 124 | WARS, SFRS2, EPAS1, PAICS, EIF4E, MTHFD2, PSME2, GMFB, DLGAP4, TYMS, CDC40, CXCL9, CXCL10, FAS, PLK4, HNRPA3P1, KITLG, C1QBP, NDUFA9, WHSC1, CA2, HNRPD, ME2, FUT4, CXCL11, GZMB, SLC4A4, RBM25, AK2, BRRN1, ATP5A1, AGPAT5, MARCH5, SEC10L1, FLJ13220, PBK, TRMT5, KLHL24, ETNK1, STAT1 | 77% | 76% | 92% | 76% | 85% | 72% |
| 125 | WARS, SFRS2, EPAS1, STAT1, EIF4E, PRDX3, MTHFD2, PSME2, GMFB, DLGAP4, TYMS, USP4, TES, CTSS, MAD2L1, CXCL9, IRF8, GTSE1, CXCL10, PLK4, CHEK1, TRIM25, NDUFA9, SLC25A11, C17orf25, CA2, HNRPD, ME2, CXCL11, IFT20, TLK1, RBM25, BRRN1, FAS, AGPAT5, FLJ10534, SEC10L1, FLJ13220, PBK, BRIP1, KLHL24 | 85% | 86% | 92% | 86% | 88% | 83% |
| 126 | HNRPD, WARS, SFRS2, EPAS1, EIF4E, PRDX3, MTHFD2, PSME2, TK1, GMFB, DLGAP4, TYMS, USP4, TES, LMAN1, ARF6, MAD2L1, CXCL9, GTSE1, CXCL10, FAS, HNRPA3P1, NDUFA9, KPNB1, SLC25A11, CA2, ME2, CXCL11, TLK1, SLC4A4, RBM25, BRRN1, AGPAT5, MARCH5, DKFZp762E1312, SEC10L1, PBK, BRIP1, KLHL24, STAT1 | 77% | 83% | 88% | 86% | 85% | 72% |
| 127 | WARS, EPAS1, EIF4E, PRDX3, MTHFD2, PSME2, TK1, GMFB, DLGAP4, TYMS, USP4, TES, LMAN1, CDC40, CXCL9, IRF8, CXCL10, PLK4, CHEK1, TRIM25, C1QBP, NDUFA9, SLC25A11, WHSC1, ME2, FUT4, CXCL11, TLK1, SLC4A4, RBM25, AK2, CAMSAP1L1, BRRN1, ATP5A1, SFRS2, FAS, SEC10L1, FLJ13220, PBK, PSAT1, TRMT5, KLHL24, STAT1 | 73% | 83% | 73% | 90% | 73% | 86% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 128 | HNRPD, EIF4E, PRDX3, MTHFD2, PSME2, TK1, GMFB, DLGAP4, TYMS, USP4, DCK, ARF6, MAD2L1, CDC40, CXCL9, IRF8, CXCL10, FAS, CHEK1, SLC25A11, C1QBP, NDUFA9, WHSC1, CA2, ME2, CXCL11, TLK1, SLC4A4, RBM25, AK2, BRRN1 SOCS6, DDAH2, RBBP4, FLJ10534, MARCH5, FLJ13220, PBK, BRIP1, ETNK1, STAT1 | 69% | 83% | 77% | 83% | 85% | 76% |
| 129 | WARS, SFRS2, EPAS1, STAT1, EIF4E, PRDX3, MTHFD2, PSME2, TK1, GMFB, DLGAP4, TYMS, CTSS, LMAN1, DCK, CDC40, SLC4A4, CXCL9, IRF8, CXCL10, FAS, C1QBP, NDUFA9, SLC25A11, WHSC1, C17orf25, CA2, ME2, RBM25, NUP210, CDC42BPA, AGPAT5, SEC10L1, FLJ13220, HNRPD, BRIP1, KLHL24, ETNK1 | 73% | 76% | 92% | 79% | 85% | 72% |
| 130 | HNRPD, WARS, SFRS2, EPAS1, PAICS, EIF4E, SFPQ, PRDX3, MTHFD2, PSME2, GMFB, DLGAP4, TYMS, CTSS, CXCL9, IRF8, RABIF, CXCL10, FAS, PLK4, CHEK1, TRIM25, KITLG, SLC25A11, C1QBP, NDUFA9, CA2, ME2, CXCL11, RBBP4, SLC4A4, RBM25, AK2, AGPAT5, FLJ10534, FLJ13220, PBK, TRMT5, KLHL24, STAT1 | 85% | 83% | 92% | 72% | 88% | 76% |
| 131 | WARS, SFRS2, PRDX3, MTHFD2, PSME2, MCM6, GMFB, DLGAP4, TYMS, CTSS, ARF6, CDC40, CXCL9, CXCL10, FAS, HNRPA3P1, TRIM25, KITLG, C1QBP, NDUFA9, KPNB1, SLC25A11, WHSC1, C17orf25, CA2, HNRPD, ME2, CXCL11, TLK1, SLC4A4, RBM25, AK2, hCAP-D3, BRRN1, SOCS6, DDAH2, RBBP4, AGPAT5, PBK, BRIP1, STAT1 | 85% | 83% | 92% | 86% | 88% | 79% |
| 132 | HNRPD, WARS, SFRS2, EIF4E, MTHFD2, PSME2, MCM6, TK1, GMFB, DLGAP4, TYMS, USP4, CTSS, LMAN1, CDC40, CXCL9, CXCL10, PLK4, HNRPA3P1, C1QBP, NDUFA9, SLC25A11, WHSC1, CA2, ME2, CXCL11, GZMB, IFT20, SLC4A4, RBM25, AK2, ATP5A1, FAS, RBBP4, BAZ1A, MARCH5, DKFZp762E1312, SEC10L1, FLJ13220, PBK, TRMT5, KLHL24, STAT1 | 77% | 83% | 88% | 76% | 85% | 76% |
| 133 | WARS, SFRS2, EPAS1, STAT1, EIF4E, PRDX3, MTHFD2, PSME2, MCM6, TK1, GMFB, DLGAP4, TYMS, TES, LMAN1, ARF6, CDC40, CXCL9, RABIF, CXCL10, FAS, PLK4, TRIM25, C1QBP, NDUFA9, SLC25A11, CA2, HNRPD, ME2, CXCL11, RBBP4, TLK1, RBM25, CDC42BPA, BAZ1A, AGPAT5, MARCH5, SEC10L1, FLJ13220, PBK, PSAT1, BRIP1 | 77% | 83% | 88% | 76% | 85% | 79% |
| 134 | WARS, SFRS2, EPAS1, PAICS, EIF4E, PRDX3, MTHFD2, PSME2, GMFB, DLGAP4, TYMS, CTSS, LMAN1, ARF6, MAD2L1, CDC40, IRF8, GTSE1, CXCL10, KITLG, C1QBP, NDUFA9, KPNB1, SLC25A11, WHSC1, ME2, CXCL11, RBBP4, TLK1, SLC4A4, RBM25, AK2, BRRN1, ATP5A1, CDC42BPA, DDAH2, FAS, MARCH5, SEC10L1, FLJ13220, PBK, HNRPD, BRIP1, STAT1 | 81% | 86% | 77% | 93% | 81% | 79% |

TABLE 9-continued

Additional Prognostic signatures (note SVM = support vector machine, 3NN = 3 nearest neighbours, 1NN = 1 nearest neighbour, Sens = sensitivity, Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 135 | WARS, SFRS2, EPAS1, EIF4E, PRDX3, MTHFD2, PSME2, GMFB, DLGAP4, TYMS, TES, CTSS, LMAN1, DCK, CDC40, CXCL9, IRF8, CXCL10, FAS, PLK4, HNRPA3P1, C1QBP, NDUFA9, SLC25A11, WHSC1, CA2, ME2, FUT4, CXCL11, GZMB, SLC4A4, RBM25, AK2, ATP5A1, DDAH2, FLJ10534, PBK, HNRPD, BRIP1, ETNK1, STAT1 | 77% | 90% | 88% | 72% | 85% | 79% |
| 136 | WARS, SFRS2, STAT1, PRDX3, MTHFD2, PSME2, MCM6, GMFB, DLGAP4, TYMS, TES, LMAN1, ARF6, CDC40, CXCL9, CXCL10, FAS, PLK4, HNRPA3P1, TRIM25, KITLG, SLC25A11, C1QBP, NDUFA9, KPNB1, C17orf25, CA2, ME2, IFT20, RBBP4, CXCL11, RBM25, AK2, hCAP-D3, ATP5A1, CDC42BPA, BAZ1A, AGPAT5, PBK, BRIP1, KLHL24 | 81% | 79% | 85% | 79% | 81% | 69% |
| 137 | WARS, SFRS2, EPAS1, EIF4E, PRDX3, MTHFD2, PSME2, MCM6, TK1, DLGAP4, TYMS, TES, LMAN1, ARF6, CDC40, CXCL9, CXCL10, FAS, KITLG, SLC25A11, C1QBP, NDUFA9, KPNB1, WHSC1, CA2, ME2, IFT20, RBBP4, TLK1, CXCL11, SLC4A4, RBM25, AK2, CDC42BPA, MARCH5, SEC10L1, FLJ13220, PBK, PSAT1, HNRPD, BRIP1, TRMT5, KLHL24, STAT1 | 85% | 83% | 81% | 83% | 73% | 72% |
| 138 | WARS, SFRS2, EPAS1, STAT1, PAICS, EIF4E, PRDX3, MTHFD2, PSME2, MCM6, GMFB, DLGAP4, TYMS, USP4, CTSS, LMAN1, ARF6, CXCL9, IRF8, CXCL10, CHEK1, C1QBP, NDUFA9, SLC25A11, WHSC1, C17orf25, CA2, ME2, CXCL11, SLC4A4, RBM25, AK2, BRRN1, CDC42BPA, FAS, BAZ1A, AGPAT5, FLJ10534, MARCH5, PBK, PSAT1, HNRPD, TRMT5, KLHL24 | 73% | 76% | 85% | 83% | 81% | 76% |
| 139 | WARS, SFRS2, EPAS1, EIF4E, PRDX3, MTHFD2, PSME2, TK1, GMFB, DLGAP4, TYMS, USP4, LMAN1, ARF6, CXCL9, CXCL10, PLK4, HNRPA3P1, TRIM25, KITLG, C1QBP, NDUFA9, KPNB1, SLC25A11, WHSC1, C17orf25, HNRPD, ME2, FUT4, CXCL11, GZMB, RBM25, AK2, hCAP-D3, BRRN1, ATP5A1, FAS, AGPAT5, SEC10L1, FLJ13220, PSAT1, TRMT5, ETNK1, STAT1 | 85% | 76% | 85% | 79% | 77% | 69% |
| 140 | HNRPD, WARS, SFRS2, EPAS1, EIF4E, PRDX3, MTHFD2, PSME2, MCM6, GBP1, GMFB, DLGAP4, TYMS, TES, CTSS, LMAN1, SLC4A4, CXCL9, CXCL10, FAS, PLK4, CHEK1, TRIM25, C1QBP, NDUFA9, SLC25A11, WHSC1, C17orf25, CA2, ME2, GZMB, RBM25, hCAP-D3, ATP5A1, AGPAT5, FLJ10534, PBK, PSAT1, BRIP1, TRMT5, STAT1 | 81% | 90% | 85% | 79% | 81% | 72% |
| 141 | WARS, SFRS2, EIF4E, PRDX3, MTHFD2, PSME2, MCM6, GMFB, DLGAP4, TYMS, USP4, MAD2L1, CDC40, CXCL9, IRF8, CXCL10, PLK4, HNRPA3P1, TRIM25, SLC25A11, NDUFA9, WHSC1, C17orf25, ME2, FUT4, CXCL11, IFT20, SLC4A4, RBM25, AK2, CAMSAP1L1, hCAP-D3, BRRN1, FAS, BAZ1A, AGPAT5, MARCH5, SEC10L1, FLJ13220, PSAT1, HNRPD, BRIP1, TRMT5, STAT1 | 85% | 83% | 88% | 83% | 73% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 142 | WARS, SFRS2, EPAS1, EIF4E, MTHFD2, PSME2, TK1, GMFB, DLGAP4, TYMS, USP4, LMAN1, CDC40, SLC4A4, CXCL9, RABIF, CXCL10, PLK4, NDUFA9, SLC25A11, WHSC1, C17orf25, CA2, HNRPD, ME2, CXCL11, IFT20, RBM25, hCAP-D3, ATP5A1, SOCS6, CDC42BPA, FAS, RBBP4, BAZ1A, DKFZp762E1312, SEC10L1, FLJ13220, PBK, PSAT1, BRIP1, STAT1 | 77% | 83% | 81% | 83% | 85% | 79% |
| 143 | HNRPD, WARS, STAT1, EIF4E, PRDX3, MTHFD2, PSME2, GMFB, DLGAP4, TYMS, USP4, TES, CTSS, CDC40, CXCL9, IRF8, CXCL10, PLK4, HNRPA3P1, KITLG, NDUFA9, KPNB1, SLC25A11, WHSC1, C17orf25, CA2, ME2, FUT4, CXCL11, SLC4A4, RBM25, hCAP-D3, DDAH2, FAS, RBBP4, AGPAT5, FLJ13220, PBK, BRIP1, TRMT5, KLHL24 | 73% | 72% | 88% | 79% | 92% | 76% |
| 144 | WARS, SFRS2, MTHFD2, PSME2, GMFB, DLGAP4, TYMS, USP4, TES, CDC40, CXCL9, CXCL10, FAS, CHEK1, NDUFA9, KPNB1, WHSC1, CA2, ME2, GZMB, TLK1, RBM25, AK2, CAMSAP1L1, hCAP-D3, FLJ10534, DKFZp762E1312, FLJ13220, HNRPD, STAT1 | 73% | 79% | 85% | 79% | 69% | 76% |
| 145 | HNRPD, WARS, SFRS2, EIF4E, MTHFD2, PSME2, GMFB, DLGAP4, TYMS, LMAN1, DCK, ARF6, CDC40, CXCL9, CXCL10, PLK4, TRIM25, C1QBP, KPNB1, SLC25A11, C17orf25, ME2, CXCL11, RBM25, hCAP-D3, DDAH2, FAS, MARCH5, STAT1 | 77% | 79% | 81% | 86% | 81% | 83% |
| 146 | WARS, STAT1, EIF4E, MTHFD2, PSME2, DLGAP4, TYMS, ARF6, CXCL9, CXCL10, KITLG, C1QBP, NDUFA9, SLC25A11, WHSC1, C17orf25, CA2, HNRPD, ME2, CXCL11, SLC4A4, RBM25, hCAP-D3, SOCS6, CDC42BPA, FAS | 81% | 79% | 88% | 79% | 85% | 69% |
| 147 | HNRPD, WARS, EPAS1, EIF4E, MTHFD2, PSME2, GMFB, DLGAP4, TYMS, ARF6, CDC40, SLC4A4, CXCL9, CXCL10, HNRPA3P1, NDUFA9, SLC25A11, CA2, ME2, TLK1, CXCL11, RBM25, ATP5A1, SFRS2, FAS, MARCH5, SEC10L1, PBK, TRMT5, STAT1 | 88% | 83% | 92% | 83% | 85% | 83% |
| 148 | WARS, SFRS2, EIF4E, PRDX3, MTHFD2, PSME2, GMFB, TYMS, TES, LMAN1, ARF6, CXCL9, CXCL10, FAS, HNRPA3P1, C1QBP, NDUFA9, SLC25A11, WHSC1, C17orf25, CA2, ME2, CXCL11, RBM25, SEC10L1, HNRPD, KLHL24, ETNK1, STAT1 | 73% | 83% | 88% | 79% | 85% | 72% |
| 149 | WARS, EIF4E, MTHFD2, PSME2, GBP1, GMFB, DLGAP4, TYMS, USP4, LMAN1, ARF6, MAD2L1, CDC40, CXCL10, HNRPA3P1, NDUFA9, C17orf25, ME2, CXCL11, SLC4A4, RBM25, AK2, CDC42BPA, DDAH2, FAS, RBBP4, BAZ1A, AGPAT5, HNRPD, BRIP1, TRMT5, STAT1 | 77% | 79% | 85% | 76% | 88% | 79% |
| 150 | WARS, SFRS2, EIF4E, PRDX3, PSME2, GMFB, DLGAP4, CXCL9, IRF8, CXCL10, FAS, PLK4, CHEK1, TRIM25, KITLG, C1QBP, NDUFA9, SLC25A11, WHSC1, C17orf25, CA2, ME2, CXCL11, RBM25, FLJ10534, SEC10L1, BRIP1, TRMT5, STAT1 | 85% | 83% | 88% | 86% | 85% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature | | SVM | | 3NN | | 1NN | |
|---|---|---|---|---|---|---|---|
| Number | Signature Genes (as gene symbols) | Sens | Spec | Sens | Spec | Sens | Spec |
| 151 | WARS, SFRS2, EIF4E, MTHFD2, PSME2, GMFB, DLGAP4, TYMS, CTSS, DCK, SLC4A4, CXCL9, CXCL10, FAS, TRIM25, SLC25A11, C1QBP, NDUFA9, WHSC1, CA2, ME2, CXCL11, TLK1, RBM25, AK2, CDC42BPA, SEC10L1, FLJ13220, KLHL24, STAT1 | 100% | 97% | 85% | 86% | 81% | 72% |
| 152 | WARS, STAT1, MTHFD2, PSME2, GMFB, DLGAP4, TYMS, DCK, MAD2L1, CDC40, CXCL9, IRF8, RABIF, CXCL10, KITLG, SLC25A11, NDUFA9, ME2, IFT20, TLK1, CXCL11, RBM25, AK2, FAS, AGPAT5, DKFZp762E1312, SEC10L1, PSAT1, HNRPD, TRMT5 | 85% | 90% | 81% | 86% | 65% | 86% |
| 153 | WARS, EPAS1, EIF4E, PRDX3, MTHFD2, GMFB, DLGAP4, TYMS, DCK, CDC40, CXCL9, CXCL10, FAS, PLK4, CHEK1, C1QBP, SLC25A11, CA2, ME2, FUT4, IFT20, SLC4A4, RBM25, SFRS2, DDAH2, PBK, HNRPD, KLHL24, ETNK1, STAT1 | 69% | 86% | 85% | 86% | 88% | 79% |
| 154 | HNRPD, WARS, STAT1, EIF4E, PRDX3, PSME2, GMFB, DLGAP4, TYMS, TES, MAD2L1, CXCL9, IRF8, CXCL10, HNRPA3P1, C1QBP, NDUFA9, SLC25A11, ME2, FUT4, IFT20, hCAP-D3, SOCS6, DDAH2, FAS, BAZ1A, PBK, KLHL24 | 88% | 83% | 81% | 83% | 85% | 72% |
| 155 | SFRS2, EPAS1, EIF4E, PRDX3, PSME2, GMFB, TYMS, TES, LMAN1, SLC4A4, CXCL9, GTSE1, CXCL10, C1QBP, NDUFA9, SLC25A11, CA2, ME2, TLK1, RBM25, CDC42BPA, FAS, FLJ10534, MARCH5, SEC10L1, PBK, HNRPD, TRMT5, KLHL24, ETNK1, STAT1 | 92% | 83% | 88% | 83% | 77% | 72% |
| 156 | WARS, STAT1, EIF4E, PRDX3, MTHFD2, GMFB, DLGAP4, TYMS, USP4, ARF6, CDC40, CXCL9, IRF8, CXCL10, FAS, PLK4, HNRPA3P1, KITLG, C1QBP, SLC25A11, ME2, FUT4, RBM25, DDAH2, RBBP4, AGPAT5, PBK, HNRPD, TRMT5, KLHL24 | 81% | 83% | 88% | 79% | 92% | 79% |
| 157 | HNRPD, WARS, SFPQ, MTHFD2, PSME2, GMFB, DLGAP4, TYMS, USP4, SLC4A4, CXCL9, CXCL10, FAS, HNRPA3P1, KITLG, SLC25A11, NDUFA9, CA2, ME2, IFT20, CXCL11, RBM25, BAZ1A, AGPAT5, SEC10L1, PBK, BRIP1, STAT1 | 92% | 86% | 85% | 69% | 85% | 69% |
| 158 | WARS, SFRS2, EIF4E, MTHFD2, PSME2, GMFB, DLGAP4, TYMS, ARF6, CXCL9, IRF8, CXCL10, PLK4, TRIM25, NDUFA9, WHSC1, C17orf25, CA2, ME2, CXCL11, RBBP4, TLK1, SLC4A4, RBM25, NUP210, FAS, AGPAT5, MARCH5, SEC10L1, HNRPD, STAT1 | 69% | 83% | 92% | 86% | 88% | 83% |
| 159 | WARS, SFRS2, EIF4E, PRDX3, MTHFD2, PSME2, GBP1, GMFB, DLGAP4, TYMS, LMAN1, ARF6, CDC40, CXCL9, CXCL10, CA2, HNRPD, ME2, CXCL11, SLC4A4, RBM25, CDC42BPA, FAS, BAZ1A, AGPAT5, FLJ13220, BRIP1, KLHL24, STAT1 | 77% | 76% | 88% | 79% | 85% | 66% |
| 160 | WARS, SFRS2, EPAS1, EIF4E, MTHFD2, PSME2, TK1, GMFB, DLGAP4, LMAN1, ARF6, CDC40, CXCL9, CXCL10, PLK4, NDUFA9, C17orf25, ME2, CXCL11, SLC4A4, RBM25, FAS, BAZ1A, DKFZp762E1312, SEC10L1, PBK, PSAT1, HNRPD, STAT1 | 77% | 76% | 77% | 83% | 77% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 161 | EIF4E, PSME2, GMFB, DLGAP4, TYMS, DCK, CDC40, CXCL9, CXCL10, FAS, TRIM25, KITLG, NDUFA9, SLC25A11, WHSC1, C17orf25, HNRPD, ME2, CXCL11, IFT20, SLC4A4, RBM25, AK2, AGPAT5, MARCH5, SEC10L1, FLJ13220, KLHL24, STAT1 | 92% | 86% | 85% | 79% | 88% | 72% |
| 162 | HNRPD, WARS, EPAS1, EIF4E, PRDX3, PSME2, TK1, GMFB, DLGAP4, TYMS, CTSS, CDC40, CXCL10, C1QBP, SLC25A11, C17orf25, ME2, CXCL11, SLC4A4, RBM25, CAMSAP1L1, CDC42BPA, FAS, MARCH5, SEC10L1, FLJ13220, PBK, BRIP1, KLHL24, STAT1 | 81% | 79% | 85% | 72% | 85% | 76% |
| 163 | WARS, SFRS2, EIF4E, MTHFD2, PSME2, TK1, DLGAP4, TYMS, USP4, TES, DCK, CDC40, CXCL10, CHEK1, HNRPA3P1, NDUFA9, SLC25A11, WHSC1, C17orf25, CA2, ME2, RBBP4, SLC4A4, RBM25, FAS, SEC10L1, FLJ13220, BRIP1, TRMT5, STAT1 | 69% | 86% | 81% | 83% | 81% | 79% |
| 164 | HNRPD, WARS, MTHFD2, TK1, GMFB, DLGAP4, TYMS, LMAN1, CDC40, GTSE1, CXCL10, CHEK1, NDUFA9, SLC25A11, WHSC1, C17orf25, CA2, ME2, FUT4, CXCL11, RBBP4, RBM25, AK2, BRRN1, FAS, AGPAT5, MARCH5, PBK, BRIP1, STAT1 | 81% | 83% | 92% | 79% | 81% | 83% |
| 165 | WARS, SFRS2, EIF4E, PRDX3, MTHFD2, PSME2, GMFB, DLGAP4, TYMS, USP4, DCK, CXCL9, CXCL10, SLC25A11, C1QBP, NDUFA9, KPNB1, WHSC1, ME2, CXCL11, SLC4A4, RBM25, CDC42BPA, FAS, AGPAT5, SEC10L1, HNRPD, BRIP1, TRMT5, STAT1 | 73% | 83% | 88% | 79% | 88% | 76% |
| 166 | WARS, EIF4E, MTHFD2, PSME2, GMFB, TYMS, TES, CDC40, IRF8, RABIF, CXCL10, PLK4, TRIM25, SLC25A11, WHSC1, C17orf25, CA2, ME2, TLK1, CXCL11, SLC4A4, RBM25, CDC42BPA, FAS, RBBP4, SEC10L1, PBK, HNRPD, BRIP1, TRMT5, STAT1 | 73% | 76% | 81% | 83% | 77% | 76% |
| 167 | WARS, SFRS2, MTHFD2, PSME2, TK1, DLGAP4, TYMS, DCK, CDC40, CXCL9, CXCL10, FAS, CHEK1, TRIM25, C1QBP, SLC25A11, WHSC1, CA2, ME2, CXCL11, GZMB, IFT20, SLC4A4, RBM25, hCAP-D3, DDAH2, SEC10L1, FLJ13220, PBK, KLHL24, STAT1 | 88% | 93% | 85% | 76% | 88% | 72% |
| 168 | WARS, SFRS2, EIF4E, MTHFD2, PSME2, MCM6, GMFB, DLGAP4, TYMS, LMAN1, DCK, CDC40, CXCL9, CXCL10, FAS, NDUFA9, WHSC1, HNRPD, ME2, SLC4A4, CXCL11, RBM25, NUP210, hCAP-D3, SEC10L1, PSAT1, KLHL24, STAT1 | 73% | 79% | 81% | 86% | 85% | 76% |
| 169 | SFRS2, EIF4E, PRDX3, MTHFD2, GMFB, DLGAP4, TYMS, USP4, LMAN1, DCK, ARF6, CDC40, CXCL9, RABIF, CXCL10, KITLG, C1QBP, SLC25A11, C17orf25, CA2, ME2, CXCL11, SLC4A4, RBM25, CAMSAP1L1, FAS, HNRPD, BRIP1, STAT1 | 73% | 79% | 85% | 86% | 88% | 76% |
| 170 | WARS, SFRS2, PAICS, EIF4E, PSME2, GMFB, DLGAP4, TYMS, ARF6, MAD2L1, SLC4A4, CXCL9, IRF8, CXCL10, FAS, NDUFA9, WHSC1, CA2, ME2, CXCL11, TLK1, RBM25, AK2, AGPAT5, MARCH5, FLJ13220, TRMT5, STAT1 | 85% | 83% | 88% | 83% | 77% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 171 | SFRS2, EPAS1, EIF4E, MTHFD2, GBP1, GMFB, CTSS, LMAN1, CDC40, CXCL9, CXCL10, FAS, CHEK1, SLC25A11, C1QBP, C17orf25, CA2, ME2, IFT20, CXCL11, RBM25, BRRN1, ATP5A1, RBBP4, HNRPD, BRIP1, STAT1 | 88% | 86% | 85% | 86% | 77% | 79% |
| 172 | WARS, SFRS2, EIF4E, MTHFD2, PSME2, TK1, GMFB, DLGAP4, TYMS, CTSS, CDC40, SLC4A4, CXCL10, KITLG, SLC25A11, C1QBP, NDUFA9, CA2, HNRPD, ME2, FUT4, CXCL11, RBM25, ATP5A1, FAS, RBBP4, BRIP1, TRMT5, STAT1 | 81% | 79% | 96% | 86% | 88% | 83% |
| 173 | WARS, SFRS2, EIF4E, MTHFD2, PSME2, GMFB, TYMS, TES, LMAN1, DCK, CXCL9, CXCL10, KITLG, KPNB1, SLC25A11, ME2, CXCL11, IFT20, TLK1, RBM25, CDC42BPA, FAS, BAZ1A, FLJ10534, MARCH5, SEC10L1, HNRPD, BRIP1, TRMT5, STAT1 | 77% | 79% | 77% | 86% | 73% | 86% |
| 174 | HNRPD, WARS, SFRS2, EPAS1, EIF4E, MTHFD2, TK1, GMFB, DLGAP4, TYMS, LMAN1, CDC40, SLC4A4, CXCL9, IRF8, RABIF, CXCL10, SLC25A11, NDUFA9, CA2, ME2, CXCL11, RBBP4, RBM25, NUP210, FAS, SEC10L1, PBK, STAT1 | 85% | 79% | 88% | 83% | 85% | 86% |
| 175 | HNRPD, WARS, EPAS1, PRDX3, MTHFD2, PSME2, DLGAP4, TYMS, CDC40, IRF8, CXCL10, FAS, SLC25A11, C1QBP, CA2, ME2, GZMB, IFT20, SLC4A4, AK2, NUP210, RBBP4, AGPAT5, MARCH5, FLJ13220, STAT1 | 85% | 90% | 88% | 83% | 85% | 72% |
| 176 | HNRPD, WARS, EIF4E, MTHFD2, PSME2, GMFB, DLGAP4, TYMS, CXCL9, CXCL10, FAS, C1QBP, NDUFA9, SLC25A11, CA2, ME2, RBBP4, SLC4A4, CXCL11, RBM25, ATP5A1, DDAH2, BAZ1A, PBK, BRIP1, STAT1 | 81% | 79% | 88% | 76% | 88% | 79% |
| 177 | HNRPD, WARS, SFRS2, EPAS1, STAT1, EIF4E, PRDX3, PSME2, DLGAP4, TYMS, TES, LMAN1, CDC40, CXCL10, FAS, C1QBP, NDUFA9, SLC25A11, CA2, ME2, GZMB, IFT20, CXCL11, SLC4A4, RBM25, AK2, AGPAT5, DKFZp762E1312, SEC10L1, BRIP1, KLHL24 | 96% | 93% | 92% | 76% | 88% | 76% |
| 178 | WARS, EIF4E, PRDX3, MTHFD2, TK1, GMFB, TYMS, CDC40, CXCL9, IRF8, CXCL10, FAS, CHEK1, TRIM25, SLC25A11, NDUFA9, CA2, ME2, IFT20, RBM25, AK2, AGPAT5, MARCH5, SEC10L1, FLJ13220, PBK, HNRPD, STAT1 | 85% | 83% | 88% | 79% | 88% | 72% |
| 179 | WARS, EIF4E, PRDX3, MTHFD2, GBP1, GMFB, DLGAP4, TYMS, USP4, IRF8, CXCL10, FAS, TRIM25, C1QBP, NDUFA9, SLC25A11, WHSC1, CA2, HNRPD, ME2, GZMB, TLK1, CXCL11, RBM25, DKFZp762E1312, PSAT1, BRIP1, TRMT5, KLHL24, STAT1 | 85% | 86% | 88% | 76% | 81% | 76% |
| 180 | WARS, EPAS1, STAT1, EIF4E, MTHFD2, PSME2, TK1, GMFB, DLGAP4, TYMS, USP4, LMAN1, CXCL9, IRF8, CXCL10, C1QBP, NDUFA9, SLC25A11, WHSC1, HNRPD, ME2, CXCL11, IFT20, TLK1, SLC4A4, CDC42BPA, SFRS2, FAS, PSAT1 | 92% | 90% | 88% | 79% | 73% | 76% |
| 181 | WARS, EIF4E, PSME2, TK1, GMFB, DLGAP4, TYMS, LMAN1, CDC40, CXCL9, FAS, PLK4, C1QBP, CA2, HNRPD, ME2, CXCL11, RBM25, RBBP4, SEC10L1, FLJ13220, PBK, BRIP1, TRMT5, KLHL24, ETNK1, STAT1 | 77% | 79% | 81% | 79% | 85% | 76% |

TABLE 9-continued

Additional Prognostic signatures (note SVM = support vector machine, 3NN = 3 nearest neighbours, 1NN = 1 nearest neighbour, Sens = sensitivity, Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 182 | WARS, SFRS2, EIF4E, MTHFD2, GMFB, DLGAP4, TYMS, LMAN1, CDC40, CXCL9, IRF8, GTSE1, CXCL10, HNRPA3P1, SLC25A11, NDUFA9, CA2, HNRPD, ME2, RBBP4, SLC4A4, RBM25, BRRN1, FAS, BAZ1A, BRIP1, STAT1 | 88% | 83% | 85% | 83% | 77% | 86% |
| 183 | HNRPD, WARS, EPAS1, EIF4E, MTHFD2, TK1, GMFB, DLGAP4, LMAN1, ARF6, MAD2L1, CDC40, CXCL9, CXCL10, HNRPA3P1, TRIM25, C1QBP, NDUFA9, SLC25A11, WHSC1, C17orf25, ME2, CXCL11, SLC4A4, RBM25, DDAH2, FAS, ETNK1, STAT1 | 88% | 90% | 81% | 86% | 81% | 79% |
| 184 | HNRPD, WARS, PAICS, MTHFD2, PSME2, DLGAP4, TYMS, USP4, CXCL9, CXCL10, KITLG, C1QBP, NDUFA9, SLC25A11, WHSC1, ME2, CXCL11, SLC4A4, RBM25, NUP210, ATP5A1, CDC42BPA, FAS, MARCH5, DKFZp762E1312, SEC10L1, PBK, BRIP1, STAT1 | 73% | 83% | 77% | 69% | 69% | 69% |
| 185 | HNRPD, WARS, SFRS2, EPAS1, EIF4E, MTHFD2, PSME2, GMFB, DLGAP4, DCK, MAD2L1, CXCL9, CXCL10, FAS, PLK4, TRIM25, KITLG, SLC25A11, WHSC1, ME2, FUT4, CXCL11, SLC4A4, RBM25, NUP210, DDAH2, RBBP4, BAZ1A, AGPAT5, FLJ10534, MARCH5, DKFZp762E1312, SEC10L1, PSAT1, BRIP1, TRMT5, STAT1 | 81% | 86% | 81% | 86% | 73% | 83% |
| 186 | WARS, SFRS2, EPAS1, EIF4E, PRDX3, MTHFD2, PSME2, GBP1, GMFB, TYMS, LMAN1, ARF6, CDC40, CXCL9, IRF8, RABIF, CXCL10, FAS, PLK4, C1QBP, NDUFA9, SLC25A11, WHSC1, C17orf25, ME2, FUT4, CXCL11, IFT20, SLC4A4, RBM25, AK2, SOCS6, MARCH5, SEC10L1, FLJ13220, PBK, HNRPD, BRIP1, TRMT5, STAT1 | 85% | 79% | 85% | 79% | 73% | 76% |
| 187 | HNRPD, WARS, SFRS2, EIF4E, MTHFD2, PSME2, GMFB, DLGAP4, TYMS, USP4, TES, LMAN1, ARF6, CDC40, SLC4A4, CXCL9, RABIF, CXCL10, FAS, PLK4, C1QBP, NDUFA9, SLC25A11, WHSC1, CA2, ME2, CXCL11, TLK1, RBM25, ATP5A1, CDC42BPA, RBBP4, AGPAT5, SEC10L1, FLJ13220, PSAT1, BRIP1, STAT1 | 77% | 83% | 85% | 79% | 81% | 79% |
| 188 | HNRPD, SFRS2, EPAS1, EIF4E, PRDX3, MTHFD2, PSME2, TK1, GMFB, DLGAP4, TYMS, USP4, CTSS, LMAN1, ARF6, MAD2L1, CDC40, CXCL9, CXCL10, FAS, PLK4, NDUFA9, WHSC1, C17orf25, CA2, ME2, CXCL11, GZMB, TLK1, SLC4A4, RBM25, AK2, NUP210, hCAP-D3, DDAH2, RBBP4, PBK, BRIP1, STAT1 | 77% | 86% | 85% | 83% | 85% | 76% |
| 189 | WARS, EIF4E, PRDX3, MTHFD2, GMFB, DLGAP4, TYMS, USP4, CTSS, ARF6, CDC40, SLC4A4, CXCL9, CXCL10, FAS, SLC25A11, C1QBP, NDUFA9, WHSC1, C17orf25, CA2, ME2, FUT4, CXCL11, GZMB, TLK1, RBM25, NUP210, CDC42BPA, AGPAT5, MARCH5, SEC10L1, PBK, HNRPD, TRMT5, KLHL24, STAT1 | 77% | 79% | 96% | 79% | 85% | 72% |
| 190 | HNRPD, WARS, SFRS2, EPAS1, EIF4E, MTHFD2, PSME2, GBP1, DLGAP4, TYMS, TES, LMAN1, ARF6, CDC40, CXCL9, IRF8, CXCL10, FAS, TRIM25, SLC25A11, NDUFA9, WHSC1, CA2, ME2, TLK1, CXCL11, SLC4A4, RBM25, AK2, hCAP-D3, DDAH2, FLJ10534, SEC10L1, BRIP1, STAT1 | 92% | 79% | 85% | 83% | 69% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 191 | WARS, EPAS1, EIF4E, PRDX3, MTHFD2, PSME2, DLGAP4, TYMS, TES, LMAN1, CDC40, CXCL9, IRF8, RABIF, CXCL10, FAS, SLC25A11, C1QBP, NDUFA9, WHSC1, CA2, ME2, CXCL11, SLC4A4, RBM25, AK2, hCAP-D3, SOCS6, CDC42BPA, FLJ10534, DKFZp762E1312, SEC10L1, FLJ13220, PBK, HNRPD, TRMT5, STAT1 | 77% | 83% | 85% | 76% | 85% | 79% |
| 192 | WARS, SFRS2, STAT1, EIF4E, PRDX3, MTHFD2, PSME2, MCM6, TK1, GMFB, DLGAP4, TYMS, CTSS, CDC40, CXCL9, CXCL10, PLK4, KITLG, SLC25A11, C1QBP, NDUFA9, C17orf25, CA2, ME2, CXCL11, IFT20, RBM25, hCAP-D3, ATP5A1, FAS, FLJ10534, MARCH5, SEC10L1, PBK, HNRPD, BRIP1, TRMT5 | 73% | 86% | 85% | 83% | 85% | 83% |
| 193 | HNRPD, WARS, EPAS1, STAT1, EIF4E, PRDX3, MTHFD2, PSME2, TK1, GMFB, DLGAP4, TYMS, TES, MAD2L1, CXCL9, CXCL10, FAS, PLK4, HNRPA3P1, C1QBP, NDUFA9, SLC25A11, WHSC1, C17orf25, CA2, ME2, SLC4A4, RBM25, hCAP-D3, SOCS6, BAZ1A, FLJ10534, SEC10L1, FLJ13220, PBK, BRIP1 | 77% | 76% | 85% | 83% | 81% | 72% |
| 194 | SFRS2, PAICS, EIF4E, PRDX3, MTHFD2, PSME2, TK1, GMFB, DLGAP4, TYMS, TES, CTSS, LMAN1, CDC40, CXCL9, CXCL10, FAS, TRIM25, C1QBP, NDUFA9, SLC25A11, WHSC1, CA2, ME2, CXCL11, IFT20, RBBP4, SLC4A4, RBM25, AK2, hCAP-D3, BRRN1, CDC42BPA, MARCH5, FLJ13220, HNRPD, STAT1 | 77% | 83% | 85% | 83% | 81% | 76% |
| 195 | WARS, SFRS2, EPAS1, EIF4E, SFPQ, MTHFD2, PSME2, MCM6, GMFB, DLGAP4, TYMS, USP4, DCK, ARF6, CDC40, CXCL10, FAS, CHEK1, HNRPA3P1, SLC25A11, NDUFA9, CA2, HNRPD, ME2, GZMB, RBBP4, TLK1, SLC4A4, CXCL11, RBM25, ATP5A1, AGPAT5, FLJ10534, FLJ13220, ETNK1, STAT1 | 81% | 86% | 88% | 76% | 85% | 79% |
| 196 | WARS, SFRS2, STAT1, EIF4E, PRDX3, MTHFD2, PSME2, MCM6, GMFB, DLGAP4, TYMS, ARF6, CDC40, SLC4A4, CXCL9, GTSE1, RABIF, CXCL10, FAS, HNRPA3P1, KITLG, NDUFA9, SLC25A11, WHSC1, C17orf25, CA2, HNRPD, ME2, CXCL11, RBBP4, RBM25, AK2, CDC42BPA, MARCH5, TRMT5, KLHL24 | 88% | 83% | 88% | 79% | 88% | 72% |
| 197 | WARS, SFRS2, EPAS1, STAT1, EIF4E, PRDX3, MTHFD2, PSME2, GMFB, DLGAP4, TYMS, DCK, CDC40, CXCL9, RABIF, CXCL10, FAS, PLK4, KITLG, C1QBP, NDUFA9, SLC25A11, WHSC1, CA2, HNRPD, ME2, FUT4, CXCL11, RBM25, CDC42BPA, MARCH5, DKFZp762E1312, SEC10L1, PBK | 77% | 79% | 85% | 79% | 88% | 79% |
| 198 | WARS, SFRS2, EPAS1, EIF4E, SFPQ, MTHFD2, PSME2, GMFB, DLGAP4, TYMS, USP4, CDC40, RABIF, CXCL10, PLK4, KITLG, C1QBP, NDUFA9, SLC25A11, WHSC1, C17orf25, ME2, CXCL11, IFT20, RBM25, CAMSAP1L1, BRRN1, FAS, AGPAT5, PSAT1, HNRPD, TRMT5, KLHL24, ETNK1, STAT1 | 85% | 90% | 77% | 83% | 77% | 66% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 199 | HNRPD, WARS, SFRS2, EPAS1, EIF4E, PRDX3, MTHFD2, PSME2, GMFB, DLGAP4, TYMS, TES, LMAN1, ARF6, CDC40, CXCL9, CXCL10, FAS, KITLG, C1QBP, NDUFA9, KPNB1, SLC25A11, CA2, ME2, GZMB, RBBP4, TLK1, CXCL11, RBM25, AK2, SOCS6, AGPAT5, SEC10L1, PBK, STAT1 | 92% | 90% | 96% | 76% | 85% | 76% |
| 200 | SFRS2, PAICS, EIF4E, PRDX3, PSME2, GMFB, DLGAP4, TYMS, DCK, ARF6, MAD2L1, CDC40, CXCL9, GTSE1, RABIF, CXCL10, FAS, C1QBP, NDUFA9, SLC25A11, C17orf25, CA2, ME2, GZMB, IFT20, CXCL11, RBM25, AK2, hCAP-D3, BRRN1, AGPAT5, DKFZp762E1312, PBK, PSAT1, HNRPD, TRMT5, ETNK1, STAT1 | 81% | 86% | 88% | 79% | 73% | 72% |
| 201 | HNRPD, WARS, SFRS2, STAT1, EIF4E, MTHFD2, PSME2, DLGAP4, TYMS, CXCL9, GTSE1, CXCL10, FAS, CHEK1, HNRPA3P1, TRIM25, KITLG, NDUFA9, SLC25A11, WHSC1, CA2, ME2, GZMB, IFT20, SLC4A4, CXCL11, RBM25, CAMSAP1L1, hCAP-D3, BRRN1, AGPAT5, MARCH5, DKFZp762E1312, SEC10L1, PBK, BRIP1 | 88% | 93% | 88% | 76% | 85% | 66% |
| 202 | WARS, SFRS2, STAT1, MTHFD2, PSME2, MCM6, GMFB, DLGAP4, TYMS, USP4, CTSS, ARF6, CDC40, CXCL9, CXCL10, FAS, HNRPA3P1, SLC25A11, CA2, HNRPD, ME2, FUT4, RBBP4, TLK1, CXCL11, SLC4A4, RBM25, AK2, CDC42BPA, AGPAT5, DKFZp762E1312, SEC10L1, FLJ13220, PBK, KLHL24, ETNK1 | 85% | 86% | 92% | 76% | 73% | 72% |
| 203 | WARS, SFRS2, STAT1, MTHFD2, PSME2, GMFB, DLGAP4, SLC4A4, CXCL9, CXCL10, FAS, CHEK1, TRIM25, KITLG, SLC25A11, C1QBP, NDUFA9, KPNB1, WHSC1, ME2, CXCL11, IFT20, RBM25, NUP210, CAMSAP1L1, BRRN1, CDC42BPA, DDAH2, AGPAT5, DKFZp762E1312, SEC10L1, FLJ13220, PBK, HNRPD, TRMT5, KLHL24 | 92% | 86% | 85% | 76% | 69% | 69% |
| 204 | WARS, SFRS2, EPAS1, EIF4E, PSME2, MCM6, GMFB, DLGAP4, TYMS, DCK, ARF6, SLC4A4, CXCL9, IRF8, CXCL10, FAS, KITLG, NDUFA9, SLC25A11, WHSC1, CA2, HNRPD, ME2, FUT4, GZMB, IFT20, RBBP4, CXCL11, RBM25, AK2, AGPAT5, MARCH5, SEC10L1, FLJ13220, PBK, BRIP1, ETNK1, STAT1 | 85% | 83% | 85% | 76% | 81% | 72% |
| 205 | WARS, SFRS2, EPAS1, EIF4E, MTHFD2, PSME2, GMFB, DLGAP4, TYMS, USP4, CTSS, LMAN1, MAD2L1, CDC40, SLC4A4, CXCL9, GTSE1, RABIF, CXCL10, FAS, PLK4, TRIM25, C1QBP, NDUFA9, SLC25A11, CA2, HNRPD, ME2, CXCL11, IFT20, RBM25, BRRN1, CDC42BPA, DDAH2, PSAT1, KLHL24, STAT1 | 96% | 86% | 81% | 79% | 85% | 72% |
| 206 | WARS, PAICS, EIF4E, MTHFD2, PSME2, TK1, GMFB, DLGAP4, TYMS, ARF6, SLC4A4, CXCL9, CXCL10, FAS, PLK4, TRIM25, SLC25A11, C1QBP, NDUFA9, KPNB1, WHSC1, C17orf25, HNRPD, ME2, CXCL11, IFT20, TLK1, RBM25, AK2, AGPAT5, SEC10L1, FLJ13220, BRIP1, TRMT5, KLHL24, STAT1 | 81% | 83% | 88% | 90% | 77% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature | | SVM | | 3NN | | 1NN | |
|---|---|---|---|---|---|---|---|
| Number | Signature Genes (as gene symbols) | Sens | Spec | Sens | Spec | Sens | Spec |
| 207 | WARS, SFRS2, EIF4E, PRDX3, MTHFD2, PSME2, GMFB, DLGAP4, TYMS, LMAN1, ARF6, CDC40, CXCL9, CXCL10, FAS, HNRPA3P1, KITLG, SLC25A11, C1QBP, NDUFA9, KPNB1, WHSC1, C17orf25, CA2, HNRPD, ME2, FUT4, CXCL11, GZMB, IFT20, SLC4A4, RBM25, AK2, SEC10L1, PBK, BRIP1, STAT1 | 85% | 90% | 96% | 79% | 85% | 79% |
| 208 | HNRPD, WARS, EPAS1, STAT1, EIF4E, PRDX3, MTHFD2, PSME2, GBP1, TK1, GMFB, DLGAP4, TYMS, TES, CDC40, CXCL9, IRF8, GTSE1, CXCL10, FAS, C1QBP, NDUFA9, C17orf25, ME2, SLC4A4, CXCL11, RBM25, NUP210, FLJ10534, MARCH5, DKFZp762E1312, FLJ13220, PBK, BRIP1, TRMT5, ETNK1 | 77% | 79% | 81% | 83% | 73% | 72% |
| 209 | WARS, EIF4E, PRDX3, MTHFD2, PSME2, DLGAP4, TYMS, USP4, LMAN1, MAD2L1, CDC40, SLC4A4, CXCL9, IRF8, GTSE1, RABIF, CXCL10, FAS, TRIM25, C1QBP, NDUFA9, SLC25A11, C17orf25, CA2, ME2, CXCL11, GZMB, IFT20, TLK1, RBM25, AK2, SOCS6, RBBP4, AGPAT5, MARCH5, SEC10L1, PBK, HNRPD, STAT1 | 85% | 86% | 88% | 79% | 85% | 76% |
| 210 | HNRPD, WARS, SFRS2, STAT1, EIF4E, SFPQ, PRDX3, MTHFD2, PSME2, MCM6, DLGAP4, TYMS, ARF6, MAD2L1, CDC40, CXCL9, RABIF, CXCL10, PLK4, CHEK1, TRIM25, C1QBP, NDUFA9, WHSC1, C17orf25, CA2, ME2, CXCL11, TLK1, BRRN1, SOCS6, FAS, AGPAT5, MARCH5, FLJ13220, PBK, TRMT5, KLHL24 | 77% | 79% | 85% | 86% | 81% | 79% |
| 211 | WARS, PAICS, EIF4E, PRDX3, MTHFD2, PSME2, TK1, GMFB, DLGAP4, TYMS, USP4, DCK, MAD2L1, CDC40, RABIF, CXCL10, FAS, HNRPA3P1, SLC25A11, NDUFA9, C17orf25, ME2, CXCL11, SLC4A4, RBM25, AK2, hCAP-D3, SOCS6, DDAH2, RBBP4, AGPAT5, DKFZp762E1312, SEC10L1, PBK, PSAT1, HNRPD, BRIP1, ETNK1, STAT1 | 77% | 79% | 85% | 76% | 81% | 72% |
| 212 | HNRPD, WARS, EPAS1, STAT1, EIF4E, MTHFD2, GBP1, TK1, GMFB, DLGAP4, TYMS, LMAN1, DCK, CDC40, CXCL9, IRF8, CXCL10, FAS, PLK4, HNRPA3P1, SLC25A11, NDUFA9, KPNB1, WHSC1, CA2, ME2, CXCL11, GZMB, RBBP4, SLC4A4, RBM25, NUP210, DDAH2, PBK, KLHL24, ETNK1 | 81% | 83% | 85% | 76% | 77% | 79% |
| 213 | HNRPD, WARS, SFRS2, STAT1, EIF4E, PRDX3, MTHFD2, GMFB, DLGAP4, TYMS, DCK, ARF6, CDC40, CXCL9, IRF8, CXCL10, FAS, TRIM25, SLC25A11, C1QBP, C17orf25, CA2, ME2, CXCL11, GZMB, IFT20, TLK1, RBM25, AK2, CDC42BPA, SEC10L1, FLJ13220, PBK, BRIP1, KLHL24, ETNK1 | 100% | 90% | 92% | 72% | 85% | 79% |
| 214 | WARS, EIF4E, MTHFD2, PSME2, TK1, GMFB, DLGAP4, TYMS, USP4, CDC40, CXCL9, IRF8, GTSE1, CXCL10, FAS, PLK4, TRIM25, C1QBP, SLC25A11, C17orf25, CA2, HNRPD, ME2, CXCL11, IFT20, AK2, BRRN1, SOCS6, CDC42BPA, SFRS2, RBBP4, MARCH5, SEC10L1, FLJ13220, PSAT1, BRIP1, TRMT5, KLHL24, STAT1 | 81% | 79% | 85% | 79% | 85% | 72% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 215 | HNRPD, WARS, SFRS2, EIF4E, PRDX3, MTHFD2, PSME2, GMFB, DLGAP4, TYMS, MAD2L1, CDC40, CXCL9, IRF8, GTSE1, CXCL10, SLC25A11, NDUFA9, WHSC1, CA2, ME2, CXCL11, IFT20, RBM25, AK2, BRRN1, CDC42BPA, FAS, RBBP4, BAZ1A, AGPAT5, SEC10L1, FLJ13220, PBK, BRIP1, KLHL24, ETNK1, STAT1 | 85% | 86% | 88% | 72% | 81% | 72% |
| 216 | HNRPD, WARS, SFRS2, EPAS1, EIF4E, PRDX3, MTHFD2, PSME2, GMFB, DLGAP4, TYMS, TES, CTSS, LMAN1, CDC40, CXCL9, IRF8, CXCL10, FAS, PLK4, HNRPA3P1, KITLG, C1QBP, NDUFA9, SLC25A11, WHSC1, C17orf25, CA2, ME2, CXCL11, RBM25, AK2, hCAP-D3, BAZ1A, AGPAT5, DKFZp762E1312, PBK, BRIP1 | 73% | 83% | 88% | 79% | 85% | 72% |
| 217 | WARS, EIF4E, MTHFD2, PSME2, MCM6, DLGAP4, TYMS, USP4, TES, DCK, ARF6, MAD2L1, CDC40, CXCL9, IRF8, CXCL10, PLK4, HNRPA3P1, TRIM25, SLC25A11, C1QBP, WHSC1, CA2, ME2, CXCL11, GZMB, IFT20, TLK1, SLC4A4, RBM25, SOCS6, DDAH2, FAS, FLJ13220, PBK, KLHL24, ETNK1, STAT1 | 85% | 86% | 81% | 79% | 77% | 76% |
| 218 | WARS, SFRS2, EPAS1, STAT1, PAICS, PRDX3, MTHFD2, PSME2, MCM6, GMFB, DLGAP4, TYMS, USP4, TES, LMAN1, SLC4A4, CXCL9, IRF8, CXCL10, FAS, PLK4, CHEK1, HNRPA3P1, TRIM25, C1QBP, NDUFA9, CA2, ME2, FUT4, CXCL11, RBM25, AK2, ATP5A1, AGPAT5, SEC10L1, FLJ13220, HNRPD, KLHL24 | 81% | 83% | 85% | 83% | 88% | 76% |
| 219 | WARS, SFRS2, EIF4E, PRDX3, MTHFD2, PSME2, GBP1, GMFB, DLGAP4, TYMS, USP4, CDC40, CXCL9, CXCL10, FAS, PLK4, HNRPA3P1, SLC25A11, NDUFA9, WHSC1, C17orf25, CA2, ME2, CXCL11, IFT20, RBM25, hCAP-D3, ATP5A1, RBBP4, AGPAT5, FLJ10534, MARCH5, SEC10L1, HNRPD, BRIP1, KLHL24, STAT1 | 81% | 79% | 85% | 79% | 88% | 76% |
| 220 | HNRPD, WARS, SFRS2, EPAS1, SFPQ, PRDX3, MTHFD2, PSME2, GMFB, TYMS, USP4, TES, LMAN1, CDC40, CXCL9, CXCL10, FAS, C1QBP, SLC25A11, WHSC1, CA2, ME2, FUT4, TLK1, CXCL11 SLC4A4, RBM25, hCAP-D3, DDAH2, BAZ1A, FLJ10534, MARCH5, FLJ13220, PBK, PSAT1, BRIP1,TRMT5, STAT1 | 73% | 79% | 85% | 79% | 85% | 83% |
| 221 | HNRPD, EPAS1, STAT1, PRDX3, MTHFD2, PSME2, TK1, GMFB, DLGAP4, TYMS, USP4, CTSS, DCK, CXCL9, CXCL10, FAS, CHEK1, HNRPA3P1, C1QBP, NDUFA9, KPNB1, SLC25A11 WHSC1, CA2, ME2, CXCL11, TLK1, RBM25, ATP5A1, DDAH2, RBBP4, SEC10L1, PBK, BRIP1, ETNK1 | 81% | 83% | 88% | 83% | 85% | 86% |
| 222 | WARS, SFRS2, EIF4E, MTHFD2, PSME2, DLGAP4, TYMS, ARF6, CXCL9, IRF8, GTSE1, RABIF, CXCL10, FAS, PLK4, KITLG, SLC25A11, C1QBP, NDUFA9, ME2, CXCL11, GZMB, IFT20, RBBP4, SLC4A4, RBM25, AK2, BAZ1A, AGPAT5, MARCH5, FLJ13220, HNRPD, BRIP1, KLHL24, ETNK1, STAT1 | 88% | 86% | 92% | 72% | 81% | 72% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 223 | HNRPD, WARS, SFRS2, STAT1, EIF4E, MTHFD2, PSME2, GMFB, DLGAP4, TYMS, LMAN1, ARF6, CXCL9, GTSE1, CXCL10, FAS, PLK4, HNRPA3P1, TRIM25, KITLG, C1QBP, SLC25A11, WHSC1, C17orf25, CA2, ME2, CXCL11, TLK1, RBM25, ATP5A1, AGPAT5, FLJ10534, MARCH5, FLJ13220, PBK, BRIP1, TRMT5 | 85% | 83% | 88% | 76% | 81% | 83% |
| 224 | HNRPD, WARS, SFRS2, EIF4E, PRDX3, MTHFD2, PSME2, GMFB, DLGAP4, TYMS, USP4, TES, CDC40, SLC4A4, CXCL9, CXCL10, FAS, TRIM25, KITLG, C1QBP, NDUFA9, C17orf25, CA2, ME2, GZMB, TLK1, CXCL11, RBM25, CAMSAP1L1, CDC42BPA, DDAH2, BAZ1A, AGPAT5, SEC10L1, PBK, KLHL24, ETNK1, STAT1 | 85% | 79% | 92% | 76% | 85% | 72% |
| 225 | WARS, EIF4E, PRDX3, MTHFD2, PSME2, GMFB, DLGAP4, TYMS, USP4, CTSS, ARF6, CDC40, CXCL9, IRF8, CXCL10, FAS, PLK4, CHEK1, TRIM25, C1QBP, NDUFA9, SLC25A11, WHSC1, CA2, HNRPD, ME2, CXCL11, GZMB, IFT20, RBBP4, SLC4A4, RBM25, ATP5A1, PBK, BRIP1, TRMT5, STAT1 | 81% | 79% | 88% | 76% | 88% | 79% |
| 226 | HNRPD, WARS, SFRS2, EIF4E, MTHFD2, PSME2, GMFB, DLGAP4, TYMS, LMAN1, DCK, CXCL9, CXCL10, FAS, HNRPA3P1, TRIM25, C1QBP, NDUFA9, SLC25A11, WHSC1, ME2, SLC4A4, CXCL11, RBM25, BRRN1, BAZ1A, AGPAT5, FLJ10534, MARCH5, SEC10L1, FLJ13220, PBK, PSAT1, BRIP1, TRMT5, ETNK1, STAT1 | 77% | 79% | 77% | 86% | 73% | 69% |
| 227 | HNRPD, WARS, SFRS2, EPAS1, PRDX3, PSME2, GBP1, TK1, DLGAP4, TYMS, DCK, ARF6, CDC40, CXCL9, GTSE1, RABIF, CXCL10, FAS, TRIM25, C1QBP, NDUFA9, SLC25A11, C17orf25, CA2, ME2, CXCL11, GZMB, IFT20, RBBP4, RBM25, AGPAT5, MARCH5, SEC10L1, FLJ13220, PBK, BRIP1, STAT1 | 81% | 90% | 92% | 76% | 88% | 69% |
| 228 | WARS, SFRS2, EPAS1, STAT1, EIF4E, MTHFD2, GMFB, DLGAP4, TYMS, TES, CTSS, CXCL9, CXCL10, FAS, PLK4, CHEK1, TRIM25, SLC25A11, NDUFA9, WHSC1, C17orf25, CA2, ME2, FUT4, CXCL11, SLC4A4, RBM25, AK2, BRRN1, CDC42BPA, DDAH2, AGPAT5, MARCH5, PBK, HNRPD, KLHL24 | 77% | 83% | 88% | 76% | 88% | 76% |
| 229 | HNRPD, WARS, SFRS2, EPAS1, PAICS, EIF4E, PRDX3, MTHFD2, PSME2, DLGAP4, TYMS, CXCL9, IRF8, RABIF, FAS, PLK4, TRIM25, SLC25A11, C1QBP, WHSC1, C17orf25, CA2, ME2, FUT4, CXCL11, GZMB, IFT20, RBM25, SOCS6, DDAH2, MARCH5, PBK, PSAT1, BRIP1, TRMT5, STAT1 | 85% | 86% | 85% | 72% | 85% | 76% |
| 230 | WARS, SFRS2, STAT1, MTHFD2, PSME2, GMFB, DLGAP4, TYMS, USP4, TES, ARF6, CDC40, CXCL9, CXCL10, FAS, HNRPA3P1, C1QBP, SLC25A11, WHSC1, ME2, CXCL11, RBBP4, SLC4A4, RBM25, AK2, hCAP-D3, CDC42BPA, FLJ10534, SEC10L1, FLJ13220, PBK, PSAT1, HNRPD, BRIP1, TRMT5, KLHL24 | 73% | 83% | 81% | 76% | 69% | 66% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 231 | SFRS2, EPAS1, EIF4E, MTHFD2, PSME2, MCM6, TK1, GMFB, DLGAP4, TYMS, CTSS, LMAN1, CXCL9, IRF8, CXCL10, CHEK1, HNRPA3P1, KITLG, SLC25A11, C1QBP, NDUFA9, WHSC1, C17orf25, ME2, FUT4, CXCL11, GZMB, RBM25, CDC42BPA, FAS, RBBP4, AGPAT5, FLJ10534, SEC10L1, FLJ13220, PBK, HNRPD, TRMT5, STAT1 | 73% | 76% | 92% | 72% | 77% | 76% |
| 232 | HNRPD, WARS, SFRS2, PAICS, EIF4E, MTHFD2, PSME2, MCM6, GBP1, TK1, GMFB, DLGAP4, TYMS, USP4, TES, CDC40, CXCL9, IRF8, RABIF, CXCL10, CHEK1, C1QBP, NDUFA9, SLC25A11, WHSC1, CA2, ME2, FUT4, CXCL11, IFT20, TLK1, SLC4A4, RBM25, NUP210, CAMSAP1L1, BRRN1, FAS, RBBP4, BAZ1A, FLJ10534, MARCH5, SEC10L1, FLJ13220, PBK, PSAT1, KLHL24, STAT1 | 73% | 79% | 88% | 86% | 81% | 83% |
| 233 | WARS, EIF4E, PRDX3, MTHFD2, PSME2, GMFB, DLGAP4, TYMS, USP4, TES, LMAN1, DCK, ARF6, MAD2L1, CDC40, SLC4A4, CXCL9, GTSE1, CXCL10, FAS, KITLG, NDUFA9, SLC25A11, WHSC1, C17orf25, CA2, HNRPD, ME2, FUT4, CXCL11, GZMB, IFT20, TLK1, RBM25, AK2, CAMSAP1L1, DDAH2, RBBP4, BAZ1A, AGPAT5, SEC10L1, PBK, BRIP1, KLHL24, ETNK1, STAT1 | 77% | 79% | 92% | 76% | 88% | 76% |
| 234 | WARS, SFRS2, EPAS1, STAT1, PAICS, EIF4E, PRDX3, MTHFD2, PSME2, GBP1, GMFB, DLGAP4, TYMS, ARF6, CDC40, CXCL9, IRF8, RABIF, CXCL10, FAS, SLC25A11, NDUFA9, C17orf25, CA2, ME2, CXCL11, GZMB, IFT20, RBBP4, TLK1, SLC4A4, RBM25, NUP210, BRRN1, ATP5A1, AGPAT5, MARCH5, SEC10L1, PBK, PSAT1, HNRPD, BRIP1, TRMT5 | 85% | 90% | 92% | 79% | 77% | 83% |
| 235 | WARS, SFRS2, EPAS1, STAT1, EIF4E, PRDX3, MTHFD2, PSME2, GMFB, DLGAP4, TYMS, USP4, CTSS, DCK, ARF6, MAD2L1, CDC40, CXCL9, CXCL10, PLK4, CHEK1, TRIM25, KITLG, SLC25A11, C1QBP, KPNB1, WHSC1, C17orf25, CA2, HNRPD, ME2, GZMB, CXCL11, RBM25, BRRN1, ATP5A1, CDC42BPA, DDAH2, FAS, BAZ1A, AGPAT5, FLJ10534, MARCH5, SEC10L1, PBK, TRMT5, KLHL24, ETNK1 | 81% | 90% | 92% | 76% | 85% | 69% |
| 236 | HNRPD, WARS, SFRS2, EPAS1, EIF4E, MTHFD2, PSME2, TK1, GMFB, DLGAP4, TYMS, USP4, TES, CTSS, DCK, ARF6, MAD2L1, CDC40, CXCL9, RABIF, CXCL10, CHEK1, HNRPA3P1, TRIM25, KITLG, C1QBP, NDUFA9, KPNB1, SLC25A11, WHSC1, CA2, ME2, GZMB, SLC4A4, CXCL11, RBM25, AK2, ATP5A1, DDAH2, FAS, BAZ1A, DKFZp762E1312, SEC10L1, FLJ13220, BRIP1, TRMT5, ETNK1, STAT1 | 81% | 83% | 88% | 72% | 81% | 76% |
| 237 | WARS, SFRS2, PAICS, EIF4E, PRDX3, MTHFD2, PSME2, TK1, GMFB, DLGAP4, TYMS, USP4, DCK, ARF6, MAD2L1, SLC4A4, CXCL9, GTSE1, CXCL10, FAS, HNRPA3P1, KITLG, SLC25A11, C1QBP, NDUFA9, KPNB1, C17orf25, CA2, HNRPD, ME2, CXCL11, GZMB, IFT20, RBBP4, RBM25, AK2, ATP5A1, BAZ1A, AGPAT5, SEC10L1, FLJ13220, PBK, BRIP1, ETNK1, STAT1 | 77% | 83% | 92% | 83% | 81% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 238 | HNRPD, WARS, SFRS2, EPAS1, EIF4E, PRDX3, MTHFD2, PSME2, GMFB, DLGAP4, TYMS, TES, CTSS, LMAN1, SLC4A4, CXCL9, IRF8, GTSE1, CXCL10, CHEK1, TRIM25, KITLG, SLC25A11, C1QBP, NDUFA9, KPNB1, WHSC1, C17orf25, CA2, ME2, FUT4, TLK1, CXCL11, RBM25, BRRN1, DDAH2, FAS, RBBP4, AGPAT5, FLJ10534, MARCH5, SEC10L1, FLJ13220, PBK, TRMT5, STAT1 | 85% | 86% | 88% | 86% | 85% | 79% |
| 239 | HNRPD, WARS, SFRS2, EPAS1, EIF4E, PRDX3, MTHFD2, PSME2, TK1, GMFB, DLGAP4, TYMS, DCK, CDC40, CXCL9, IRF8, GTSE1, RABIF, CXCL10, FAS, CHEK1, SLC25A11, C1QBP, NDUFA9, WHSC1, C17orf25, CA2, ME2, IFT20, CXCL11, SLC4A4, RBM25, AK2, hCAP-D3, ATP5A1, SOCS6, DDAH2, FLJ10534, MARCH5, SEC10L1, PBK, PSAT1, BRIP1, STAT1 | 69% | 79% | 88% | 83% | 81% | 76% |
| 240 | WARS, SFRS2, EPAS1, STAT1, EIF4E, PRDX3, MTHFD2, TK1, GMFB, DLGAP4, TYMS, CTSS, LMAN1, ARF6, MAD2L1, CXCL9, IRF8, RABIF, CXCL10, FAS, HNRPA3P1, TRIM25, KITLG, C1QBP, NDUFA9, SLC25A11, WHSC1, C17orf25, HNRPD, ME2, GZMB, SLC4A4, CXCL11, RBM25, AK2, CAMSAP1L1, hCAP-D3, BRRN1, CDC42BPA, RBBP4, BAZ1A, FLJ10534, SEC10L1, BRIP1, KLHL24, ETNK1 | 81% | 83% | 96% | 69% | 81% | 76% |
| 241 | HNRPD, WARS, SFRS2, EIF4E, PRDX3, MTHFD2, PSME2, TK1, GMFB, DLGAP4, TYMS, LMAN1, MAD2L1, CDC40, CXCL9, RABIF, CXCL10, FAS, PLK4, TRIM25, SLC25A11, NDUFA9, KPNB1, WHSC1, CA2, ME2, CXCL11, TLK1, SLC4A4, RBM25, hCAP-D3, BRRN1, SOCS6, CDC42BPA, DDAH2, RBBP4, BAZ1A, AGPAT5, DKFZp762E1312, SEC10L1, PBK, BRIP1, KLHL24, ETNK1, STAT1 | 73% | 79% | 88% | 83% | 92% | 79% |
| 242 | WARS, STAT1, EIF4E, MTHFD2, PSME2, TK1, GMFB, DLGAP4, TYMS, USP4, CTSS, LMAN1, DCK, ARF6, MAD2L1, CDC40, CXCL9, RABIF, CXCL10, FAS, PLK4, TRIM25, KITLG, SLC25A11, C1QBP, NDUFA9, KPNB1, C17orf25, CA2, ME2, CXCL11, GZMB, SLC4A4, RBM25, AK2, hCAP-D3, DDAH2, RBBP4, BAZ1A, PSAT1, HNRPD, BRIP1, TRMT5, KLHL24, ETNK1 | 81% | 83% | 85% | 79% | 81% | 69% |
| 243 | WARS, SFRS2, EPAS1, EIF4E, MTHFD2, PSME2, GMFB, DLGAP4, TYMS, USP4, CTSS, LMAN1, CDC40, SLC4A4, CXCL9, CXCL10, FAS, PLK4, CHEK1, KITLG, C1QBP, NDUFA9, WHSC1, CA2, HNRPD, ME2, CXCL11, GZMB, TLK1, RBM25, AK2, hCAP-D3, BRRN1, CDC42BPA, RBBP4, BAZ1A, AGPAT5, SEC10L1, FLJ13220, PBK, BRIP1, KLHL24, ETNK1, STAT1 | 85% | 83% | 92% | 79% | 77% | 72% |
| 244 | WARS, SFRS2, EPAS1, STAT1, EIF4E, PRDX3, MTHFD2, PSME2, GBP1, TK1, GMFB, DLGAP4, TYMS, USP4, ARF6, CDC40, SLC4A4, CXCL9, RABIF, CXCL10, FAS, PLK4, CHEK1, KITLG, SLC25A11, C1QBP, NDUFA9, WHSC1, CA2, HNRPD, ME2, CXCL11, GZMB, IFT20, RBM25, CAMSAP1L1, BRRN1, CDC42BPA, BAZ1A, AGPAT5, FLJ10534, DKFZp762E1312, PBK, ETNK1 | 81% | 83% | 88% | 79% | 81% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 245 | HNRPD, WARS, SFRS2, EPAS1, PAICS, EIF4E, PRDX3, MTHFD2, PSME2, MCM6, GMFB, DLGAP4, TYMS, TES, DCK, CDC40, SLC4A4, CXCL9, CXCL10, PLK4, CHEK1, HNRPA3P1, KITLG, C1QBP, NDUFA9, SLC25A11, WHSC1, CA2, ME2, GZMB, RBBP4, CXCL11, RBM25, AK2, NUP210, CAMSAP1L1, hCAP-D3, CDC42BPA, FAS, MARCH5, SEC10L1, PBK, ETNK1, STAT1 | 77% | 86% | 88% | 76% | 77% | 76% |
| 246 | WARS, SFRS2, EPAS1, EIF4E, PRDX3, MTHFD2, PSME2, GBP1, GMFB, DLGAP4, TYMS, TES, LMAN1, CDC40, SLC4A4, CXCL9, RABIF, CXCL10, FAS, PLK4, HNRPA3P1, SLC25A11, C1QBP, NDUFA9, KPNB1, WHSC1, C17orf25, CA2, ME2, FUT4, GZMB, TLK1, CXCL11, RBM25, CAMSAP1L1, DDAH2, AGPAT5, MARCH5, SEC10L1, FLJ13220, PBK, HNRPD, BRIP1, ETNK1, STAT1 | 77% | 83% | 92% | 79% | 81% | 79% |
| 247 | WARS, SFRS2, EPAS1, EIF4E, PRDX3, MTHFD2, PSME2, GBP1, GMFB, DLGAP4, TYMS, USP4, TES, MAD2L1, CDC40, SLC4A4, CXCL9, IRF8, GTSE1, CXCL10, PLK4, KITLG, C1QBP, NDUFA9, KPNB1, SLC25A11, WHSC1, C17orf25, CA2, ME2, IFT20, RBBP4, CXCL11, RBM25, AK2, CAMSAP1L1, CDC42BPA, FAS, AGPAT5, FLJ10534, MARCH5, SEC10L1, PBK, HNRPD, BRIP1, KLHL24, ETNK1, STAT1 | 77% | 83% | 85% | 79% | 85% | 72% |
| 248 | HNRPD, WARS, SFRS2, EIF4E, PRDX3, MTHFD2, PSME2, MCM6, GBP1, TK1, GMFB, DLGAP4, TYMS, USP4, DCK, CDC40, CXCL9, GTSE1, RABIF, CXCL10, FAS, PLK4, TRIM25, C1QBP, NDUFA9, SLC25A11, WHSC1, C17orf25, CA2, ME2, FUT4, GZMB, IFT20, RBBP4, CXCL11, SLC4A4, RBM25, BRRN1, AGPAT5, FLJ10534, MARCH5, FLJ13220, PSAT1, TRMT5, KLHL24, ETNK1, STAT1 | 77% | 86% | 88% | 76% | 81% | 69% |
| 249 | HNRPD, WARS, SFRS2, EPAS1, EIF4E, MTHFD2, PSME2, GMFB, DLGAP4, TYMS, USP4, MAD2L1, SLC4A4, CXCL9, GTSE1, CXCL10, FAS, PLK4, TRIM25, KITLG, NDUFA9, KPNB1, WHSC1, C17orf25, CA2, ME2, FUT4, CXCL11, GZMB, IFT20, TLK1, RBM25, CAMSAP1L1, BRRN1, SOCS6, CDC42BPA, BAZ1A, AGPAT5, MARCH5, SEC10L1, FLJ13220, KLHL24, ETNK1, STAT1 | 92% | 97% | 88% | 76% | 85% | 79% |
| 250 | HNRPD, WARS, SFRS2, EPAS1, EIF4E, SFPQ, PRDX3, MTHFD2, PSME2, GMFB, DLGAP4, TYMS, USP4, ARF6, CDC40, CXCL9, CXCL10, FAS, CHEK1, TRIM25, NDUFA9, KPNB1, SLC25A11, C17orf25, CA2, ME2, CXCL11, IFT20, TLK1, SLC4A4, RBM25, AK2, BRRN1, ATP5A1, DDAH2, BAZ1A, AGPAT5, MARCH5, SEC10L1, FLJ13220, PBK, PSAT1, BRIP1, STAT1 | 92% | 90% | 92% | 76% | 85% | 79% |
| 251 | WARS, EPAS1, STAT1, EIF4E, SFPQ, PRDX3, MTHFD2, PSME2, TK1, GMFB, DLGAP4, TYMS, LMAN1, ARF6, SLC4A4, CXCL9, IRF8, GTSE1, CXCL10, FAS, PLK4, HNRPA3P1, SLC25A11, C1QBP, NDUFA9, CA2, HNRPD, ME2, FUT4, CXCL11, GZMB, IFT20, TLK1, RBM25, AK2, ATP5A1, SOCS6, DDAH2, RBBP4, AGPAT5, MARCH5, SEC10L1, FLJ13220, BRIP1, TRMT5 | 77% | 90% | 92% | 76% | 85% | 72% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM | | 3NN | | 1NN | |
|---|---|---|---|---|---|---|---|
| | | Sens | Spec | Sens | Spec | Sens | Spec |
| 252 | WARS, SFRS2, EPAS1, PAICS, EIF4E, PRDX3, MTHFD2, PSME2, GBP1, GMFB, DLGAP4, TYMS, USP4, CTSS, DCK, CDC40, SLC4A4, GTSE1, RABIF, CXCL10, FAS, PLK4, HNRPA3P1, C1QBP, SLC25A11, WHSC1, HNRPD, ME2, FUT4, CXCL11, IFT20, TLK1, RBM25, AK2, NUP210, BRRN1, ATP5A1, AGPAT5, FLJ10534, DKFZp762E1312, SEC10L1, FLJ13220, PBK, TRMT5, KLHL24, ETNK1, STAT1 | 65% | 83% | 77% | 90% | 73% | 76% |
| 253 | HNRPD, WARS, EPAS1, STAT1, EIF4E, PRDX3, MTHFD2, PSME2, GMFB, DLGAP4, TYMS, USP4, TES, LMAN1, DCK, SLC4A4, CXCL9, CXCL10, FAS, PLK4, C1QBP, NDUFA9, KPNB1, SLC25A11, WHSC1, C17orf25, CA2, ME2, FUT4, CXCL11, RBBP4, TLK1, RBM25, CAMSAP1L1, ATP5A1, MARCH5, SEC10L1, PBK, PSAT1, BRIP1, TRMT5, KLHL24, ETNK1 | 73% | 83% | 85% | 79% | 81% | 76% |
| 254 | HNRPD, WARS, EPAS1, EIF4E, MTHFD2, PSME2, MCM6, GBP1, GMFB, DLGAP4, TYMS, USP4, CTSS, DCK, ARF6, SLC4A4, CXCL9, IRF8, CXCL10, FAS, PLK4, CHEK1, HNRPA3P1, C1QBP, NDUFA9, SLC25A11, WHSC1, C17orf25, CA2, ME2, FUT4, IFT20, RBBP4, CXCL11, RBM25, NUP210, hCAP-D3, SFRS2, DDAH2, BAZ1A, AGPAT5, FLJ10534, DKFZp762E1312, SEC10L1, FLJ13220, KLHL24, STAT1 | 77% | 76% | 92% | 86% | 88% | 79% |
| 255 | HNRPD, WARS, SFRS2, EPAS1, EIF4E, PRDX3, MTHFD2, PSME2, GBP1, TK1, GMFB, DLGAP4, TYMS, LMAN1, CDC40, CXCL9, CXCL10, PLK4, CHEK1, TRIM25, KITLG, C1QBP, NDUFA9, WHSC1, C17orf25, CA2, ME2, CXCL11, SLC4A4, RBM25, AK2, NUP210, DDAH2, FAS, BAZ1A, AGPAT5, FLJ10534, MARCH5, DKFZp762E1312, SEC10L1, PBK, PSAT1, BRIP1, KLHL24, STAT1 | 81% | 79% | 85% | 79% | 85% | 76% |
| 256 | WARS, SFRS2, EPAS1, STAT1, EIF4E, SFPQ, PRDX3, MTHFD2, TK1, GMFB, DLGAP4, TYMS, USP4, LMAN1, ARF6, CDC40, SLC4A4, CXCL9, RABIF, CXCL10, FAS, PLK4, CHEK1, TRIM25, KITLG, SLC25A11, C1QBP, NDUFA9, C17orf25, CA2, ME2, TLK1, RBM25, NUP210, AGPAT5, FLJ10534, SEC10L1, FLJ13220, PBK, PSAT1, HNRPD, BRIP1, TRMT5, KLHL24 | 77% | 83% | 85% | 79% | 81% | 83% |
| 257 | WARS, SFRS2, EIF4E, MTHFD2, PSME2, GBP1, TK1, GMFB, DLGAP4, TYMS, LMAN1, MAD2L1, CDC40, CXCL9, CXCL10, FAS, CHEK1, HNRPA3P1, KITLG, SLC25A11, C1QBP, NDUFA9, KPNB1, WHSC1, CA2, HNRPD, ME2, GZMB, TLK1, SLC4A4, CXCL11, RBM25, AK2, CAMSAP1L1, DDAH2, AGPAT5, FLJ10534, MARCH5, DKFZp762E1312, PBK, PSAT1, BRIP1, TRMT5, KLHL24, ETNK1, STAT1 | 73% | 86% | 88% | 83% | 77% | 72% |

TABLE 9-continued

Additional Prognostic signatures (note SVM = support vector machine, 3NN = 3 nearest neighbours, 1NN = 1 nearest neighbour, Sens = sensitivity, Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 258 | WARS, SFRS2, EPAS1, EIF4E, MTHFD2, PSME2, TK1, GMFB, DLGAP4, TYMS, LMAN1, ARF6, CDC40, CXCL9, CXCL10, FAS, PLK4, CHEK1, HNRPA3P1, SLC25A11, C1QBP, NDUFA9, WHSC1, C17orf25, HNRPD, ME2, CXCL11, IFT20, RBBP4, SLC4A4, RBM25, AK2, ATP5A1, SOCS6, FLJ10534, MARCH5, DKFZp762E1312, SEC10L1, FLJ13220, PBK, PSAT1, BRIP1, TRMT5, ETNK1, STAT1 | 77% | 83% | 73% | 86% | 73% | 76% |
| 259 | HNRPD, WARS, EPAS1, PAICS, MTHFD2, PSME2, MCM6, GMFB, DLGAP4, TYMS, CDC40, CXCL9, RABIF, CXCL10, FAS, PLK4, HNRPA3P1, TRIM25, SLC25A11, C1QBP, NDUFA9, WHSC1, CA2, ME2, CXCL11, GZMB, IFT20, RBBP4, TLK1, RBM25, AK2, CAMSAP1L1, ATP5A1, CDC42BPA, DDAH2, BAZ1A, AGPAT5, FLJ10534, MARCH5, SEC10L1, FLJ13220, PBK, PSAT1, BRIP1, ETNK1, STAT1 | 85% | 93% | 92% | 72% | 77% | 72% |
| 260 | HNRPD, WARS, SFRS2, PAICS, EIF4E, PRDX3, MTHFD2, PSME2, GMFB, DLGAP4, TYMS, ARF6, MAD2L1, CDC40, CXCL9, GTSE1, RABIF, CXCL10, PLK4, CHEK1, HNRPA3P1, TRIM25, NDUFA9, SLC25A11, WHSC1, C17orf25, CA2, ME2, FUT4, CXCL11, IFT20, SLC4A4, RBM25, AK2, NUP210, ATP5A1, SOCS6, FAS, AGPAT5, FLJ10534, MARCH5, SEC10L1, PBK, PSAT1, BRIP1, ETNK1, STAT1 | 77% | 79% | 85% | 76% | 85% | 69% |
| 261 | HNRPD, WARS, SFRS2, STAT1, MTHFD2, TK1, GMFB, DLGAP4, TYMS, USP4, CTSS, ARF6, SLC4A4, CXCL9, GTSE1, CXCL10, FAS, HNRPA3P1, TRIM25, SLC25A11, C1QBP, NDUFA9, KPNB1, WHSC1, C17orf25, CA2, ME2, CXCL11, GZMB, IFT20, RBM25, hCAP-D3, ATP5A1, SOCS6, DDAH2, BAZ1A, MARCH5, SEC10L1, FLJ13220, PBK, PSAT1, BRIP1, ETNK1 | 85% | 83% | 88% | 72% | 77% | 76% |
| 262 | HNRPD, WARS, SFRS2, EPAS1, EIF4E, MTHFD2, PSME2, TK1, GMFB, DLGAP4, TYMS, USP4, LMAN1, DCK, CDC40, CXCL9, CXCL10, FAS, PLK4, CHEK1, HNRPA3P1, KITLG, C1QBP, NDUFA9, SLC25A11, WHSC1, C17orf25, CA2, ME2, CXCL11, IFT20, SLC4A4, RBM25, AK2, ATP5A1, SOCS6, BAZ1A, AGPAT5, FLJ10534, SEC10L1, PBK, PSAT1, BRIP1, KLHL24, ETNK1, STAT1 | 77% | 79% | 85% | 79% | 85% | 76% |
| 263 | HNRPD, WARS, SFRS2, EPAS1, STAT1, EIF4E, PRDX3, PSME2, MCM6, GBP1, GMFB, DLGAP4, USP4, CTSS, ARF6, CDC40, SLC4A4, CXCL9, GTSE1, RABIF, CXCL10, FAS, CHEK1, HNRPA3P1, KITLG, C1QBP, NDUFA9, KPNB1, WHSC1, CA2, ME2, CXCL11, RBM25, CDC42BPA, RBBP4, AGPAT5, MARCH5, SEC10L1, FLJ13220, PBK, PSAT1, TRMT5, KLHL24 | 81% | 83% | 88% | 79% | 81% | 79% |
| 264 | WARS, SFRS2, EPAS1, EIF4E, SFPQ, PRDX3, MTHFD2, PSME2, GBP1, TK1, GMFB, DLGAP4, TYMS, CTSS, LMAN1, CDC40, SLC4A4, CXCL9, IRF8, CXCL10, FAS, PLK4, TRIM25, SLC25A11, C1QBP, NDUFA9, WHSC1, CA2, HNRPD, ME2, CXCL11, GZMB, TLK1, RBM25, AK2, hCAP-D3, ATP5A1, CDC42BPA, BAZ1A, AGPAT5, MARCH5, SEC10L1, PBK, TRMT5, KLHL24, STAT1 | 88% | 86% | 88% | 83% | 85% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM | | 3NN | | 1NN | |
|---|---|---|---|---|---|---|---|
| | | Sens | Spec | Sens | Spec | Sens | Spec |
| 265 | HNRPD, WARS, EPAS1, PAICS, EIF4E, SFPQ, PRDX3, MTHFD2, PSME2, TK1, GMFB, DLGAP4, TYMS, USP4, CTSS, LMAN1, ARF6, CDC40, SLC4A4, CXCL9, IRF8, CXCL10, FAS, PLK4, CHEK1, TRIM25, KITLG, C1QBP, NDUFA9, KPNB1, SLC25A11, WHSC1, ME2, GZMB, TLK1, CXCL11, RBM25, AK2, CAMSAP1L1, AGPAT5, FLJ10534, SEC10L1, PBK, BRIP1, KLHL24, STAT1 | 92% | 90% | 85% | 76% | 69% | 76% |
| 266 | WARS, SFRS2, EPAS1, EIF4E, PRDX3, MTHFD2, PSME2, GMFB, DLGAP4, TYMS, USP4, TES, CTSS, MAD2L1, SLC4A4, CXCL9, IRF8, CXCL10, FAS, PLK4, TRIM25, C1QBP, NDUFA9, SLC25A11, WHSC1, C17orf25, CA2, ME2, CXCL11, GZMB, RBM25, AK2, ATP5A1, RBBP4, AGPAT5, MARCH5, SEC10L1, PBK, HNRPD, BRIP1, TRMT5, KLHL24, ETNK1, STAT1 | 77% | 86% | 88% | 76% | 85% | 79% |
| 267 | WARS, EPAS1, EIF4E, PRDX3, MTHFD2, PSME2, GMFB, DLGAP4, TYMS, TES, LMAN1, DCK, ARF6, CDC40, SLC4A4, CXCL9, IRF8, GTSE1, CXCL10, FAS, CHEK1, SLC25A11, C1QBP, NDUFA9, WHSC1, C17orf25, CA2, ME2, CXCL11, IFT20, RBM25, AK2, NUP210, SOCS6, CDC42BPA, SFRS2, RBBP4, BAZ1A, FLJ10534, MARCH5, FLJ13220, PBK, PSAT1, HNRPD, KLHL24, STAT1 | 85% | 83% | 85% | 79% | 81% | 76% |
| 268 | HNRPD, WARS, SFRS2, EPAS1, EIF4E, PRDX3, MTHFD2, PSME2, MCM6, GBP1, GMFB, DLGAP4, TYMS, USP4, ARF6, CDC40, SLC4A4, IRF8, GTSE1, CXCL10, FAS, HNRPA3P1, TRIM25, KITLG, NDUFA9, SLC25A11, CA2, ME2, CXCL11, GZMB, TLK1, RBM25, AK2, hCAP-D3, CDC42BPA, AGPAT5, FLJ10534, MARCH5, SEC10L1, FLJ13220, PBK, PSAT1, BRIP1, TRMT5, STAT1 | 88% | 93% | 92% | 76% | 81% | 72% |
| 269 | HNRPD, WARS, SFRS2, EIF4E, PRDX3, MTHFD2, PSME2, MCM6, TK1, GMFB, DLGAP4, TYMS, USP4, ARF6, CDC40, SLC4A4, CXCL9, GTSE1, CXCL10, HNRPA3P1, KITLG, C1QBP, NDUFA9, SLC25A11, WHSC1, C17orf25, CA2, ME2, FUT4, CXCL11, GZMB, RBM25, AK2, CDC42BPA, FAS, RBBP4, BAZ1A, SEC10L1, FLJ13220, PBK, PSAT1, KLHL24, ETNK1, STAT1 | 81% | 79% | 92% | 76% | 81% | 69% |
| 270 | HNRPD, WARS, SFRS2, EPAS1, EIF4E, PRDX3, MTHFD2, PSME2, TK1, GMFB, DLGAP4, TYMS, CTSS, ARF6, MAD2L1, CDC40, CXCL9, IRF8, GTSE1, CXCL10, FAS, CHEK1, HNRPA3P1, TRIM25, KITLG, SLC25A11, NDUFA9, KPNB1, WHSC1, CA2, ME2, FUT4, CXCL11, GZMB, RBM25, AK2, CDC42BPA, BAZ1A, AGPAT5, DKFZp762E1312, SEC10L1, PBK, TRMT5, KLHL24, ETNK1, STAT1 | 88% | 86% | 88% | 79% | 85% | 72% |
| 271 | WARS, SFRS2, EPAS1, STAT1, EIF4E, MTHFD2, PSME2, MCM6, TK1, GMFB, DLGAP4, TYMS, USP4, LMAN1, ARF6, MAD2L1, CDC40, SLC4A4, CXCL9, IRF8, GTSE1, CXCL10, PLK4, C1QBP, NDUFA9, SLC25A11, WHSC1, CA2, HNRPD, ME2, FUT4, GZMB, RBM25, AK2, ATP5A1, CDC42BPA, FAS, AGPAT5, FLJ10534, SEC10L1, FLJ13220, PBK, BRIP1, TRMT5, KLHL24, ETNK1 | 77% | 69% | 92% | 79% | 81% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 272 | HNRPD, WARS, SFRS2, EPAS1, EIF4E, PRDX3, MTHFD2, PSME2, TK1, GMFB, DLGAP4, TYMS, USP4, CTSS, LMAN1, DCK, SLC4A4, CXCL9, IRF8, CXCL10, FAS, HNRPA3P1, KITLG, C1QBP, NDUFA9, SLC25A11, CA2, ME2, FUT4, IFT20, RBBP4, TLK1, CXCL11, RBM25, BRRN1, CDC42BPA, AGPAT5, FLJ10534, MARCH5, SEC10L1, PBK, BRIP1, TRMT5, KLHL24, ETNK1, STAT1 | 73% | 83% | 92% | 83% | 85% | 76% |
| 273 | WARS, SFRS2, EPAS1, STAT1, EIF4E, MTHFD2, PSME2, GBP1, TK1, GMFB, DLGAP4, TYMS, USP4, ARF6, CXCL9, IRF8, RABIF, CXCL10, FAS, PLK4, CHEK1, KITLG, SLC25A11, C1QBP, NDUFA9, WHSC1, CA2, ME2, CXCL11, IFT20, RBBP4, TLK1, RBM25, ATP5A1, CDC42BPA, FLJ13220, PBK, HNRPD, BRIP1, TRMT5, KLHL24, ETNK1 | 88% | 83% | 85% | 83% | 77% | 79% |
| 274 | HNRPD, WARS, SFRS2, EPAS1, EIF4E, PRDX3, MTHFD2, PSME2, GBP1, GMFB, DLGAP4, TYMS, TES, DCK, MAD2L1, CXCL9, CXCL10, FAS, PLK4, HNRPA3P1, KITLG, SLC25A11, NDUFA9, WHSC1, C17orf25, CA2, ME2, IFT20, RBBP4, CXCL11, SLC4A4, RBM25, NUP210, CAMSAP1L1, BRRN1, CDC42BPA, DDAH2, AGPAT5, FLJ10534, MARCH5, SEC10L1, FLJ13220, PBK, TRMT5, KLHL24, ETNK1, STAT1 | 81% | 86% | 88% | 83% | 85% | 76% |
| 275 | WARS, SFRS2, PAICS, EIF4E, MTHFD2, PSME2, MCM6, GBP1, TK1, GMFB, DLGAP4, TYMS, USP4, TES, LMAN1, CDC40, CXCL9, CXCL10, PLK4, TRIM25, KITLG, SLC25A11, C1QBP, NDUFA9, C17orf25, HNRPD, ME2, CXCL11, IFT20, TLK1, SLC4A4, RBM25, hCAP-D3, ATP5A1, DDAH2, FAS, AGPAT5, FLJ10534, MARCH5, SEC10L1, FLJ13220, PBK, PSAT1, BRIP1, KLHL24, STAT1 | 73% | 86% | 77% | 83% | 69% | 79% |
| 276 | HNRPD, WARS, SFRS2, STAT1, EIF4E, PRDX3, MTHFD2, PSME2, MCM6, TK1, GMFB, DLGAP4, TYMS, USP4, DCK, ARF6, CDC40, CXCL9, IRF8, CXCL10, FAS, PLK4, TRIM25, KITLG, C1QBP, NDUFA9, SLC25A11, WHSC1, CA2, ME2, CXCL11, GZMB, RBBP4, TLK1, RBM25, AK2, NUP210, ATP5A1, AGPAT5, MARCH5, SEC10L1, PBK, BRIP1, TRMT5 | 85% | 79% | 88% | 79% | 81% | 79% |
| 277 | HNRPD, WARS, SFRS2, EPAS1, STAT1, EIF4E, PRDX3, MTHFD2, PSME2, MCM6, GBP1, GMFB, DLGAP4, TYMS, TES, CTSS, LMAN1, DCK, SLC4A4, CXCL9, GTSE1, CXCL10, PLK4, CHEK1, TRIM25, C1QBP, NDUFA9, KPNB1, WHSC1, C17orf25, ME2, CXCL11, RBM25, BRRN1, ATP5A1, CDC42BPA, DDAH2, FAS, AGPAT5, MARCH5, PBK, BRIP1, TRMT5, KLHL24, ETNK1 | 81% | 83% | 88% | 76% | 77% | 69% |
| 278 | WARS, STAT1, EIF4E, SFPQ, PRDX3, MTHFD2, MCM6, TK1, GMFB, DLGAP4, TYMS, TES, CTSS, MAD2L1, CDC40, SLC4A4, CXCL9, RABIF, CXCL10, FAS, KITLG, SLC25A11, C1QBP, NDUFA9, C17orf25, CA2, HNRPD, ME2, GZMB, TLK1, CXCL11, RBM25, BRRN1, CDC42BPA, SFRS2, DDAH2, AGPAT5, SEC10L1, PBK, PSAT1, BRIP1, TRMT5, KLHL24 | 77% | 72% | 88% | 83% | 77% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 279 | HNRPD, WARS, EPAS1, STAT1, EIF4E, SFPQ, PRDX3, MTHFD2, PSME2, MCM6, TK1, GMFB, DLGAP4, TYMS, USP4, TES, DCK, ARF6, CDC40, SLC4A4, CXCL9, RABIF, CXCL10, FAS, TRIM25, NDUFA9, SLC25A11, WHSC1, C17orf25, CA2, ME2, GZMB, TLK1, CXCL11, RBM25, AK2, hCAP-D3, CDC42BPA, DDAH2, RBBP4, FLJ10534, SEC10L1, FLJ13220, PBK, PSAT1, BRIP1, KLHL24 | 77% | 86% | 92% | 76% | 77% | 76% |
| 280 | WARS, SFRS2, STAT1, EIF4E, MTHFD2, PSME2, MCM6, GBP1, TK1, GMFB, DLGAP4, TYMS, USP4, TES, CTSS, LMAN1, ARF6, CDC40, SLC4A4, CXCL9, CXCL10, FAS, PLK4, KITLG, C1QBP, KPNB1, WHSC1, CA2, ME2, FUT4, GZMB, CXCL11, RBM25, AK2, CDC42BPA, RBBP4, BAZ1A, AGPAT5, MARCH5, SEC10L1, PBK, HNRPD, BRIP1, KLHL24, ETNK1 | 81% | 79% | 92% | 79% | 85% | 72% |
| 281 | HNRPD, WARS, SFRS2, EPAS1, STAT1, EIF4E, PRDX3, MTHFD2, PSME2, TK1, GMFB, DLGAP4, TYMS, CTSS, LMAN1, DCK, CDC40, SLC4A4, CXCL9, IRF8, CXCL10, TRIM25, SLC25A11, C1QBP, NDUFA9, KPNB1, WHSC1, ME2, CXCL11, TLK1, RBM25, hCAP-D3, CDC42BPA, FAS, BAZ1A, AGPAT5, SEC10L1, FLJ13220, PBK, TRMT5, ETNK1 | 85% | 79% | 77% | 86% | 73% | 76% |
| 282 | HNRPD, WARS, SFRS2, EPAS1, EIF4E, PRDX3, MTHFD2, PSME2, GBP1, GMFB, DLGAP4, TYMS, TES, CTSS, LMAN1, MAD2L1, SLC4A4, CXCL9, CXCL10, FAS, CHEK1, SLC25A11, C1QBP, NDUFA9, KPNB1, WHSC1, C17orf25, CA2, ME2, FUT4, CXCL11, TLK1, RBM25, hCAP-D3, ATP5A1, CDC42BPA, DDAH2, AGPAT5, FLJ10534, DKFZp762E1312, SEC10L1, FLJ13220, PBK, TRMT5, STAT1 | 77% | 83% | 88% | 83% | 88% | 86% |
| 283 | WARS, SFRS2, PAICS, EIF4E, PRDX3, MTHFD2, PSME2, TK1, GMFB, DLGAP4, TYMS, USP4, TES, ARF6, CDC40, CXCL9, CXCL10, FAS, PLK4, TRIM25, SLC25A11, C1QBP, NDUFA9, WHSC1, C17orf25, CA2, ME2, FUT4, IFT20, SLC4A4, CXCL11, RBM25, AK2, BRRN1, ATP5A1, CDC42BPA, AGPAT5, MARCH5, SEC10L1, FLJ13220, PBK, HNRPD, BRIP1, TRMT5, KLHL24, ETNK1, STAT1 | 81% | 83% | 85% | 76% | 85% | 72% |
| 284 | HNRPD, WARS, SFRS2, EPAS1, EIF4E, PRDX3, MTHFD2, PSME2, GBP1, TK1, GMFB, DLGAP4, TYMS, USP4, LMAN1, ARF6, SLC4A4, CXCL9, IRF8, CXCL10, FAS, KITLG, C1QBP, NDUFA9, SLC25A11, WHSC1, C17orf25, CA2, ME2, GZMB, CXCL11, RBM25, AK2, hCAP-D3, CDC42BPA, DDAH2, RBBP4, AGPAT5, MARCH5, DKFZp762E1312, SEC10L1, FLJ13220, PBK, BRIP1, TRMT5, KLHL24, STAT1 | 81% | 76% | 88% | 79% | 85% | 72% |
| 285 | WARS, SFRS2, EPAS1, STAT1, EIF4E, PRDX3, MTHFD2, PSME2, GMFB, DLGAP4, TYMS, USP4, CTSS, DCK, ARF6, CDC40, SLC4A4, CXCL9, CXCL10, FAS, CHEK1, TRIM25, SLC25A11, C1QBP, C17orf25, CA2, ME2, GZMB, IFT20, RBBP4, CXCL11, RBM25, AK2, NUP210, SOCS6, DDAH2, AGPAT5, FLJ10534, MARCH5, DKFZp762E1312, SEC10L1, PBK, HNRPD, TRMT5 | 85% | 86% | 92% | 76% | 81% | 72% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 286 | WARS, EPAS1, STAT1, PAICS, EIF4E, PRDX3, MTHFD2, PSME2, TK1, DLGAP4, TYMS, MAD2L1, CDC40, CXCL9, IRF8, CXCL10, FAS, TRIM25, KITLG, C1QBP, NDUFA9, SLC25A11, WHSC1, C17orf25, HNRPD, ME2, CXCL11, IFT20, RBBP4, SLC4A4, RBM25, AK2, NUP210, SOCS6, CDC42BPA, BAZ1A, AGPAT5, SEC10L1, FLJ13220, PBK, PSAT1, BRIP1, TRMT5 | 73% | 76% | 81% | 79% | 73% | 66% |
| 287 | WARS, SFRS2, EPAS1, EIF4E, PRDX3, PSME2, GMFB, DLGAP4, TYMS, CTSS, ARF6, MAD2L1, CDC40, CXCL9, CXCL10, FAS, TRIM25, SLC25A11, C1QBP, NDUFA9, KPNB1, WHSC1, C17orf25, CA2, HNRPD, ME2, CXCL11, GZMB, IFT20, TLK1, SLC4A4, RBM25, CAMSAP1L1, hCAP-D3, RBBP4, BAZ1A, AGPAT5, MARCH5, FLJ13220, PBK, TRMT5, ETNK1, STAT1 | 88% | 90% | 88% | 79% | 77% | 79% |
| 288 | HNRPD, WARS, SFRS2, EPAS1, STAT1, EIF4E, SFPQ, PRDX3, MTHFD2, PSME2, TK1, GMFB, DLGAP4, TYMS, ARF6, CDC40, CXCL9, CXCL10, FAS, SLC25A11, NDUFA9, WHSC1, C17orf25, CA2, ME2, CXCL11, IFT20, SLC4A4, RBM25, AK2, SOCS6, DDAH2, RBBP4, BAZ1A, DKFZp762E1312, FLJ13220, PBK, PSAT1, BRIP1, ETNK1 | 81% | 90% | 85% | 76% | 85% | 69% |
| 289 | WARS, SFRS2, EPAS1, STAT1, PAICS, EIF4E, PRDX3, MTHFD2, PSME2, GMFB, DLGAP4, TYMS, USP4, CTSS, LMAN1, CDC40, CXCL9, IRF8, RABIF, CXCL10, FAS, TRIM25, SLC25A11, C1QBP, WHSC1, C17orf25, CA2, HNRPD, ME2, CXCL11, GZMB, TLK1, RBM25, CAMSAP1L1, hCAP-D3, CDC42BPA, BAZ1A, AGPAT5, MARCH5, DKFZp762E1312, FLJ13220, PBK, PSAT1, BRIP1, KLHL24 | 77% | 86% | 88% | 83% | 73% | 69% |
| 290 | WARS, SFRS2, EIF4E, PRDX3, MTHFD2, PSME2, TK1, GMFB, DLGAP4, TYMS, USP4, ARF6, MAD2L1, SLC4A4, CXCL9, IRF8, CXCL10, FAS, TRIM25, SLC25A11, NDUFA9, KPNB1, WHSC1, C17orf25, CA2, ME2, GZMB, IFT20, RBBP4, CXCL11, RBM25, AK2, BRRN1, CDC42BPA, AGPAT5, FLJ10534, MARCH5, SEC10L1, FLJ13220, PBK, HNRPD, BRIP1, KLHL24, ETNK1, STAT1 | 85% | 83% | 85% | 83% | 81% | 72% |
| 291 | HNRPD, WARS, SFRS2, EPAS1, STAT1, EIF4E, SFPQ, PRDX3, MTHFD2, GMFB, DLGAP4, TYMS, USP4, TES, CTSS, ARF6, MAD2L1, CDC40, CXCL9, CXCL10, FAS, PLK4, CHEK1, KITLG, SLC25A11, NDUFA9, KPNB1, CA2, ME2, FUT4, CXCL11, GZMB, TLK1, SLC4A4, RBM25, ATP5A1, DDAH2, MARCH5, DKFZp762E1312, PBK, BRIP1, KLHL24 | 85% | 86% | 92% | 79% | 85% | 86% |
| 292 | WARS, SFRS2, EPAS1, STAT1, EIF4E, PRDX3, MTHFD2, PSME2, TK1, GMFB, DLGAP4, TYMS, USP4, CTSS, CXCL9, IRF8, RABIF, CXCL10, FAS, PLK4, TRIM25, C1QBP, NDUFA9, SLC25A11, C17orf25, CA2, HNRPD, ME2, CXCL11, GZMB, SLC4A4, RBM25, ATP5A1, CDC42BPA, DDAH2, MARCH5, DKFZp762E1312, SEC10L1, FLJ13220, PBK, PSAT1, BRIP1, KLHL24, ETNK1, UBD, GTSE1, MYO1B, TMED5, RBBP8 | 81% | 83% | 85% | 72% | 69% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 293 | HNRPD, WARS, EIF4E, PRDX3, MTHFD2, PSME2, GMFB, DLGAP4, TYMS, USP4, MAD2L1, CXCL9, IRF8, CXCL10, FAS, SLC25A11, NDUFA9, WHSC1, ME2, CXCL11, IFT20, RBBP4, SLC4A4, RBM25, AK2, NUP210, CAMSAP1L1, ATP5A1, DDAH2, AGPAT5, MARCH5, SEC10L1, FLJ13220, PBK, PSAT1, BRIP1, STAT1, FLJ22471, LAPTM5, DEPDC1, INDO, YDD19 | 81% | 79% | 77% | 79% | 69% | 72% |
| 294 | WARS, SFRS2, PSME2, GMFB, DLGAP4, TYMS, TES, CDC40, CXCL9, CXCL10, HNRPA3P1, C1QBP, SLC25A11, WHSC1, C17orf25, CA2, ME2, TLK1, SLC4A4, CXCL11, AK2, hCAP-D3, DDAH2, FAS, AGPAT5, FLJ10534, PSAT1, HNRPD, BRIP1, KLHL24, STAT1, IVD | 73% | 79% | 88% | 79% | 85% | 76% |
| 295 | WARS, SFRS2, EPAS1, EIF4E, SFPQ, MTHFD2, PSME2, TK1, GMFB, DLGAP4, TYMS, USP4, LMAN1, CDC40, SLC4A4, CXCL9, IRF8, RABIF, CXCL10, FAS, PLK4, CHEK1, HNRPA3P1, TRIM25, SLC25A11, NDUFA9, KPNB1, WHSC1, CA2, HNRPD, ME2, GZMB, IFT20, CXCL11, RBM25, hCAP-D3, BAZ1A, AGPAT5, MARCH5, PBK, BRIP1, KLHL24, ETNK1, STAT1, TACC3, IL2RB, AK2 | 85% | 86% | 85% | 76% | 73% | 76% |
| 296 | HNRPD, WARS, SFRS2, PAICS, EIF4E, PRDX3, MTHFD2, PSME2, TK1, GMFB, DLGAP4, TYMS, CDC40, SLC4A4, CXCL9, CXCL10, HNRPA3P1, KITLG, C1QBP, NDUFA9, SLC25A11, WHSC1, CA2, ME2, FUT4, CXCL11, IFT20, RBBP4, RBM25, AK2, DDAH2, FAS, FLJ10534, SEC10L1, FLJ13220, PBK, BRIP1, TRMT5, KLHL24, STAT1, FEM1C, ITGB5 | 81% | 86% | 92% | 86% | 85% | 76% |
| 297 | WARS, EIF4E, PSME2, GMFB, DLGAP4, TYMS, USP4, CDC40, SLC4A4, CXCL10, TRIM25, C1QBP, NDUFA9, SLC25A11, CA2, ME2, CXCL11, RBM25, CAMSAP1L1, ATP5A1, SOCS6, FLJ10534, DKFZp762E1312, SEC10L1, HNRPD, STAT1, LMAN1, LOC92249, NFS1 | 77% | 79% | 73% | 86% | 81% | 86% |
| 298 | WARS, SFRS2, EIF4E, PRDX3, MTHFD2, PSME2, TK1, GMFB, DLGAP4, TYMS, USP4, TES, CTSS, DCK, MAD2L1, CXCL9, GTSE1, CXCL10, FAS, HNRPA3P1, KITLG, C1QBP, NDUFA9, SLC25A11, WHSC1, CA2, HNRPD, ME2, FUT4, CXCL11, SLC4A4, RBM25, CDC42BPA, DDAH2, RBBP4, FLJ10534, MARCH5, SEC10L1, FLJ13220, PBK, BRIP1, ETNK1, STAT1, ZWINT, ZG16, TPRT, PURA | 81% | 76% | 81% | 72% | 77% | 76% |
| 299 | HNRPD, WARS, STAT1, EIF4E, SFPQ, PRDX3, MTHFD2, PSME2, GMFB, DLGAP4, TYMS, MAD2L1, SLC4A4, CXCL9, CXCL10, FAS, NDUFA9, WHSC1, ME2, GZMB, TLK1, CXCL11, RBM25, AGPAT5, FLJ13220, KLHL24, SLAMF8, PBX1, CAP350 | 85% | 79% | 81% | 69% | 77% | 72% |
| 300 | HNRPD, WARS, STAT1, EIF4E, PRDX3, MTHFD2, PSME2, GBP1, TK1, GMFB, DLGAP4, TYMS, USP4, LMAN1, DCK, ARF6, CXCL9, CXCL10, FAS, TRIM25, KITLG, C1QBP, NDUFA9, KPNB1, SLC25A11, WHSC1, CA2, ME2, FUT4, CXCL11, GZMB, IFT20, SLC4A4, RBM25, BRRN1, ATP5A1, SFRS2, DDAH2, RBBP4, SEC10L1, FLJ13220, PBK, PSAT1, KLHL24, ETNK1, FLJ20273, VAPB, LARP4, CD74, BTN2A2 | 77% | 79% | 85% | 76% | 85% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 301 | WARS, SFRS2, EPAS1, EIF4E, SFPQ, PRDX3, MTHFD2, PSME2, TK1, GMFB, DLGAP4, TYMS, USP4, CTSS, CDC40, SLC4A4, CXCL9, IRF8, CXCL10, FAS, PLK4, CHEK1, TRIM25, KITLG, SLC25A11, C1QBP, NDUFA9, WHSC1, HNRPD, ME2, CXCL11, GZMB, RBBP4, RBM25, CAMSAP1L1, BRRN1, CDC42BPA, AGPAT5, FLJ10534, SEC10L1, PBK, BRIP1, KLHL24, ETNK1, STAT1, H2AFZ, PGGT1B | 81% | 76% | 88% | 69% | 77% | 69% |
| 302 | WARS, EIF4E, MTHFD2, PSME2, GBP1, GMFB, DLGAP4, TYMS, CDC40, SLC4A4, CXCL10, FAS, CHEK1, HNRPA3P1, KITLG, SLC25A11, CA2, ME2, FUT4, CXCL11, IFT20, TLK1, RBM25, AK2, SFRS2, TRMT5, KLHL24, STAT1, FKBP9 | 85% | 86% | 88% | 83% | 81% | 79% |
| 303 | HNRPD, WARS, SFRS2, EPAS1, EIF4E, PRDX3, MTHFD2, PSME2, MCM6, TK1, DLGAP4, TYMS, TES, MAD2L1, CDC40, CXCL9, CXCL10, FAS, PLK4, CHEK1, TRIM25, C1QBP, NDUFA9, WHSC1, CA2, ME2, CXCL11, GZMB, RBBP4, SLC4A4, RBM25, CAMSAP1L1, DDAH2, AGPAT5, MARCH5, SEC10L1, PBK, BRIP1, TRMT5, ETNK1, STAT1, CHAF1A, ITGB5, HNRPDL | 77% | 79% | 88% | 79% | 81% | 76% |
| 304 | HNRPD, WARS, SFRS2, MTHFD2, PSME2, TK1, GMFB, DLGAP4, TYMS, LMAN1, DCK, MAD2L1, CXCL9, CXCL10, FAS, KITLG, KPNB1, SLC25A11, WHSC1, ME2, CXCL11, IFT20, SLC4A4, RBM25, BRRN1, ATP5A1, CDC42BPA, BAZ1A, MARCH5, SEC10L1, PBK, PSAT1, BRIP1, KLHL24, STAT1, RBM28 | 81% | 79% | 81% | 83% | 81% | 72% |
| 305 | HNRPD, WARS, SFRS2, EIF4E, MTHFD2, PSME2, GMFB, DLGAP4, TYMS, USP4, CDC40, CXCL9, CXCL10, PLK4, HNRPA3P1, TRIM25, SLC25A11, KPNB1, ME2, SLC4A4, RBM25, hCAP-D3, FAS, RBBP4, BAZ1A, DKFZp762E1312, SEC10L1, KLHL24, STAT1, PSME1, BUB3, SOCS6 | 77% | 83% | 77% | 83% | 88% | 79% |
| 306 | WARS, EPAS1, STAT1, EIF4E, MTHFD2, PSME2, GMFB, DLGAP4, TYMS, USP4, TES, CTSS, ARF6, SLC4A4, CXCL9, RABIF, CXCL10, FAS, PLK4, KITLG, SLC25A11, C1QBP, NDUFA9, KPNB1, WHSC1, CA2, HNRPD, ME2, FUT4, CXCL11, IFT20, RBM25, CAMSAP1L1, SOCS6, DDAH2, AGPAT5, FLJ10534, MARCH5, SEC10L1, FLJ13220, PBK, BRIP1, KLHL24, ETNK1, RPS2, CHAF1A, LGALS3BP | 73% | 79% | 85% | 79% | 81% | 76% |
| 307 | WARS, SFRS2, MTHFD2, PSME2, GMFB, DLGAP4, TYMS, CXCL9, GTSE1, RABIF, CXCL10, HNRPA3P1, TRIM25, KITLG, C1QBP, NDUFA9, WHSC1, CA2, ME2, FUT4, RBM25, hCAP-D3, ATP5A1, DDAH2, FAS, STAT1, CDCA8, HMGB3 | 85% | 93% | 85% | 83% | 81% | 83% |
| 308 | WARS, MTHFD2, PSME2, GBP1, MAD2L1, CXCL9, IRF8, CXCL10, CHEK1, KITLG, ME2, CXCL11, IFT20, RBM25, AK2, ATP5A1, FAS, AGPAT5, SEC10L1, FLJ13220, HNRPD, KLHL24, ETNK1, STAT1, ECGF1 | 81% | 76% | 81% | 83% | 77% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 309 | WARS, SFRS2, EPAS1, EIF4E, PRDX3, MTHFD2, PSME2, TK1, GMFB, DLGAP4, TYMS, TES, CDC40, SLC4A4, CXCL9, GTSE1, CXCL10, FAS, PLK4, CHEK1, KITLG, C1QBP, NDUFA9, SLC25A11, WHSC1, C17orf25, ME2, FUT4, CXCL11, IFT20, RBBP4, RBM25, AK2, NUP210, BRRN1, CDC42BPA, AGPAT5, FLJ10534, MARCH5, SEC10L1, FL13220, PBK, TRMT5, ETNK1, STAT1, SELL, GART | 81% | 83% | 88% | 76% | 73% | 76% |
| 310 | WARS, SFRS2, EPAS1, STAT1, EIF4E, SFPQ, MTHFD2, PSME2, TK1, GMFB, DLGAP4, TYMS, USP4, CTSS, ARF6, CDC40, CXCL9, GTSE1, CXCL10, FAS, PLK4, CHEK1, TRIM25, SLC25A11, C1QBP, NDUFA9, WHSC1, ME2, FUT4, CXCL11, IFT20, RBBP4, SLC4A4, RBM25, hCAP-D3, DDAH2, AGPAT5, FLJ10534, MARCH5, SEC10L1, FLJ13220, PSAT1, HNRPD, BRIP1, KLHL24, ETNK1, WFDC1, YTHDF3, K-ALPHA-1, PAWR | 73% | 72% | 85% | 83% | 69% | 72% |
| 311 | HNRPD, WARS, SFRS2, STAT1, EIF4E, PRDX3, MTHFD2, PSME2, TK1, GMFB, DLGAP4, TYMS, TES, LMAN1, MAD2L1, CDC40, CXCL9, IRF8, CXCL10, PLK4, HNRPA3P1, KITLG, C1QBP, NDUFA9, SLC25A11, WHSC1, ME2, FUT4, CXCL11, IFT20, RBM25, BRRN1, CDC42BPA, FAS, AGPAT5, DKFZp762E1312, SEC10L1, FLJ13220, PBK, BRIP1, KLHL24, SMC2L1, IRF1 | 81% | 83% | 88% | 83% | 73% | 79% |
| 312 | WARS, EPAS1, STAT1, MTHFD2, PSME2, MCM6, GMFB, DLGAP4, TYMS, USP4, CTSS, LMAN1, CXCL9, IRF8, CXCL10, KITLG, C1QBP, NDUFA9, SLC25A11, ME2, SLC4A4, RBM25, hCAP-D3, SOCS6, FAS, RBBP4, BAZ1A, AGPAT5, PSAT1, BRIP1, ETNK1, LPP, PPM1D, LAP3, TXNDC | 73% | 79% | 81% | 79% | 77% | 76% |
| 313 | WARS, EIF4E, PRDX3, PSME2, TK1, GMFB, DLGAP4, TYMS, LMAN1, CXCL10, SLC25A11, C1QBP, NDUFA9, KPNB1, C17orf25, CA2, ME2, RBBP4, SLC4A4, RBM25, FAS, SEC10L1, PBK, HNRPD, ETNK1, STAT1, KIAA0828, SPCS3, NARS | 77% | 76% | 85% | 79% | 77% | 83% |
| 314 | HNRPD, WARS, SFRS2, EPAS1, EIF4E, SFPQ, PRDX3, MTHFD2, PSME2, MCM6, TK1, GMFB, DLGAP4, TYMS, USP4, LMAN1, ARF6, CDC40, SLC4A4, CXCL9, IRF8, CXCL10, FAS, PLK4, KITLG, C1QBP, NDUFA9, SLC25A11, WHSC1, CA2, ME2, GZMB, CXCL11, RBM25, CAMSAP1L1, CDC42BPA, FLJ10534, MARCH5, FLJ13220, PBK, PSAT1, BRIP1, KLHL24, STAT1, NUP160, HLA-E | 81% | 76% | 85% | 79% | 81% | 79% |
| 315 | WARS, EIF4E, SFPQ, PRDX3, MTHFD2, MCM6, GMFB, DLGAP4, TYMS, CDC40, CXCL9, CXCL10, CHEK1, HNRPA3P1, C1QBP, SLC25A11, WHSC1, CA2, ME2, CXCL11, SLC4A4, RBM25, AK2, SFRS2, FAS, MARCH5, FLJ13220, KLHL24, ETNK1, STAT1, SOCS1 | 73% | 79% | 85% | 83% | 77% | 72% |
| 316 | WARS, EIF4E, MTHFD2, PSME2, GMFB, DLGAP4, USP4, DCK, CDC40, CXCL9, CXCL10, FAS, SLC25A11, C1QBP, KPNB1, WHSC1, CA2, ME2, FUT4, CXCL11, RBM25, DDAH2, SEC10L1, PBK, HNRPD, TRMT5, KLHL24, STAT1, PPA2, GTSE1, TNFRSF11A, RYK | 81% | 83% | 81% | 79% | 85% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 317 | WARS, SFRS2, EPAS1, PSME2, TK1, GMFB, DLGAP4, TYMS, CTSS, LMAN1, CDC40, SLC4A4, CXCL9, IRF8, CXCL10, PLK4, CHEK1, SLC25A11, C1QBP, KPNB1, WHSC1, CA2, ME2, GZMB, TLK1, CXCL11, RBM25, hCAP-D3, FAS, RBBP4, FLJ10534, MARCH5, HNRPD, STAT1, KIF2C, HAT1 | 77% | 90% | 85% | 79% | 85% | 83% |
| 318 | WARS, EIF4E, PRDX3, PSME2, GBP1, TYMS, LMAN1, CXCL9, CXCL10, FAS, CHEK1, SLC25A11, NDUFA9, CA2, ME2, RBBP4, TLK1, CXCL11, SLC4A4, BRRN1, PBK, HNRPD, STAT1, TGFB2 | 69% | 83% | 77% | 86% | 81% | 83% |
| 319 | WARS, SFRS2, EPAS1, EIF4E, SFPQ, PRDX3, MTHFD2, PSME2, TK1, DLGAP4, TYMS, LMAN1, SLC4A4, CXCL9, CXCL10, PLK4, SLC25A11, WHSC1, C17orf25, CA2, ME2, CXCL11, GZMB, IFT20, RBM25, NUP210, CAMSAP1L1, ATP5A1, FAS, RBBP4, AGPAT5, FLJ10534, PBK, PSAT1, HNRPD, STAT1, HLA-DMB | 92% | 90% | 88% | 79% | 73% | 79% |
| 320 | SFRS2, EIF4E, PRDX3, MTHFD2, PSME2, DLGAP4, TYMS, CXCL10, FAS, PLK4, CHEK1, HNRPA3P1, TRIM25, SLC25A11, C1QBP, NDUFA9, CA2, ME2, CXCL11, SLC4A4, RBM25, ATP5A1, FLJ13220, PSAT1, BRIP1, STAT1, RIF1, SCC-112, U2AF2 | 73% | 86% | 73% | 76% | 81% | 79% |
| 321 | HNRPD, WARS, STAT1, EIF4E, SFPQ, PRDX3, MTHFD2, PSME2, MCM6, TK1, GMFB, DLGAP4, TYMS, CTSS, LMAN1, DCK, CDC40, SLC4A4, CXCL9, CXCL10, FAS, PLK4, TRIM25, SLC25A11, NUUFA9, WHSC1, C17orf25, CA2, ME2, FUT4, CXCL11, IFT20, RBM25, AK2, BRRN1, SFRS2, DDAH2, MARCH5, SEC10L1, FLJ13220, PBK, PSAT1, BRIP1, KLHL24, CD8A, GTF2H2, C14orf156, BIRC5 | 77% | 83% | 81% | 79% | 81% | 76% |
| 322 | HNRPD, WARS, SFRS2, EPAS1, STAT1, EIF4E, SFPQ, PRDX3, MTHFD2, PSME2, MCM6, TK1, GMFB, DLGAP4, TYMS, USP4, CTSS, DCK, CXCL9, RABIF, CXCL10, FAS, TRIM25, NDUFA9, KPNB1, WHSC1, CA2, ME2, RBBP4, SLC4A4, RBM25, NUP210, hCAP-D3, SOCS6, BAZ1A, PBK, PSAT1, BRIP1, KLHL24, MAX, HADHSC | 77% | 79% | 81% | 83% | 88% | 76% |
| 323 | WARS, SFRS2, EIF4E, MTHFD2, PSME2, TK1, GMFB, DLGAP4, TYMS, TES, CTSS, ARF6, MAD2L1, CDC40, CXCL9, IRF8, CXCL10, TRIM25, SLC25A11, C1QBP, NDUFA9, CA2, ME2, CXCL11, GZMB, SLC4A4, RBM25, AK2, NUP210, BRRN1, ATP5A1, DDAH2, FAS, MARCH5, SEC10L1, PBK, HNRPD, ETNK1, STAT1, AP1G1 | 88% | 83% | 88% | 76% | 85% | 79% |
| 324 | WARS, STAT1, PRDX3, MTHFD2, PSME2, TK1, GMFB, DLGAP4, TYMS, CTSS, LMAN1, ARF6, MAD2L1, CDC40, CXCL9, CXCL10, FAS, PLK4, TRIM25, KITLG, C1QBP, NDUFA9, KPNB1, SLC25A11, WHSC1, CA2, HNRPD, ME2, FUT4, CXCL11, RBM25, CAMSAP1L1, hCAP-D3, BRRN1, ATP5A1, SOCS6, RBBP4, SEC10L1, PBK, BRIP1, KLHL24, ETNK1, MIS12, RBMS3, RUNX1, TTC19 | 73% | 76% | 81% | 83% | 85% | 86% |
| 325 | HNRPD, WARS, SFRS2, EIF4E, MTHFD2, PSME2, GMFB, DLGAP4, TYMS, MAD2L1, CXCL10, FAS, HNRPA3P1, NDUFA9, SLC25A11, CA2, ME2, GZMB, CXCL11, hCAP-D3, RBBP4, BAZ1A, AGPAT5, FLJ10534, ETNK1, STAT1, JAK2, RNGTT | 85% | 76% | 92% | 76% | 85% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 326 | WARS, PAICS, EIF4E, SFPQ, MTHFD2, PSME2, GMFB, DLGAP4, TYMS, USP4, TES, ARF6, CDC40, CXCL9, RABIF, CXCL10, FAS, TRIM25, KITLG, C1QBP, NDUFA9, SLC25A11, WHSC1, ME2, FUT4, CXCL11, SLC4A4, RBM25, CAMSAP1L1, hCAP-D3, CDC42BPA, AGPAT5, PBK, PSAT1, HNRPD, BRIP1, STAT1, CDC2, ATP13A3, ZC3HAV1, FANCA | 73% | 76% | 81% | 79% | 77% | 66% |
| 327 | WARS, EIF4E, MTHFD2, PSME2, TK1, GMFB, TYMS, CXCL9, CXCL10, FAS, SLC25A11, WHSC1, C17orf25, CA2, ME2, RBM25, NUP210, BAZ1A, FLJ10534, MARCH5, SEC10L1, HNRPD, BRIP1, KLHL24, ETNK1, STAT1, SGPP1, CLCA4, FOXM1 | 77% | 79% | 85% | 79% | 69% | 79% |
| 328 | HNRPD, WARS, SFRS2, EPAS1, STAT1, EIF4E, MTHFD2, PSME2, GBP1, TK1, GMFB, DLGAP4, TYMS, TES, LMAN1, DCK, ARF6, CDC40, CXCL9, CXCL10, FAS, PLK4, TRIM25, KITLG, SLC25A11, C1QBP, NDUFA9, KPNB1, WHSC1, C17orf25, CA2, ME2, TLK1, CXCL11, SLC4A4, RBM25, AK2, hCAP-D3, BAZ1A, AGPAT5, SEC10L1, FLJ13220, PBK, KLHL24, ETNK1, MCAM, BUB3, YTHDC2, APOL6, NUP210 | 88% | 83% | 85% | 79% | 81% | 76% |
| 329 | WARS, SFRS2, EPAS1, EIF4E, MTHFD2, PSME2, MCM6, TK1, GMFB, DLGAP4, TYMS, USP4, TES, LMAN1, ARF6, CDC40, CXCL9, IRF8, GTSE1, RABIF, CXCL10, FAS, HNRPA3P1, C1QBP, NDUFA9, KPNB1, SLC25A11, WHSC1, C17orf25, CA2, HNRPD, ME2, CXCL11, GZMB, SLC4A4, RBM25, AK2, SOCS6, CDC42BPA, RBBP4, AGPAT5, MARCH5, SEC10L1, PSAT1, BRIP1, KLHL24, ETNK1, STAT1, CACNB3, BUB1B, ESPL1, H2AFZ | 88% | 86% | 85% | 76% | 77% | 72% |
| 330 | WARS, SFRS2, EPAS1, EIF4E, MTHFD2, PSME2, TK1, GMFB, DLGAP4, USP4, CXCL9, CXCL10, NDUFA9, KPNB1, SLC25A11, C17orf25, ME2, CXCL11, RBBP4, hCAP-D3, ATP5A1, FAS, AGPAT5, FLJ10534, PBK, PSAT1, HNRPD, BRIP1, ETNK1, STAT1, LHCGR | 77% | 79% | 73% | 79% | 65% | 69% |
| 331 | WARS, EIF4E, MTHFD2, PSME2, GBP1, DLGAP4, TYMS, CTSS, CDC40, SLC4A4, IRF8, CXCL10, FAS, TRIM25, SLC25A11, C1QBP, NDUFA9, ME2, FUT4, RBBP4, TLK1, RBM25, AK2, FLJ10534, MARCH5, FLJ13220, ETNK1, STAT1, C18orf9, C10orf3, AURKB, IFI16, PTPRC | 69% | 72% | 73% | 86% | 81% | 76% |
| 332 | HNRPD, WARS, PAICS, EIF4E, PRDX3, MTHFD2, TK1, GMFB, TYMS, CTSS, CXCL9, FAS, KITLG, NDUFA9, SLC25A11, C17orf25, ME2, FUT4, CXCL11, IFT20, SLC4A4, RBM25, CDC42BPA, SFRS2, AGPAT5, MARCH5, SEC10L1, FLJ13220, PBK, PSAT1, BRIP1, KLHL24, STAT1, AK2 | 77% | 83% | 88% | 76% | 77% | 72% |
| 333 | WARS, EIF4E, PRDX3, MTHFD2, PSME2, MCM6, GMFB, DLGAP4, TYMS, USP4, CTSS, LMAN1, CXCL9, CXCL10, FAS, PLK4, HNRPA3P1, TRIM25, SLC25A11, WHSC1, ME2, CXCL11, IFT20, SLC4A4, RBM25, BAZ1A, AGPAT5, DKFZp762E1312, SEC10L1, PBK, HNRPD, BRIP1, ETNK1, STAT1, TOP2A, NUSAP1, USP14, PRF1, SCYL2 | 88% | 86% | 85% | 66% | 65% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 334 | WARS, SFRS2, EPAS1, EIF4E, MTHFD2, PSME2, GMFB, DLGAP4, TYMS, USP4, CXCL10, FAS, WHSC1, C17orf25, ME2, IFT20, TLK1, CXCL11, SLC4A4, RBM25, AK2, CDC42BPA, HNRPD, ETNK1, STAT1, HLA-DRA, POLE2, PAICS, NUP210 | 88% | 93% | 88% | 86% | 73% | 83% |
| 335 | HNRPD, WARS, EIF4E, PRDX3, MTHFD2, PSME2, GBP1, TK1, GMFB, DLGAP4, TYMS, USP4, LMAN1, CDC40, CXCL9, PLK4, SLC25A11, WHSC1, C17orf25, CA2, ME2, IFT20, CXCL11, RBM25, hCAP-D3, FAS, FLJ10534, DKFZp762E1312, SEC10L1, ETNK1, STAT1, WDHD1 | 81% | 83% | 92% | 79% | 88% | 83% |
| 336 | WARS, SFRS2, EPAS1, EIF4E, PRDX3, MTHFD2, PSME2, MCM6, GBP1, GMFB, DLGAP4, TYMS, USP4, CTSS, MAD2L1, CXCL9, IRF8, GTSE1, CXCL10, FAS, CHEK1, KITLG, SLC25A11, C1QBP, NDUFA9, WHSC1, C17orf25, CA2, ME2, CXCL11, GZMB, IFT20, TLK1, SLC4A4, RBM25, hCAP-D3, BAZ1A, MARCH5, DKFZp762E1312, SEC10L1, FLJ13220, PSAT1, HNRPD, BRIP1, KLHL24, ETNK1, STAT1, CUTL1, FAM64A | 77% | 86% | 85% | 76% | 81% | 76% |
| 337 | WARS, SFRS2, EPAS1, EIF4E, MTHFD2, PSME2, GMFB, DLGAP4, TYMS, CTSS, LMAN1, CDC40, CXCL9, IRF8, SLC25A11, C1QBP, NDUFA9, CA2, ME2, FUT4, CXCL11, RBM25, AK2, CDC42BPA, FAS, RBBP4, AGPAT5, MARCH5, SEC10L1, PBK, HNRPD, BRIP1, TRMT5, STAT1, TMEPAI, ZNF304, KLF7 | 77% | 79% | 92% | 69% | 92% | 79% |
| 338 | WARS, SFRS2, EPAS1, STAT1, EIF4E, SFPQ, PRDX3, MTHFD2, PSME2, GBP1, GMFB, DLGAP4, TYMS, CDC40, SLC4A4, CXCL9, RABIF, CXCL10, FAS, CHEK1, TRIM25, SLC25A11, C1QBP, NDUFA9, WHSC1, CA2, HNRPD, ME2, GZMB, RBBP4, CXCL11, RBM25, AK2, NUP210, BRRN1, ATP5A1, CDC42BPA, AGPAT5, FLJ10534, MARCH5, SEC10L1, FLJ13220, PBK, PSAT1, BRIP1, MCM10, HLA-DMA, RABEP1, YARS, P15RS | 81% | 93% | 92% | 79% | 81% | 72% |
| 339 | WARS, STAT1, EIF4E, MTHFD2, PSME2, GMFB, DLGAP4, MAD2L1, FAS, PLK4, TRIM25, KITLG, SLC25A11, KPNB1, WHSC1, ME2, CXCL11, SLC4A4, RBM25, AK2, AGPAT5, KLHL24, CDKN1C, RFC5, FEN1, TFRC | 73% | 79% | 77% | 79% | 69% | 83% |
| 340 | WARS, EIF4E, MTHFD2, PSME2, TK1, GMFB, DLGAP4, TYMS, TES, LMAN1, DCK, CDC40, CXCL9, IRF8, GTSE1, CXCL10, FAS, PLK4, TRIM25, SLC25A11, C1QBP, NDUFA9, C17orf25, CA2, ME2, FUT4, CXCL11, SLC4A4, RBM25, AK2, CDC42BPA, RBBP4, BAZ1A, AGPAT5, FLJ10534, SEC10L1, FLJ13220, PBK, PSAT1, HNRPD, KLHL24, ETNK1, STAT1, SPFH1, SP3, CDC20, RAP1GDS1, M11S1 | 73% | 79% | 85% | 83% | 81% | 72% |
| 341 | WARS, EPAS1, EIF4E, PRDX3, MTHFD2, PSME2, TK1, GMFB, DLGAP4, TYMS, USP4, LMAN1, ARF6, SLC4A4, CXCL9, CXCL10, FAS, TRIM25, KITLG, C1QBP, NDUFA9, SLC25A11, WHSC1, C17orf25, HNRPD, ME2, GZMB, TLK1, CXCL11, RBM25, AK2, BRRN1, DDAH2, AGPAT5, FLJ10534, SEC10L1, FLJ13220, PBK, PSAT1, TRMT5, KLHL24, ETNK1, STAT1, AVEN, HLA-DPA1, CD59 | 96% | 90% | 81% | 72% | 73% | 72% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature | | SVM | | 3NN | | 1NN | |
|---|---|---|---|---|---|---|---|
| Number | Signature Genes (as gene symbols) | Sens | Spec | Sens | Spec | Sens | Spec |
| 342 | WARS, SFRS2, EPAS1, PRDX3, MTHFD2, TK1, GMFB, DLGAP4, TYMS, TES, LMAN1, SLC4A4, GTSE1, CXCL10, FAS, TRIM25, C1QBP, NDUFA9, SLC25A11 WHSC1, C17orf25, CA2, HNRPD, ME2, FUT4, CXCL11, R8M25, CDC42BPA, RBBP4, BAZ1A, AGPAT5, MARCH5, SEC10L1, BRIP1, TRMT5, KLHL24, STAT1, MPP5, EIF4A1, TRIP13, APOL3 | 81% | 83% | 92% | 79% | 85% | 79% |
| 343 | WARS, SFRS2, EIF4E, PRDX3, MTHFD2, PSME2, TK1, GMFB, DLGAP4, TYMS, LMAN1, CDC40, CXCL9, CXCL10, FAS, CHEK1, HNRPA3P1, SLC25A11, C1QBP, WHSC1, CA2, HNRPD, ME2, CXCL11, TLK1, SLC4A4, RBM25, AK2, ATP5A1, SOCS6, BAZ1A, AGPAT5, MARCH5, DKFZp762E1312, SEC10L1, PBK, BRIP1, KLHL24, STAT1, GPR161, SGCD | 69% | 79% | 85% | 83% | 88% | 76% |
| 344 | WARS, SFRS2, EIF4E, PRDX3, PSME2, GMFB, DLGAP4, TYMS, USP4, MAD2L1, CDC40, SLC4A4, CXCL10, FAS, CHEK1, KITLG, NDUFA9, KPNB1, SLC25A11, CA2, HNRPD, ME2, FUT4, GZMB, CXCL11, RBM25, BRRN1, CDC42BPA, MARCH5, KLHL24, ETNK1, STAT1, ADH1C, WHSC1, HIP2 | 77% | 86% | 92% | 79% | 88% | 86% |
| 345 | WARS, SFRS2, EPAS1, PAICS, EIF4E, MTHFD2, PSME2, TK1, GMFB, DLGAP4, TYMS, USP4, DCK, ARF6, SLC4A4, CXCL9, RABIF, CXCL10, FAS, TRIM25, SLC25A11, C1QBP, NDUFA9, WHSC1, C17orf25, CA2, HNRPD, ME2, FUT4, GZMB, IFT20, CXCL11, RBM25, AK2, CAMSAP1L1, BRRN1, DDAH2, RBBP4, AGPAT5, PBK, PSAT1, BRIP1, KLHL24, STAT1, XPO7, TRAFD1, YTHDC2, RNF138 | 81% | 86% | 88% | 83% | 88% | 72% |
| 346 | WARS, SFRS2, EPAS1, PRDX3, MTHFD2, PSME2, MCM6, DLGAP4, TYMS, USP4, CDC40, SLC4A4, CXCL9, RABIF, CXCL10, FAS, SLC25A11, C1QBP, NDUFA9, WHSC1, CA2, ME2, CXCL11, RBM25, NUP210, BRRN1, DDAH2, RBBP4, BAZ1A, DKFZp762E1312, SEC10L1, PSAT1, HNRPD, KLHL24, ETNK1, STAT1, ACADSB, AMIGO2, CCL5, KIAA0286 | 81% | 83% | 85% | 76% | 81% | 72% |
| 347 | SFRS2, EPAS1, EIF4E, SFPQ, PRDX3, MTHFD2, PSME2, GMFB, DLGAP4, TYMS, LMAN1, DCK, ARF6, CDC40, CXCL9, GTSE1, CXCL10, FAS, SLC25A11, KPNB1, WHSC1, CA2, HNRPD, ME2, CXCL11, SLC4A4, RBM25, AK2, ATP5A1, CDC42BPA, BAZ1A, FLJ10534, FLJ13220, PBK, BRIP1, KLHL24, STAT1, PSMB9, HBP1, CPD, AIM2 | 81% | 83% | 92% | 79% | 85% | 79% |
| 348 | WARS, EPAS1, EIF4E, PRDX3, MTHFD2, MCM6, GMFB, DLGAP4, CDC40, CXCL10, CHEK1, KPNB1, CA2, ME2, RBBP4, CXCL11, SLC4A4, RBM25, CDC42BPA, FAS, FLJ10534, SEC10L1, FLJ13220, HNRPD, STAT1, TTK, YBX2, BCL7C, SI | 73% | 86% | 73% | 86% | 73% | 79% |
| 349 | WARS, SFRS2, STAT1, EIF4E, PRDX3, MTHFD2, TK1, GMFB, DLGAP4, TYMS, USP4, TES, CTSS, CXCL9, CXCL10, FAS, SLC25A11, KPNB1, C17orf25, ME2, GZMB, SLC4A4, NUP210, hCAP-D3, HNRPD, TRMT5, KLHL24, PRO2730 | 88% | 79% | 96% | 69% | 88% | 76% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 350 | EPAS1, EIF4E, PRDX3, PSME2, GMFB, DLGAP4, TYMS, USP4, CTSS, SLC4A4, CXCL10, HNRPA3P1, KITLG, SLC25A11, WHSC1, CA2, HNRPD, ME2, FUT4, RBM25, CAMSAP1L1, FAS, AGPAT5, FLJ10534, MARCH5, SEC10L1, PSAT1, BRIP1, KLHL24, STAT1, MCM2, GGA2, SPAG5, VRK1, EBNA1BP2 | 73% | 83% | 92% | 79% | 81% | 76% |
| 351 | WARS, SFRS2, EIF4E, MTHFD2, PSME2, TK1, GMFB, DLGAP4, TYMS, LMAN1, MAD2L1, SLC4A4, CXCL9, RABIF, CXCL10, FAS, CHEK1, KITLG, SLC25A11, NDUFA9, C17orf25, CA2, ME2, IFT20, CXCL11, RBM25, hCAP-D3, CDC42BPA, AGPAT5, MARCH5, HNRPD, KLHL24, STAT1, MYCBP, GBP1, ITGA4, PBXIP1, CENPA | 85% | 76% | 88% | 83% | 88% | 76% |
| 352 | HNRPD, WARS, SFRS2, EPAS1, EIF4E, PRDX3, MTHFD2, PSME2, GMFB, DLGAP4, TYMS, TES, CTSS, ARF6, CDC40, SLC4A4, CXCL9, CXCL10, FAS, TRIM25, KITLG, NDUFA9, SLC25A11, C17orf25, CA2, ME2, FUT4, GZMB, CXCL11, BRRN1, SOCS6, CDC42BPA, BAZ1A, DKFZp762E1312, SEC10L1, PBK, PSAT1, BRIP1, TRMT5, ETNK1, STAT1, PPIG, NUP98, FUSIP1, SH3GLB1 | 77% | 79% | 92% | 76% | 77% | 76% |
| 353 | WARS, SFRS2, EPAS1, EIF4E, PRDX3, MTHFD2, PSME2, GMFB, DLGAP4, TYMS, DCK, CDC40, CXCL9, GTSE1, RABIF, CXCL10, KITLG, C1QBP, NDUFA9, SLC25A11, C17orf25, CA2, ME2, GZMB, IFT20, SLC4A4, RBM25, DDAH2, FAS, AGPAT5, FLJ10534, MARCH5, FLJ13220, PBK, HNRPD, KLHL24, ETNK1, STAT1, C5orf4, KIF23, SSPN | 85% | 83% | 88% | 79% | 73% | 72% |
| 354 | HNRPD, WARS, SFRS2, STAT1, EIF4E, SFPQ, PSME2, GBP1, GMFB, DLGAP4, TYMS, CTSS, ARF6, CDC40, SLC4A4, CXCL10, FAS, C1QBP, NDUFA9, SLC25A11, WHSC1, CA2, ME2, IFT20, RBBP4, CXCL11, RBM25, NUP210, BAZ1A, AGPAT5, MARCH5, PBK, KLHL24, MAP2K4, UBE2L6 | 85% | 83% | 92% | 83% | 81% | 76% |
| 355 | HNRPD, WARS, EIF4E, MTHFD2, MCM6, DLGAP4, TYMS, CDC40, CXCL9, CXCL10, FAS, TRIM25, C1QBP, ME2, CXCL11, RBM25, AK2, CDC42BPA, SEC10L1, PBK, KLHL24, ETNK1, STAT1, DNA2L, TAP2, SYNPO | 88% | 90% | 73% | 79% | 73% | 76% |
| 356 | HNRPD, WARS, EIF4E, MTHFD2, GBP1, GMFB, DLGAP4, TYMS, USP4, DCK, CDC40, CXCL9, IRF8, GTSE1, CXCL10, HNRPA3P1, TRIM25, C1QBP, NDUFA9, SLC25A11, WHSC1, CA2, ME2, FUT4, CXCL11, RBBP4, TLK1, SLC4A4, RBM25, AK2, NUP210, ATP5A1, SFRS2, FAS, AGPAT5, FLJ10534, MARCH5, SEC10L1, PBK, KLHL24, ETNK1, STAT1, EXOSC9, KIF15, FBXL14, ABCE1 | 69% | 83% | 85% | 83% | 81% | 79% |
| 357 | WARS, EPAS1, EIF4E, PRDX3, MTHFD2, PSME2, MCM6, TK1, GMFB, DLGAP4, TYMS, TES, CTSS, LMAN1, CDC40, SLC4A4, CXCL9, IRF8, CXCL10, FAS, PLK4, HNRPA3P1, C1QBP, NDUFA9, SLC25A11, WHSC1, C17orf25, CA2, HNRPD, ME2, CXCL11, RBM25, AK2, CDC42BPA, RBBP4, AGPAT5, FLJ10534, SEC10L1, FLJ13220, PBK, BRIP1, STAT1, CCL5, FLJ20516, BUB1, MRPL42 | 85% | 86% | 88% | 79% | 81% | 72% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 358 | HNRPD, WARS, EIF4E, MTHFD2, PSME2, GBP1, GMFB, DLGAP4, TYMS, USP4, ARF6, MAD2L1, CDC40, SLC4A4, CXCL9, CXCL10, FAS, PLK4, C1QBP, SLC25A11, WHSC1, CA2, ME2, CXCL11, RBBP4, RBM25, AK2, CDC42BPA, BAZ1A, AGPAT5, SEC10L1, PBK, PSAT1, BRIP1, ETNK1, STAT1, GZMA, EIF4A1, PSMA3, CD2, CCNB1 | 77% | 83% | 85% | 79% | 81% | 69% |
| 359 | WARS, PSME2, GMFB, DLGAP4, TYMS, CDC40, CXCL9, GTSE1, CXCL10, FAS, TRIM25, SLC25A11, C1QBP, NDUFA9, WHSC1, C17orf25, ME2, CXCL11, RBM25, CAMSAP1L1, AGPAT5, FLJ13220, PSAT1, TRMT5, KLHL24, ETNK1, STAT1, RRM1, CXCL13, NKG7, MGAT2, LCP2 | 77% | 79% | 81% | 76% | 77% | 66% |
| 360 | HNRPD, SFRS2, EPAS1, STAT1, EIF4E, MTHFD2, PSME2, TK1, GMFB, DLGAP4, TYMS, CXCL9, CXCL10, FAS, CHEK1, HNRPA3P1, KPNB1, SLC25A11, WHSC1, C17orf25, ME2, CXCL11, IFT20, TLK1, SLC4A4, RBM25, CDC42BPA, BAZ1A, AGPAT5, MARCH5, SEC10L1, PBK, PSAT1, KLHL24, C1orf112, TCF7L2, RARRES3, SERBP1, TBX2 | 88% | 90% | 85% | 79% | 73% | 76% |
| 361 | HNRPD, WARS, EIF4E, SFPQ, MTHFD2, PSME2, GMFB, DLGAP4, TYMS, TES, CTSS, ARF6, CXCL9, IRF8, RABIF, CXCL10, FAS, PLK4, HNRPA3P1, KITLG, SLC25A11, C1QBP, NDUFA9, WHSC1, C17orf25, ME2, CXCL11, IFT20, TLK1, RBM25, AK2, NUP210, hCAP-D3, CDC42BPA, DDAH2, AGPAT5, FLJ10534, SEC10L1, PBK, KLHL24, STAT1, PTGER3, HCAP-G | 81% | 83% | 88% | 76% | 77% | 69% |
| 362 | HNRPD, WARS, SFRS2, EPAS1, STAT1, EIF4E, SFPQ, PRDX3, MTHFD2, PSME2, TK1, GMFB, DLGAP4, TYMS, CTSS, LMAN1, MAD2L1, CDC40, CXCL9, IRF8, CXCL10, KITLG, C1QBP, NDUFA9, SLC25A11, WHSC1, ME2, CXCL11, GZMB, IFT20, RBBP4, SLC4A4, RBM25, hCAP-D3, BRRN1, FAS, FLJ10534, SEC10L1, PSAT1, KLHL24, NUP50, MCCC2, RABGEF1 | 81% | 90% | 85% | 79% | 77% | 83% |
| 363 | WARS, SFRS2, EPAS1, EIF4E, MTHFD2, GMFB, DLGAP4, TYMS, USP4, CDC40, CXCL9, CXCL10, FAS, HNRPA3P1, TRIM25, C1QBP, SLC25A11, ME2, CXCL11, IFT20, RBM25, AK2, hCAP-D3, CDC42BPA, RBBP4, BAZ1A, DKFZp762E1312, SEC10L1, PBK, HNRPD, ETNK1, STAT1, PSMA6, ZNF345, UBAP1 | 92% | 90% | 77% | 83% | 69% | 72% |
| 364 | WARS, EPAS1, PAICS, EIF4E, MTHFD2, PSME2, GMFB, TYMS, TES, LMAN1, SLC4A4, CXCL9, RABIF, FAS, CHEK1, HNRPA3P1, TRIM25, SLC25A11, C1QBP, WHSC1, ME2, CDC42BPA, FLJ10534, SEC10L1, PBK, STAT1, ZBTB20, NAT2 | 77% | 86% | 88% | 76% | 85% | 76% |
| 365 | WARS, SFRS2, EIF4E, MTHFD2, PSME2, GMFB, DLGAP4, TYMS, USP4, MAD2L1, CXCL9, CXCL10, FAS, C1QBP, NDUFA9, KPNB1, SLC25A11, WHSC1, CA2, ME2, IFT20, SLC4A4, RBM25, AK2, CDC42BPA, DDAH2, PSAT1, HNRPD, BRIP1, KLHL24, ETNK1, STAT1, HMMR, CTSL | 85% | 86% | 85% | 76% | 81% | 69% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 366 | WARS, EIF4E, PRDX3, MTHFD2, PSME2, GMFB, DLGAP4, TYMS, USP4, CTSS, DCK, CXCL9, CXCL10, FAS, TRIM25, WHSC1, C17orf25, CA2, ME2, FUT4, IFT20, CXCL11, SLC4A4, RBM25, CDC42BPA, RBBP4, AGPAT5, MARCH5, FLJ13220, PBK, HNRPD, TRMT5, KLHL24, ETNK1, STAT1, PBX1, ZDHHC3, CLEC2D | 88% | 83% | 85% | 72% | 69% | 76% |
| 367 | HNRPD, WARS, SFRS2, EIF4E, MTHFD2, PSME2, TK1, GMFB, DLGAP4, TYMS, TES, LMAN1, ARF6, CDC40, CXCL9, IRF8, GTSE1, RABIF, CXCL10, FAS, KITLG, C1QBP, NDUFA9, SLC25A11, WHSC1, ME2, TLK1, SLC4A4, CXCL11, RBM25, hCAP-D3, DDAH2, RBBP4, BAZ1A, AGPAT5, SEC10L1, PBK, TRMT5, KLHL24, ETNK1, STAT1, NEK2, KIAA0841, RNMT, C4orf16 | 73% | 83% | 85% | 83% | 73% | 66% |
| 368 | WARS, SFRS2, EPAS1, STAT1, MTHFD2, PSME2, GMFB, DLGAP4, TYMS, TES, CDC40, SLC4A4, CXCL9, RABIF, CXCL10, FAS, PLK4, CHEK1, HNRPA3P1, TRIM25, C1QBP, KPNB1, SLC25A11, WHSC1, CA2, HNRPD, ME2, FUT4, RBBP4, CXCL11, RBM25, NUP210, SOCS6, CDC42BPA, FLJ10534, MARCH5, FLJ13220, PBK, PSAT1, BRIP1, KLHL24, APOL1, PDGFA, FBXO5, CACYBP, ABCE1 | 73% | 83% | 81% | 79% | 81% | 72% |
| 369 | WARS, SFRS2, EPAS1, STAT1, PAICS, EIF4E, MTHFD2, PSME2, GMFB, DLGAP4, TYMS, USP4, DCK, CDC40, SLC4A4, CXCL9, GTSE1, CXCL10, PLK4, SLC25A11, NDUFA9, KPNB1, WHSC1, C17orf25, CA2, ME2, FUT4, IFT20, TLK1, CXCL11, RBM25, AK2, CDC42BPA, DDAH2, FAS, BAZ1A, AGPAT5, SEC10L1, FLJ13220, PBK, PSAT1, HNRPD, BRIP1, BMP5, ETNK1, PTGER3, VAMP4, CCNB2 | 88% | 86% | 81% | 83% | 81% | 79% |
| 370 | WARS, EPAS1, PRDX3, MTHFD2, PSME2, TK1, GMFB, DLGAP4, TYMS, TES, CTSS, MAD2L1, CDC40, SLC4A4, CXCL9, GTSE1, RABIF, CXCL10, FAS, PLK4, TRIM25, KITLG, SLC25A11, C1QBP, CA2, ME2, CXCL11, RBBP4, TLK1, RBM25, AK2, BRRN1, SFRS2, BAZ1A, AGPAT5, FLJ13220, PSAT1, HNRPD, BRIP1, KLHL24, STAT1, TAP1, LCP2, ITGAL, CCNT2, FYB | 81% | 79% | 81% | 79% | 81% | 76% |
| 371 | HNRPD, WARS, PRDX3, MTHFD2, PSME2, MCM6, TK1, GMFB, DLGAP4, TYMS, DCK, ARF6, CXCL9, CXCL10, C1QBP, NDUFA9, SLC25A11, ME2, IFT20, CXCL11, RBM25, AK2, BRRN1, ATP5A1, CDC42BPA, SFRS2, FAS, BAZ1A, AGPAT5, FLJ13220, PBK, PSAT1, BRIP1, KLHL24, STAT1, NEIL3, PCDHGC3, NUSAP1 | 88% | 79% | 85% | 79% | 73% | 72% |
| 372 | SFRS2, EPAS1, EIF4E, PRDX3, MTHFD2, PSME2, MCM6, TK1, GMFB, DLGAP4, TYMS, TES, DCK, MAD2L1, CXCL9, IRF8, CXCL10, FAS, TRIM25, KITLG, C1QBP, NDUFA9, SLC25A11, WHSC1, CA2, HNRPD, ME2, CXCL11, IFT20, RBBP4, SLC4A4, RBM25, AK2, CDC42BPA, DDAH2, BAZ1A, AGPAT5, FLJ10534, MARCH5, SEC10L1, FLJ13220, PBK, KLHL24, ETNK1, STAT1, TNFAIP2 | 77% | 79% | 81% | 83% | 85% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature | | SVM | | 3NN | | 1NN | |
|---|---|---|---|---|---|---|---|
| Number | Signature Genes (as gene symbols) | Sens | Spec | Sens | Spec | Sens | Spec |
| 373 | WARS, STAT1, EIF4E, SFPQ, MTHFD2, PSME2, GMFB, DLGAP4, TYMS, ARF6, CDC40, SLC4A4, CXCL9, RABIF, CXCL10, FAS, SLC25A11, C1QBP, NDUFA9, KPNB1, WHSC1, C17orf25, CA2, ME2, FUT4, CXCL11, GZMB, TLK1, RBM25, AK2, FLJ10534, FLJ13220, HNRPD, BRIP1, GEMIN4, PTPRC | 85% | 86% | 92% | 79% | 81% | 72% |
| 374 | WARS, SFRS2, EPAS1, PAICS, EIF4E, MTHFD2, PSME2, MCM6, GBP1, GMFB, DLGAP4, TYMS, TES, CTSS, DCK, MAD2L1, CDC40, SLC4A4, CXCL9, IRF8, GTSE1, CXCL10, FAS, PLK4, TRIM25, KITLG, C1QBP, NDUFA9, KPNB1, SLC25A11, WHSC1, CA2, ME2, CXCL11, RBM25, AK2, hCAP-D3, CDC42BPA, DDAH2, AGPAT5, MARCH5, SEC10L1, FLJ13220, PBK, HNRPD, BRIP1, KLHL24, STAT1, APOBEC3G, KIF11, GBP2, RAB6A, ITGB5 | 77% | 90% | 81% | 76% | 85% | 76% |
| 375 | WARS, EIF4E, MTHFD2, PSME2, MCM6, GMFB, DLGAP4, TYMS, MAD2L1, CDC40, CXCL9, CXCL10, FAS, SLC25A11, C1QBP, NDUFA9, ME2, FUT4, CXCL11, RBM25, hCAP-D3, BRRN1, MARCH5, SEC10L1, FLJ13220, HNRPD, STAT1, AP2B1, KIF2, K-ALPHA-1, GPHN | 73% | 72% | 85% | 90% | 81% | 83% |
| 376 | HNRPD, WARS, SFRS2, EPAS1, PAICS, EIF4E, PRDX3, MTHFD2, PSME2, GBP1, TK1, GMFB, DLGAP4, TYMS, USP4, CTSS, LMAN1, CXCL9, IRF8, RABIF, CXCL10, FAS, HNRPA3P1, KITLG, SLC25A11, C1QBP, NDUFA9, WHSC1, ME2, CXCL11, TLK1, SLC4A4, RBM25, ATP5A1, RBBP4, FLJ10534, MARCH5, FLJ13220, PSAT1, BRIP1, KLHL24, STAT1, KIF18A, KIF2C, NF2, DLG7, PSMA5 | 77% | 83% | 77% | 86% | 73% | 86% |
| 377 | WARS, SFRS2, EPAS1, EIF4E, MTHFD2, PSME2, GMFB, DLGAP4, TYMS, CDC40, CXCL9, CXCL10, FAS, PLK4, TRIM25, KITLG, C1QBP, NDUFA9, SLC25A11, HNRPD, ME2, CXCL11, IFT20, RBM25, ATP5A1, DDAH2, AGPAT5, FLJ13220, PSAT1, BRIP1, KLHL24, STAT1, SLC4A4, CD7, DNM1L, RPL39, CDKN3 | 81% | 90% | 85% | 90% | 88% | 72% |
| 378 | HNRPD, WARS, SFRS2, EPAS1, STAT1, EIF4E, PRDX3, MTHFD2, PSME2, TK1, DLGAP4, TYMS, USP4, LMAN1, DCK, MAD2L1, CDC40, SLC4A4, CXCL9, GTSE1, RABIF, CXCL10, FAS, PLK4, CHEK1, HNRPA3P1, TRIM25, C1QBP, NDUFA9, SLC25A11, WHSC1, ME2, CXCL11, GZMB, IFT20, RBBP4, TLK1, RBM25, AK2, ATP5A1, AGPAT5, KLHL24, ETNK1, CD3Z, DHX15, MTHFD1 | 85% | 90% | 85% | 72% | 73% | 79% |
| 379 | WARS, STAT1, EIF4E, MTHFD2, PSME2, GMFB, DLGAP4, TYMS, LMAN1, DCK, SLC4A4, CXCL9, IRF8, RABIF, CXCL10, FAS, TRIM25, NDUFA9, SLC25A11, WHSC1, HNRPD, ME2, CXCL11, TLK1, RBM25, CAMSAP1L1, CDC42BPA, RBBP4, MARCH5, SEC10L1, FLJ13220, PSAT1, BRIP1, KLHL24, ETNK1, ATF6, RRM2, KPNA2 | 81% | 83% | 77% | 83% | 77% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 380 | HNRPD, WARS, SFRS2, EPAS1, EIF4E, MTHFD2, PSME2, GBP1, TK1, DLGAP4, TYMS, LMAN1, MAD2L1, CXCL9, IRF8, CXCL10, FAS, HNRPA3P1, KITLG, NDUFA9, KPNB1, SLC25A11, ME2, CXCL11, TLK1, SLC4A4, RBM25, AK2, AGPAT5, FLJ10534, MARCH5, SEC10L1, PBK, PSAT1, BRIP1, KLHL24, STAT1, BTN3A3 | 73% | 83% | 81% | 86% | 69% | 72% |
| 381 | WARS, EIF4E, PRDX3, MTHFD2, PSME2, TK1, GMFB, DLGAP4, TYMS, USP4, TES, CDC40, CXCL9, CXCL10, FAS, KITLG, NDUFA9, SLC25A11, WHSC1, CA2, ME2, RBM25, AK2, ATP5A1, SEC10L1, PBK, HNRPD, BRIP1, KLHL24, STAT1, CHEK1, C20orf45, CKS2 | 85% | 83% | 92% | 86% | 85% | 76% |
| 382 | WARS, SFRS2, EPAS1, EIF4E, MTHFD2, PSME2, GBP1, GMFB, DLGAP4, TYMS, USP4, ARF6, MAD2L1, CXCL9, RABIF, CXCL10, FAS, PLK4, CHEK1, HNRPA3P1, KITLG, SLC25A11, WHSC1, C17orf25, ME2, FUT4, CXCL11, IFT20, SLC4A4, RBM25, ATP5A1, CDC42BPA, RBBP4, MARCH5, SEC10L1, FLJ13220, PBK, PSAT1, ETNK1, STAT1, HMGN2, SFRS10 | 92% | 90% | 81% | 79% | 73% | 76% |
| 383 | WARS, EPAS1, EIF4E, PRDX3, MTHFD2, PSME2, GBP1, GMFB, DLGAP4, TYMS, USP4, DCK, CDC40, CXCL9, IRF8, RABIF, CXCL10, FAS, PLK4, HNRPA3P1, TRIM25, KITLG, C1QBP, NDUFA9, SLC25A11, C17orf25, CA2, HNRPD, ME2, CXCL11, RBM25, SFRS2, DDAH2, RBBP4, AGPAT5, FLJ13220, PBK, ETNK1, STAT1, TMEM48 | 85% | 83% | 88% | 76% | 81% | 72% |
| 384 | WARS, SFRS2, EPAS1, EIF4E, SFPQ, GMFB, DLGAP4, TYMS, USP4, SLC4A4, CXCL9, RABIF, CXCL10, FAS, KPNB1, CA2, ME2, FUT4, CXCL11, RBM25, CAMSAP1L1, KLHL24, STAT1, TRAF3IP3, SOS1 | 88% | 90% | 88% | 83% | 81% | 76% |
| 385 | WARS, SFRS2, EIF4E, PRDX3, MTHFD2, PSME2, DLGAP4, TYMS, USP4, MAD2L1, SLC4A4, CXCL9, GTSE1, RABIF, CXCL10, FAS, HNRPA3P1, TRIM25, SLC25A11, NDUFA9, WHSC1, CA2, ME2, GZMB, TLK1, CXCL11, RBM25, AK2, BRRN1, ATP5A1, DDAH2, AGPAT5, MARCH5, SEC10L1, PBK, PSAT1, HNRPD, BRIP1, KLHL24, STAT1, C16orf30 | 85% | 86% | 88% | 79% | 73% | 79% |
| 386 | WARS, SFRS2, PA1CS, EIF4E, PRDX3, MTHFD2, PSME2, MCM6, TK1, GMFB, DLGAP4, TYMS, LMAN1, CXCL9, IRF8, GTSE1, CXCL10, FAS, TRIM25, KITLG, SLC25A11, C1QBP, NDUFA9, KPNB1, WHSC1, HNRPD, ME2, CXCL11, IFT20, RBBP4, TLK1, SLC4A4, RBM25, CAMSAP1L1, ATP5A1, DDAH2, FLJ10534, MARCH5, DKFZp762E1312, SEC10L1, PBK, TRMT5, STAT1, PGD, ZNF148 | 69% | 76% | 69% | 86% | 81% | 86% |
| 387 | HNRPD, WARS, EPAS1, PRDX3, MTHFD2, PSME2, TK1, DLGAP4, TYMS, USP4, TES, LMAN1, CXCL9, CXCL10, FAS, PLK4, TRIM25, C1QBP, SLC25A11, WHSC1, ME2, RBBP4, TLK1, SLC4A4, NUP210, SFRS2, SEC10L1, ETNK1, STAT1, SNRPC, RAC2 | 73% | 86% | 88% | 83% | 81% | 83% |
| 388 | WARS, SFRS2, PAICS, EIF4E, MTHFD2, PSME2, GMFB, DLGAP4, TYMS, TES, LMAN1, CDC40, CXCL10, NDUFA9, KPNB1, SLC25A11, ME2, CXCL11, SLC4A4, RBM25, NUP210, hCAP-D3, FAS, RBBP4, ETNK1, STAT1, DHX40, KIAA0090 | 73% | 79% | 73% | 86% | 77% | 83% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 389 | HNRPD, WARS, SFRS2, EPAS1, STAT1, EIF4E, MTHFD2, PSME2, GMFB, DLGAP4, TYMS, LMAN1, ARF6, CXCL10, FAS, PLK4, TRIM25, SLC25A11, C1QBP, NDUFA9, ME2, CXCL11, GZMB, TLK1, SLC4A4, RBM25, hCAP-D3, ATP5A1, CDC42BPA, DDAH2, AGPAT5, FLJ10534, MARCH5, FLJ13220, SLA | 85% | 86% | 88% | 76% | 81% | 83% |
| 390 | WARS, EPAS1, EIF4E, PRDX3, TK1, GMFB, DLGAP4, USP4, CXCL9, CXCL10, FAS, CHEK1, KITLG, C1QBP, NDUFA9, SLC25A11, WHSC1, ME2, IFT20, RBM25, HNRPD, BRIP1, ETNK1, STAT1, MASA, SYDE1, C9orf16, ZNF518 | 88% | 86% | 81% | 83% | 81% | 86% |
| 391 | WARS, SFRS2, MTHFD2, GMFB, DLGAP4, TYMS, CXCL9, RABIF, CXCL10, HNRPA3P1, TRIM25, KITLG, SLC25A11, ME2, RBBP4, CXCL11, RBM25, SOCS6, FAS, AGPAT5, MARCH5, SEC10L1, HNRPD, BRIP1, STAT1, KIAA0265, CCNA2, LRP8, CNAP1 | 85% | 79% | 92% | 79% | 88% | 76% |
| 392 | HNRPD, WARS, SFRS2, EIF4E, PRDX3, MTHFD2, PSME2, GBP1, TK1, GMFB, DLGAP4, USP4, CTSS, ARF6, CXCL9, IRF8, GTSE1, CXCL10, TRIM25, C1QBP, SLC25A11, WHSC1, CA2, ME2, FUT4, CXCL11, GZMB, SLC4A4, RBM25, AK2, CAMSAP1L1, ATP5A1, SOCS6, CDC42BPA, FAS, RBBP4, BAZ1A, AGPAT5, MARCH5, SEC10L1, PBK, BRIP1, KLHL24, STAT1, GTPBP3, MOBK1B, MDS032, WDR45L | 85% | 90% | 88% | 79% | 85% | 69% |
| 393 | HNRPD, WARS, SFRS2, STAT1, EIF4E, MTHFD2, PSME2, MCM6, GMFB, DLGAP4, TYMS, USP4, TES, DCK, CDC40, CXCL9, IRF8, CXCL10, FAS, PLK4, SLC25A11, C1QBP, NDUFA9, KPNB1, C17orf25, ME2, IFT20, RBBP4, TLK1, SLC4A4, CXCL11, RBM25, AK2, NUP210, ATP5A1, CDC42BPA, SEC10L1, FLJ13220, PBK, PSAT1, BRIP1, KLHL24, ETNK1, FLJ20641, PIK3CD | 81% | 79% | 77% | 86% | 69% | 66% |
| 394 | WARS, SFRS2, EIF4E, PRDX3, MTHFD2, PSME2, GBP1, TK1, GMFB, DLGAP4, TYMS, USP4, MAD2L1, CDC40, CXCL9, IRF8, CXCL10, WHSC1, C17orf25, CA2, HNRPD, ME2, CXCL11, GZMB, SLC4A4, RBM25, AK2, FAS, SEC10L1, KLHL24, STAT1, KIAA0907 | 81% | 90% | 85% | 79% | 85% | 72% |
| 395 | WARS, SFRS2, EPAS1, PAICS, EIF4E, PRDX3, MTHFD2, PSME2, DLGAP4, TYMS, TES, DCK, CDC40, SLC4A4, IRF8, CXCL10, PLK4, C1QBP, NDUFA9, SLC25A11, WHSC1, CA2, ME2, FUT4, GZMB, TLK1, CXCL11, RBM25, hCAP-D3, FAS, AGPAT5, MARCH5, SEC10L1, PSAT1, HNRPD, BRIP1, STAT1, NUMB, HMGB2 | 85% | 86% | 85% | 72% | 69% | 76% |
| 396 | WARS, EIF4E, MTHFD2, GMFB, DLGAP4, CTSS, CDC40, CXCL10, FAS, HNRPA3P1, C1QBP, NDUFA9, SLC25A11, HNRPD, ME2, FUT4, CXCL11, RBM25, ATP5A1, FLJ10534, SEC10L1, FLJ13220, PBK, BRIP1, STAT1, KPNA2, IBRDC3, RIG, NP | 81% | 83% | 81% | 90% | 73% | 79% |

TABLE 9-continued

Additional Prognostic signatures (note SVM = support vector machine,
3NN = 3 nearest neighbours, 1NN = 1 nearest neighbour, Sens = sensitivity,
Spec = specificity, for prediction of recurrence)

| Signature Number | Signature Genes (as gene symbols) | SVM Sens | SVM Spec | 3NN Sens | 3NN Spec | 1NN Sens | 1NN Spec |
|---|---|---|---|---|---|---|---|
| 397 | WARS, EPAS1, EIF4E, MTHFD2, PSME2, TK1, GMFB, DLGAP4, TYMS, USP4, LMAN1, DCK, CDC40, CXCL9, IRF8, GTSE1, CXCL10, FAS, TRIM25, KITLG, SLC25A11, C1QBP, NDUFA9, KPNB1, WHSC1, C17orf25, CA2, HNRPD, ME2, CXCL11, GZMB, RBM25, AK2, NUP210, ATP5A1, DDAH2, FLJ10534, MARCH5, FLJ13220, PBK, PSAT1, BRIP1, TRMT5, KLHL24, ETNK1, STAT1, SFRS7, SMURF2, SCC-112 | 81% | 83% | 92% | 76% | 73% | 76% |
| 398 | WARS, SFRS2, PRDX3, PSME2, TK1, GMFB, DLGAP4, TYMS, TES, MAD2L1, CXCL9, GTSE1, CXCL10, PLK4, TRIM25, C1QBP, NDUFA9, KPNB1, WHSC1, C17orf25, CA2, ME2, CXCL11, GZMB, IFT20, SLC4A4, RBM25, AK2, hCAP-D3, ATP5A1, FAS, MARCH5, PBK, HNRPD, ETNK1, STAT1, HEM1, DKK1, PRDX1, ELOVL6, CD86 | 92% | 97% | 88% | 76% | 81% | 79% |
| 399 | HNRPD, WARS, SFRS2, EPAS1, EIF4E, PRDX3, MTHFD2, PSME2, MCM6, GMFB, DLGAP4, TYMS, USP4, LMAN1, CDC40, SLC4A4, CXCL9, GTSE1, CXCL10, FAS, PLK4, SLC25A11, C1QBP, NDUFA9, KPNB1, WHSC1, C17orf25, CA2, ME2, CXCL11, IFT20, RBM25, BRRN1, CDC42BPA, RBBP4, AGPAT5, MARCH5, SEC10L1, PBK, TRMT5, KLHL24, STAT1, PEG3, ASPM, NR5A2 | 85% | 79% | 88% | 79% | 88% | 76% |
| 400 | WARS, SFRS2, PAICS, EIF4E, SFPQ, PRDX3, MTHFD2, PSME2, GMFB, DLGAP4, TYMS, USP4, CTSS, LMAN1, DCK, MAD2L1, CXCL9, IRF8, CXCL10, PLK4, KITLG, C1QBP, NDUFA9, KPNB1, SLC25A11, WHSC1, C17orf25, CA2, HNRPD, ME2, CXCL11, TLK1, SLC4A4, RBM25, AK2, ATP5A1, FAS, RBBP4, BAZ1A, FLJ10534, SEC10L1, FLJ13220, PBK, PSAT1, BRIP1, KLHL24, STAT1, AMD1 | 65% | 79% | 92% | 86% | 85% | 76% |
| 401 | HNRPD, WARS, EIF4E, MTHFD2, PSME2, GBP1, TK1, GMFB, DLGAP4, TYMS, USP4, TES, MAD2L1, CXCL9, CXCL10, FAS, TRIM25, NDUFA9, WHSC1, C17orf25, CA2, ME2, CXCL11, TLK1, SLC4A4, RBM25, BRRN1, DDAH2, MARCH5, PBK, PSAT1, BRIP1, KLHL24, STAT1, LOC146909, ECT2, BM039, GTF3C4 | 85% | 79% | 85% | 86% | 81% | 76% |
| 402 | WARS, EPAS1, STAT1, EIF4E, MTHFD2, TK1, GMFB, DLGAP4, TYMS, USP4, CTSS, DCK, ARF6, CDC40, CXCL9, CXCL10, PLK4, HNRPA3P1, TRIM25, KITLG, SLC25A11, NDUFA9, WHSC1, C17orf25, CA2, HNRPD, ME2, CXCL11, IFT20, TLK1, SLC4A4, RBM25, AK2, CAMSAP1L1, ATP5A1, SOCS6, SFRS2, DDAH2, FAS, RBBP4, MARCH5, SEC10L1, FLJ13220, PBK, PSAT1, BRIP1, KLHL24, MS4A12, SMCHD1, RANBP2L1, SP110, SE57-1 | 81% | 79% | 88% | 79% | 81% | 79% |
| 403 | WARS, SFRS2, EPAS1, STAT1, EIF4E, MTHFD2, PSME2, MCM6, TK1, GMFB, DLGAP4, TYMS, TES, CDC40, SLC4A4, CXCL9, IRF8, GTSE1, CXCL10, FAS, CHEK1, SLC25A1, C1QBP, NDUFA9, WHSC1, C17orf25, CA2, ME2, FUT4, TLK1, RBM25, CAMSAP1L1, hCAP-D3, DDAH2, RBBP4, FLJ10534, PBK, PSAT1, BRIP1, KLHL24, ETNK1, CAND1 | 73% | 86% | 81% | 83% | 69% | 79% |

Example 20

Specific Application of Prediction Methods

In selection of the gene signatures described here, two different statistical methods were used to characterise the signatures: k-nearest neighbours, and support vector machines. These methods are provided as packages to the R statistical software system (ref), through the packages class (ref) and e1071 (ref).
The signatures described in this document were tested as follows. In both cases, the data used to develop the prediction models for a given signature were the gene expression values (raw normalised intensities from the Affymetrix array data) for the probes corresponding to genes that comprise that signature, across both recurrent and non-recurrent samples:

- For k-nearest neighbours, we used leave-one-out cross validation with k=1 and k=3 to obtain sensitivity (proportion of positive, i.e. recurrent, samples correctly classified) and specificity (proportion of negative samples, i.e. non-recurrent samples correctly classified) described in table 9
- The dataset was used to generate leave-one-out cross-validation sensitivity and specificity data using the following support-vector machine parameters: The support vector machine models were generated using a linear kernel, and all other parameters used were the default values obtained from the svm function of the e1071 package.

Note the genes comprising the signatures were themselves obtained from the list of significantly differentially expressed probes, and those from the list of genes which were found to correlate with genes from the NZ 22-gene signature. In some cases there was more than one significant (or correlated) probe per gene. In these cases, the prediction models used the median intensity data across all significant probes (i.e. those in the significant probe list, see table 1) for that gene.

REFERENCES

1. Arnold C N, Goel A, Blum H E, Richard Boland C. Molecular pathogenesis of colorectal cancer. Cancer 2005; 104:2035-47.
2. Anwar S, Frayling I M, Scott N A, Carlson G L. Systematic review of genetic influences on the prognosis of colorectal cancer. Br J Surg 2004; 91:1275-91.
3. Wang Y, Jatkoe T, Zhang Y, et al. Gene expression profiles and molecular markers to predict recurrence of Dukes' B colon cancer. J Clin Oncol 2004; 22: 1564-71.
4. Eschrich S, Yang I, Bloom G, et al. Molecular staging for survival prediction of colorectal cancer patients. J Clin Oncol 2005; 23:3526-35.
5. Barrier A, Lemoine A, Boelle P Y, et al. Colon cancer prognosis prediction by gene expression profiling. Oncogene 2005; 24:6155-64.
6. Simon R. Roadmap for developing and validating therapeutically relevant genomic classifiers. J Clin Oncol 2005; 23:7332-41.
7. Michiels S, Koscielny S, Hill C. Prediction of cancer outcome with microarrays: a multiple random validation strategy. Lancet 2005; 365:488-92.
8. Marshall E. Getting the noise out of gene arrays. Science 2004; 306:630-31.
9. Birkenkamp-Demtroder K, Christensen L L, Olesen S H, et al. Gene expression in colorectal cancer. Cancer Res 2002; 62:4352-63.
10. Ihaka R, Gentleman R. R: A language for data analysis and graphics. Journal of Computational and Graphical Statistics 1996; 5:299-314.
11. Smyth G K. Linear models and empirical Bayes methods for assessing differential expression in microarray experiments. Statistical Applications in Genetics and Molecular Biology 2004; 3:Article 3.
12. Gentleman R C, Carey V J, Bates D M, et al. Bioconductor: open software development for computational biology and bioinformatics. Genome Biol 2004; 5:R80.
13. Smyth G K, Speed T P. Normalization of cDNA microarray data. In: Carter D, ed. METHODS: Selecting Candidate Genes from DNA Array Screens: Application to Neuroscience. Vol. 31; 2003:265-73.
14. Irizarry R A, Hobbs B, Collin F, et al. Exploration, normalization, and summaries of high density oligonucleotide array probe level data. Biostatistics 2003; 4:249-64.
15. Harrington D P, Fleming T R. A class of rank test procedures for censored survival data. Biometrika 1982; 69:553-66.
16. Barnes C J, Li F, Mandal M, Yang Z, Sahin A A, Kumar R. Heregulin induces expression, ATPase activity, and nuclear localization of G3BP, a Ras signaling component, in human breast tumors. Cancer Res 2002; 62:1251-55.
17. Niki T, Izumi S, Saegusa Y, et al. MSSP promotes ras/myc cooperative cell transforming activity by binding to c-Myc. Genes Cells 2000; 5:127-41.
18. Rein D T, Roehrig K, Schondorf T, et al. Expression of the hyaluronan receptor RHAMM in endometrial carcinomas suggests a role in tumor progression and metastasis. J Cancer Res Clin Oncol 2003; 129:161-64.
19. Fernandez P, Carretero J, Medina P P, et al. Distinctive gene expression of human lung adenocarcinomas carrying LKBI mutations. Oncogene 2004; 23:5084-91.
20. Frey U H, Eisenhardt A, Lummen G, et al. The T393C polymorphism of the G alpha s gene (GNAS1) is a novel prognostic marker in bladder cancer. Cancer Epidemiol Biomarkers Prev 2005; 14:871-77.
21. Niini T, Vettenranta K, Hollmen J, et al. Expression of myeloid-specific genes in childhood acute lymphoblastic leukemia—a cDNA array study. Leukemia 2002; 16:2213-21.
22. Yasui K, Mihara S, Zhao C, et al. Alteration in copy numbers of genes as a mechanism for acquired drug resistance. Cancer Res 2004; 64:1403-10.
23. Nomura J, Matsumoto K, Iguchi-Ariga S M, Ariga H. Positive regulation of Fas gene expression by MSSP and abrogation of Fas-mediated apoptosis induction in MSSP-deficient mice. Exp Cell Res 2005; 305:324-32.
24. Mayeur G L, Fraser C S, Peiretti F, Block K L, Hershey J W. Characterization of eIF3k: a newly discovered subunit of mammalian translation initiation factor eIF3. Eur J Biochem 2003; 270:4133-39.
25. Hsieh Y J, Wang Z, Kovelman R, Roeder R G. Cloning and characterization of two evolutionarily conserved subunits (TFIIIC102 and TFIIIC63) of human TFIIIC and their involvement in functional interactions with TFIIIB and RNA polymerase III. Mol Cell Biol 1999; 19:4944-52.
26. Matsumoto S, Abe Y, Fujibuchi T, et al. Characterization of a MAPKK-like protein kinase TOPK. Biochem Biophys Res Commun 2004; 325:997-1004.
27. Dong V M, McDermott D H, Abdi R. Chemokines and diseases. Eur J Dermatol 2003; 13:224-30.

28. Abe Y, Matsumoto S, Kito K, Ueda N. Cloning and expression of a novel MAPKK-like protein kinase, lymphokine-activated killer T-cell-originated protein kinase, specifically expressed in the testis and activated lymphoid cells. J Biol Chem 2000; 275:21525-31.
29. Logan G J, Smyth C M, Earl J W, et al. HeLa cells cocultured with peripheral blood lymphocytes acquire an immuno-inhibitory phenotype through up-regulation of indoleamine 2,3-dioxygenase activity. Immunology 2002; 105:478-87.
30. Lubeseder-Martellato C, Guenzi E, Jorg A, et al. Guanylate-binding protein-1 expression is selectively induced by inflammatory cytokines and is an activation marker of endothelial cells during inflammatory diseases. Am J Pathol 2002; 161:1749-59.
31. Phillips S M, Banerjea A, Feakins R, Li S R, Bustin S A, Dorudi S. Tumor-infiltrating lymphocytes in colorectal cancer with microsatellite instability are activated and cytotoxic. Br J Surg 2004; 91:469-75.
32. Oliveira S H, Taub D D, Nagel J, et al. Stem cell factor induces eosinophil activation and degranulation: mediator release and gene array analysis. Blood 2002; 100:4291-97.
33. Xanthoulea S, Pasparakis M, Kousteni S, et al. Tumor necrosis factor (TNF) receptor shedding controls thresholds of innate immune activation that balance opposing TNF functions in infectious and inflammatory diseases. J Exp Med 2004; 200:367-76.
34. Brennan D J, O'Brien S L, Fagan A, et al. Application of DNA microarray technology in determining breast cancer prognosis and therapeutic response. Expert Opin Biol Ther 2005; 5:1069-83.
35. Canna K, McArdle P A, McMillan D C, et al. The relationship between tumor T-lymphocyte infiltration, the systemic inflammatory response and survival in patients undergoing curative resection for colorectal cancer. Br J Cancer 2005; 92:651-54.
36. Rossi D, Zlotnik A. The biology of chemokines and their receptors. Annu Rev Immunol 2000; 18:217-42.
37. Miyazaki M, Nakatsura T, Yokomine K, et al. DNA vaccination of HSP105 leads to tumor rejection of colorectal cancer and melanoma in mice through activation of both CD4 T cells and CD8 T cells. Cancer Sci 2005; 96:695-705.
38. Ein-Dor L, Kela I, Getz G, Givol D, Domany E. Outcome signature genes in breast cancer: is there a unique set? Bioinformatics 2005; 21:171-78.
39. Becker R A, Chambers, JM and Wilks A R The New S Language. Wadsworth & Brooks/Cole 1988.
40. Gentleman R., Carey V J, Huber W., Irizarry R A, Dudoit S. Bioinformatics and Computational Biology Solutions Using R and Bioconductor. Springer 2005.
41. Bauer D F. Constructing confidence sets using rank statistics. Journal of the American Statistical Association 1972; 67:687-690.
42. Lonnstedt I. and Speed T P. Replicated microarray data. Statistica Sinica 2002; 12:31-46.
43. Efron, B. and Tibshirani, R. An Introduction to the Bootstrap. Chapman & Hall. 2005
44. Harraway J. Introductory Statistical Methods and the Analysis of Variance. University of Otago Press 1993.
45. McCabe G P, Moore D S Introduction to the Practice of Statistics W.H. Freeman & Co. 2005
46. Casella G, Berger R L Statistical Inference Wadsworth 2001
47. McLaughlan G J, Do K, Ambroise C Analyzing Microarray Gene Expression Data (Wiley Series in Probability and Statistics) 2004
48. Wright G W, Simon R M A random variance model for detection of differential gene expression in small microarray experiments. Bioinformatics 2003; 19:2448-2455
49. Hastie T, Tibshirani R, Friedman J The Elements of Statistical Learning Data Mining, Inference and Prediction Springer 2003
50. Neter J, Kutner M H, Wasserman W, Nachtsheim C J, Applied Linear Statistical Models McGraw-Hill/Irwin 1996
51. Venables, WN, Ripley, BD Modern Applied Statistics with S. $4^{th}$ ed. Springer 2002.
52. Ripley, B. D. Pattern Recognition and Neural Networks Cambridge University Press 1996
53. Cristianini N, Shawe-Taylor J An Introduction to Support Vector Machines (and other kernel-based learning methods) Cambridge University Press 2000
54. Breiman L, Friedman J, Stone C J, Olshen R A Classification and Regression Trees Chapman & Hall/CRC 1984
55. Good, PI Resampling Methods: A Practical Guide to Data Analysis Birkhauser 1999

Wherein in the description reference has been made to integers or components having known equivalents, such equivalents are herein incorporated as if individually set fourth.

Although the invention has been described by way of example and with reference to possible embodiments thereof, it is to be appreciated that improvements and/or modifications may be made without departing from the scope thereof.

What is claimed is:

1. A method for treating a patient previously treated for colorectal cancer, consisting of the steps:
   (i) obtaining a CRC tumor sample from a patient, isolating mRNA from said CRC tumor sample;
   (ii) reverse transcribing said mRNA into cDNA;
   (iii) using polymerase chain reaction (PCR) analysis of said cDNA obtained from the CRC tumor sample to determine the amounts of cDNA derived from the genes encoding WD repeat domain 44 (WDR44), rna binding motif, single stranded interacting protein 1, isoform d (RBMS1), Ras-GTPase activating protein SH3 domain-binding protein 2 (SACMIL), sterol o-acyltransferase acyl-coenzyme a: cholesterol acyltransferase 1 (SOAT1), pdz-binding kinase (PBK), ras-gtpase activating protein sh3 domain-binding protein 2 (G3BP2), zinc finger and BTB domain containing 20 (ZBTB20), zinc finger protein 410 (ZNF410), COMM domain containing 2 (COMMD2), proteasome (prosome, macropain) 26s subunit, atpase, 1 (PSMC1), COX10 homolog, cytochrome c oxidase assembly protein, heme A: farnesyltransferase (yeast) (COX10), general transcription factor iiic, polypeptide 5 (63kd) (GTF3C5), hyaluronan-mediated motility receptor (rhamm) (HMMR), ubiquitin-conjugating enzyme e21 3 (UBE2L3), gnas complex locus (GNAS), protein phosphatase 2 (formerly 2a), regulatory subunit b (pr 52), alpha isoform (PP2R2A), ribonuclease, rnase a family, 2 (liver, eosinophil-derived neurotoxin) (RNASE2), short coiled-coil protein (SCOC), proteasome (prosome, macropain) 26s subunit, non-atpase, 9 (PSMD9), eukaryotic translation initiation factor 3, subunit 7 (zeta, 66/67kd) (EIF3 S7), ATPase, Ca++ transporting, plasma membrane 4 (ATP2B4), and atp-binding cassette, sub-family c, member 9, isoform sur2a-delta-14 (ABCC9) by contacting said cDNA from said patient with sets of three oligonucleotides, one oligonucleotide of each set comprising a synthetic forward primer having a length of between 17-30 mer and 20-80% G+C content, another oligonucleotide of said set comprising a synthetic reverse primer having a length of 17-30 mer and 20-80% G+C content, and a third oligonucleotide of said set comprising a reporter fluorescent dye and a quencher fluorescent dye-labeled probe, specific for one of the genes;

(iv) calculating the odds ratio for disease recurrence;

(v) if the odds ratio is 8.4 or higher, the patient is treated with a higher or longer dose of chemotherapeutic agent, pursue aggressive or experimental treatments, and (vi) if the odds ratio is less than 8.4, the patient is treated with surgery alone.

2. The method of claim 1, wherein the step of determining the amounts of at least one oligonucleotide derived from the genes is carried out using a nucleotide complementary to at least a portion of said cDNA of said gene.

* * * * *

UNITED STATES PATENT AND TRADEMARK OFFICE
CERTIFICATE OF CORRECTION

PATENT NO. : 10,422,005 B2
APPLICATION NO. : 12/214782
DATED : September 24, 2019
INVENTOR(S) : Hjalmar Nekarda et al.

Page 1 of 1

It is certified that error appears in the above-identified patent and that said Letters Patent is hereby corrected as shown below:

In the Claims

In Column 170 Line 55, please replace the word "famesyltransferase" with the word --farnesyltransferase--.

Signed and Sealed this
Twenty-ninth Day of October, 2019

Andrei Iancu
*Director of the United States Patent and Trademark Office*